United States Patent
Tsang et al.

(10) Patent No.: US 11,413,243 B2
(45) Date of Patent: Aug. 16, 2022

(54) FUSOGENIC COMPOUNDS FOR DELIVERY OF BIOLOGICALLY ACTIVE MOLECULES

(71) Applicant: Nitto Denko Corporation, Osaka (JP)

(72) Inventors: Kwok Yin Tsang, Irvine, CA (US); Bharat Majeti, San Diego, CA (US); John Gaudette, Poway, CA (US); Roger Adami, Carlsbad, CA (US); Hao Bai, San Diego, CA (US); Wenbin Ying, Oceanside, CA (US)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 16/182,571

(22) Filed: Nov. 6, 2018

(65) Prior Publication Data
US 2019/0133948 A1 May 9, 2019

Related U.S. Application Data

(60) Provisional application No. 62/582,252, filed on Nov. 6, 2017.

(51) Int. Cl.
| | |
|---|---|
| *A61K 9/127* | (2006.01) |
| *A61K 47/10* | (2017.01) |
| *A61K 47/69* | (2017.01) |
| *A61K 31/7105* | (2006.01) |
| *A61K 47/14* | (2017.01) |
| *C07C 201/00* | (2006.01) |
| *B82Y 5/00* | (2011.01) |

(52) U.S. Cl.
CPC ........ *A61K 9/1272* (2013.01); *A61K 31/7105* (2013.01); *A61K 47/10* (2013.01); *A61K 47/14* (2013.01); *A61K 47/6911* (2017.08); *C07C 201/00* (2013.01); *B82Y 5/00* (2013.01)

(58) Field of Classification Search
CPC ................................................. A61K 31/7105
USPC .......................................................... 560/196
See application file for complete search history.

(56) References Cited

U.S. PATENT DOCUMENTS

| | | | |
|---|---|---|---|
| 2011/0223257 A1 | 9/2011 | Zhao et al. | |
| 2013/0022665 A1 | 1/2013 | Niitsu et al. | |
| 2013/0115274 A1 | 5/2013 | Knopov et al. | |
| 2013/0171127 A1* | 7/2013 | Niitsu .................... | A61K 45/06 424/94.67 |
| 2013/0330401 A1 | 12/2013 | Payne et al. | |

FOREIGN PATENT DOCUMENTS

| | | |
|---|---|---|
| EA | 201490847 A1 | 12/2014 |
| EA | 026374 B1 | 4/2017 |
| EP | 2069500 B1 | 9/2014 |
| EP | 2998289 A1 | 3/2016 |
| RU | 2615143 C2 | 4/2017 |
| RU | 2015119409 A | 10/2017 |
| WO | WO 2005/026372 | 3/2005 |
| WO | WO 2011/076807 A2 | 6/2011 |
| WO | WO 2011/119852 A1 | 9/2011 |
| WO | WO 2013/063468 A1 | 5/2013 |
| WO | WO 2014/076195 A1 | 5/2014 |

OTHER PUBLICATIONS

Gennaro A. R., *Remington'S Pharmaceutical Sciences*, Mack Publishing Co., Easton, PA (18$^{th}$ Ed.—1990); TOC.
Greene and Wuts, [Eds.] *Protective Groups in Organic Synthesis*, (3$^{rd}$ Edition—1991); TOC.
Hermanson Greg T., *Bioconjugate Techniques*, Academic Press (1996); TOC.
International Search Report and Written Opinion dated Feb. 4, 2019 in corresponding PCT/US2018/059504, filed Nov. 6, 2018 in 7 pages.
Gao et al., "Amphiphilic dendritic peptides: Synthesis and behavior as an organogelator and liquid crystal", Beilstein Journal of Organic Chemistry, vol. 7, pp. 198-203 (2011).
International Preliminary Report on Patentability issued in International Application No. PCT/US2018/059504, dated May 12, 2020.
Invitation pursuant to Rule 63(1) EPC, issued in EP Application No. 18872775.4, dated Jul. 1, 2021.
Supplementary European Search Report issued in EP Application No. 18872775.4, dated Oct. 29, 2021.
Office Action issued in Indian Application No. 202017020619, dated Nov. 30, 2021.
Office Action issued in Russian Application No. 2020117606, dated Apr. 22, 2022.
Dyson et al., "May's Chemistry of Synthetic Drugs", MIR Publishers, 5$^{th}$ Edition, 1964, p. 12-19.
Pokrovsky, "Medicinal Products", Popular Medical Encyclopedia, 4$^{th}$ Edition, 1997, p. 317.

\* cited by examiner

*Primary Examiner* — Ana Z Muresan

(74) *Attorney, Agent, or Firm* — Knobbe Martens Olson & Bear, LLP

(57) ABSTRACT

This invention includes fusogenic compounds, and compositions and methods of use thereof. The fusogenic compounds can be used for making nanoparticle compositions for use in biopharmaceuticals and therapeutics. More particularly, this invention relates to compounds, compositions and methods for providing nanoparticles to incorporate or encapsulate active agents, to deliver and distribute the active agents to cells, tissues, organs, and subjects.

23 Claims, 68 Drawing Sheets

Chemical Formula: $C_{222}H_{386}N_{12}O_{39}$
Exact Mass: 3844.86
Molecular Weight: 3847.58

Chemical Formula: $C_{154}H_{256}N_2O_{27}$
Exact Mass: 2565.87
Molecular Weight: 2567.73

Chemical Formula: $C_{222}H_{402}N_{12}O_{39}$
Exact Mass: 3860.98
Molecular Weight: 3863.70

Chemical Formula: $C_{190}H_{354}N_{12}O_{39}$
Exact Mass: 3428.61
Molecular Weight: 3430.97

Chemical Formula: $C_{170}H_{316}N_{10}O_{31}$
Exact Mass: 2994.35
Molecular Weight: 2996.44

Chemical Formula: $C_{198}H_{340}N_{10}O_{29}$
Exact Mass: 3322.54
Molecular Weight: 3324.94

Chemical Formula: $C_{200}H_{344}N_{10}O_{31}$
Exact Mass: 3382.56
Molecular Weight: 3384.99

Chemical Formula: $C_{196}H_{336}N_{10}O_{31}$
Exact Mass: 3326.50
Molecular Weight: 3328.88

Chemical Formula: $C_{206}H_{352}N_{14}O_{27}$
Molecular Weight: 3457.15
LC-MS, [M+2H] : 3458.3

Chemical Formula: $C_{118}H_{206}N_8O_{21}$
Molecular Weight: 2072.98

LC-MS, [M+H] : 2075.0

Chemical Formula: $C_{118}H_{206}N_8O_{21}$
Molecular Weight: 2072.98

LC-MS, [M+2H] : 2075.0

FUSOGENIC COMPOUNDS FOR DELIVERY OF BIOLOGICALLY ACTIVE MOLECULES

BACKGROUND OF THE INVENTION

Therapeutic agents such as drug compounds, nucleic acid molecules and other active agents operate by uptake into cells, tissues, and organs of a subject. Transfection of agents and molecules into cells is often a limiting step in therapeutic action.

When the active agent molecules are sensitive to attack or degradation in serum or other biological settings, it becomes necessary to protect the molecules in order to achieve their medicinal effect.

For example, one way to carry out transfection of nucleic acids is to incorporate or encapsulate the active molecules in a nanoparticle. A drawback of such methodology can be low rates of cell penetration.

There is a long-standing need for molecules having fusogenic properties to provide nanoparticles that have favorable transfection properties to increase rates of cell penetration and deliver active agents to cells.

What is needed are compositions and compounds for forming nanoparticles for active agents. There is a continuing need for molecules and compositions for efficient transfection and distribution of nucleic acid molecules and other agents to cells and subjects.

BRIEF SUMMARY

This invention relates to the fields of biopharmaceuticals and therapeutics. More particularly, this invention relates to compounds, compositions and methods containing fusogenic molecules for providing nanoparticles to deliver and distribute active agents or drug compounds to cells, tissues, organs, and subjects. This invention relates to molecules and compositions thereof for use in biopharmaceuticals and therapeutics. More particularly, this invention relates to compounds, compositions and methods for providing nanoparticles to deliver and distribute active agents or drug compounds to cells, tissues, organs, and subjects.

This invention provides a range of fusogenic compounds. The fusogenic compounds of this invention can be used to form nanoparticles to deliver and distribute active agents.

Examples of active agents of this disclosure include biologically active molecules, nucleic acids, DNA, RNA, mRNA, siRNA, and microRNA, among other forms.

Embodiments of this invention include the following:

A fusogenic compound having Formula I

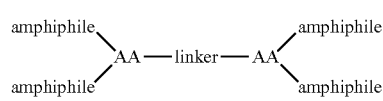

Formula I wherein each amphiphile independently comprises one to two lipophilic chains, wherein the lipophilic chains each independently comprise 8 to 22 carbon atoms;

wherein each AA is independently an amino acid comprising a side chain having an amino group, wherein the amino acid is attached to an amphiphile at each of its amino groups and is attached to the linker at its C terminus;

wherein linker has the structure

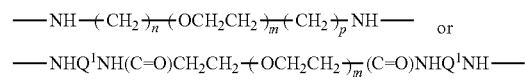

wherein $Q^1$ is branched or unbranched C(2-8)alkandiyl, branched or unbranched C(2-8)alkenediyl, branched or unbranched C(2-8)alkynediyl, or

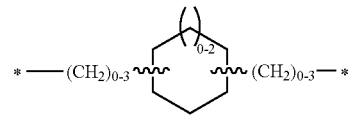

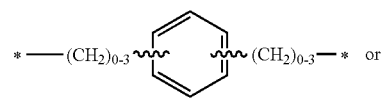

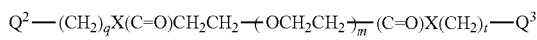

wherein $Q^2$ is

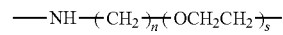

wherein $Q^3$ is

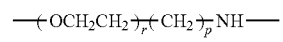

wherein X is —O—, —S—, or —NH—;
n, p, q and t are independently for each occurrence 1 to 3;
m is independently 1 to 10;
r and s are independently for each occurrence 1 to 5.

The fusogenic compound above, wherein AA is selected from the following structures, and any stereoisomer thereof:

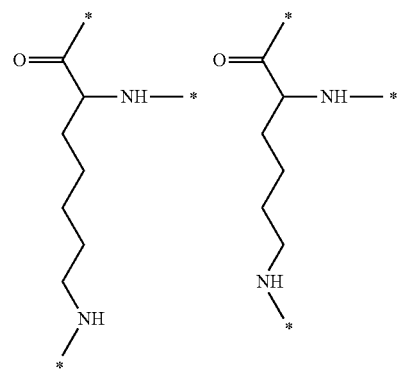

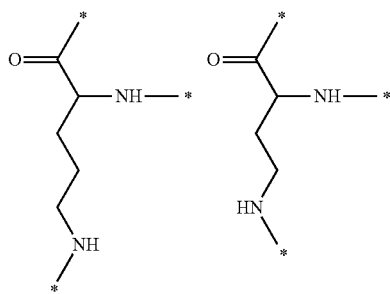

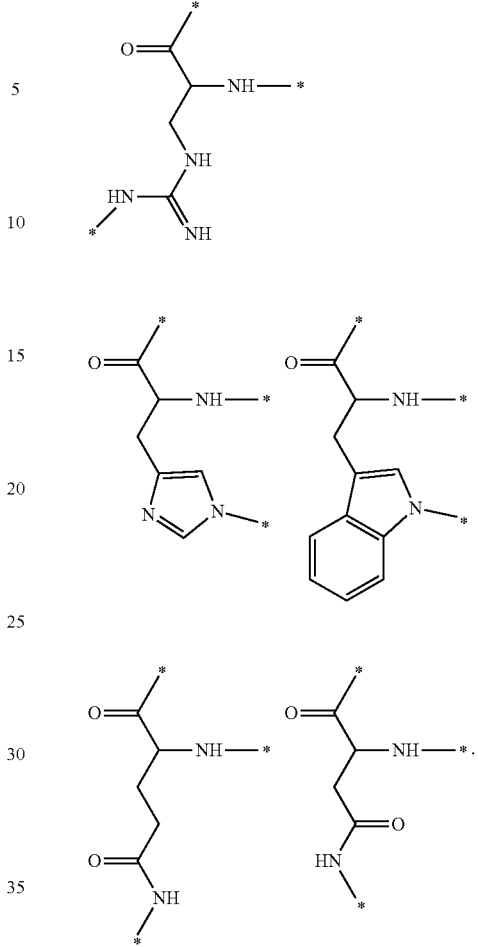

The fusogenic compound above, wherein one or two of the amphiphiles are absent and replaced by an alkyl group, or a pharmaceutically acceptable organic chemical group having 1-400 atoms selected from carbon, oxygen, nitrogen, sulfur, fluorine, and hydrogen.

The fusogenic compound above, wherein the pharmaceutically acceptable organic chemical group is alkyl, alkenyl, alkynyl, acetyl, Boc, Fmoc, TFA, or CBZ, preferably alkyl, acetyl, more preferably acetyl.

The fusogenic compound above, wherein the compound is selected from the following:

[Compound T13]

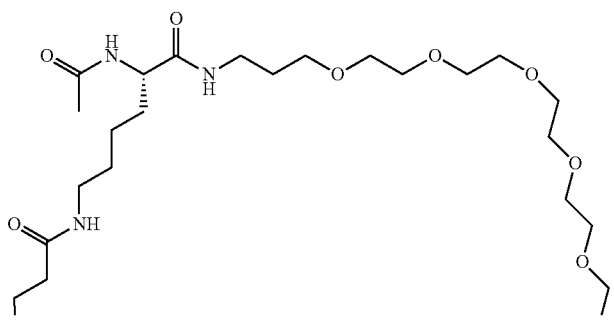

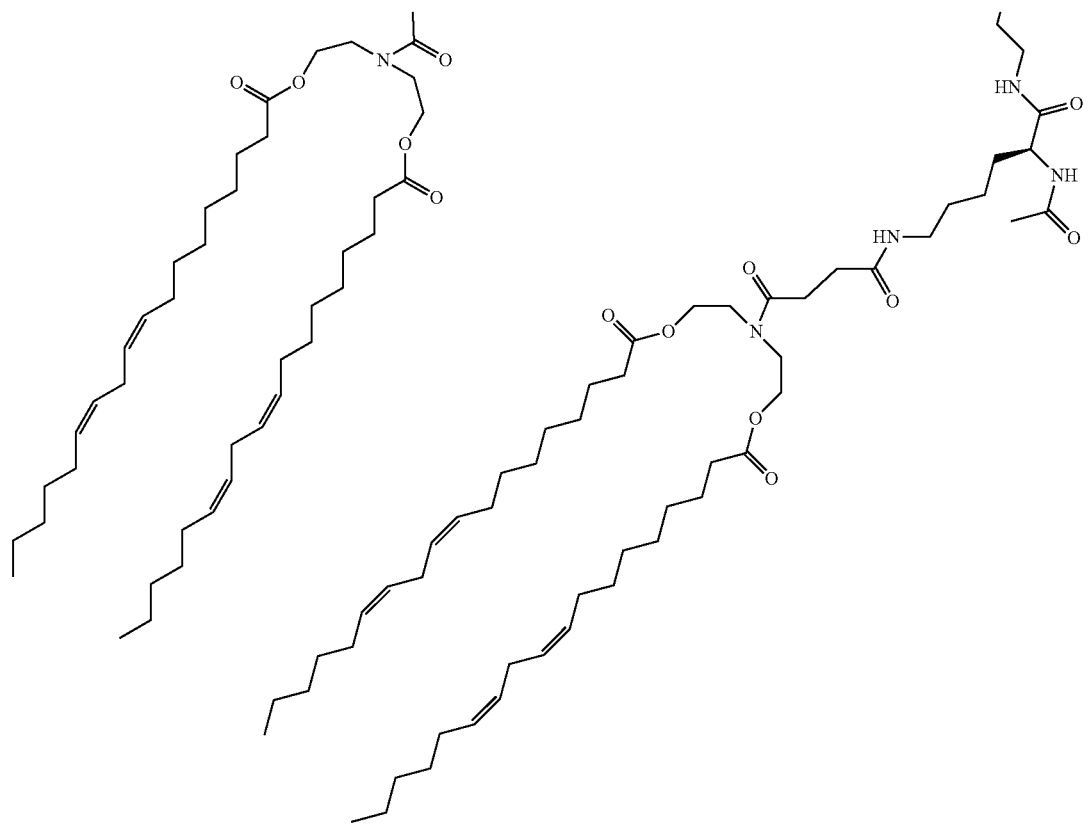
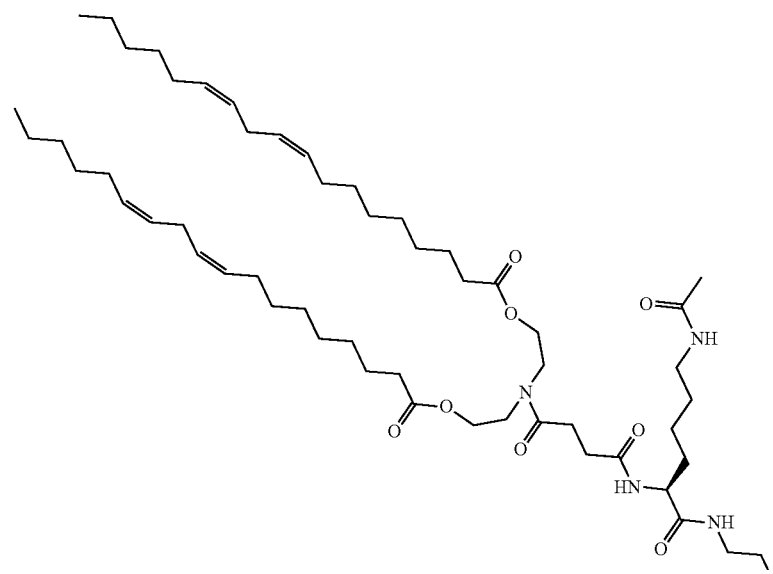
[Compound T14]

-continued

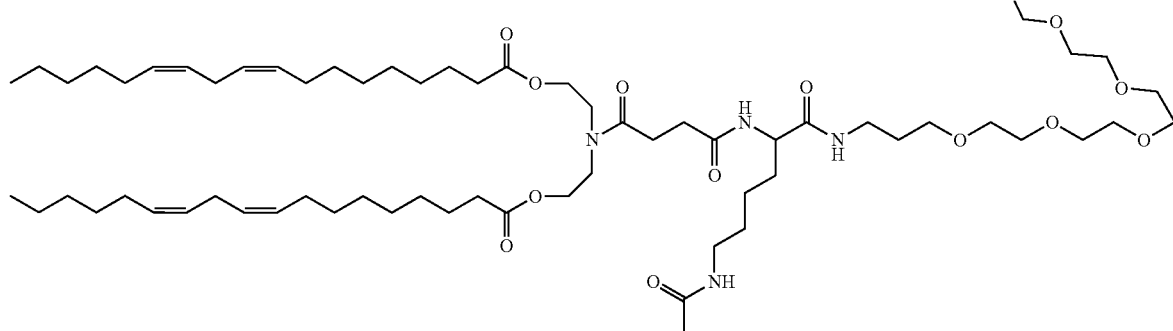

The fusogenic compound above, wherein one or more of the amphiphiles have the structure shown in Formula II

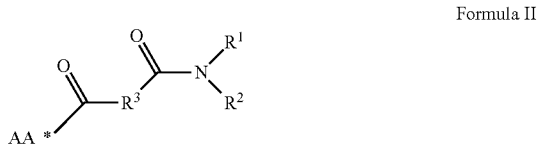

Formula II wherein $R^1$ and $R^2$ are

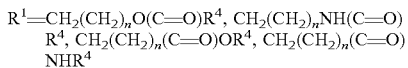

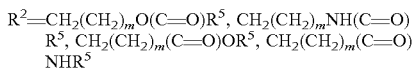

wherein n and m are each independently from 1 to 2; and $R^4$ and $R^5$ are independently for each occurrence a C(12-20) alkyl group, or a C(12-20) alkenyl group;
wherein $R^3$ is selected from branched or unbranched C(1-8)alkandiyl, substituted or unsubstituted C(2-8)alkendiyl, substituted or unsubstituted C(2-8)alkyndiyl, substituted or unsubstituted C(3-8)cycloalkandiyl, substituted or unsubstituted arylene, substituted or unsubstituted C(4-8)heteroarylene, and substituted or unsubstituted heterocycloalkandiyl, and combinations thereof; wherein $R^3$ is optionally interrupted by one or more of —O—, —S—, —SO—, —SO$_2$—, —NH—, —NR$^6$—, —NH(C=O)—, —O(C=O)—, wherein $R^6$ is C(1-6)alkyl-, C(1-6)alkoxy-, or C(1-6)alkoxy-C(1-6)alkoxy-.

$R^3$ is preferably branched or unbranched C(2-8)alkandiyl, substituted or unsubstituted C(2-8)alkendiyl, substituted or unsubstituted C(2-8)alkyndiyl, C(3-8)cycloalkandiyl, substituted or unsubstituted C(4-8)arylene, and even more preferably branched or unbranched C(2-8)alkandiyl, substituted or unsubstituted C(3-8)cycloalkandiyl.

As used herein, the term "and combinations thereof" in reference to formulas indicates further variations in structure based on combining the listed groups. For example, the combination of C(1-8)alkandiyl and C(4-8)heteroarylene refers to C(1-8)alkandiyl-C(4-8)heteroarylene, as well as C(1-8)alkandiyl-C(4-8)heteroarylene-C(1-8)alkandiyl.

The fusogenic compound above, wherein $R^3$ is selected from
branched or unbranched C(2-8)alkandiyl,
substituted or unsubstituted C(2-8)alkendiyl,
substituted or unsubstituted C(2-8)alkyndiyl
substituted or unsubstituted C(3-8)cycloalkandiyl
substituted or unsubstituted C(4-8)heteroarylene

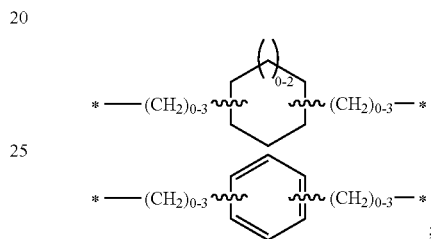

preferably branched or unbranched C(2-8)alkandiyl, substituted or unsubstituted C(3-8)cycloalkandiyl.

The fusogenic compound above, wherein one or more of the amphiphiles have the structure shown in Formula III

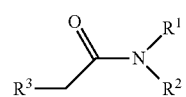

Formula III wherein $R^1$ and $R^2$ are

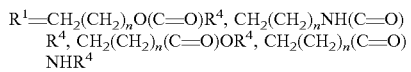

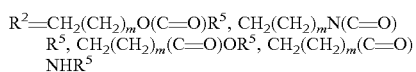

wherein n and m are each independently from 1 to 2; and $R^4$ and $R^5$ are independently for each occurrence a C(12-20) alkyl group, or a C(12-20) alkenyl group;
wherein $R^3$ is selected from
-alkyl-(C=O)—, which is attached to AA;
-alkyl-O(C=O)—, which is attached to AA;
-alkyl-NH(C=O)—, which is attached to AA;
-alkyl-(C=O)-alkyl-(C=O)—, which is attached to AA;
-alkyl-O(C=O)-alkyl-(C=O)—, which is attached to AA
-alkyl-NH(C=O)-alkyl-(C=O)—, which is attached to AA
-alkenyl-(C=O)—, which is attached to AA;
-alkenyl-O(C=O)—, which is attached to AA;
-alkenyl-NH(C=O)—, which is attached to AA;
-alkenyl-(C=O)-alkenyl-(C=O)—, which is attached to AA;
-alkenyl-O(C=O)-alkenyl-(C=O)—, which is attached to AA -alkenyl-NH(C=O)-alkenyl-(C=O)—, which is attached to AA -alkynyl-(C=O)—, which is attached to AA;

-alkynyl-O(C=O)—, which is attached to AA;

-alkynyl-NH(C=O)—, which is attached to AA;

-alkynyl-(C=O)-alkynyl-(C=O)—, which is attached to AA;

-alkynyl-O(C=O)-alkynyl-(C=O)—, which is attached to AA

-alkynyl-NH(C=O)-alkynyl-(C=O)—, which is attached to AA wherein any alkyl of $R^3$ is branched or unbranched C(1-6)alkyl, any alkenyl of $R^3$ is branched or unbranched C(2-6)alkenyl, and any alkynyl of $R^3$ is branched or unbranched C(2-6)alkynyl;

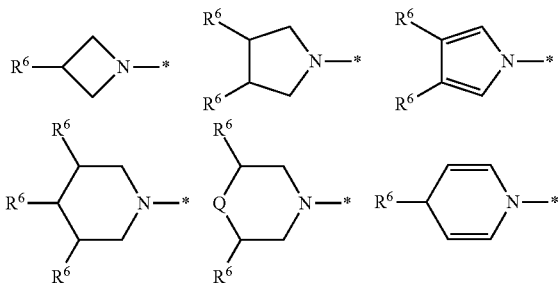

and positional isomers thereof;

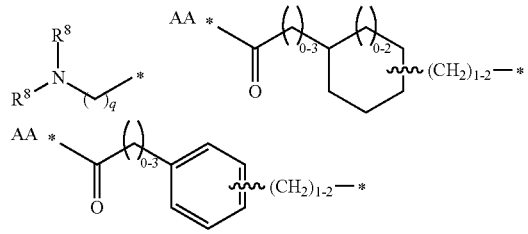

wherein
each $R^6$ is independently selected from H, alkyl, alkoxy, and alkoxyalkoxy, with the proviso that one $R^6$ is —(C=O)— or -alkyl-(C=O)— which is attached to AA;

each $R^8$ is independently selected from H, alkyl, with the proviso that one $R^8$ is —(C=O)— or -alkyl-(C=O)— which is attached to AA;

q is from zero to four;

Q is O or N.

The fusogenic compound above, wherein alkyl of $R^6$ and $R^8$ are each independently branched or unbranched C(1-6) alkyl, alkoxy of $R^6$ is C(1-6)alkoxy, and alkoxyalkoxy of $R^6$ is C(1-6)alkoxyC(1-6)alkoxy.

The fusogenic compound above, wherein $R^4$ and $R^5$ are independently
for each occurrence a C(14-18) alkyl group, or a C(14-18) alkenyl group, preferably a C(14-18) alkenyl group having 2 to 4 double bonds.

The fusogenic compound above, wherein the compound is selected from the following:

[Compound R4]
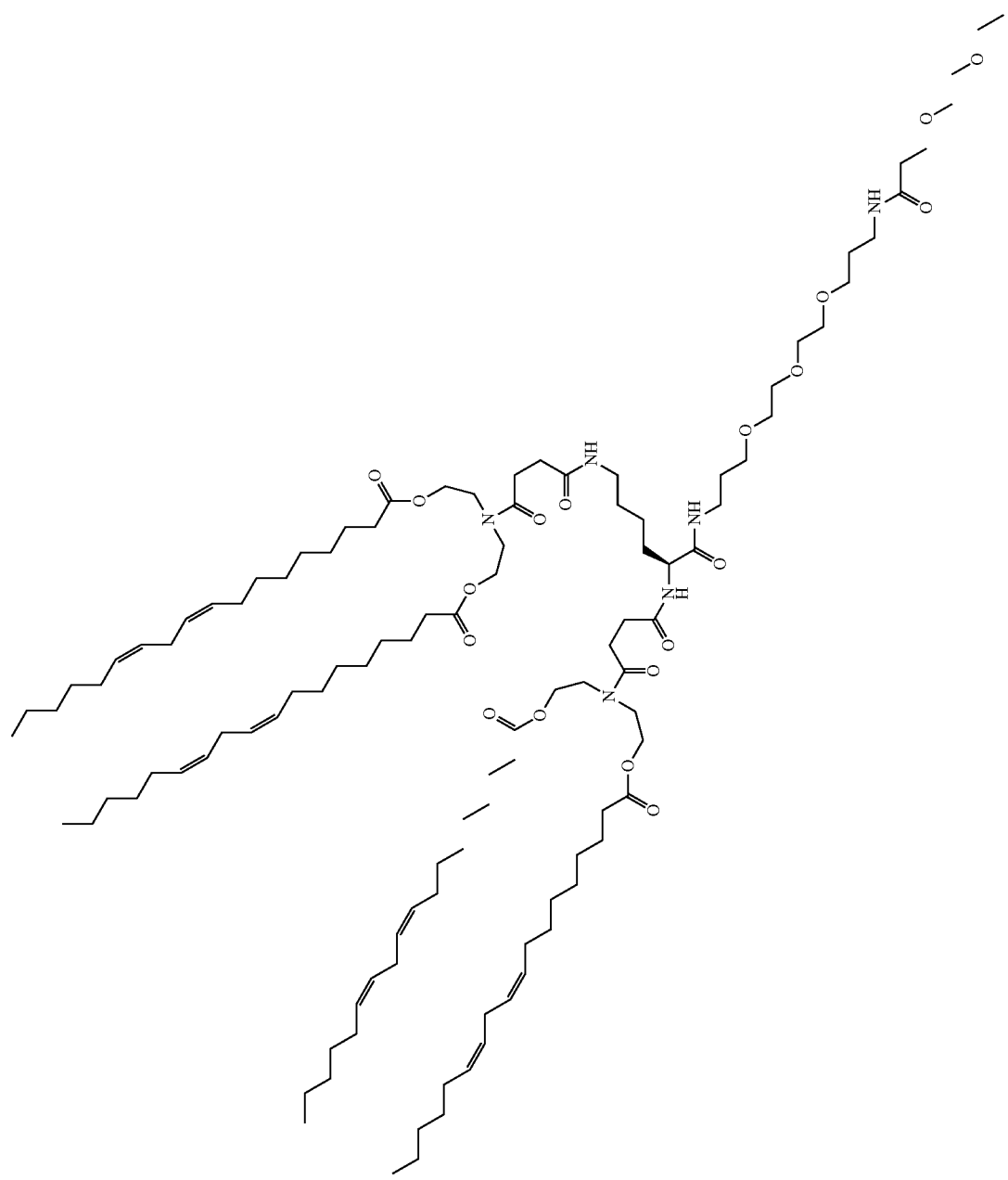

-continued
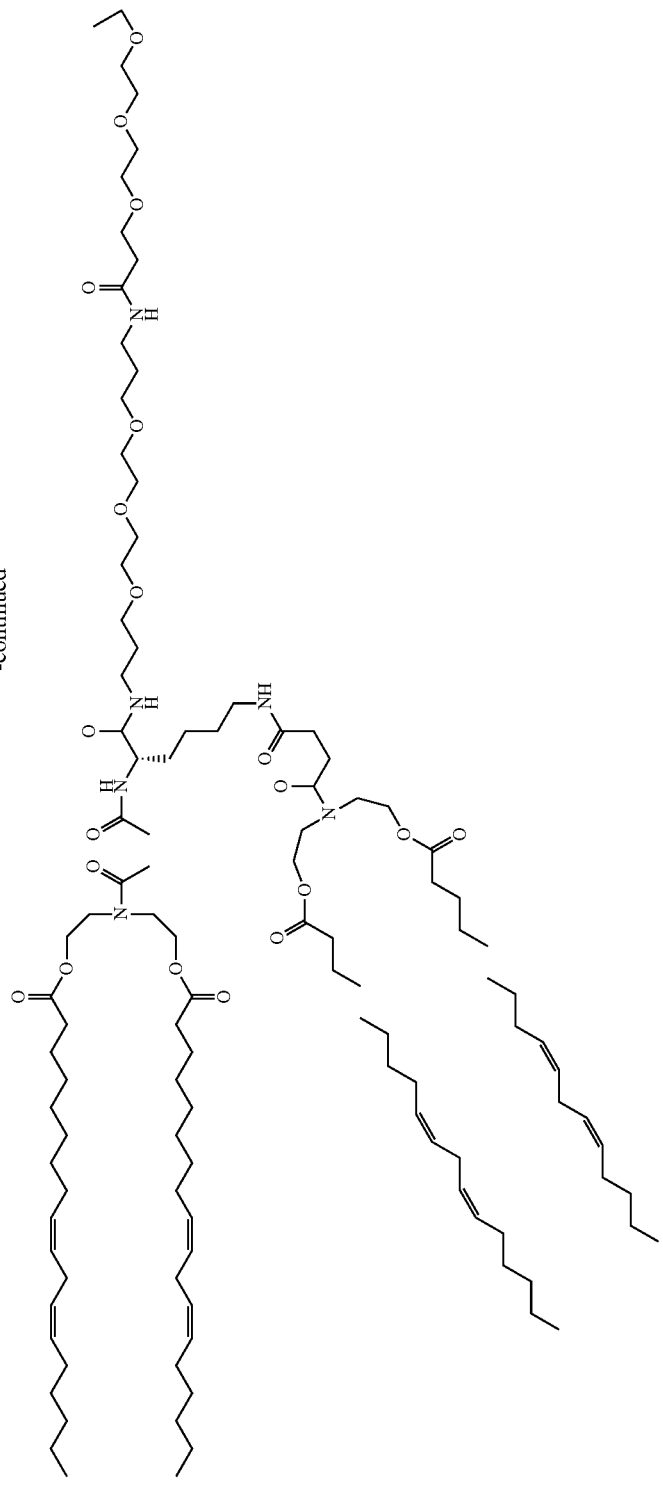

[Compound S6]
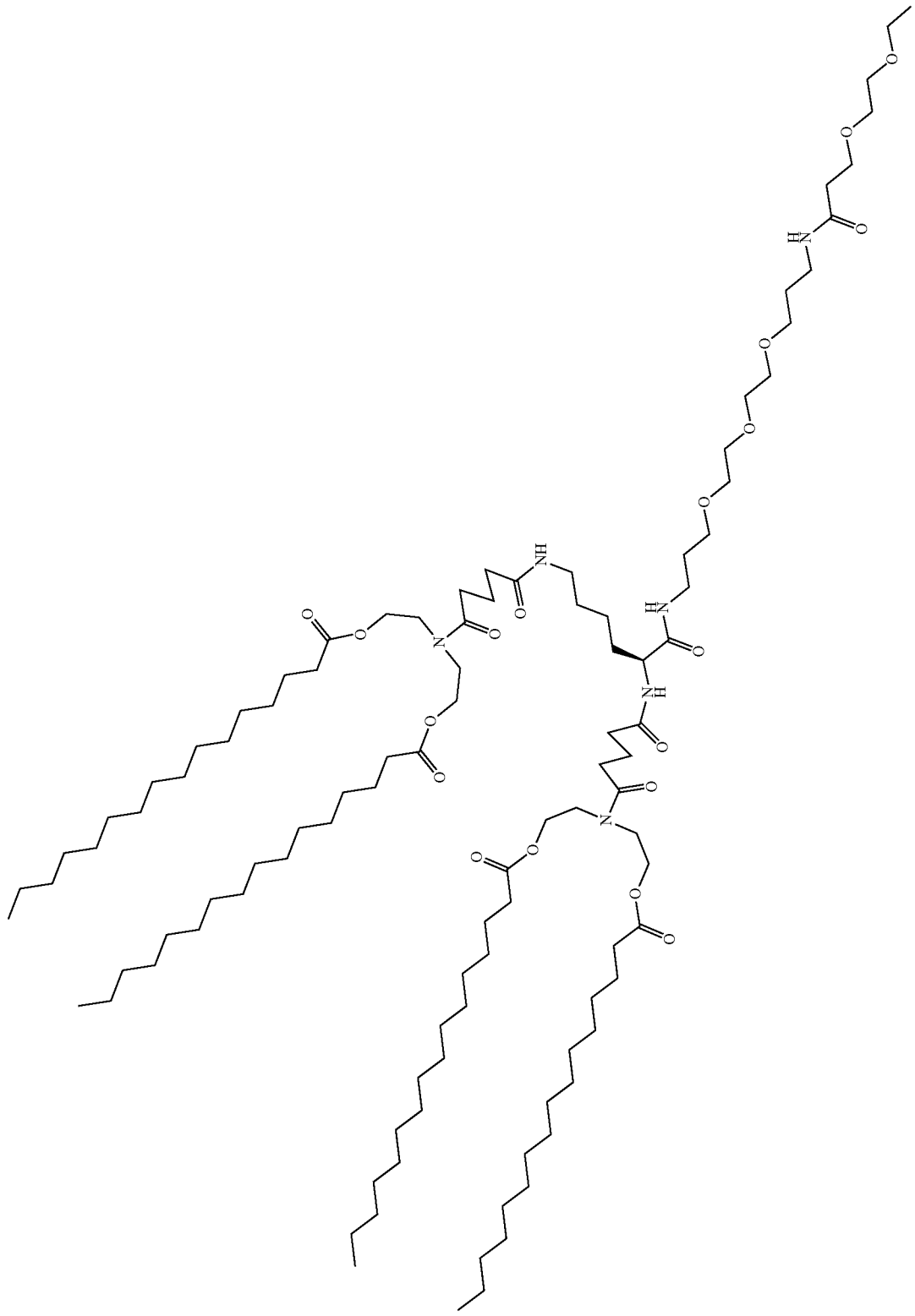

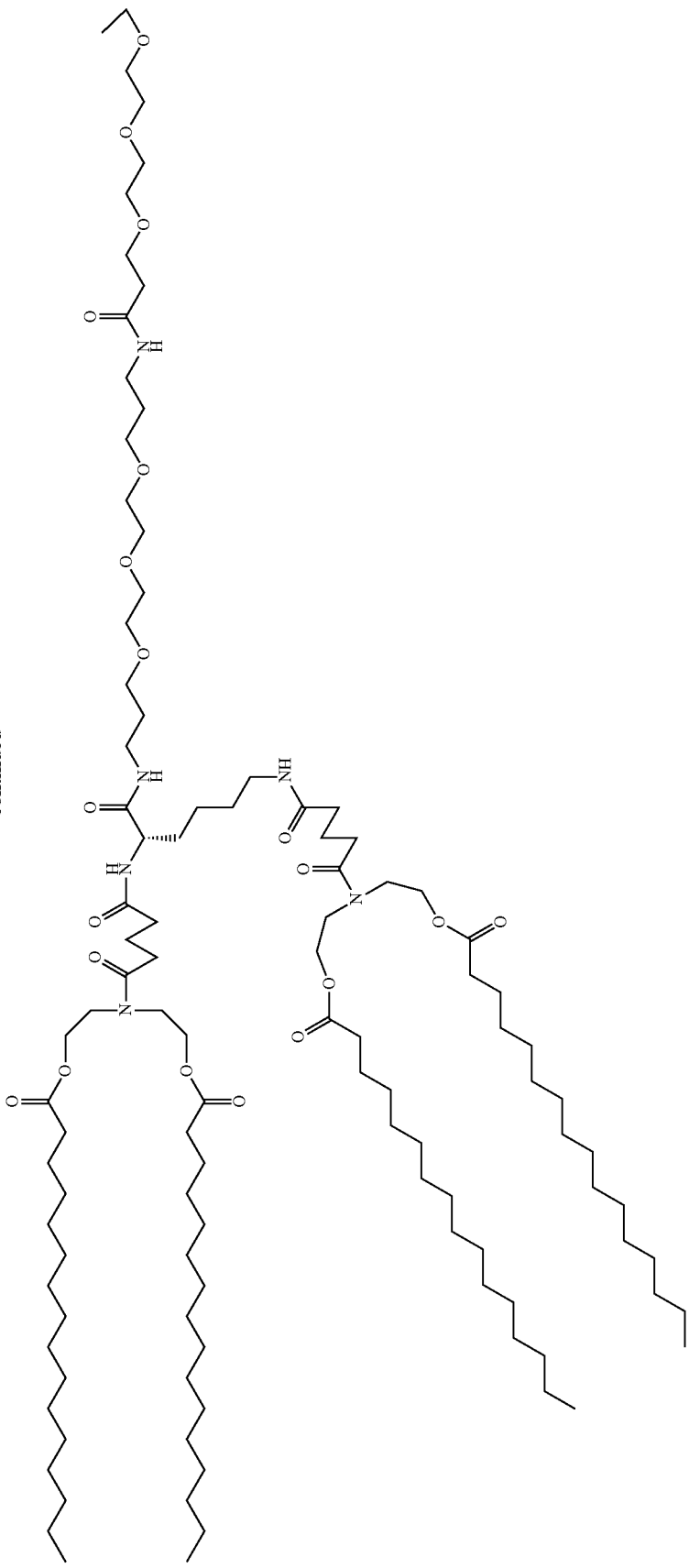

[Compound S7]
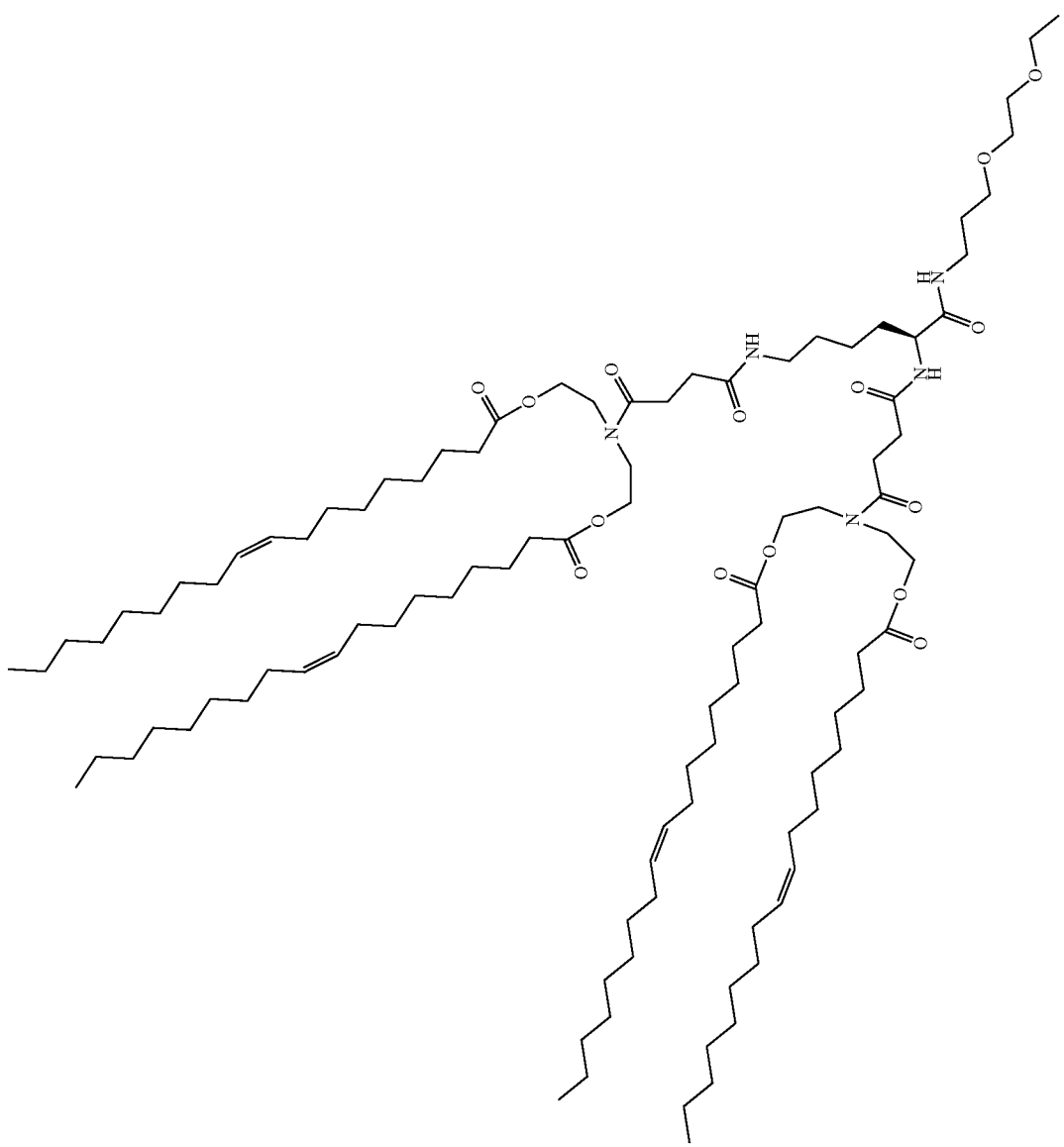

-continued
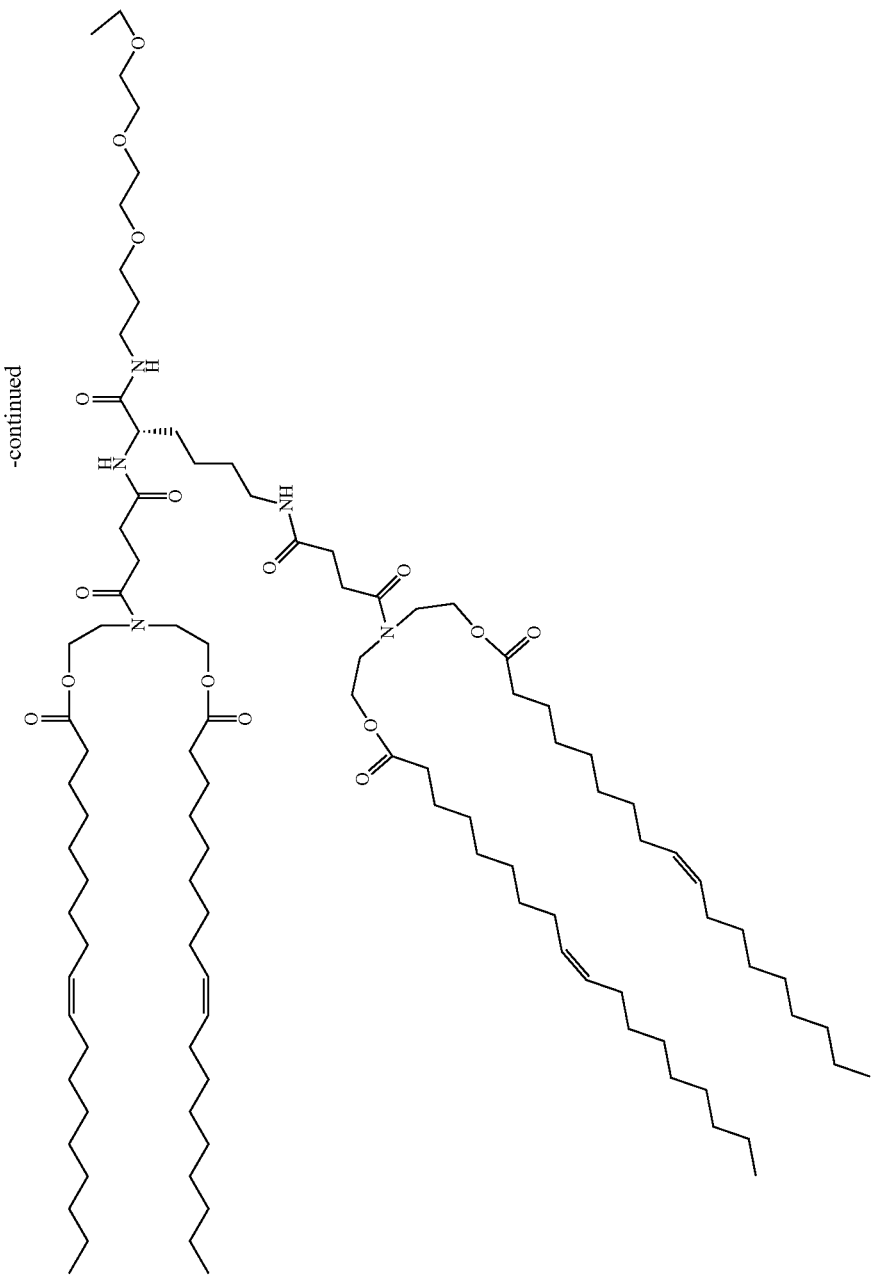

[Compound S8]
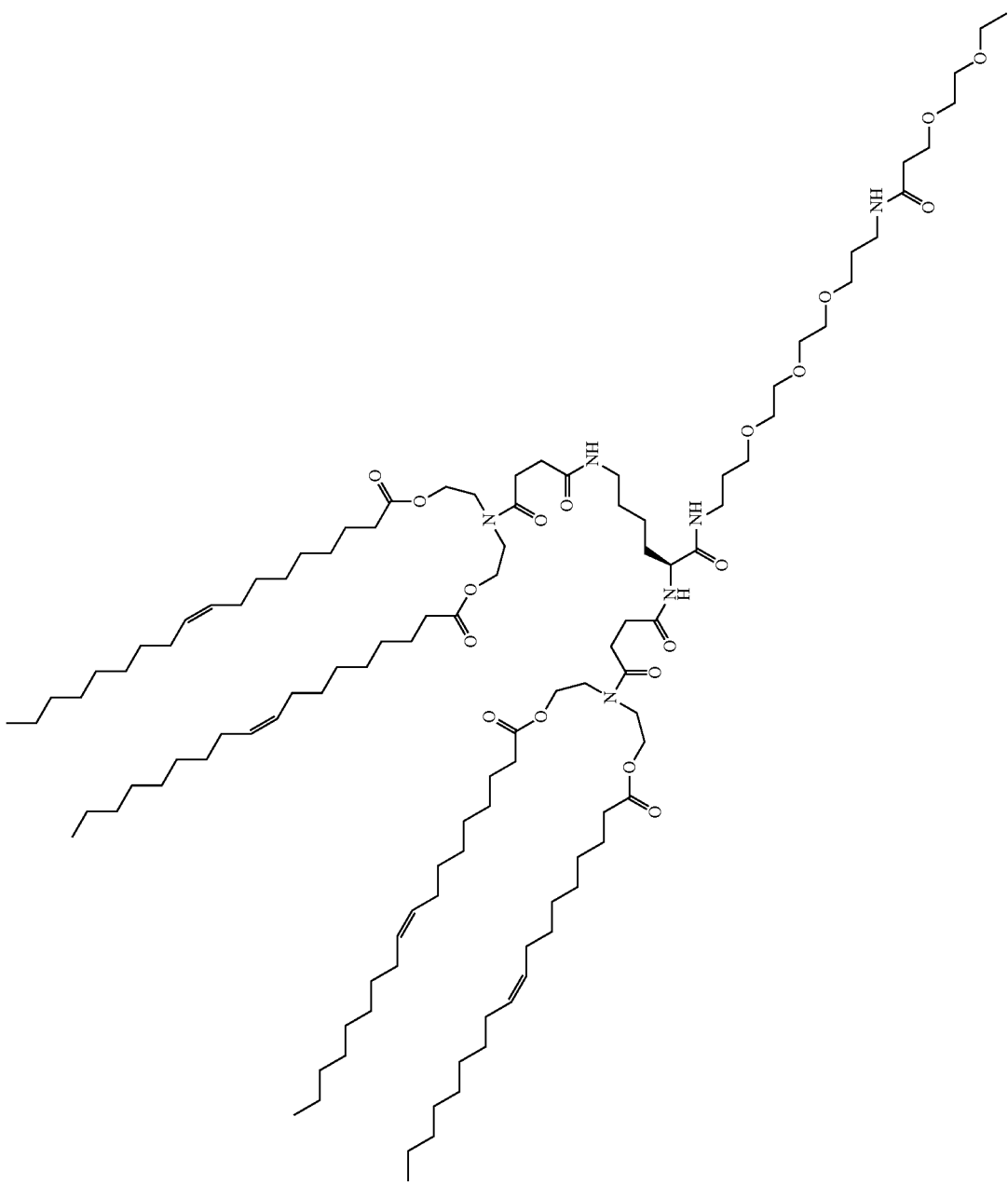

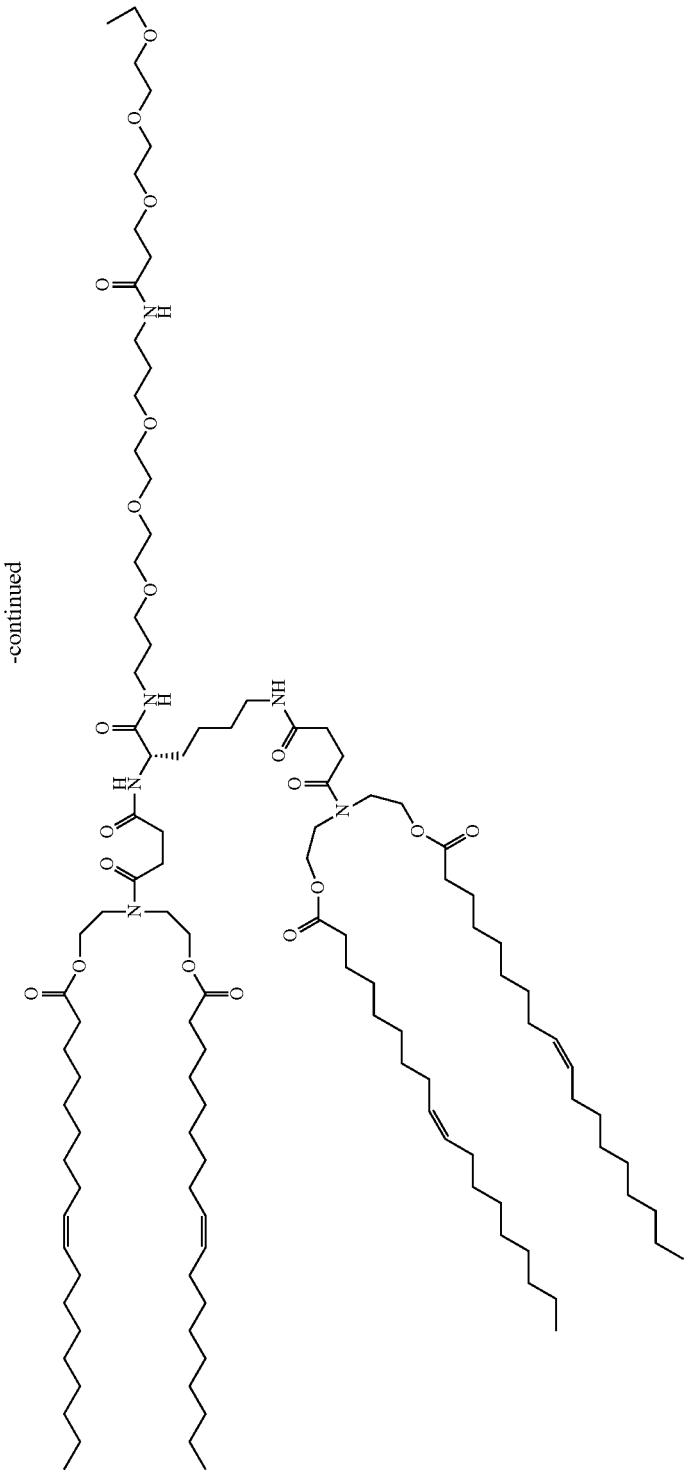

[Compound T1]
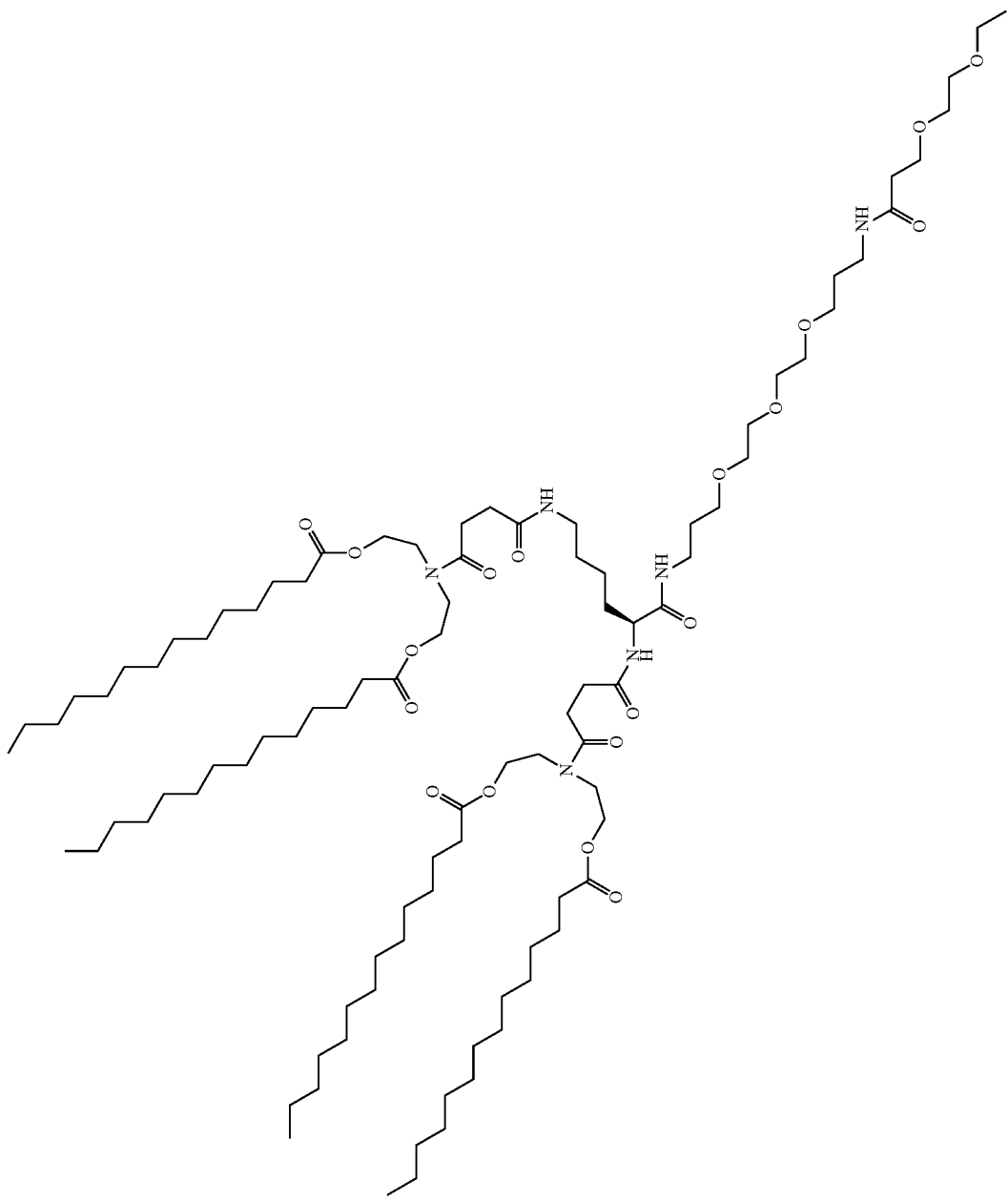

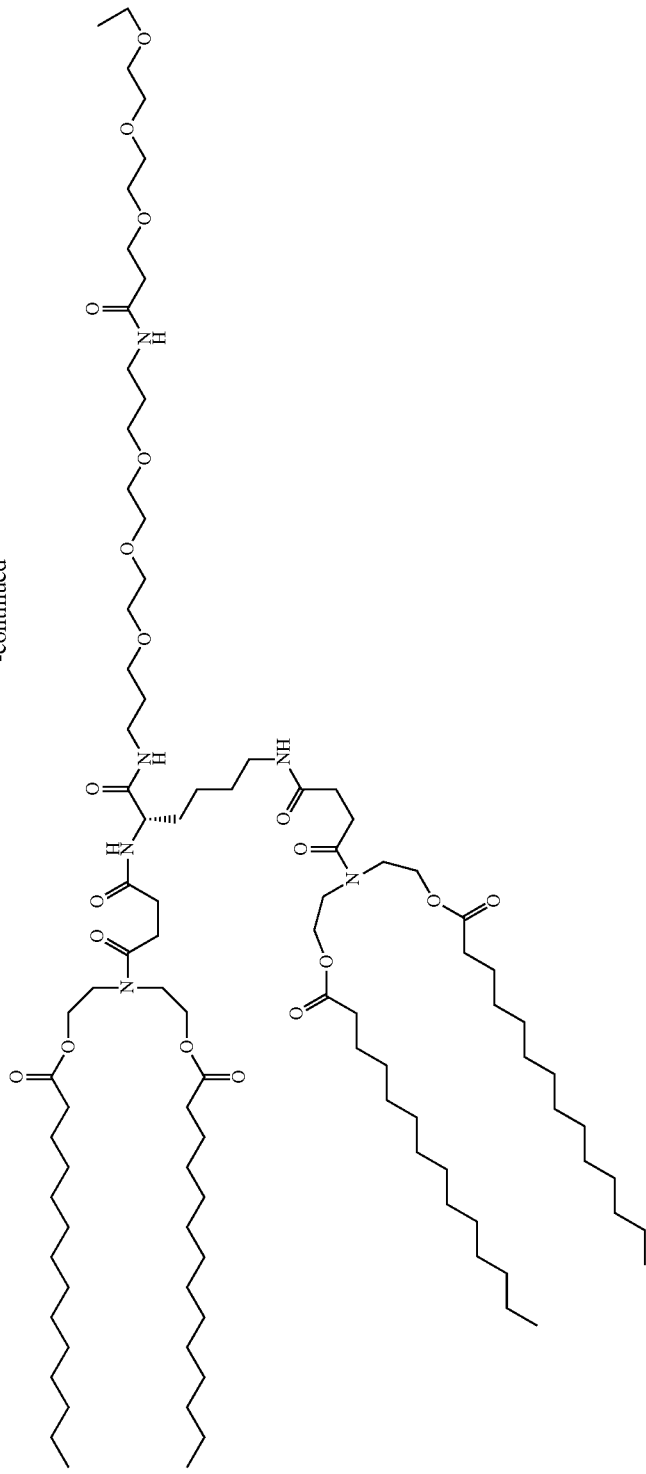

-continued
[Compound T2]
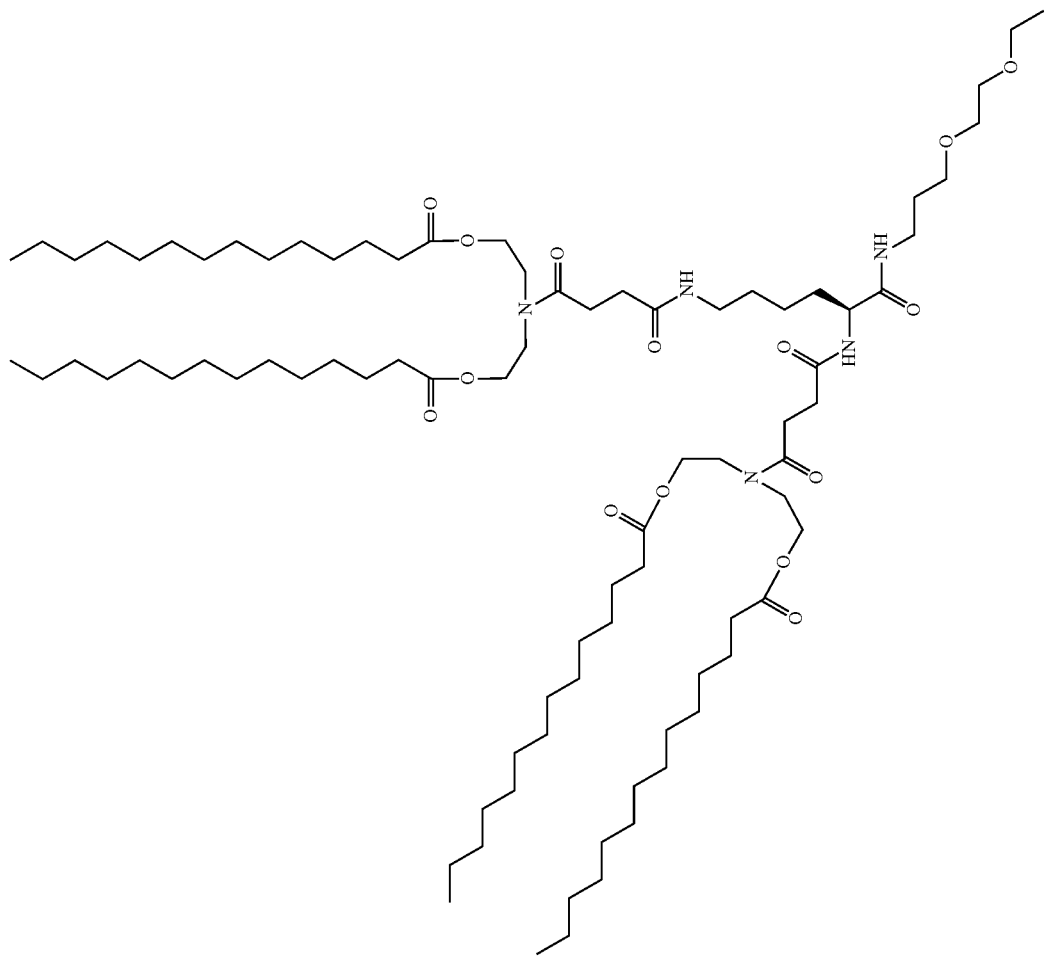

-continued
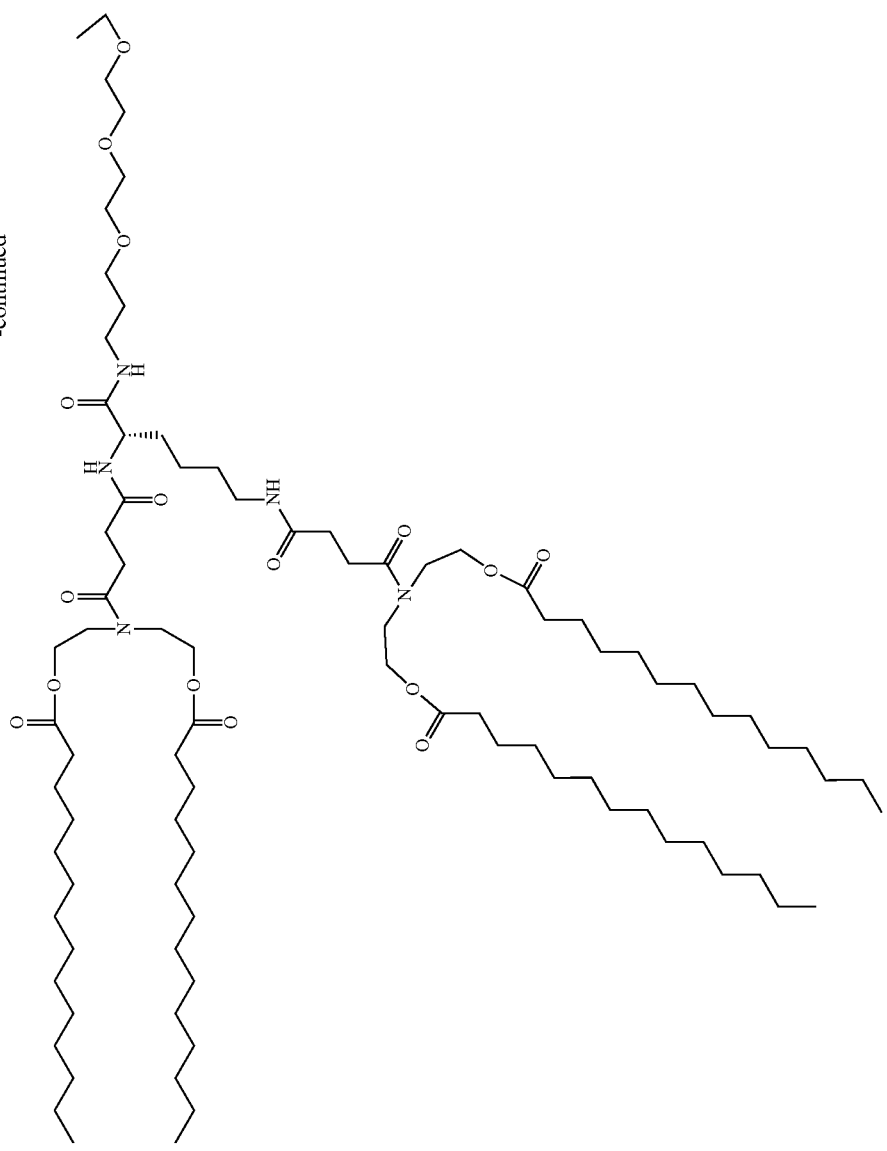

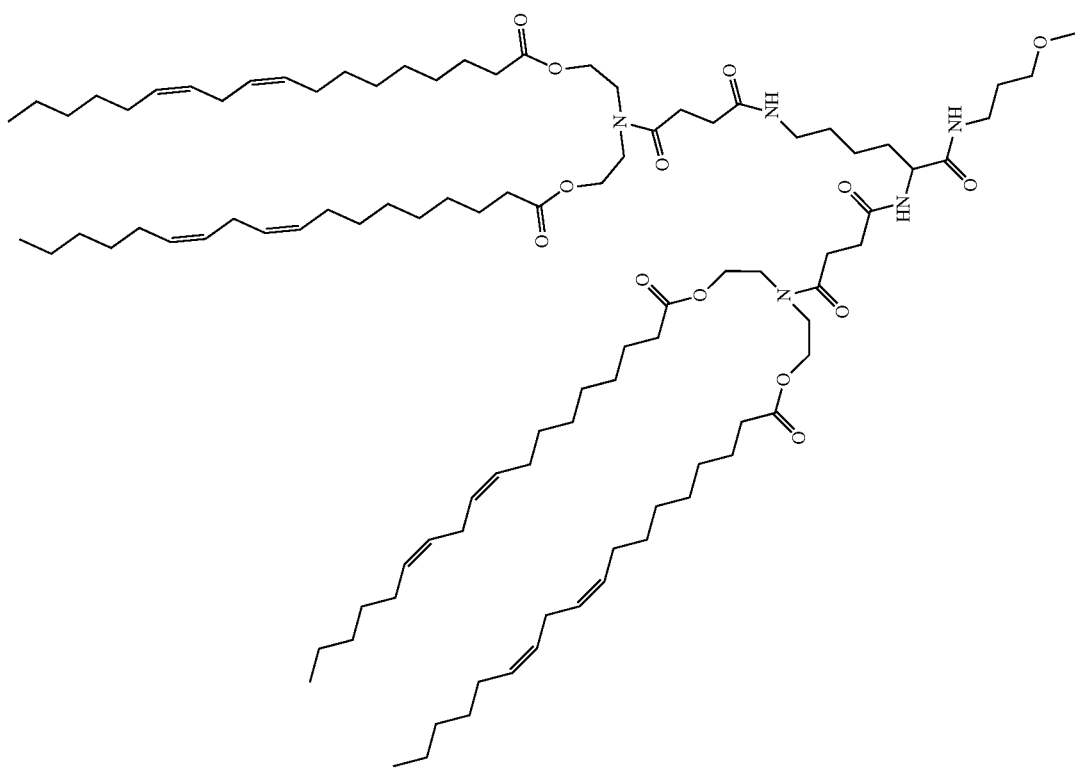

-continued
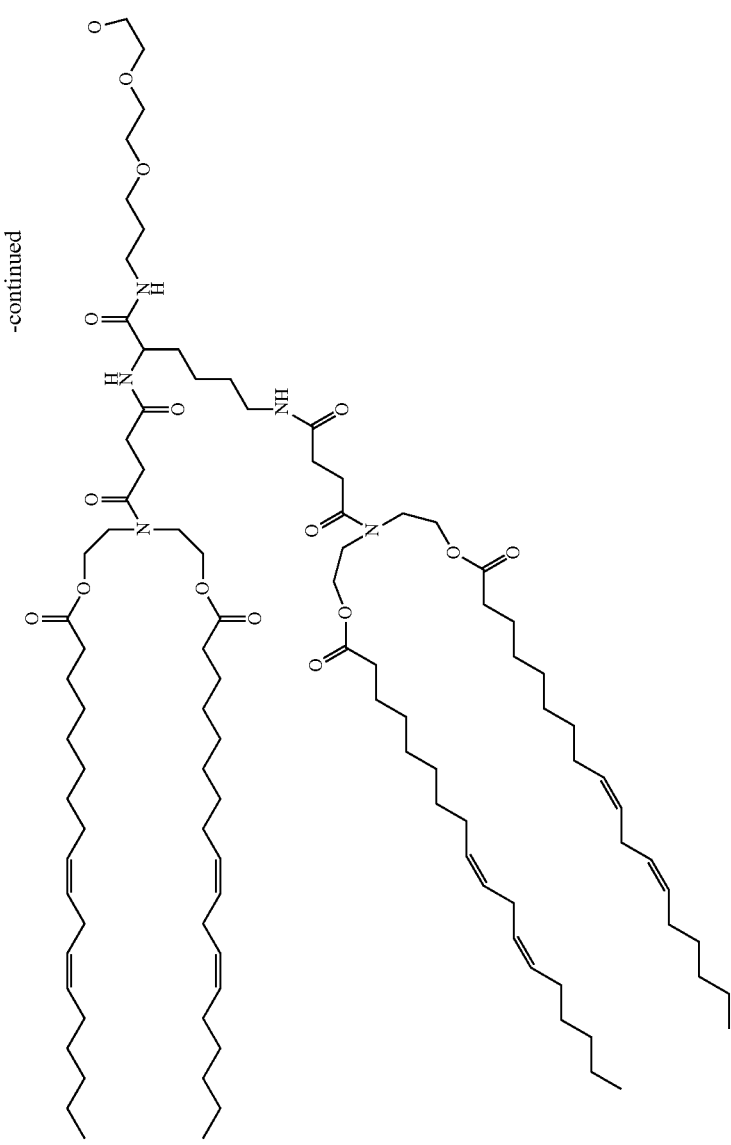

-continued
[Compound T5]
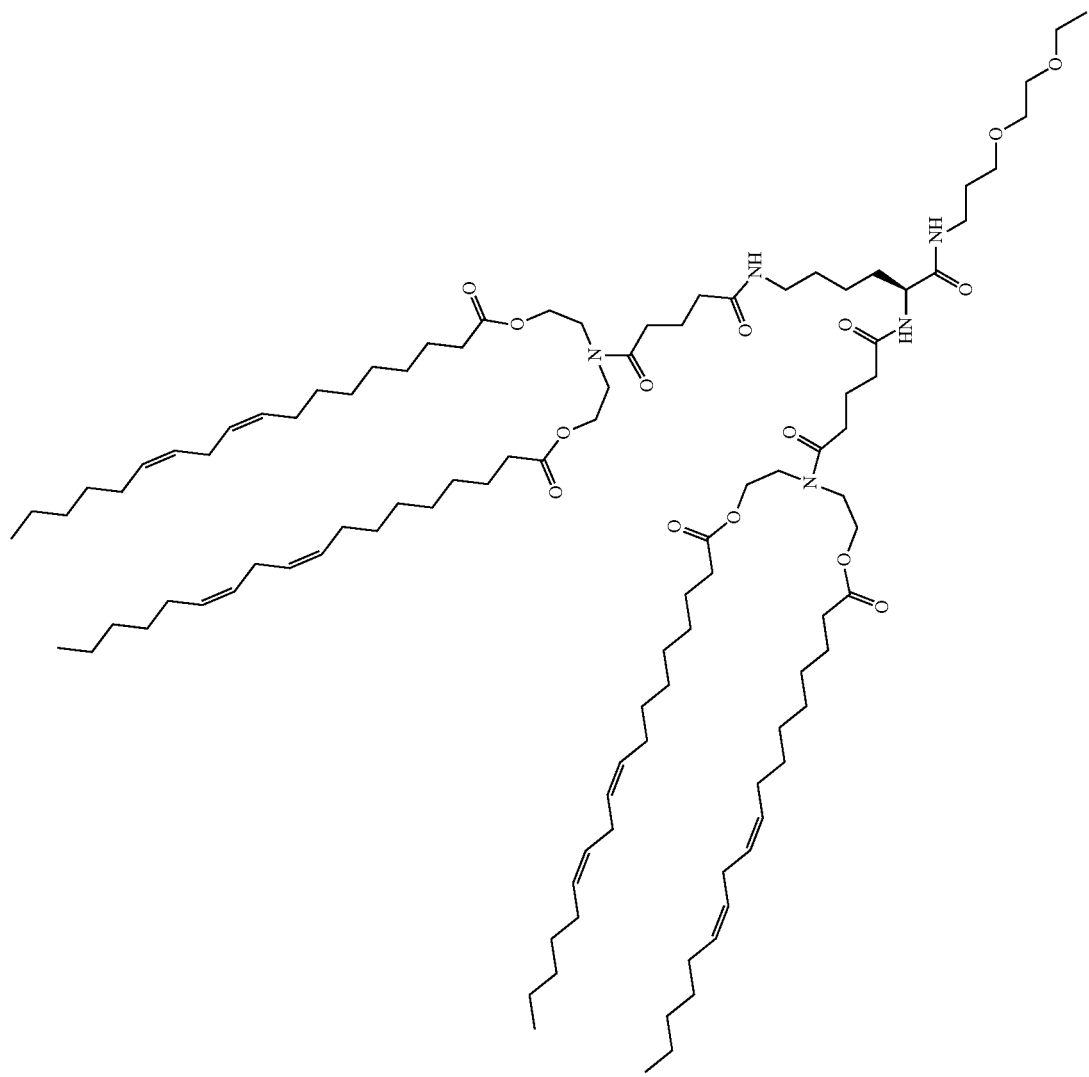

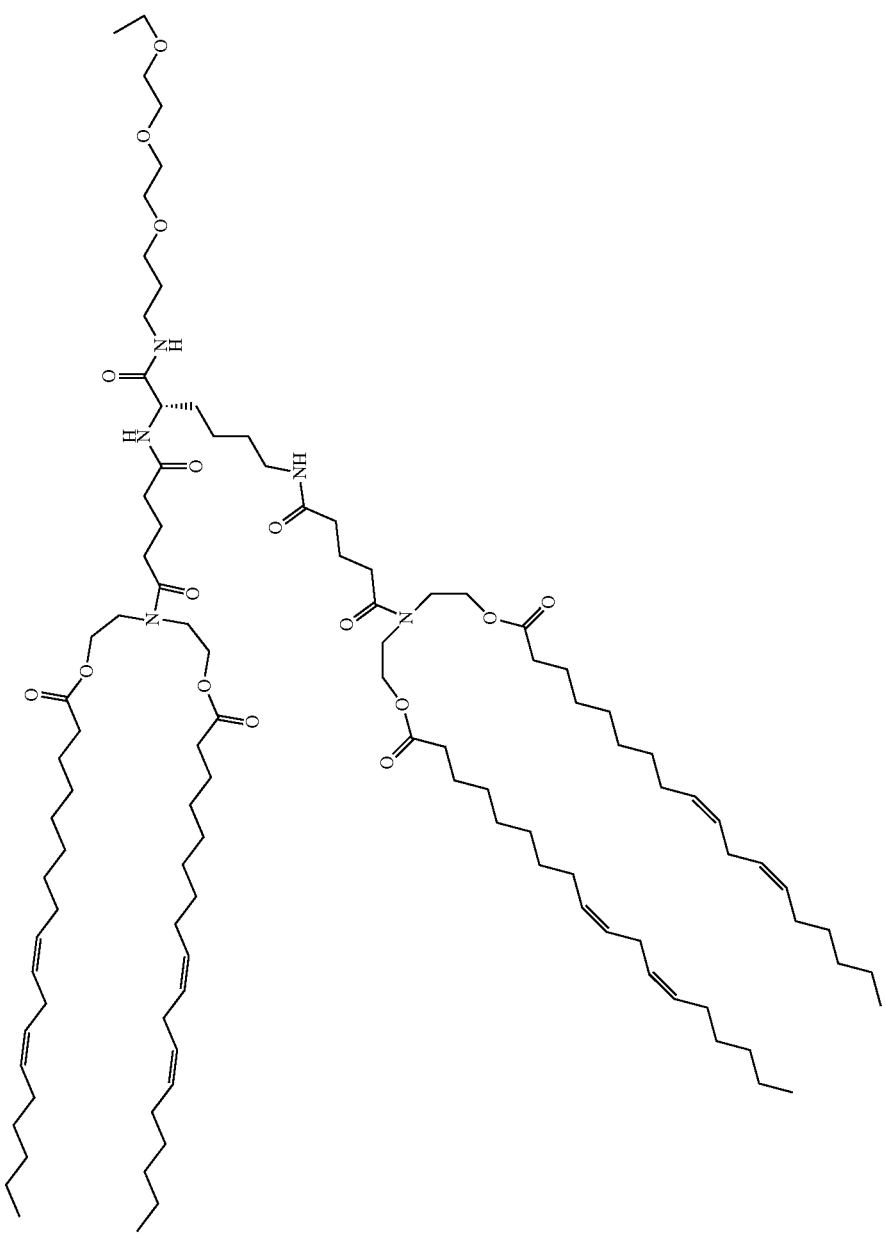

[Compound T6]
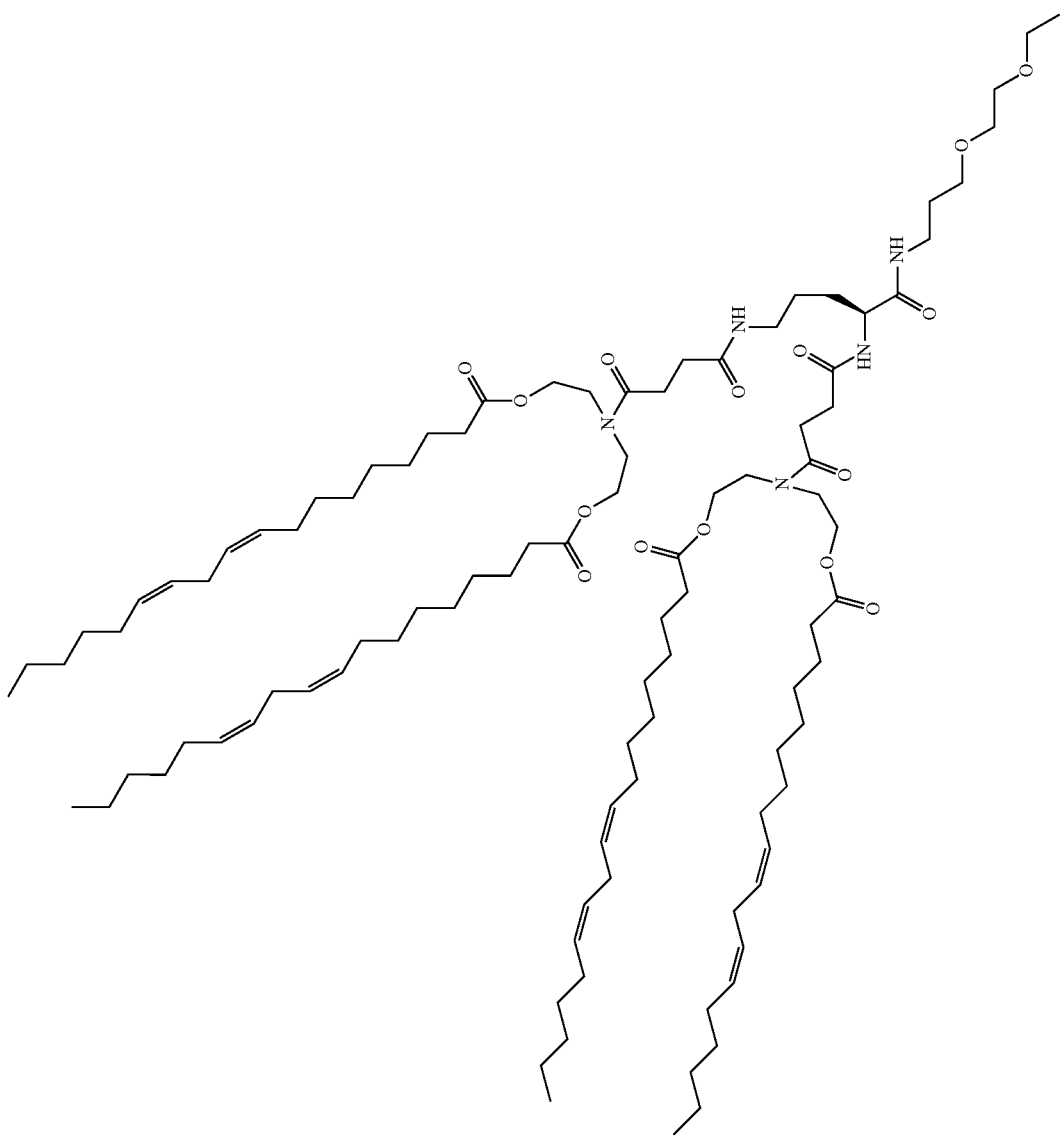

-continued
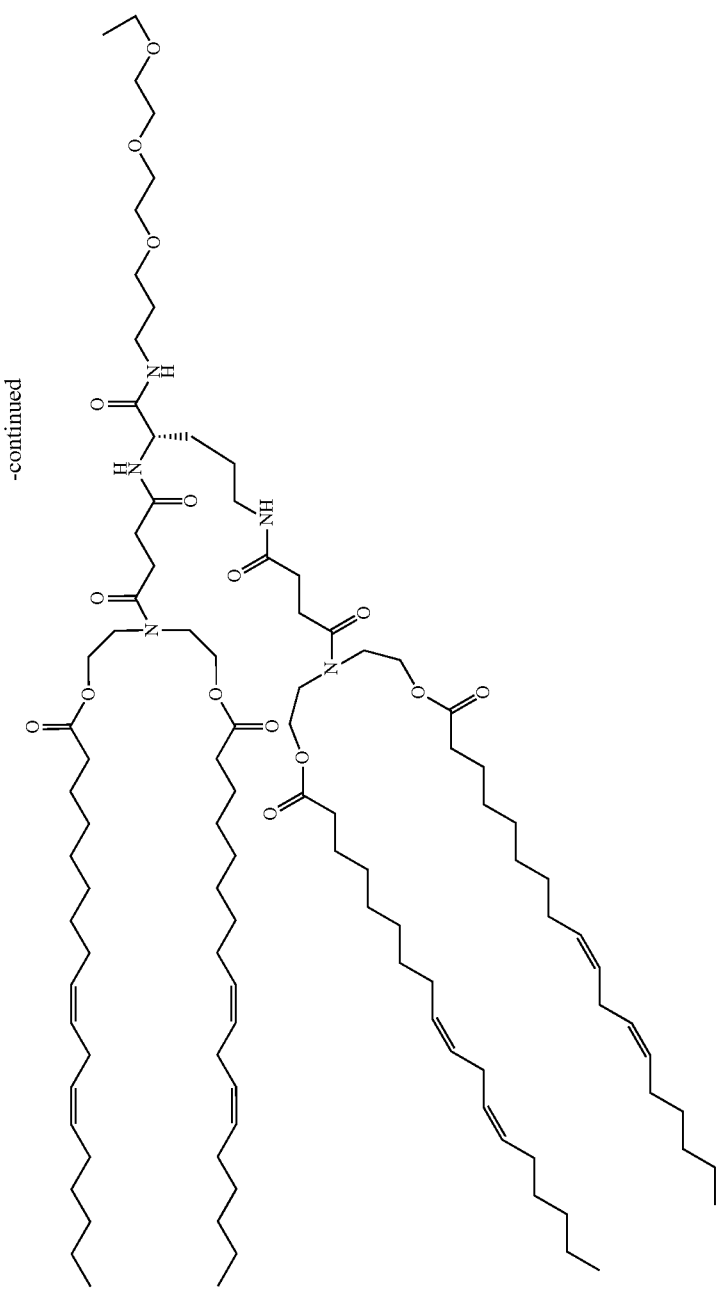

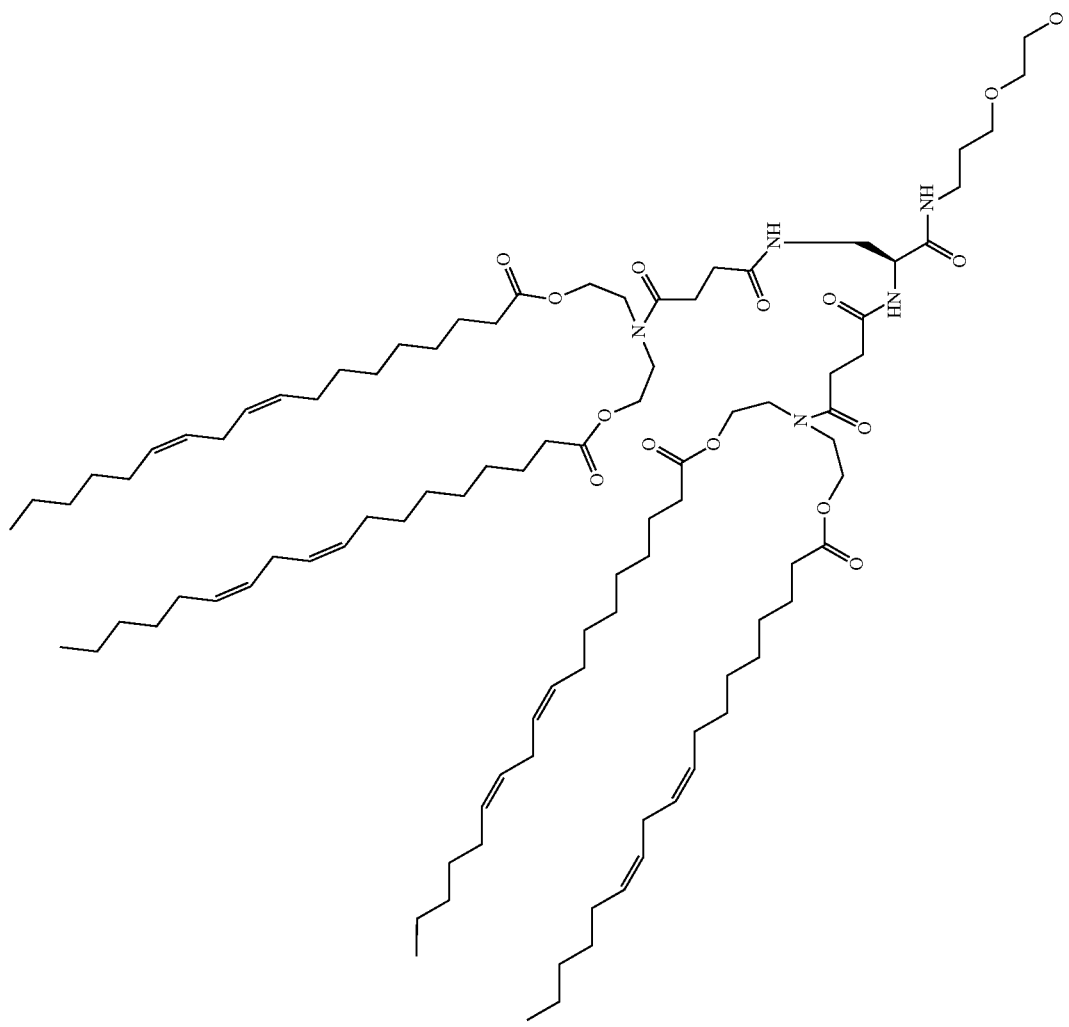
[Compound T7]

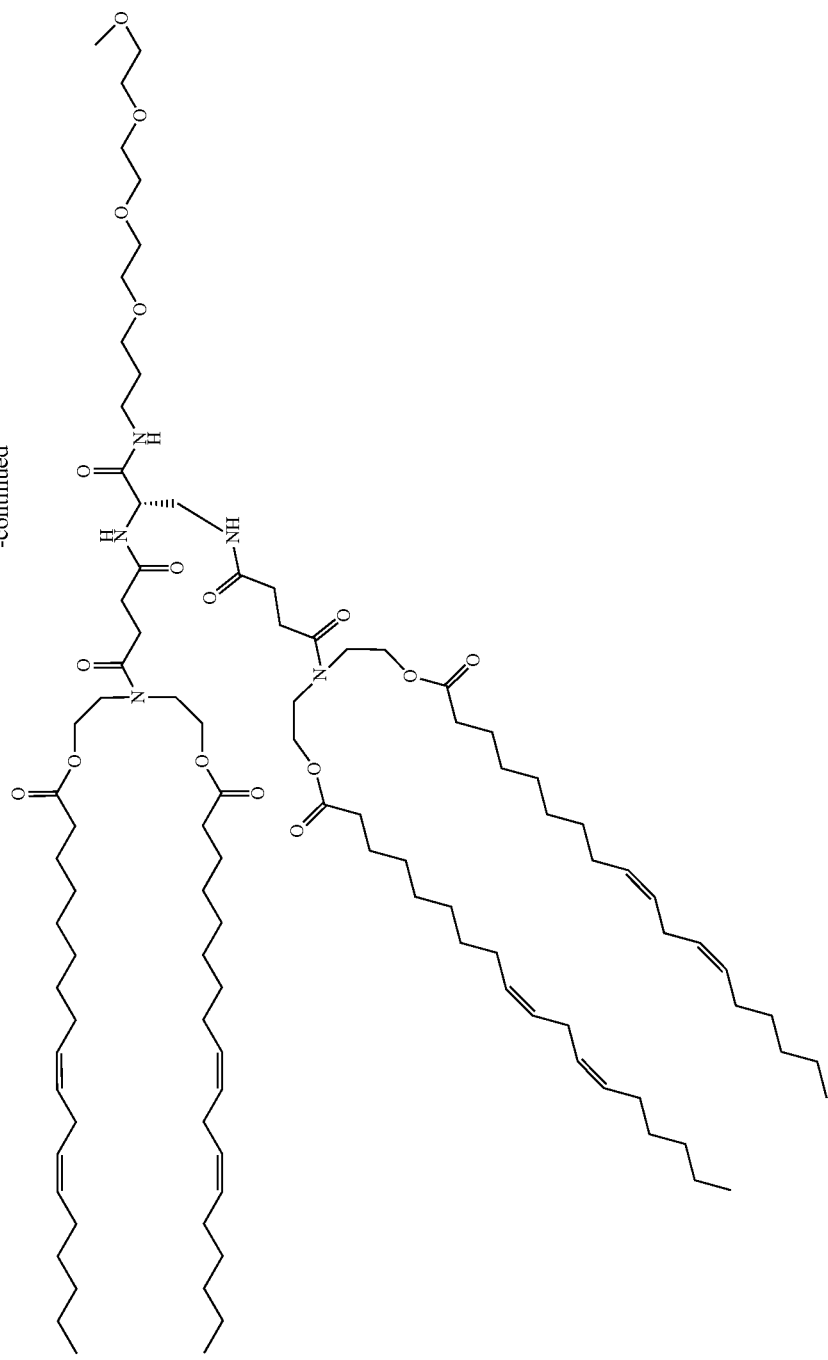

[Compound T8]
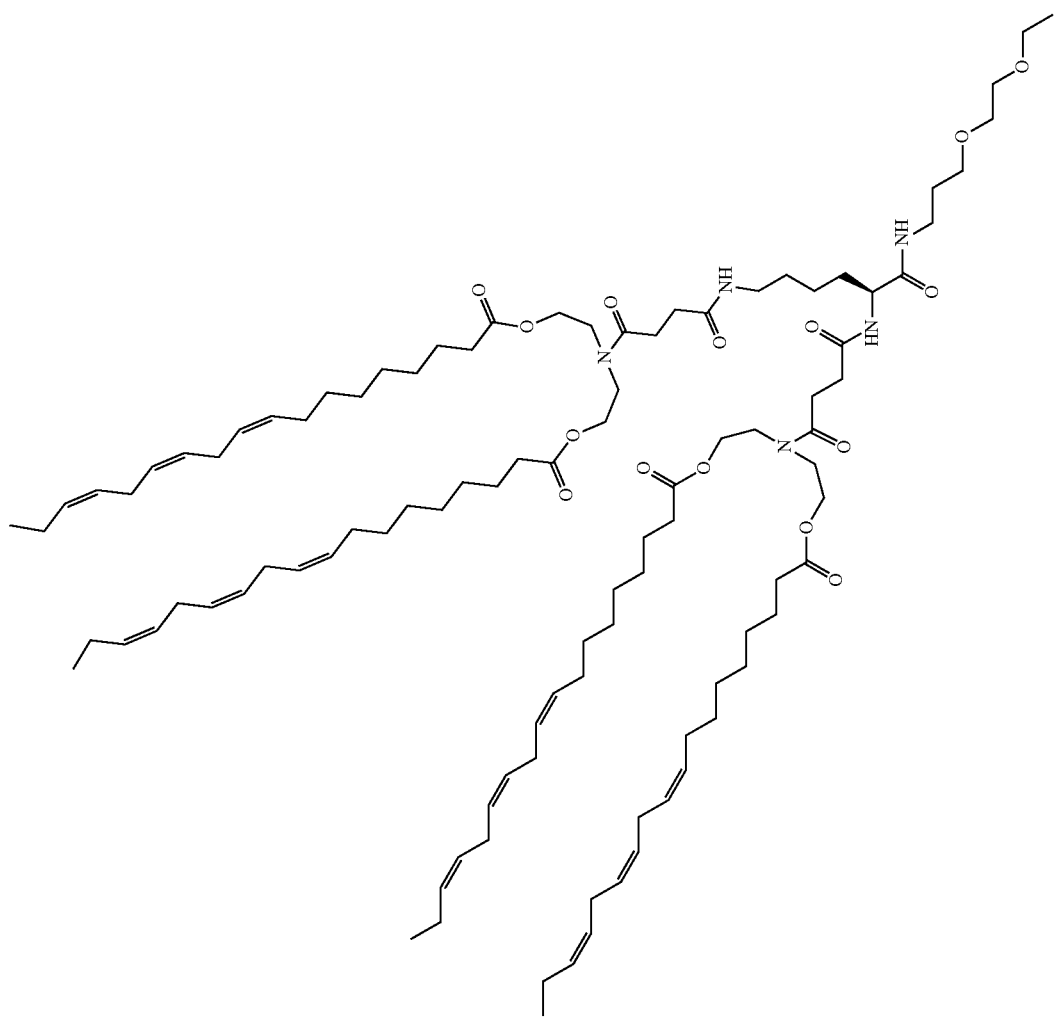

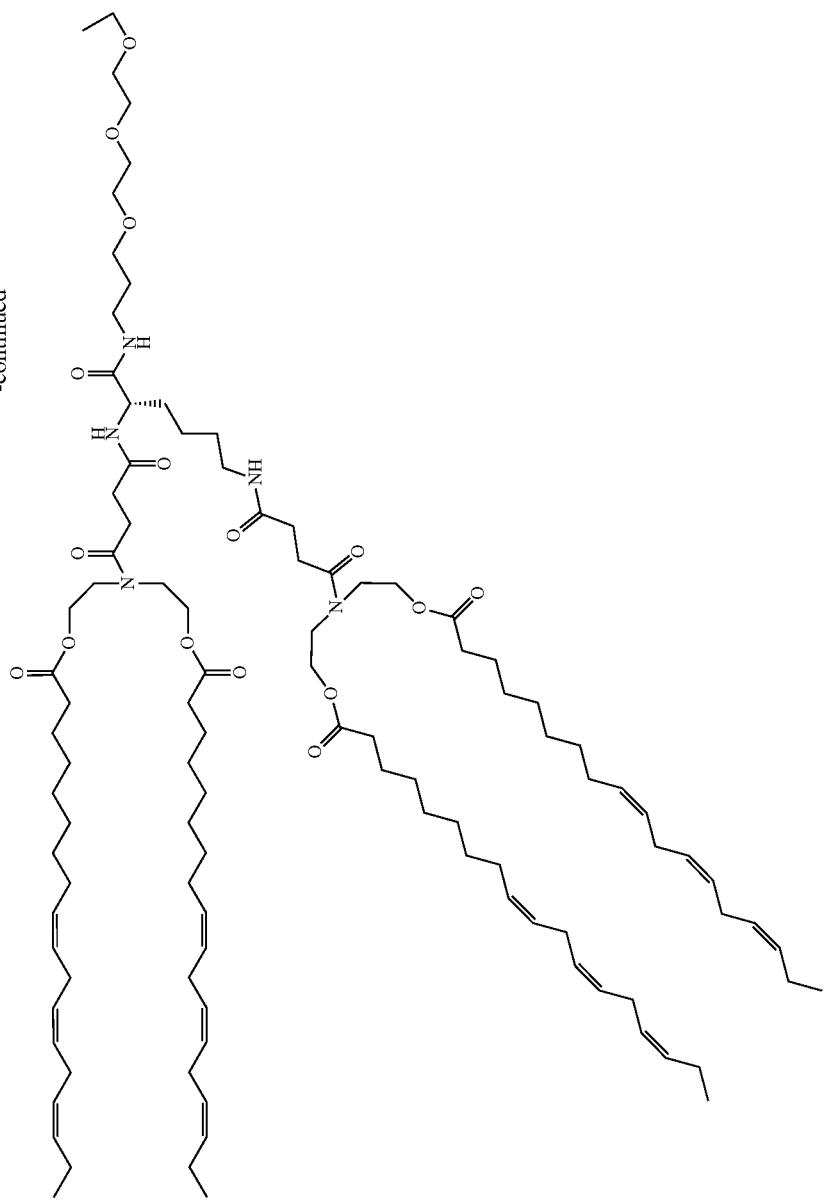

-continued
[Compound T3]
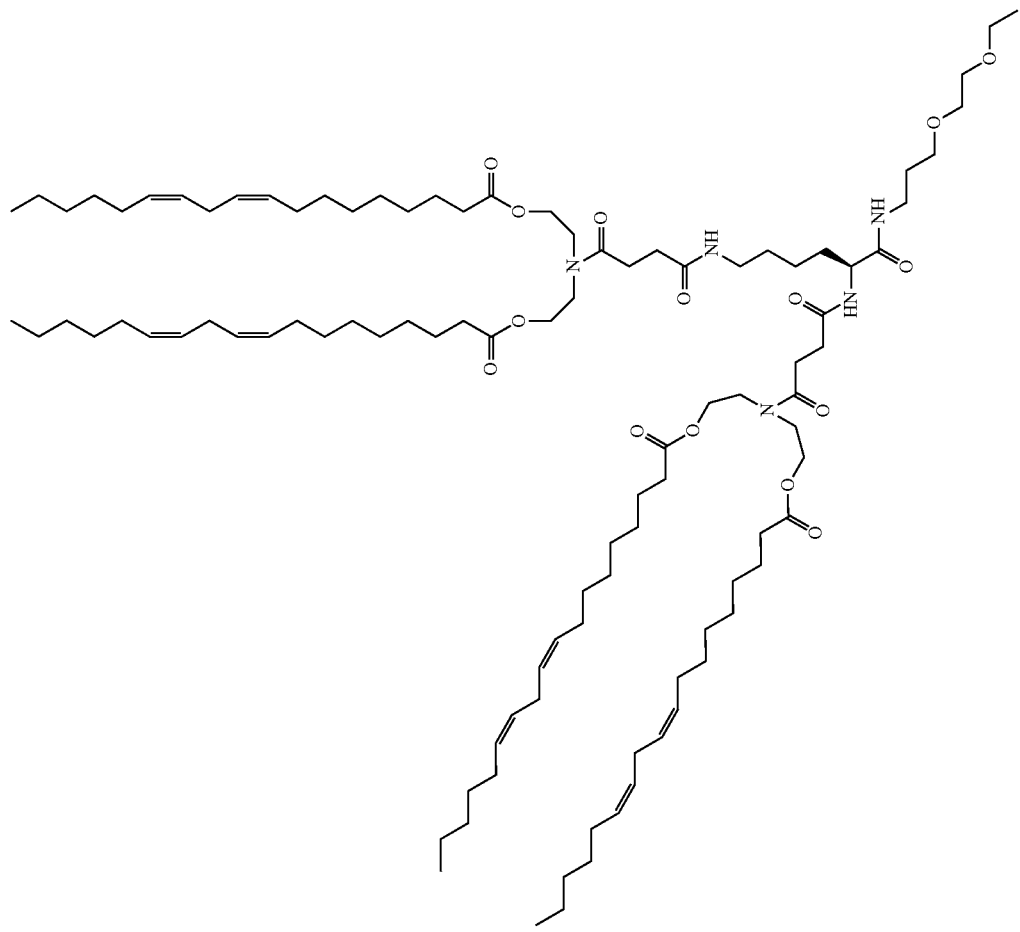

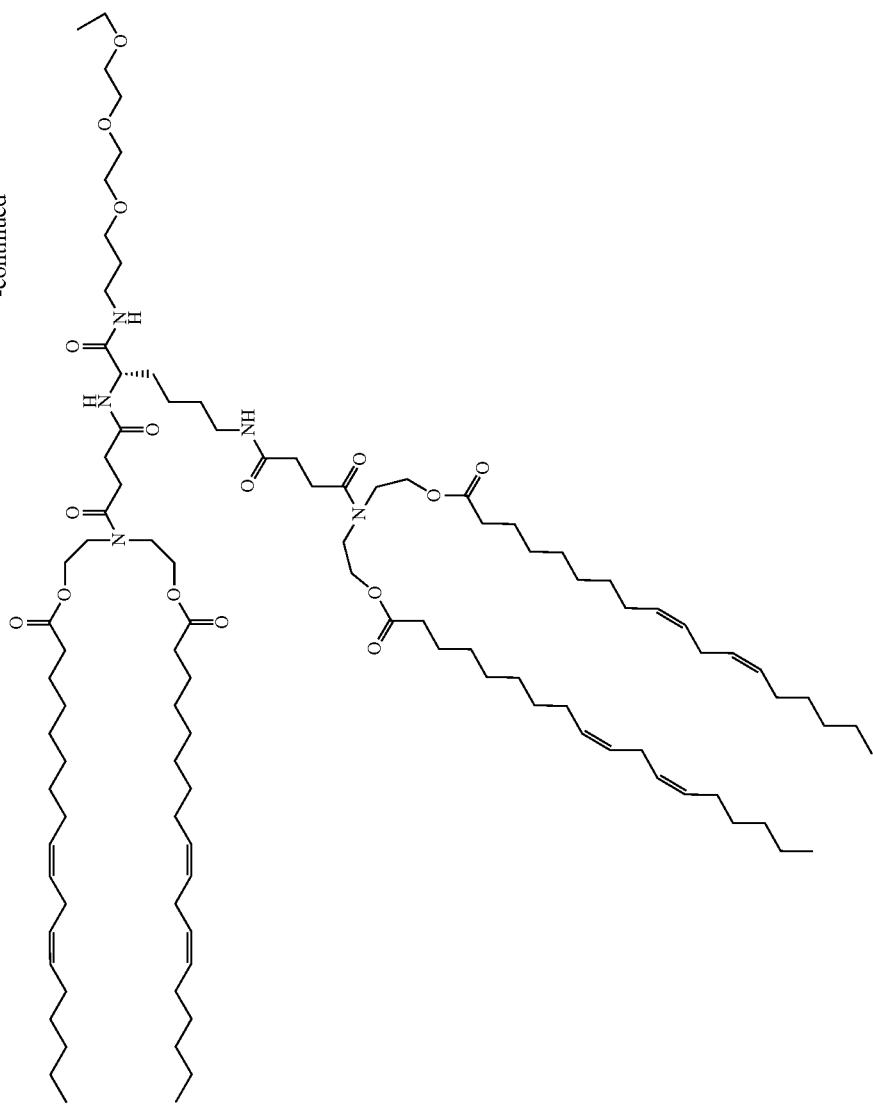

The fusogenic compound above, wherein one or more of the amphiphiles have the structure shown in Formula III

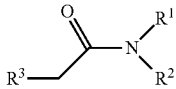

Formula III wherein R¹ and R² are

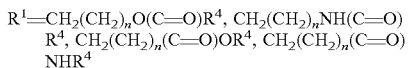

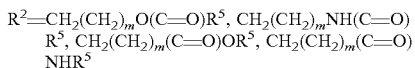

wherein
n and m are each independently from 1 to 2;
R⁴ and R⁵ are independently for each occurrence a C(12-20) alkyl group, or a C(12-20) alkenyl group;
R³ is a C(1-12) alkyl group or a C(4-12) alkenyl group that is substituted with a —(C=O)— or -alkyl-(C=O)— which is attached to AA.

The fusogenic compound above, wherein R⁴ and R⁵ are independently for each occurrence a C(14-18) alkyl group, or a C(14-18) alkenyl group, preferably a C(14-18) alkenyl group having 2 to 4 double bonds.

The fusogenic compound above, wherein one or more of the amphiphiles have the structure shown in Formula IV

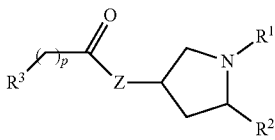

Formula IV wherein R¹ and R² are

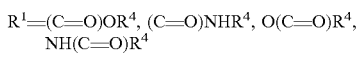

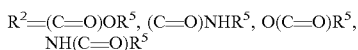

wherein R⁴ and R⁵ are independently for each occurrence a C(12-20) alkyl group, or a C(12-20) alkenyl group;
Z is O or NH; p is 0 to 5;
wherein R³ is selected from branched or unbranched C(1-8)alkandiyl-(C=O)— which is attached to AA, substituted or unsubstituted C(2-8)alkendiyl-(C=O)— which is attached to AA, substituted or unsubstituted C(2-8) alkyndiyl-(C=O)— which is attached to AA, substituted or unsubstituted C(3-8)cycloalkandiyl-(C=O)— which is attached to AA, substituted or unsubstituted arylene-(C=O)— which is attached to AA, substituted or unsubstituted C(4-8)heteroarylene-(C=O)— which is attached to AA, and substituted or unsubstituted heterocycloalkandiyl-(C=O)— which is attached to AA; wherein R³ is optionally interrupted by one or more of —O—, —S—, —SO—, —SO₂—, —NH—, —NR⁶—, —NH(C=O)—, —O(C=O)—, wherein R⁶ is C(1-6)alkyl-, C(1-6) alkoxy-, or C(1-6)alkoxy-C(1-6)alkoxy-.
R³ is preferably branched or unbranched C(2-8)alkandiyl, substituted or unsubstituted C(2-8)alkendiyl, substituted or unsubstituted C(2-8)alkyndiyl, C(3-8)cycloalkandiyl, substituted or unsubstituted C(4-8)arylene, and even more preferably branched or unbranched C(2-8)alkandiyl, substituted or unsubstituted C(3-8)cycloalkandiyl.

The fusogenic compound above, wherein one or more of the amphiphiles have the structure shown in Formula IV

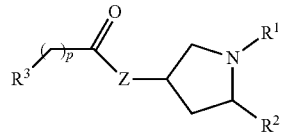

Formula IV wherein R¹ and R² are

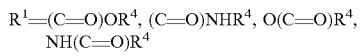

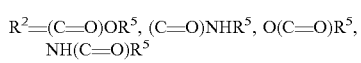

wherein R⁴ and R⁵ are independently for each occurrence a C(12-20) alkyl group, or a C(12-20) alkenyl group;
Z is O or NH; p is 0 to 5;
wherein R³ is selected from C(1-12) alkyl group or C(2-12) alkenyl group that is substituted with a —(C=O)— which is attached to AA

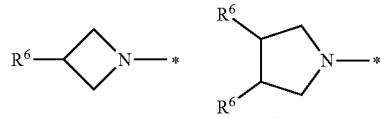

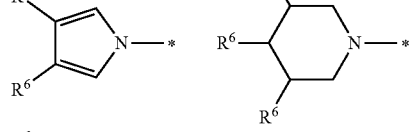

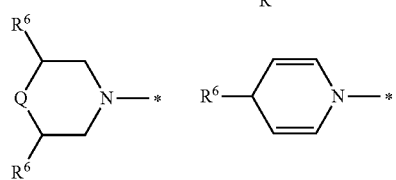

and positional isomers thereof;

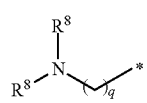

wherein
each R⁶ is independently selected from H, alkyl, alkoxy, and alkoxyalkoxy, with the proviso that one R⁶ is —(C=O)— or -alkyl-(C=O)— which is attached to AA;
each R⁸ is independently selected from H, alkyl, with the proviso that one R⁸ is —(C=O)— or -alkyl-(C=O)— which is attached to AA;

q is from zero to four;
Q is O or N.
The fusogenic compound above, wherein $R^4$ and $R^5$ are independently for each occurrence a C(14-18) alkyl group, or a C(14-18) alkenyl group, preferably a C(14-18) alkenyl group having 2 to 4 double bonds.
The fusogenic compound above, wherein the compound is compound T10:
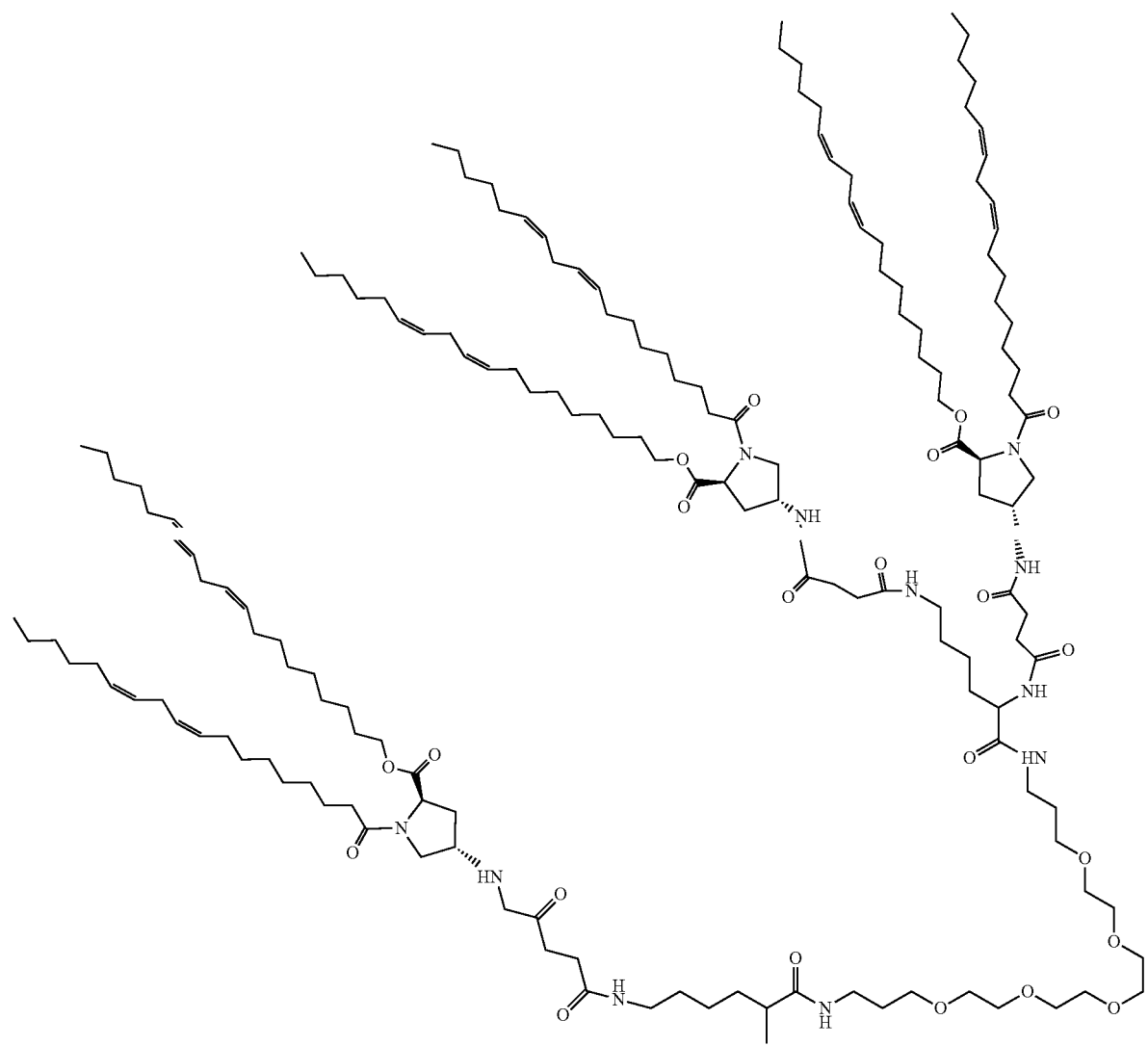
[Compound T10]

-continued

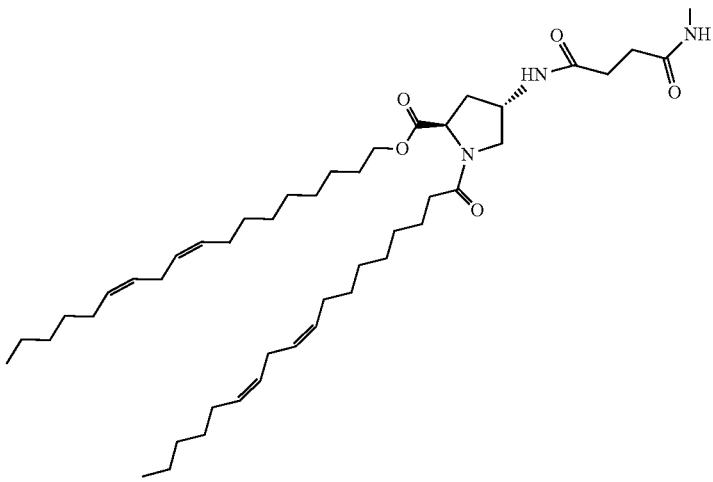

The fusogenic compound above, wherein one or more of the amphiphiles have the structure shown in Formula IV

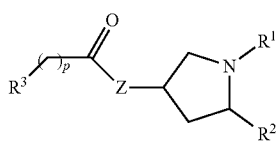

Formula IV wherein $R^1$ and $R^2$ are
$R^1$ is a C(12-20) alkyl group, or a C(12-20) alkenyl group;
$R^2$ is $(CH_2)_n XR^4$, wherein n is 0 to 3, X is O, S, SO, $SO_2$, NH;
wherein $R^4$ is a C(12-20) alkyl group, or a C(12-20) alkenyl group;
wherein Z is O or NH;
wherein p is 1;
wherein $R^3$ is selected from
C(1-12) alkyl group or C(2-12) alkenyl group that is substituted with a —(C=O)— which is attached to AA.

The fusogenic compound above, wherein one or more of the amphiphiles have the structure shown in Formula V

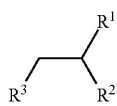

Formula V wherein $R^1$ and $R^2$ are $R^1$=(C=O)$OR^4$, (C=O)$NHR^4$, O(C=O)$R^4$, NH(C=O)$R^4$ $R^2$=(C=O)$OR^5$, (C=O)$NHR^5$, O(C=O)$R^5$, NH(C=O)$R^5$ wherein $R^4$ and $R^5$ are independently for each occurrence a C(12-20) alkyl group, or a C(12-20) alkenyl group;
wherein $R^3$ is selected from branched or unbranched
—O(C=O)—C(1-8)alkandiyl-(C=O)—
which is attached to AA, substituted or unsubstituted
—O(C=O)—C(2-8)alkendiyl-(C=O)—
which is attached to AA, substituted or unsubstituted
—O(C=O)—C(2-8)alkyndiyl-(C=O)—
which is attached to AA, substituted or unsubstituted
—O(C=O)—C(3-8)cycloalkandiyl-(C=O)— which is attached to AA, substituted or unsubstituted —O(C=O)-arylene-(C=O)— which is attached to AA, substituted or unsubstituted —O(C=O)—C(4-8)heteroarylene-(C=O)— which is attached to AA, and substituted or unsubstituted —O(C=O)-heterocycloalkandiyl-(C=O)— which is attached to AA; wherein $R^3$ is optionally interrupted by one or more of —O—, —S—, —SO—, —$SO_2$—, —NH—, —$NR^6$—, —NH(C=O)—, —O(C=O)—, wherein $R^6$ is C(1-6)alkyl-, C(1-6)alkoxy-, or C(1-6)alkoxy-C(1-6)alkoxy-.

$R^3$ is preferably branched or unbranched C(2-8)alkandiyl, substituted or unsubstituted C(2-8)alkendiyl, substituted or unsubstituted C(2-8)alkyndiyl, C(3-8)cycloalkandiyl, substituted or unsubstituted C(4-8)arylene, and even more preferably branched or unbranched C(2-8)alkandiyl, substituted or unsubstituted C(3-8)cycloalkandiyl.

The fusogenic compound above, wherein $R^4$ and $R^5$ are independently for each occurrence a C(14-18) alkyl group, or a C(14-18) alkenyl group, preferably a C(14-18) alkenyl group having 2 to 4 double bonds.

The fusogenic compound above, wherein the compound is compound T12:
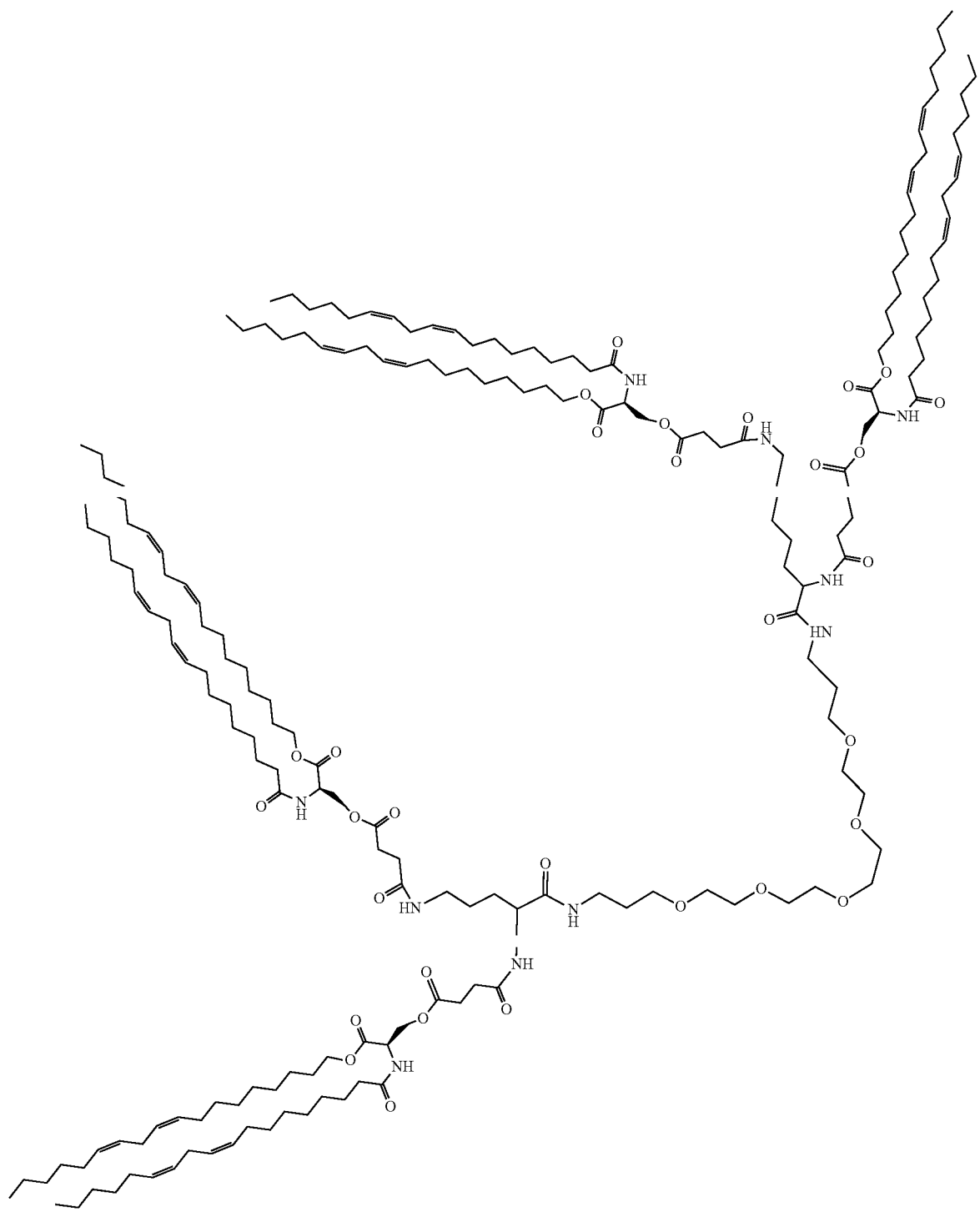
[Compound T12]

The fusogenic compound above, wherein one or more of the amphiphiles have the structure shown in Formula V

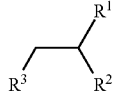

Formula V wherein R$^1$ and R$^2$ are

R$^1$=(C=O)OR$^4$, (C=O)NHR$^4$, O(C=O)R$^4$, NH(C=O)R$^4$

R$^2$=(C=O)OR$^5$, (C=O)NHR$^5$, O(C=O)R$^5$, NH(C=O)R$^5$ wherein R$^4$ and R$^5$ are independently for each occurrence a C(12-20) alkyl group, or a C(12-20) alkenyl group;
wherein R$^3$ is selected from
- —(C=O)— or -alkyl-(C=O)—, which is attached to AA;
- —O(C=O)— or -alkyl-O(C=O)—, which is attached to AA;
- —O(C=O)-alkandiyl-(C=O)—, which is attached to AA
- —O(C=O)-alkendiyl-(C=O)—, which is attached to AA
- —O(C=O)-alkyndiyl-(C=O)—, which is attached to AA
- —NH(C=O)— or -alkyl-NH(C=O)—, which is attached to AA;
- -alkyl-(C=O)-alkyl-(C=O)—, which is attached to AA;
- -alkyl-O(C=O)-alkyl-(C=O)—, which is attached to AA
- -alkyl-NH(C=O)-alkyl-(C=O)—, which is attached to AA;
- -alkenyl-(C=O)—, which is attached to AA;
- -alkenyl-O(C=O)—, which is attached to AA;
- -alkenyl-NH(C=O)—, which is attached to AA;
- -alkenyl-(C=O)-alkendiyl-(C=O)—, which is attached to AA;
- -alkenyl-O(C=O)-alkendiyl-(C=O)—, which is attached to AA
- -alkenyl-NH(C=O)-alkendiyl-(C=O)—, which is attached to AA
- -alkynyl-(C=O)—, which is attached to AA;
- -alkynyl-O(C=O)—, which is attached to AA;
- -alkynyl-NH(C=O)—, which is attached to AA;
- -alkynyl-(C=O)-alkyndiyl-(C=O)—, which is attached to AA;
- -alkynyl-O(C=O)-alkyndiyl-(C=O)—, which is attached to AA
- -alkynyl-NH(C=O)-alkyndiyl-(C=O)—, which is attached to AA

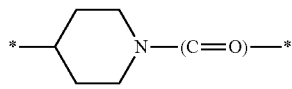

which is attached to AA

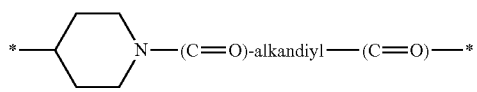

which is attached to AA

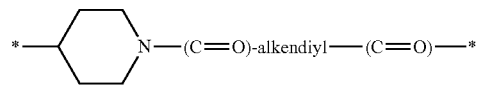

which is attached to AA

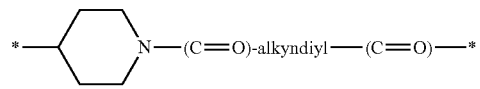

which is attached to AA

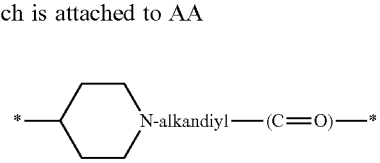

which is attached to AA

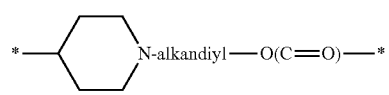

which is attached to AA

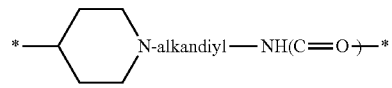

which is attached to AA

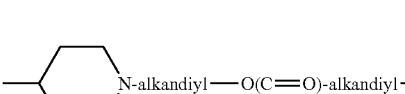

which is attached to AA which is attached to AA and positional isomers thereof;
wherein any alkyl of R$^3$ is branched or unbranched C(1-6) alkyl, any alkenyl of R$^3$ is branched or unbranched C(2-6)alkenyl, and any alkynyl of R$^3$ is branched or unbranched C(2-6)alkynyl.

The fusogenic compound above, wherein one or more of the amphiphiles have the structure shown in Formula VI

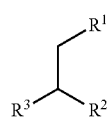

Formula VI wherein R$^1$ and R$^2$ are

R$^1$=(C=O)OR$^4$, (C=O)NHR$^4$, O(C=O)R$^4$, NH(C=O)R$^4$

R$^2$=(C=O)OR$^5$, (C=O)NHR$^5$, O(C=O)R$^5$, NH(C=O)R$^5$ wherein

R⁴ and R⁵ are independently for each occurrence a C(12-20) alkyl group, or a C(12-20) alkenyl group;

wherein R³ is selected from branched or unbranched C(1-8)alkandiyl-(C=O)— which is attached to AA, substituted or unsubstituted C(2-8)alkendiyl-(C=O)— which is attached to AA, substituted or unsubstituted C(2-8) alkyndiyl-(C=O)— which is attached to AA, substituted or unsubstituted C(3-8)cycloalkandiyl-(C=O)— which is attached to AA, substituted or unsubstituted arylene-(C=O)— which is attached to AA, substituted or unsubstituted C(4-8)heteroarylene-(C=O)— which is attached to AA, and substituted or unsubstituted heterocycloalkandiyl-(C=O)— which is attached to AA; wherein R³ is optionally interrupted by one or more of —O—, —S—, —SO—, —SO₂—, —NH—, —NR⁶—, —NH(C=O)—, —O(C=O)—, wherein R⁶ is C(1-6)alkyl-, C(1-6)alkoxy-, or C(1-6)alkoxy-C(1-6)alkoxy-.

R³ is preferably branched or unbranched C(2-8)alkandiyl, substituted or unsubstituted C(2-8)alkendiyl, substituted or unsubstituted C(2-8)alkyndiyl, C(3-8)cycloalkandiyl, substituted or unsubstituted C(4-8)arylene, and even more preferably branched or unbranched C(2-8)alkandiyl, substituted or unsubstituted C(3-8)cycloalkandiyl.

The fusogenic compound above, wherein one or more of the amphiphiles have the structure shown in Formula VI

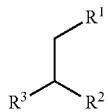

Formula VI wherein R¹ and R² are

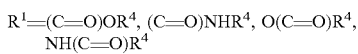

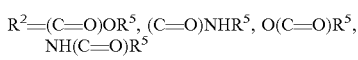

wherein

R⁴ and R⁵ are independently for each occurrence a C(12-20) alkyl group, or a C(12-20) alkenyl group;

R³ is selected from
- -alkyl-(C=O)—, which is attached to AA;
- -alkyl-O(C=O)—, which is attached to AA;
- -alkyl-NH(C=O)—, which is attached to AA;
- -alkyl-(C=O)-alkyl-(C=O)—, which is attached to AA;
- -alkyl-O(C=O)-alkyl-(C=O)—, which is attached to AA
- -alkyl-NH(C=O)-alkyl-(C=O)—, which is attached to AA
- -alkenyl-(C=O)—, which is attached to AA;
- -alkenyl-O(C=O)—, which is attached to AA;
- -alkenyl-NH(C=O)—, which is attached to AA;
- -alkenyl-(C=O)-alkenyl-(C=O)—, which is attached to AA;
- -alkenyl-O(C=O)-alkenyl-(C=O)—, which is attached to AA
- -alkenyl-NH(C=O)-alkenyl-(C=O)—, which is attached to AA
- -alkynyl-(C=O)—, which is attached to AA;
- -alkynyl-O(C=O)—, which is attached to AA;
- -alkynyl-NH(C=O)—, which is attached to AA;
- -alkynyl-(C=O)-alkynyl-(C=O)—, which is attached to AA;
- -alkynyl-O(C=O)-alkynyl-(C=O)—, which is attached to AA
- -alkynyl-NH(C=O)-alkynyl-(C=O)—, which is attached to AA

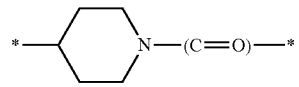

which is attached to AA

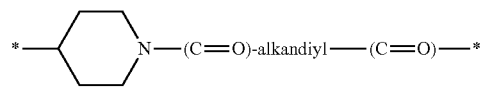

which is attached to AA

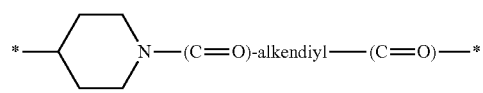

which is attached to AA

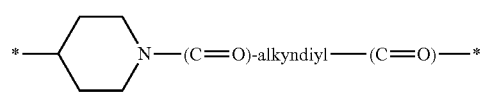

which is attached to AA

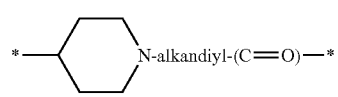

which is attached to AA

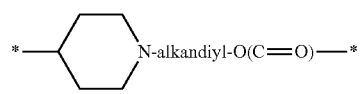

which is attached to AA

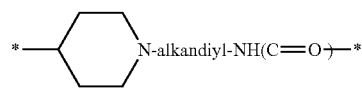

which is attached to AA

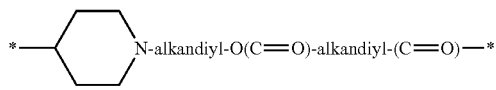

which is attached to AA and positional isomers thereof; wherein any alkyl of $R^3$ is branched or unbranched C(1-6) alkyl, any alkenyl of $R^3$ is branched or unbranched C(2-6)alkenyl, and any alkynyl of $R^3$ is branched or unbranched C(2-6)alkynyl.

The fusogenic compound above, wherein $R^4$ and $R^5$ are independently for each occurrence a C(14-18) alkyl group, or a C(14-18) alkenyl group, preferably a C(14-18) alkenyl group having 2 to 4 double bonds.

The fusogenic compound above, wherein the compound is compound T11

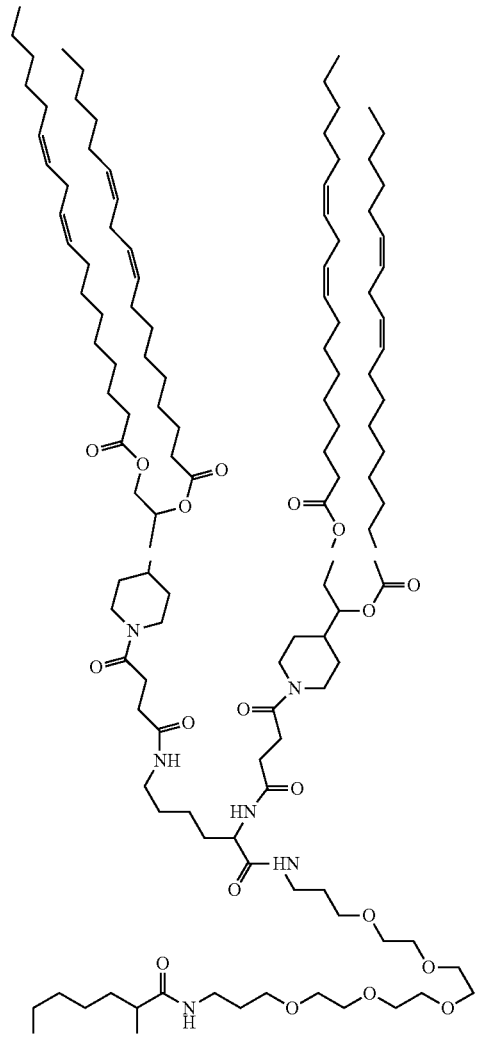

[Compound T11]

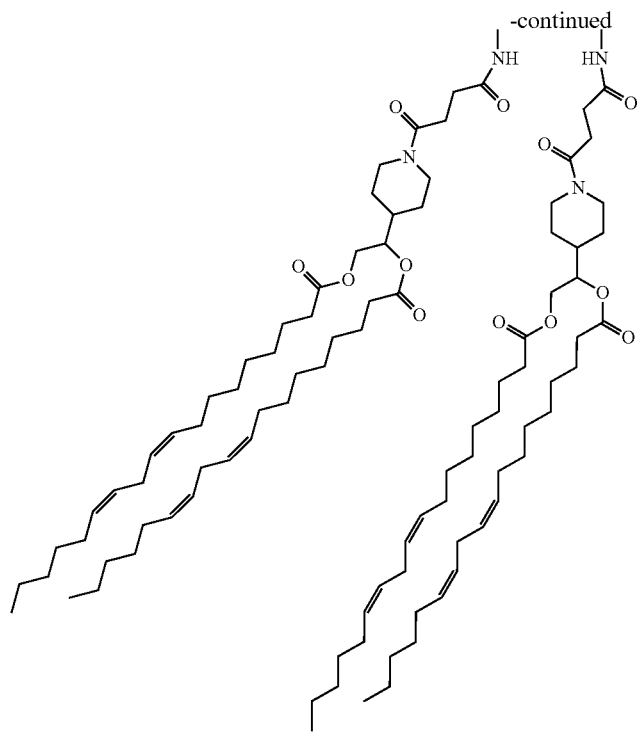

A fusogenic compound having Formula VII

Formula VII

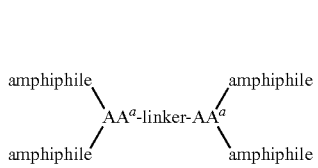

wherein each amphiphile independently comprises one to two lipophilic chains, wherein the lipophilic chains each independently comprise 8 to 22 carbon atoms;
wherein each AA$^a$ is independently an amino acid comprising a side chain having an acyl group, wherein the amino acid is attached to an amphiphile at each of its acyl groups and is attached to the linker at its N terminus;
wherein linker has the structure

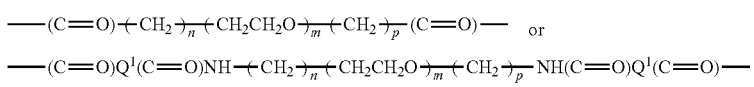

wherein Q$^1$ is branched or unbranched C(2-8)alkandiyl, branched or unbranched C(2-8)alkenediyl, branched or unbranched C(2-8)alkynediyl, or

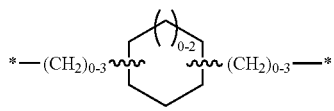

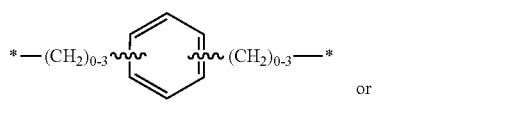

wherein Q$^2$ is

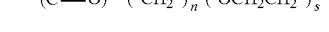

wherein Q$^3$ is

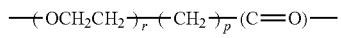

wherein X is —O—, —S— or —NH—;
n and p are independently for each occurrence 1 to 3;
m is independently 1 to 10;
r and s are independently for each occurrence 1 to 5.

The fusogenic compound above, wherein AA$^a$ is selected from the following structures, and any stereoisomer thereof:

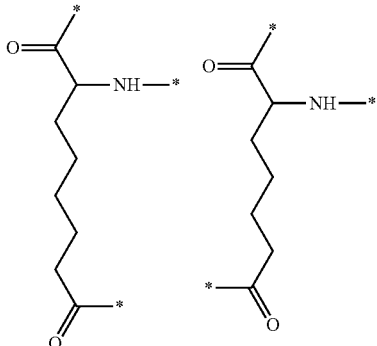

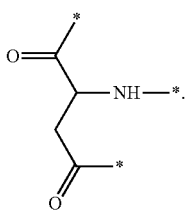

The fusogenic compound above, wherein one or two of the amphiphiles are absent and replaced by an alkyl group, or a pharmaceutically acceptable organic chemical group having 1-400 atoms selected from carbon, oxygen, nitrogen, sulfur, fluorine, and hydrogen.

The fusogenic compound above, wherein the pharmaceutically acceptable organic chemical group is selected from alkyl, alkenyl, alkynyl, alkyl ether, aryl ether, alkoxy, and alkoxyakoxy.

The fusogenic compound above, wherein the pharmaceutically acceptable organic chemical group is selected from methoxy, ethoxy, t-butyl ether, and benzyl oxy.

The fusogenic compound above, wherein one or more of the amphiphiles have the structure shown in Formula VIII Formula VIII

wherein $R^1$ and $R^2$ are

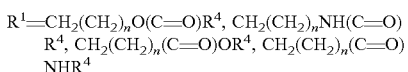

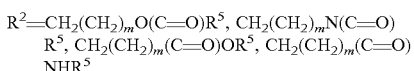

wherein n and m are each independently from 1 to 2;

$R^4$ and $R^5$ are independently for each occurrence a C(12-20) alkyl group, or a C(12-20) alkenyl group.

The fusogenic compound above, wherein one or more of the amphiphiles have the structure shown in Formula IX Formula IX

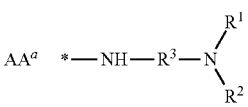

wherein $R^1$ and $R^2$ are

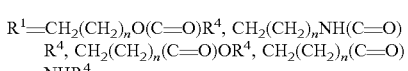

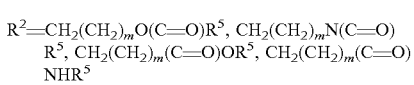

wherein n and m are each independently from 1 to 2;

$R^4$ and $R^5$ are independently for each occurrence a C(12-20) alkyl group, or a C(12-20) alkenyl group;

wherein $R^3$ is selected from branched or unbranched C(1-8)alkandiyl, substituted or unsubstituted C(2-8)alkendiyl, substituted or unsubstituted C(2-8)alkyndiyl, substituted or unsubstituted C(3-8)cycloalkandiyl, substituted or unsubstituted arylene, substituted or unsubstituted C(4-8) heteroarylene, and substituted or unsubstituted heterocycloalkandiyl; wherein $R^3$ is optionally interrupted by one or more of —O—, —S—, —SO—, —SO$_2$—, —NH—, —NR$^6$—, —NH(C═O)—, —O(C═O)—, wherein $R^6$ is C(1-6)alkyl-, C(1-6)alkoxy-, or C(1-6)alkoxy-C(1-6)alkoxy-.

$R^3$ is preferably branched or unbranched C(2-8)alkandiyl, substituted or unsubstituted C(2-8)alkendiyl, substituted or unsubstituted C(2-8)alkyndiyl, C(3-8)cycloalkandiyl, substituted or unsubstituted C(4-8)arylene, and even more preferably branched or unbranched C(2-8)alkandiyl, substituted or unsubstituted C(3-8)cycloalkandiyl.

The fusogenic compound above, wherein $R^4$ and $R^5$ are independently for each occurrence a C(14-18) alkyl group, or a C(14-18) alkenyl group, preferably a C(14-18) alkenyl group having 2 to 4 double bonds.

The fusogenic compound above, wherein the compound is compound T9:
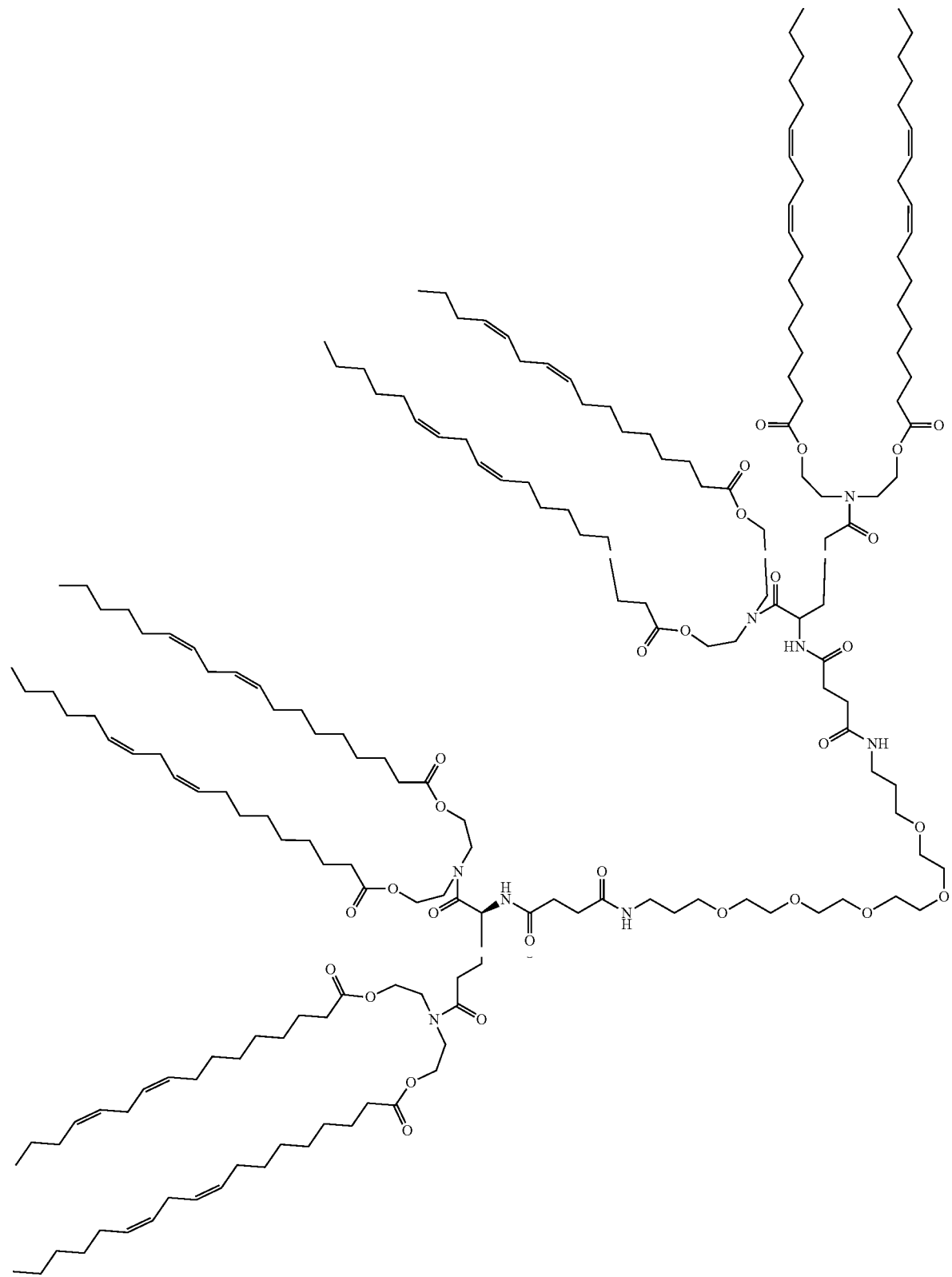
[Compound T9]

The fusogenic compound above, wherein one or more of the amphiphiles have the structure shown in Formula X

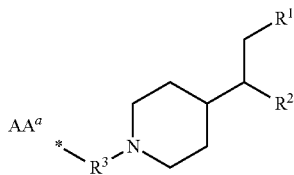

Formula X wherein
$R^1$ and $R^2$ are

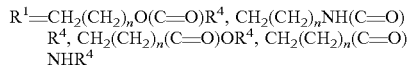

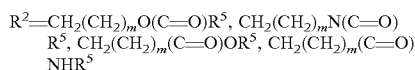

$R^4$ and $R^5$ are independently for each occurrence a C(12-20) alkyl group, or a C(12-20) alkenyl group;
wherein $R^3$ is absent or selected from branched or unbranched *—NH—C(1-8)alkandiyl-(C=O)—, substituted or unsubstituted *—NH—C(2-8)alkendiyl-(C=O)—, substituted or unsubstituted *—NH—C(2-8)alkyndiyl-(C=O)—, substituted or unsubstituted *—NH—C(3-8)cycloalkandiyl-(C=O)—, substituted or unsubstituted*—NH-arylene-(C=O)—, substituted or unsubstituted *—NH—C(4-8)heteroarylene-(C=O)—, and substituted or unsubstituted *—NH-heterocycloalkandiyl-(C=O)—, wherein * indicates the terminus attached to AA$^a$; wherein $R^3$ is optionally interrupted by one or more of —O—, —S—, —SO—, —SO$_2$—, —NH—, —NR$^6$—, —NH(C=O)—, —O(C=O)—, wherein $R^6$ is C(1-6)alkyl-, C(1-6)alkoxy-, or C(1-6)alkoxy-C(1-6)alkoxy-.

$R^3$ is preferably branched or unbranched C(2-8)alkandiyl, substituted or unsubstituted C(2-8)alkendiyl, substituted or unsubstituted C(2-8)alkyndiyl, C(3-8)cycloalkandiyl, substituted or unsubstituted C(4-8)arylene, and even more preferably branched or unbranched C(2-8)alkandiyl, substituted or unsubstituted C(3-8)cycloalkandiyl.

The fusogenic compound above, wherein one or more of the amphiphiles have the structure shown in Formula XI

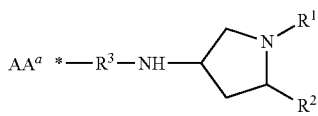

Formula XI wherein
$R^1$ and $R^2$ are
$R^1$=(C=O)OR$^4$, (C=O)NHR$^4$, O(C=O)R$^4$, NH(C=O)R$^4$
$R^2$=(C=O)OR$^5$, (C=O)NHR$^5$, O(C=O)R$^5$, NH(C=O)R$^5$
$R^4$ and $R^5$ are independently for each occurrence a C(12-20) alkyl group, or a C(12-20) alkenyl group;
wherein $R^3$ is absent or selected from branched or unbranched *—NH—C(1-8)alkandiyl-(C=O)—, substituted or unsubstituted *—NH—C(2-8)alkendiyl-(C=O)—, substituted or unsubstituted *—NH—C(2-8)alkyndiyl-(C=O)—, substituted or unsubstituted *—NH—C(3-8)cycloalkandiyl-(C=O)—, substituted or unsubstituted*—NH-arylene-(C=O)—, substituted or unsubstituted *—NH—C(4-8)heteroarylene-(C=O)—, and substituted or unsubstituted *—NH-heterocycloalkandiyl-(C=O)—, wherein * indicates the terminus attached to AA$^a$; wherein $R^3$ is optionally interrupted by one or more of —O—, —S—, —SO—, —SO$_2$—, —NH—, —NR$^6$—, —NH(C=O)—, —O(C=O)—, wherein $R^6$ is C(1-6)alkyl-, C(1-6)alkoxy-, or C(1-6)alkoxy-C(1-6)alkoxy-.

$R^3$ is preferably branched or unbranched C(2-8)alkandiyl, substituted or unsubstituted C(2-8)alkendiyl, substituted or unsubstituted C(2-8)alkyndiyl, C(3-8)cycloalkandiyl, substituted or unsubstituted C(4-8)arylene, and even more preferably branched or unbranched C(2-8)alkandiyl, substituted or unsubstituted C(3-8)cycloalkandiyl.

The fusogenic compound above, wherein one or more of the amphiphiles have the structure shown in Formula III

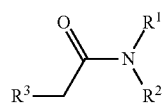

Formula III wherein $R^1$ and $R^2$ are

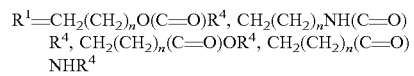

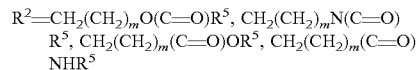

wherein n and m are each independently from 1 to 2; and $R^4$ and $R^5$ are independently for each occurrence a C(12-20) alkyl group, or a C(12-20) alkenyl group;
wherein
$R^3$ is selected from
—(C=O)-alkyl-NH—, which is attached to AA$^a$;
—(C=O)-alkenyl-NH—, which is attached to AA$^a$;
—(C=O)-alkynyl-NH—, which is attached to AA$^a$;
wherein any alkyl of $R^3$ is branched or unbranched C(1-6)alkyl, any alkenyl of $R^3$ is branched or unbranched C(2-6)alkenyl, and any alkynyl of $R^3$ is branched or unbranched C(2-6)alkynyl;

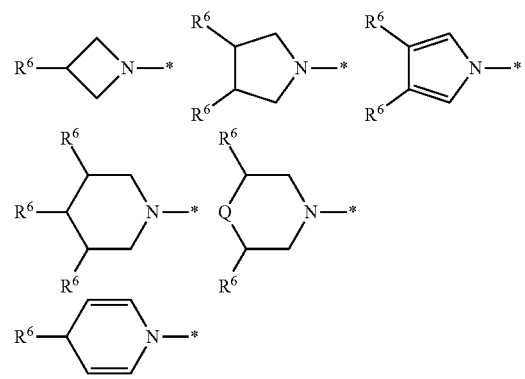

and positional isomers thereof;

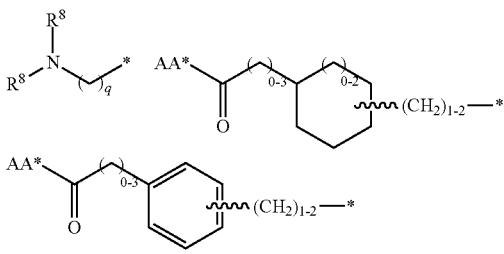

wherein
each $R^6$ is independently selected from H, alkyl, alkoxy, and alkoxyalkoxy, with the proviso that one $R^6$ is —(C=O)-alkyl-NH— which NH is attached to $AA^a$;
each $R^8$ is independently selected from H, alkyl, with the proviso that one $R^8$ is —(C=O)— alkyl-NH— which NH is attached to $AA^a$;
q is from zero to four;
Q is O or N.

The fusogenic compound above, wherein one or more of the amphiphiles have the structure shown in Formula V Formula V

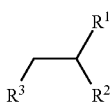

wherein $R^1$ and $R^2$ are

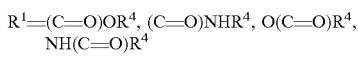

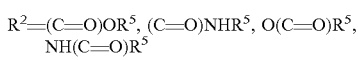

wherein $R^4$ and $R^5$ are independently for each occurrence a C(12-20) alkyl group, or a C(12-20) alkenyl group;
wherein
wherein $R^3$ is absent or selected from branched or unbranched *—NH—C(1-8)alkandiyl-(C=O)—, substituted or unsubstituted *—NH—C(2-8)alkendiyl-(C=O)—, substituted or unsubstituted *—NH—C(2-8)alkyndiyl-(C=O)—, substituted or unsubstituted *—NH—C(3-8)cycloalkandiyl-(C=O)—, substituted or unsubstituted-NH-arylene-(C=O)—, substituted or unsubstituted *—NH—C(4-8)heteroarylene-(C=O)—, and substituted or unsubstituted
*—NH-heterocycloalkandiyl-(C=O)—, wherein * indicates the terminus attached to $AA^a$;
wherein $R^3$ is optionally interrupted by one or more of —O—, —S—, —SO—, —SO$_2$—, —NH—, —NR$^6$—, —NH(C=O)—, —O(C=O)—, wherein $R^6$ is C(1-6) alkyl-, C(1-6)alkoxy-, or C(1-6)alkoxy-C(1-6)alkoxy-.

$R^3$ is as above, with preferably branched or unbranched C(2-8)alkandiyl, substituted or unsubstituted C(2-8)alkendiyl, substituted or unsubstituted C(2-8)alkyndiyl, C(3-8) cycloalkandiyl, substituted or unsubstituted C(4-8)arylene, and even more preferably branched or unbranched C(2-8) alkandiyl, substituted or unsubstituted C(3-8)cycloalkandiyl.

Embodiments of this invention further contemplate compositions containing a fusogenic compound above and a pharmaceutically acceptable carrier. The composition may contain nanoparticles or liposomes.

A pharmaceutical composition of this invention may include a fusogenic compound, an active agent, and a pharmaceutically acceptable carrier. In a composition, the fusogenic compound may be from 0.01 mol % to 20 mol % of the lipids of the composition. The composition may contain nanoparticles or liposomes.

The fusogenic molecules and formulations of this invention can be used for delivery of an active agent.

In some embodiments, the active agent is one or more nucleic acids.

In certain embodiments, the active agent is one or more DNAs, RNAs, mRNAs, siRNAs, or microRNAs. The active agent may be one or more RNA molecules.

The active agent may be one or more RNAi molecules, one or more mRNA molecules, and modified forms thereof.

Embodiments of this invention include compositions for use in distributing an active agent for treating a condition or disease in a subject. The composition may contain an active agent, a fusogenic compound, an ionizable lipid, a structural lipid, a stabilizer lipid, and a lipid for reducing immunogenicity of the composition.

This invention includes methods for preventing, ameliorating or treating a disease or condition in a subject in need comprising administering to the subject a composition above. The compositions of this invention may be used in the treatment of the human or animal body.

Embodiments of this invention also include the following:
A compound of formula(A)

formula A

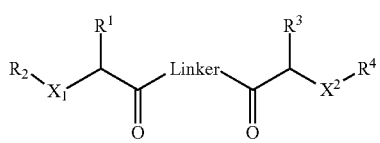

wherein linker is a divalent group comprising PEG portion,
$X_1$ and $X_2$ are independently C1-C5 alkanediyl group,
$R_1$, $R_2$, $R_3$ and $R_4$ are independently

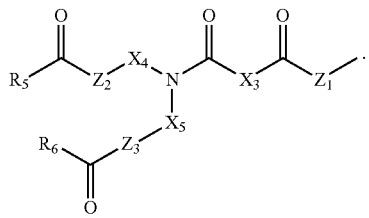

$X_3$ is single bond, C1-C5 alkanediyl group or C2-C5 alkenediyl group,
$X_4$ and $X_5$ are independently C2-5 alkanediyl group,
$Z_1$, $Z_2$ and $Z_3$ are independently —O—, —S— or —NH—, and
$R_5$ and $R_6$ are independently C11-23 alkyl or C11-23 alkenyl group.

Embodiments of this invention also include the following:
A compound of formula(B)

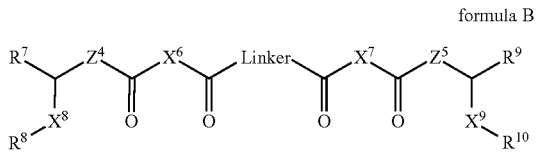

formula B wherein linker is a divalent group comprising PEG portion,
$X_6$ and $X_7$ are independently C1-C5 alkanediyl group,
$X_8$ and $X_9$ are independently C1-C5 alkanediyl group,
$Z_4$ and $Z_5$ are independently —O—, —S— or —NH—,
$R_7$, $R_8$, $R_9$ and $R_{10}$ are independently

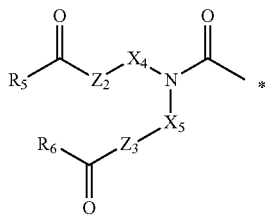

$X_4$ and $X_5$ are independently C2-5 alkanediyl group,
$Z_2$ and $Z_3$ are independently —O—, —S— or —NH—, and
$R_5$ and $R_6$ are independently C11-23 alkyl or C11-23 alkenyl group.

The compound above, wherein the linker is

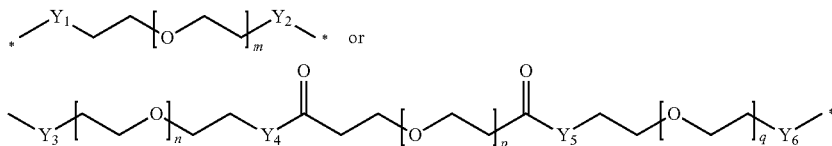

wherein m is an integer of 1-12,
$Y_1$ is —O—, —NH— or —NHCH$_2$—,
$Y_2$ is —O—, —NH— or —CH$_2$NH—,
n and q are independently an integer of 1-5,
p is integer of 0-5,
$Y_3$ and $Y_5$ are independently —O—, —NH— or —NHCH$_2$—, and
$Y_4$ and $Y_6$ are independently —O—, —NH— or —CH$_2$NH—.

The compound above, wherein $X_1$ and $X_2$ are independently C1-C5 straight alkanediyl group, preferably C2-C4 straight alkanediyl group, more preferably C4 straight alkanediyl group.

The compound above, wherein $R_1$, $R_2$, $R_3$ and $R_4$ are same group.

The compound above, wherein $X_3$ is single bond or C1-C5 straight alkanediyl group, $X_3$ is preferably C2-C4 straight alkanediyl group, more preferably ethylene, i.e. ethanediyl group.

The compound above, wherein $X_4$ and $X_5$ are independently C2-5 straight alkanediyl group, $X_4$ and $X_5$ are preferably C2-4 straight alkanediyl group, more preferably ethylene, i.e. ethanediyl group.

The compound above, wherein $Z_1$ is —NH—.
The compound above, wherein $Z_2$ and $Z_3$ are —O—.

The compound above, wherein $R_5$ and $R_6$ are independently C11-23 straight alkenyl group.

The compound above, wherein $R_5$ and $R_6$ are independently C11-23 straight alkenyl group with 1-6 double-bond(s), wherein the number of double bonds is preferably 1-3, more preferably 2-3, further more preferably 2.

The compound above, wherein $R_5$ and $R_6$ are independently C11-23 straight alkenyl group with 2 double-bonds.

The compound above, wherein $R_5$ and $R_6$ are independently C13-17 straight alkenyl group, $R_5$ and $R_6$ are preferably C15-17 straight alkenyl group, more preferably C17 straight alkenyl group.

The compound above, wherein $R_5$ and $R_6$ are independently C17 straight alkenyl group.

The compound above, wherein $R_5$ and $R_6$ is heptadeca-8,11-dienyl group.

A composition which comprises a cationic lipid, an ionizable lipid and a lipid of the compound above in a lipid nanoparticle comprising a bilayer of lipid molecules.

The composition above, which further comprises a nucleic acid.

The composition above, wherein the nucleic acid is siRNA, mRNA or microRNA.

The composition above, wherein the composition is a pharmaceutical composition.

BRIEF DESCRIPTION OF THE DRAWINGS

This patent or application file contains at least one drawing executed in color. Copies of this patent or patent application publication with color drawings will be provided by the US Patent Office upon request and payment of the necessary fee.

As shown in FIG. 24, liposomal delivery formulation #5, which contained 2% (of total lipids) of a fusogenic compound R4 of this invention, provided activity for gene expression knockdown in stellate cells of an example siRNA targeted to HSP47 that was surprisingly increased, as compared to the control formulation #1, which did not contain a fusogenic compound of this invention.

As shown in FIG. 49, delivery of the mRNA to various tissues and cells was determined with a MAXDISCOVER GFP ELISA. Surprisingly, GFP mRNA was selectively transfected and/or translated in lung, with lower transfection and/or translation in muscle, liver, heart, and kidney.

As shown in FIG. 50, the relative delivery, transfection, and/or translation of the mRNA in various tissues and cells was determined with a Promega E4510 assay kit. Surprisingly, Fluc mRNA was selectively delivered, transfected, and/or translated in lung and spleen, with lower delivery, transfection, and/or translation in liver, heart, kidney, and muscle.

As shown in FIG. 51, the relative delivery, transfection, and/or translation of the mRNA in various tissues and cells was determined with a Promega E4510 assay kit. Fluc mRNA was selectively delivered, transfected, and/or translated in lung and spleen, with lower delivery, transfection, and/or translation in pancreas, kidney, liver, testis, and small intestine.

As shown in FIG. 52, the relative delivery, transfection, and/or translation of the mRNA in various tissues was determined with luminescence imaging 7 hours after injection.

As shown in FIG. 53, the relative delivery of mRNA was far greater in formulations containing the fusogenic molecule of this invention (2035-03-03) than for the same formulation without the fusogenic molecule (2035-13-01).

DETAILED DESCRIPTION OF THE INVENTION

This invention provides a range of fusogenic molecules. The fusogenic compounds of this invention can be used in delivering therapeutic agents to cells, tissues or organs, organisms, and subjects.

In some aspects, this invention provides platform compounds for forming fusogenic molecules. The fusogenic molecules may be formed by attaching one or a plurality of neutral molecules such as hydrocarbon molecules, aliphatic molecule, saturated fatty acid molecule, unsaturated fatty acid molecule, monounsaturated fatty acid molecule or polyunsaturated fatty acid molecule to the platform structure.

Figure 1:
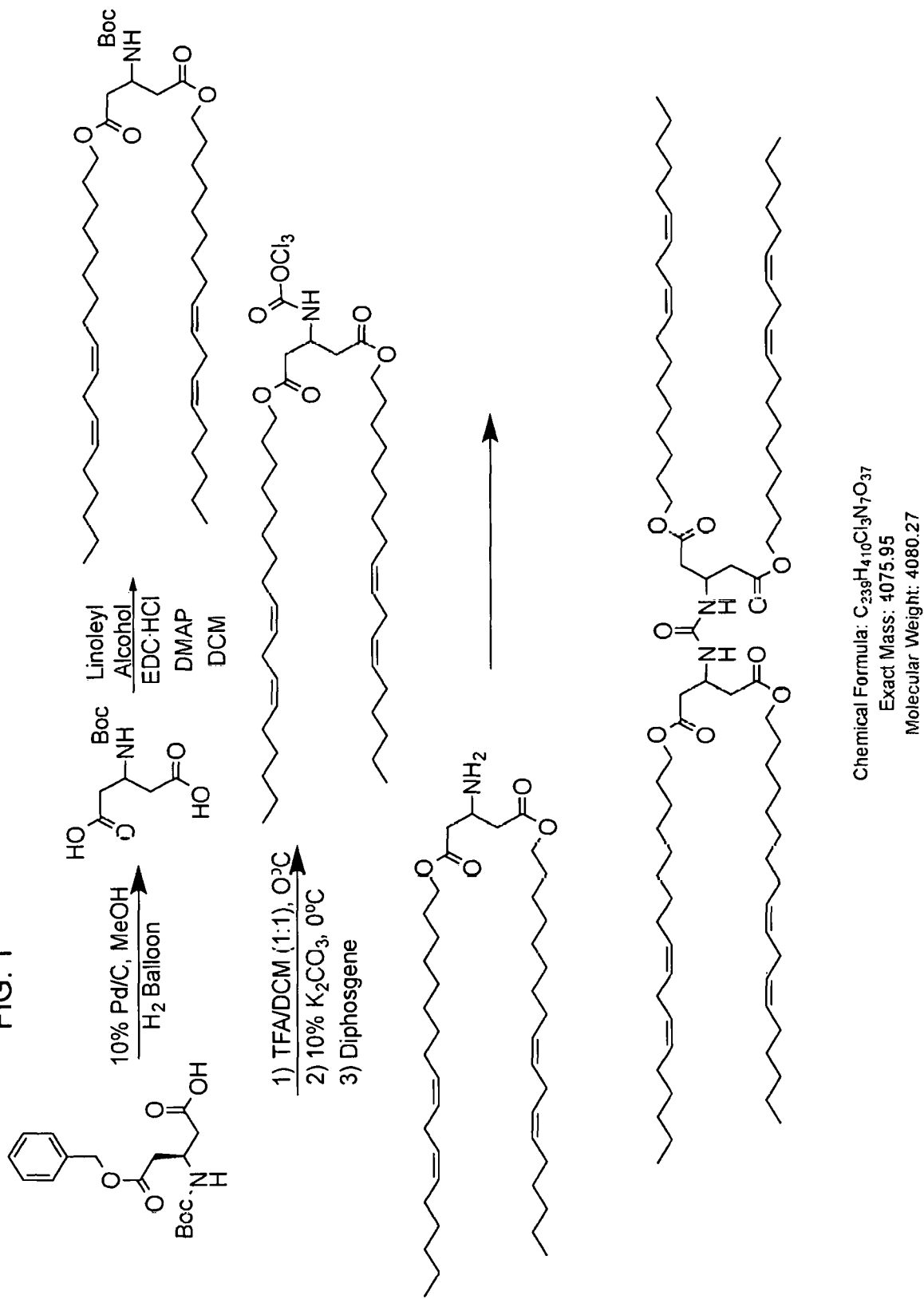
FIG. 1 shows a scheme for the preparation of Compound R1.
Figure 2:
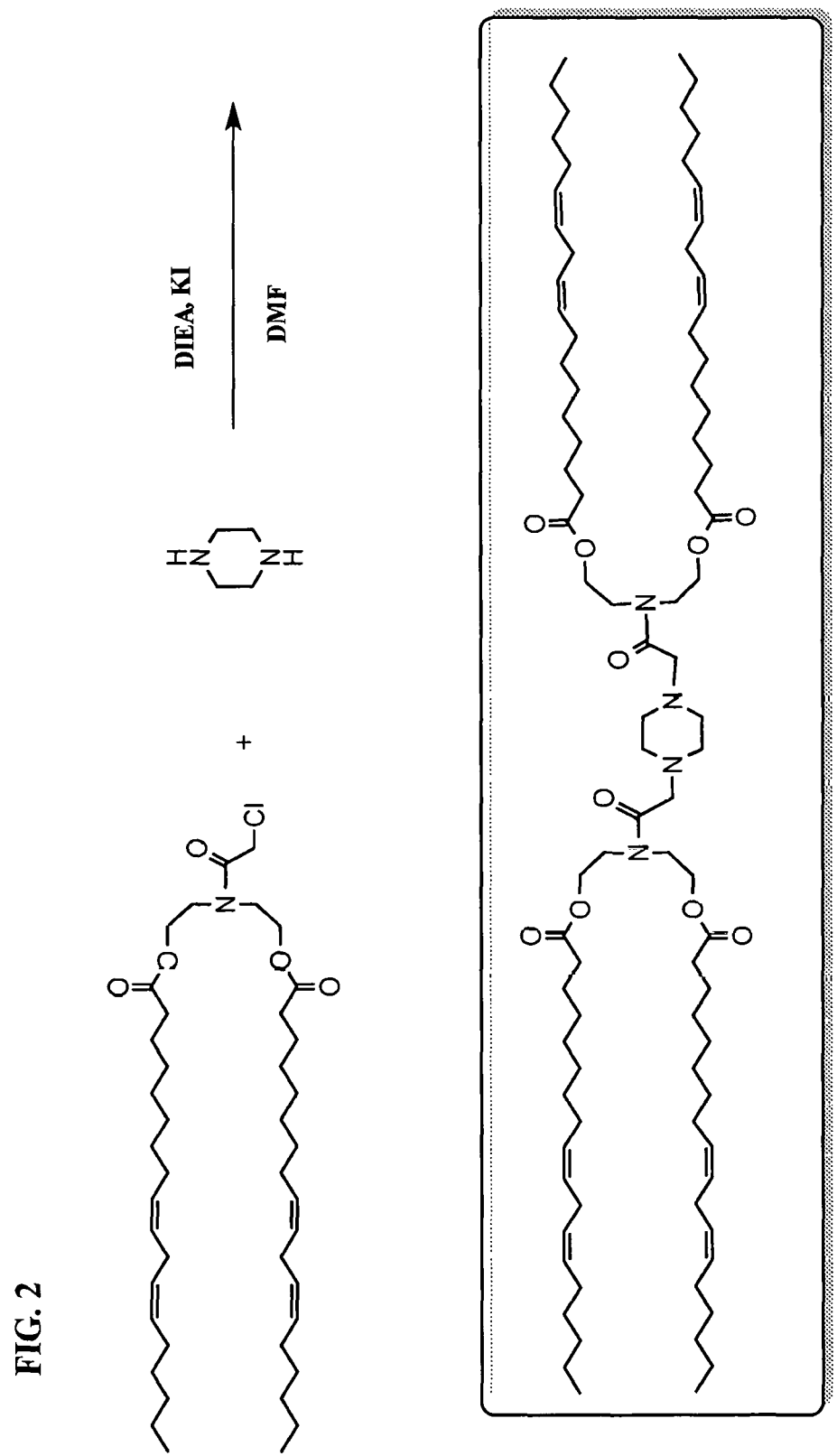
FIG. 2 shows a scheme for the preparation of Compound R2.
Figure 3A:
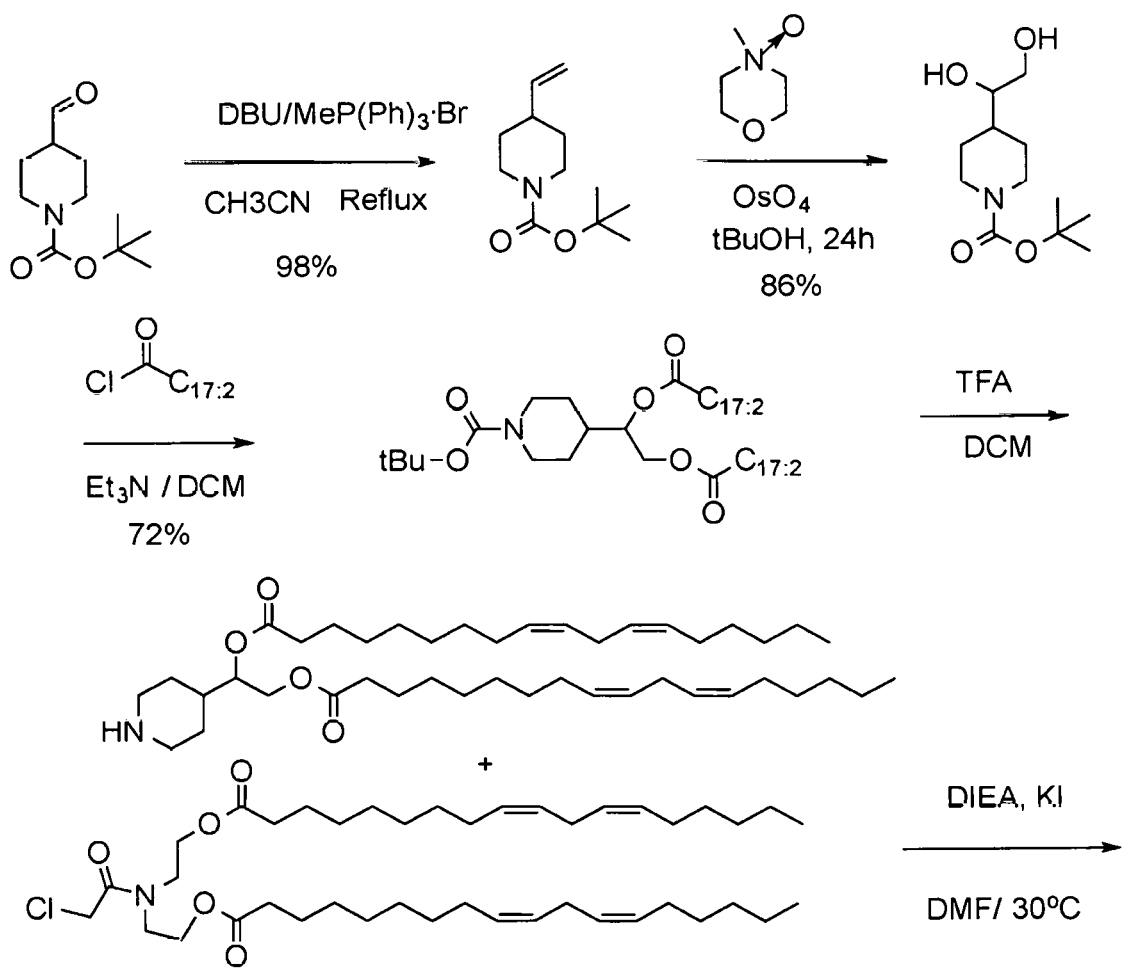
FIG. 3A shows a scheme for the preparation of Compound R3.
Figure 3B:
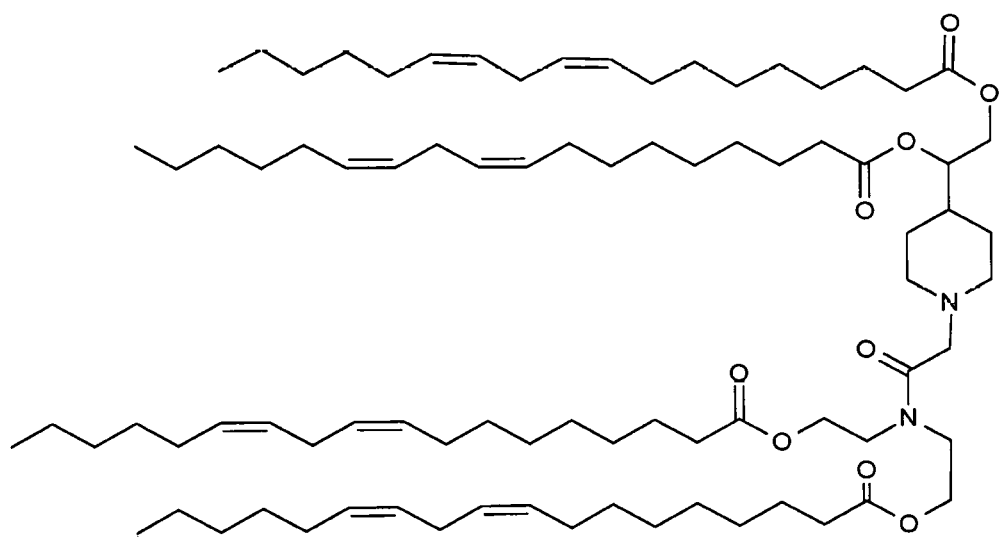
FIG. 3B shows the structure of Compound R3.
Figure 4A:
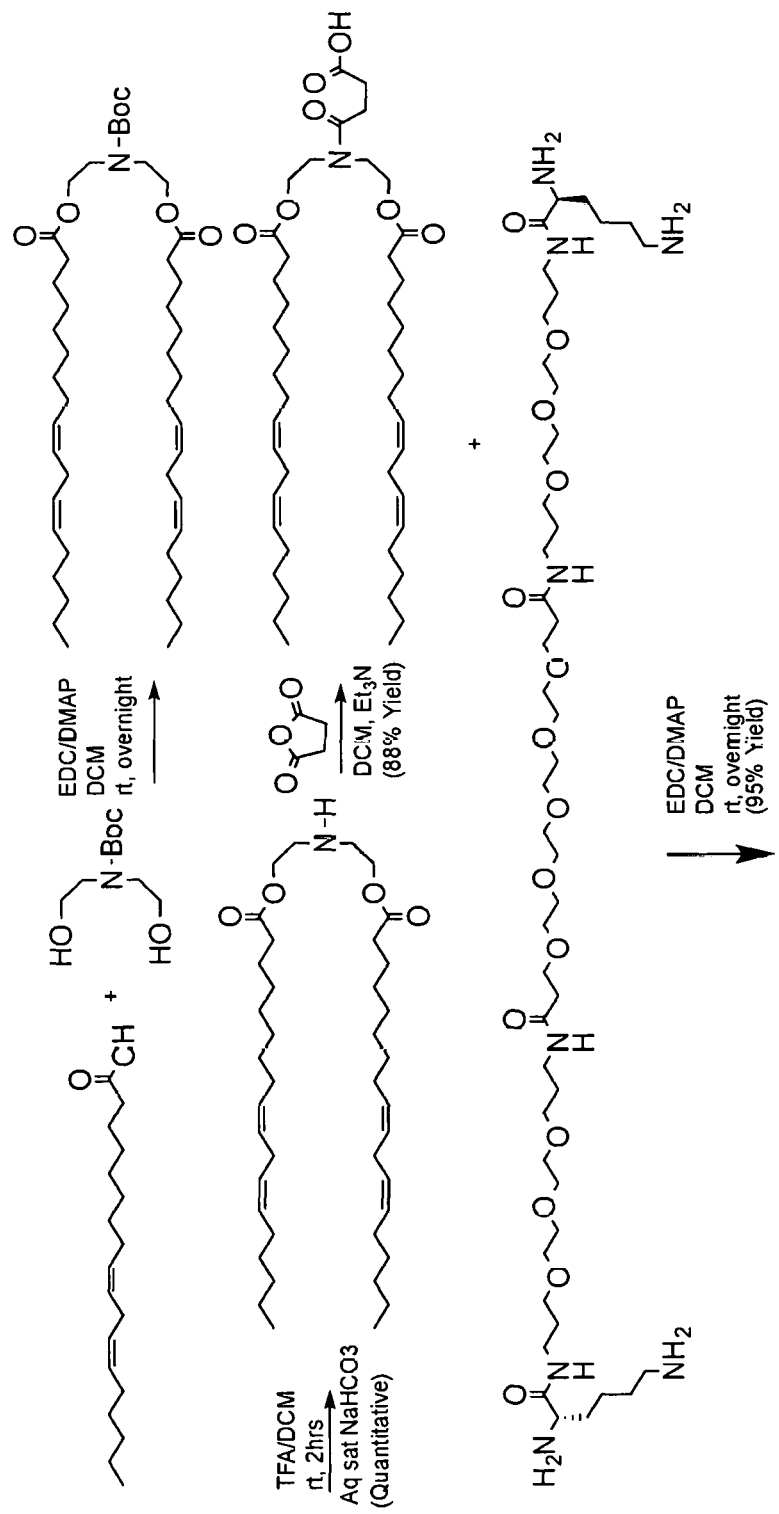
FIG. 4A shows a scheme for the preparation of Compound R4.
Figure 4B:
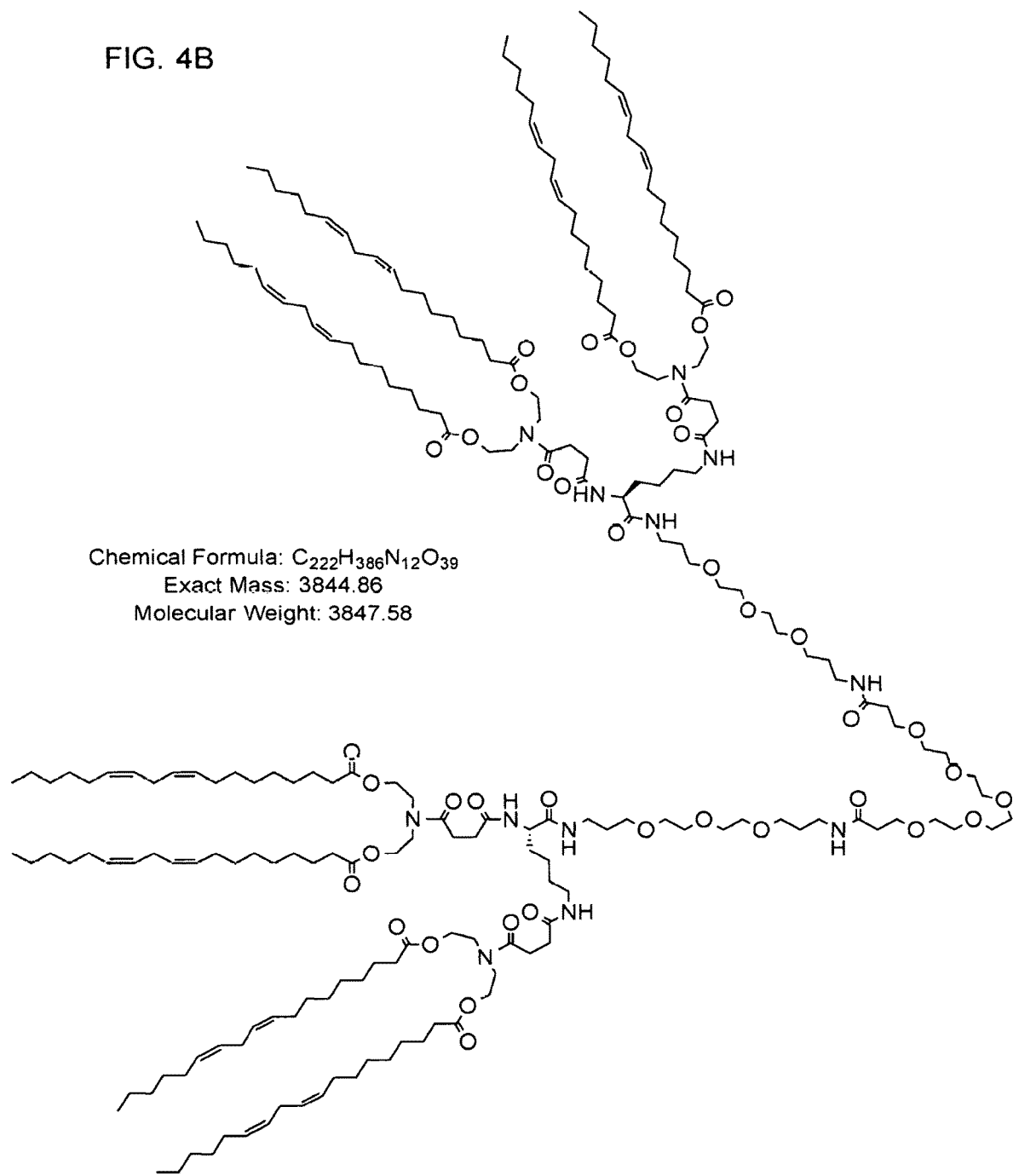
FIG. 4B shows the structure of Compound R4.
Figure 5:
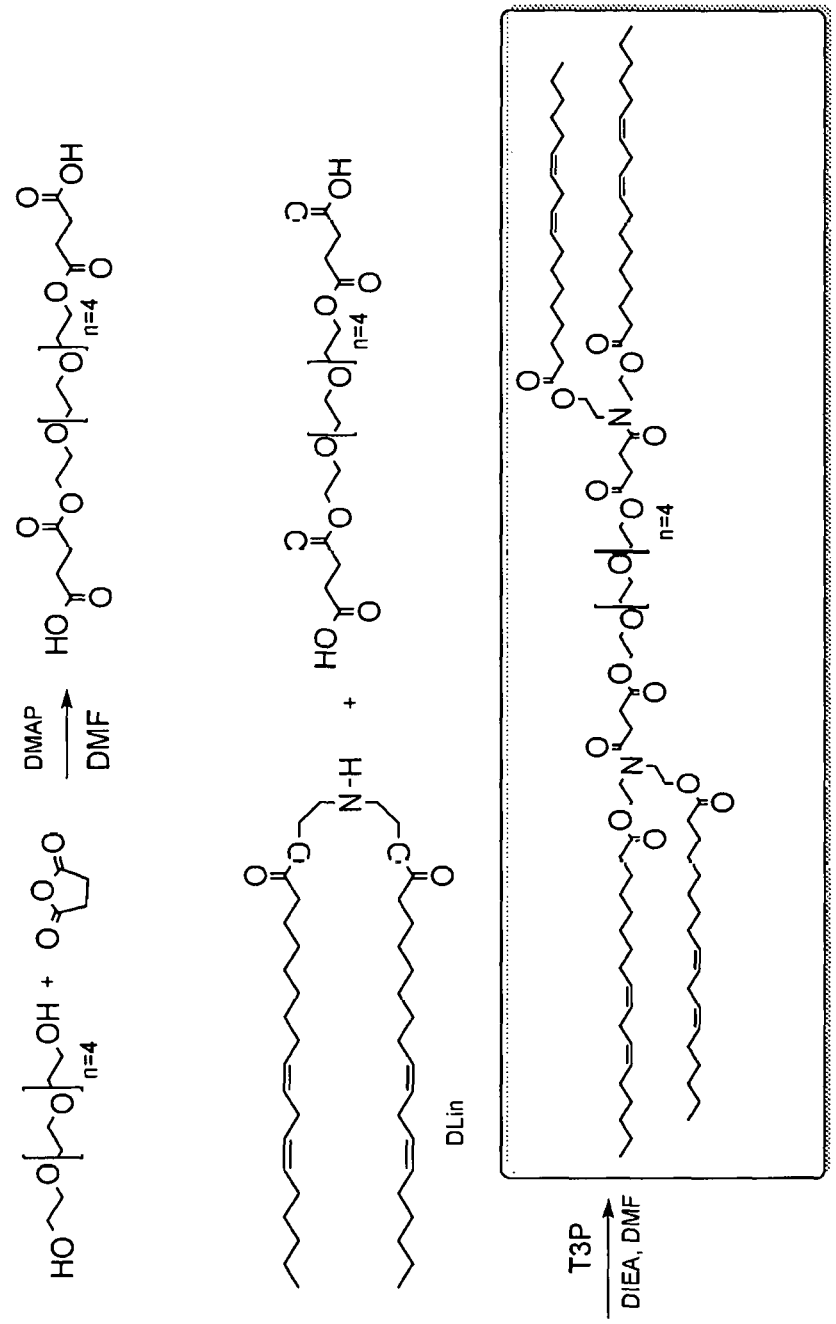
FIG. 5 shows a scheme for the preparation of Compound R5.
Figure 6:
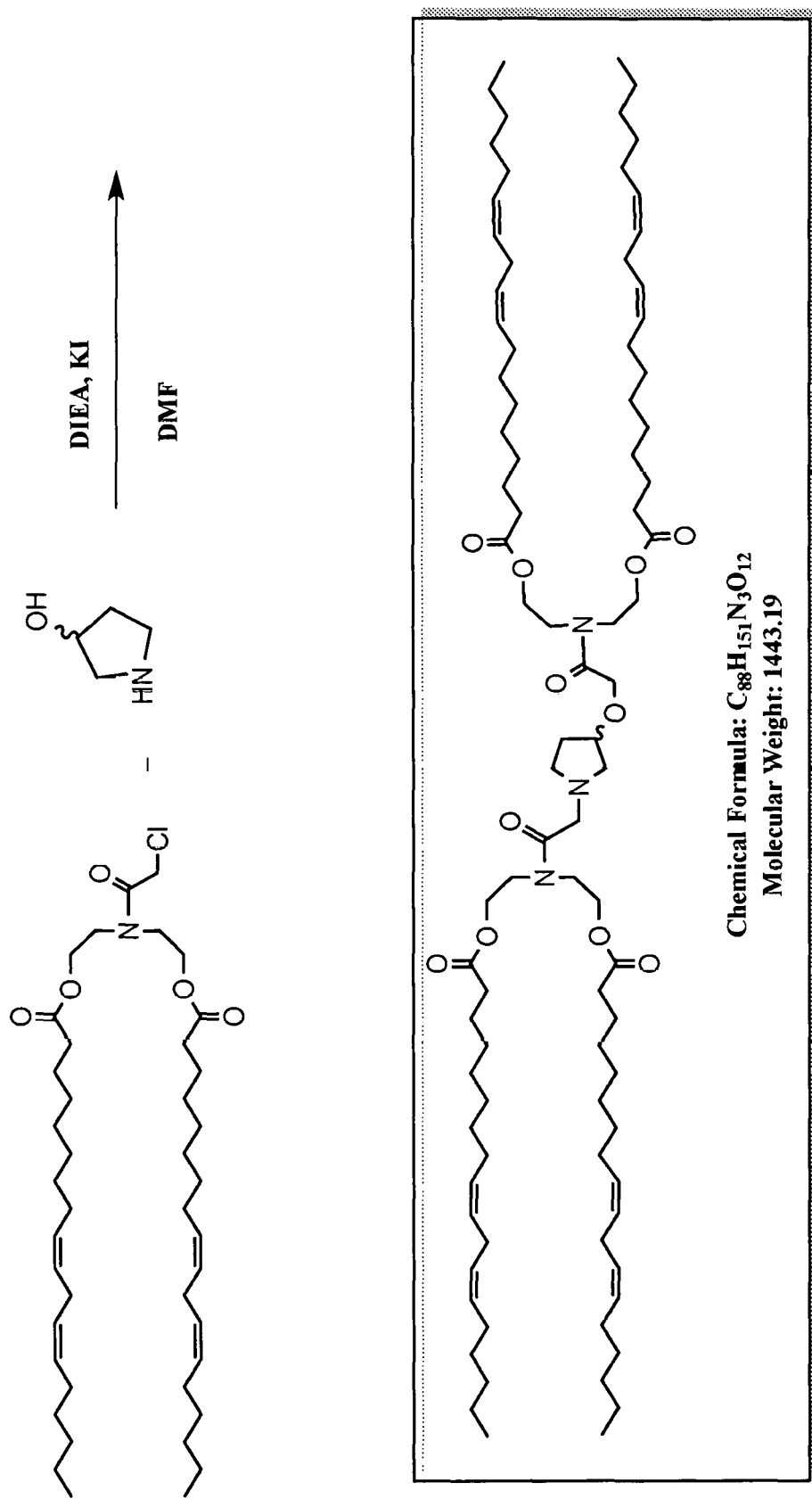
FIG. 6 shows a scheme for the preparation of Compound R6.
Figure 7:
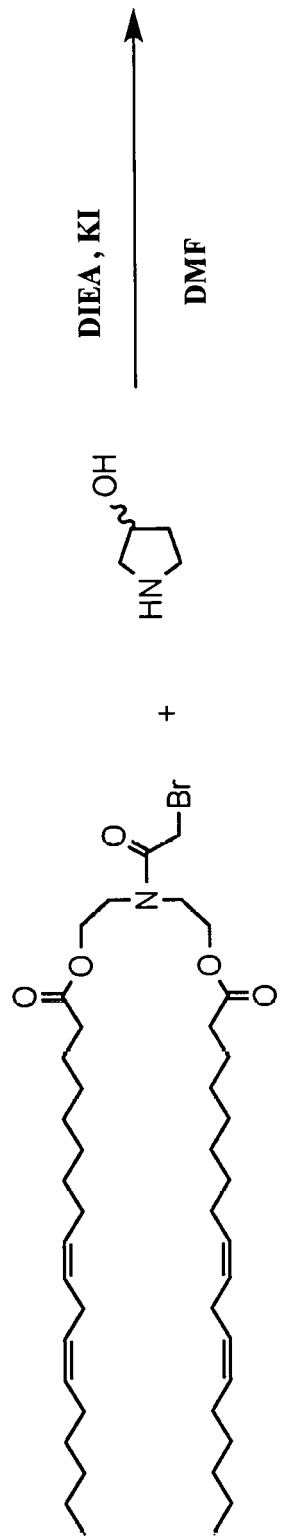
FIG. 7 shows an alternative scheme for the preparation of Compound R6.
Figure 7:
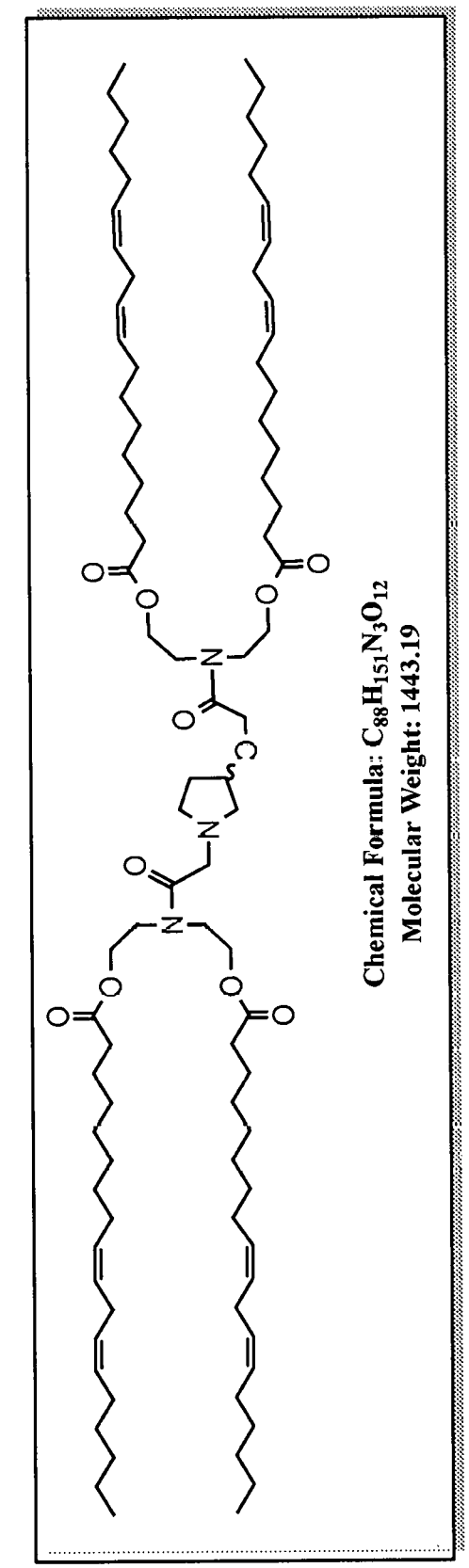
Figure 8:
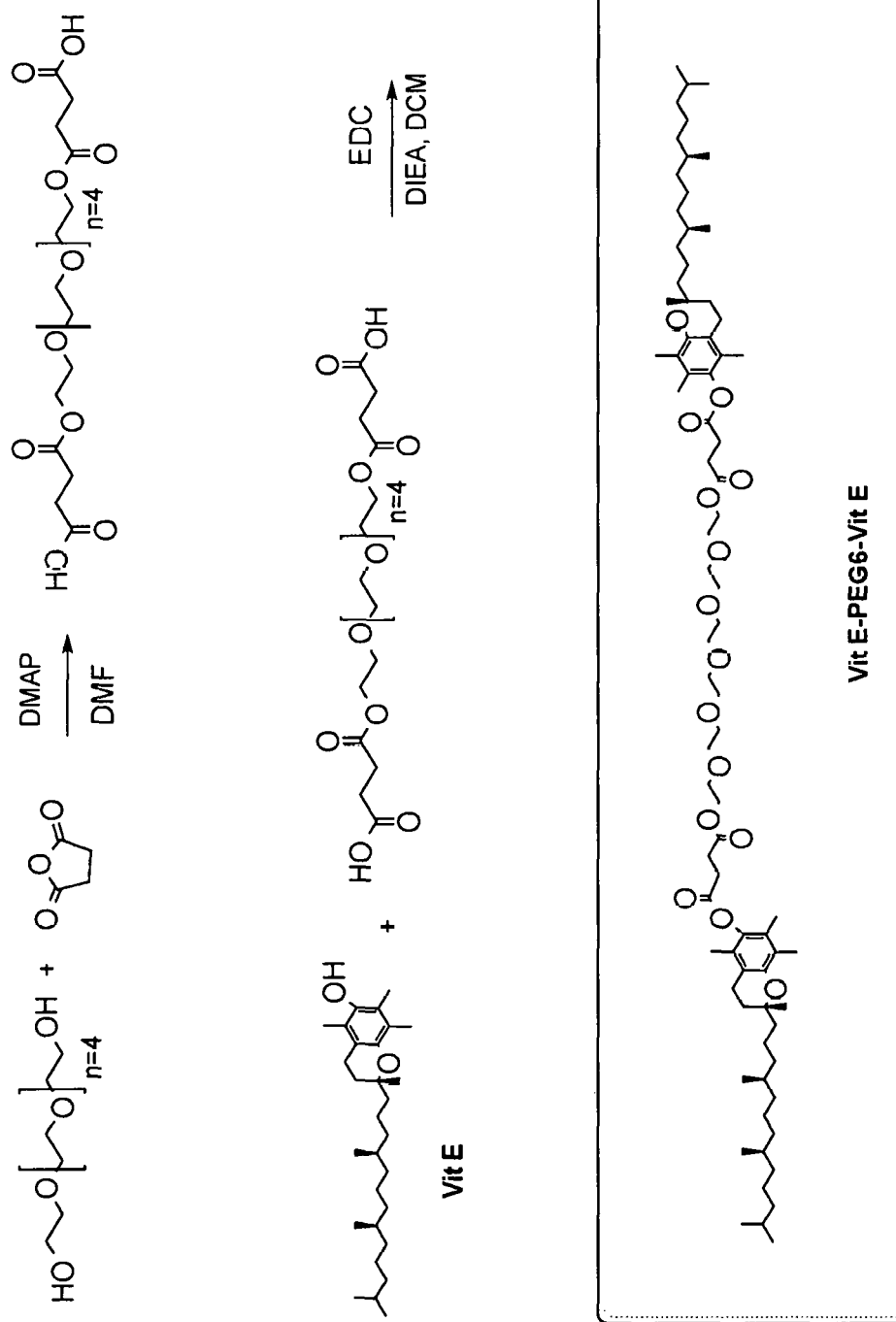
FIG. 8 shows a scheme for the preparation of Compound S2.
Figure 9:
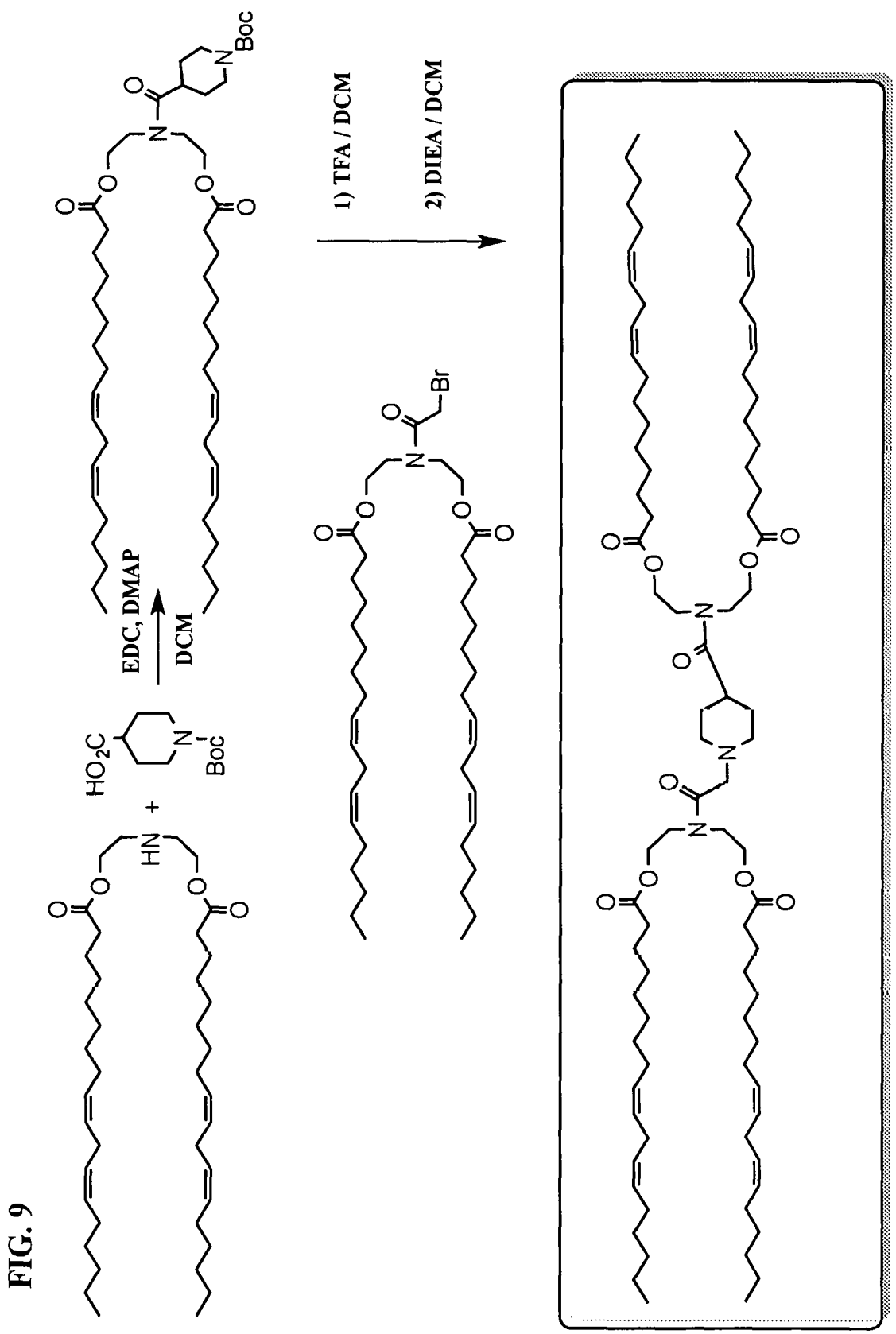
FIG. 9 shows a scheme for the preparation of Compound S3.
Figure 10A:
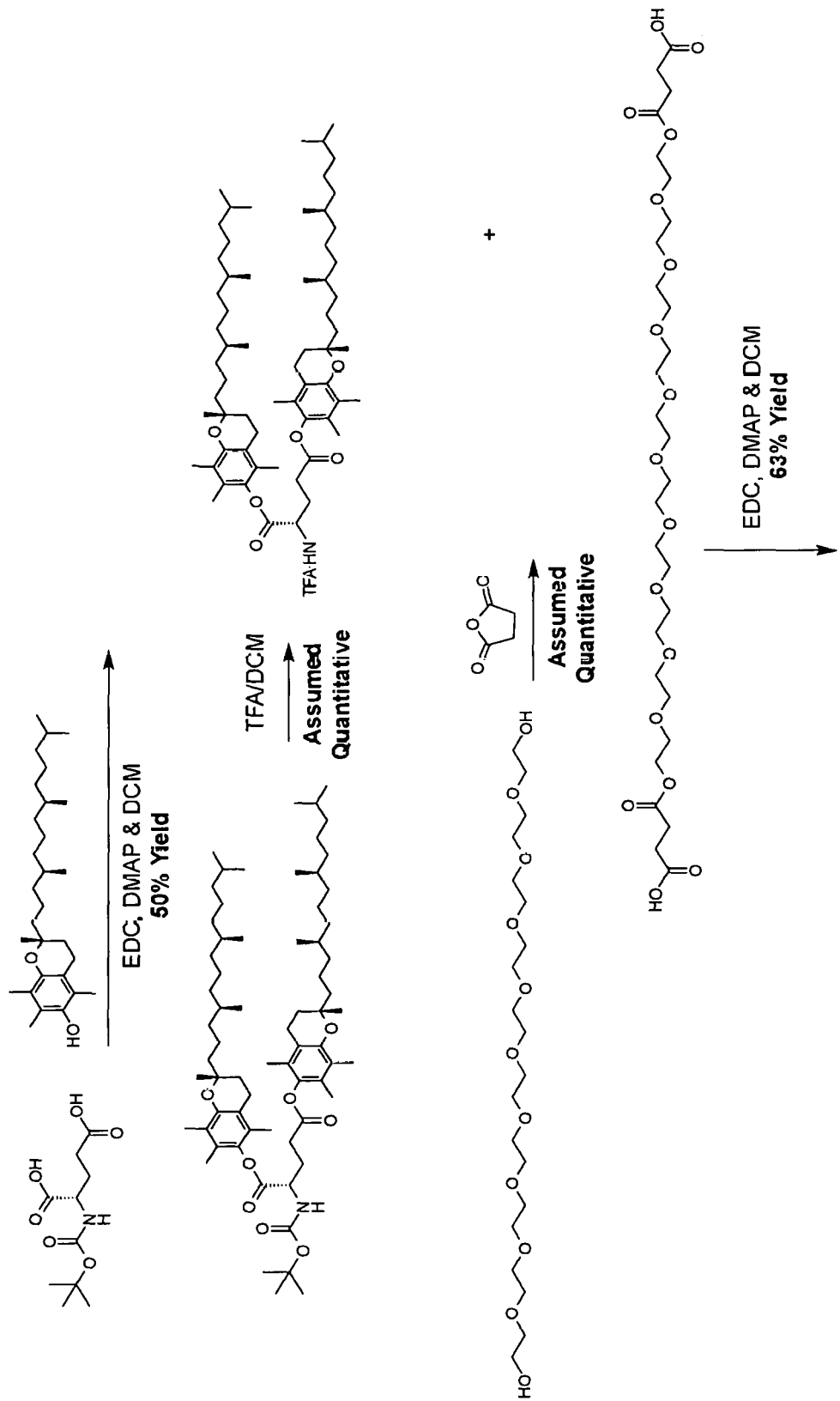
FIG. 10A shows a scheme for the preparation of Compound S4.
Figure 10B:
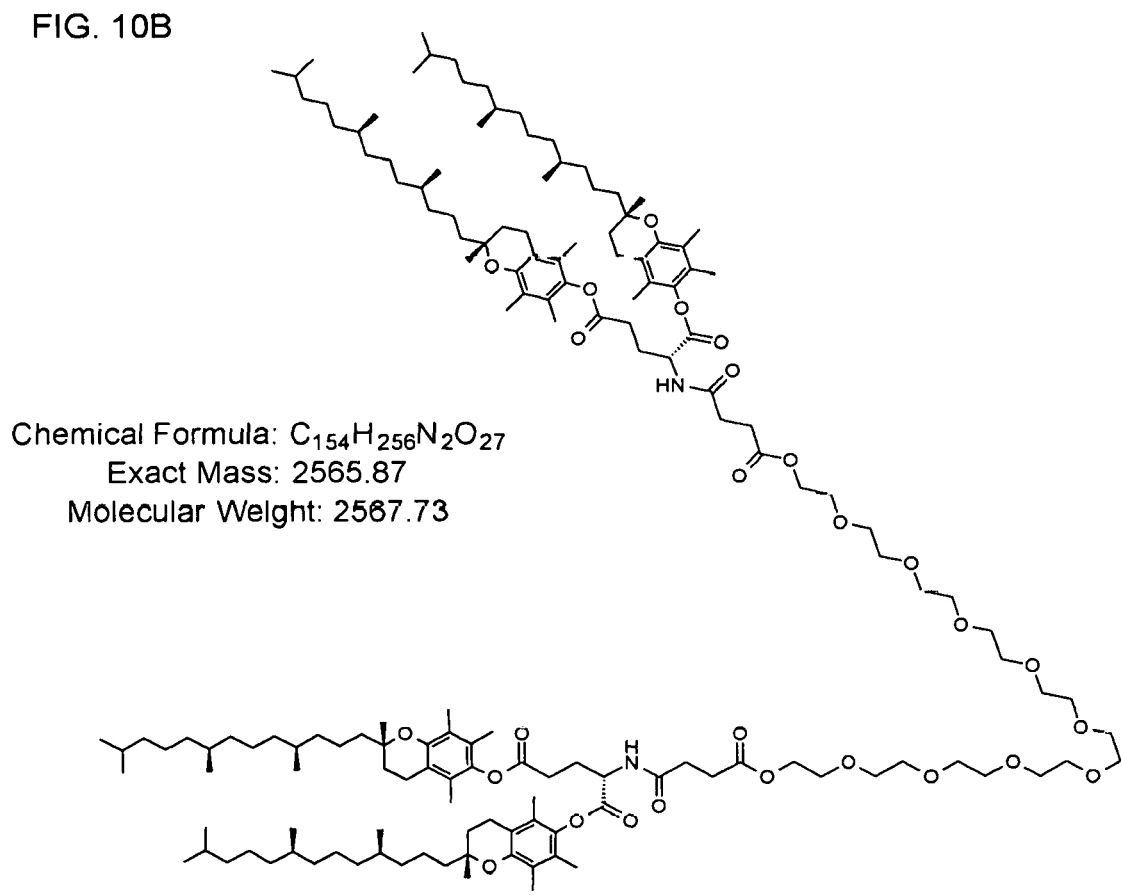
FIG. 10B show the structure of Compound S4.
Figure 11:
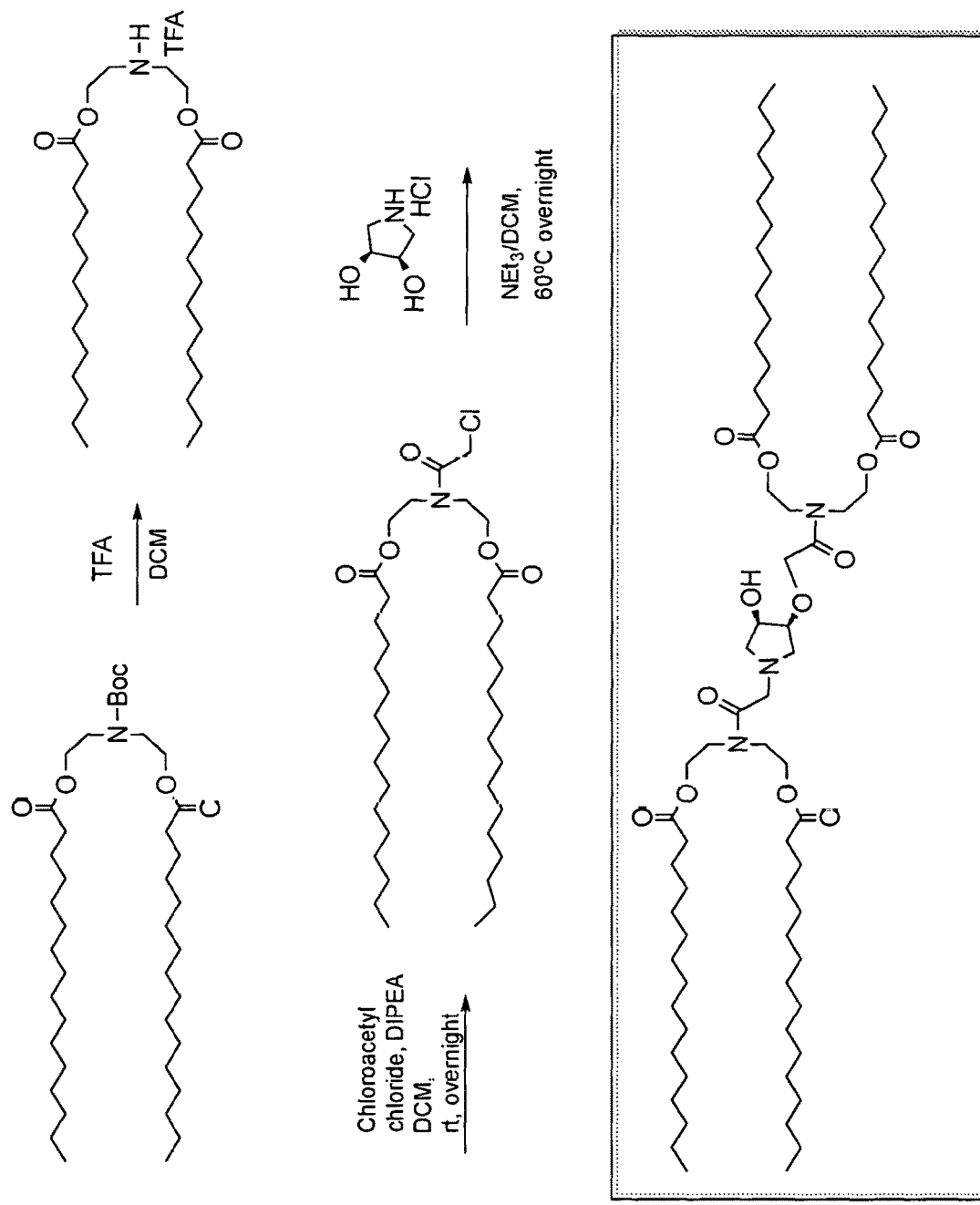
FIG. 11 shows a scheme for the preparation of Compound S5.
Figure 12A:
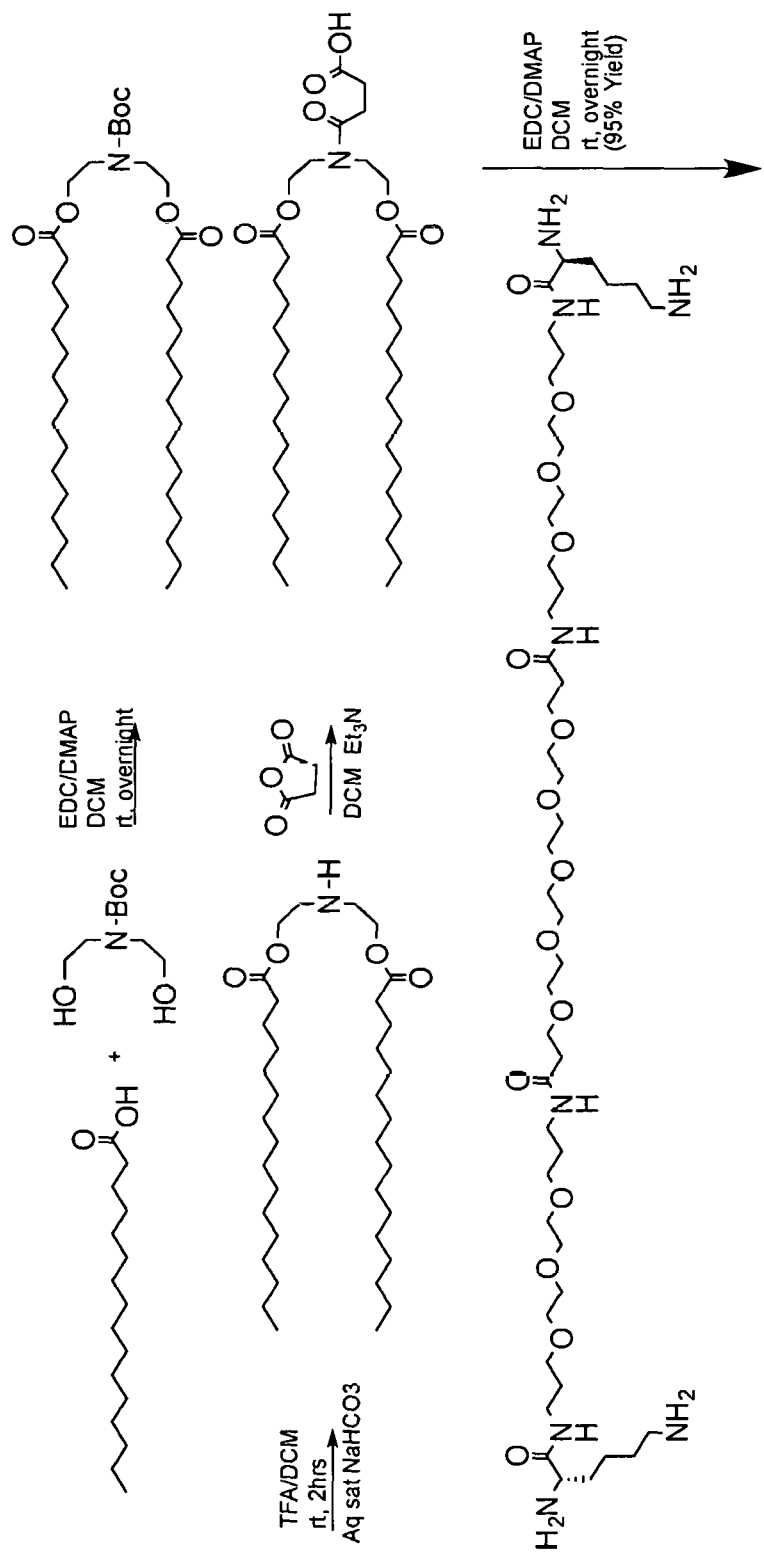
FIG. 12A shows a scheme for the preparation of Compound S6.
Figure 12B:
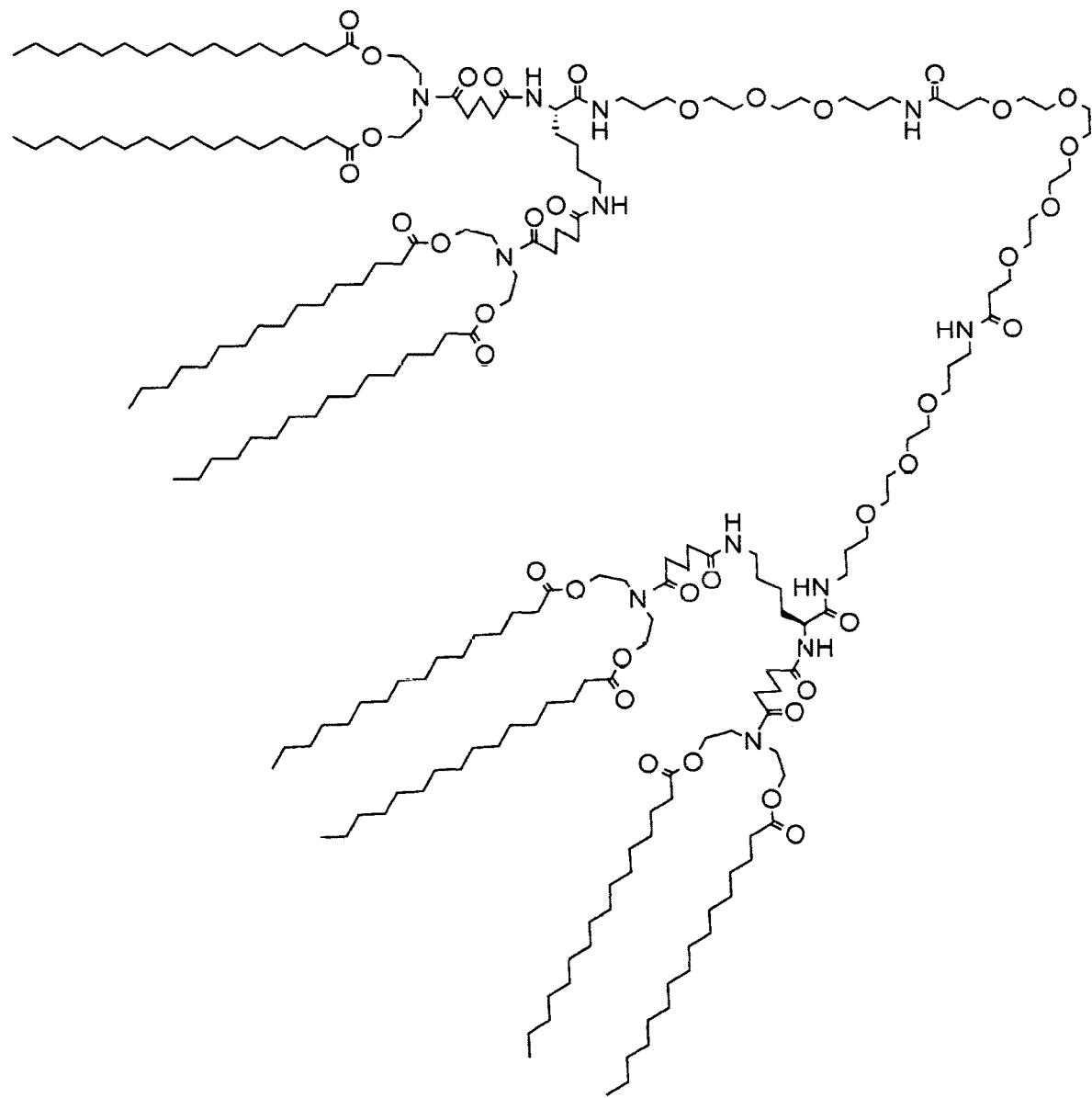
FIG. 12B shows the structure of Compound S6.
Figure 13A:
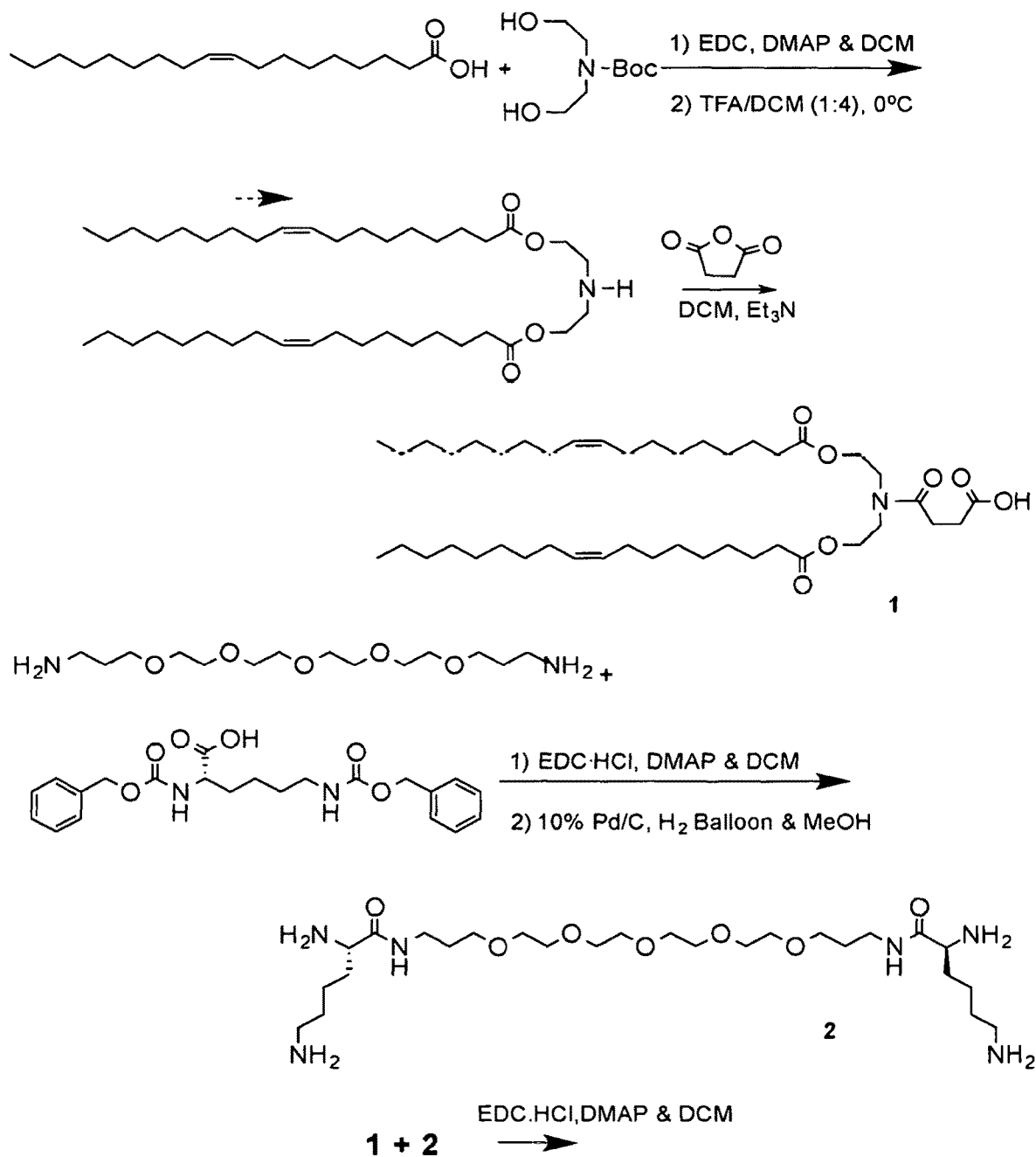
FIG. 13A shows a scheme for the preparation of Compound S7.
Figure 13B:
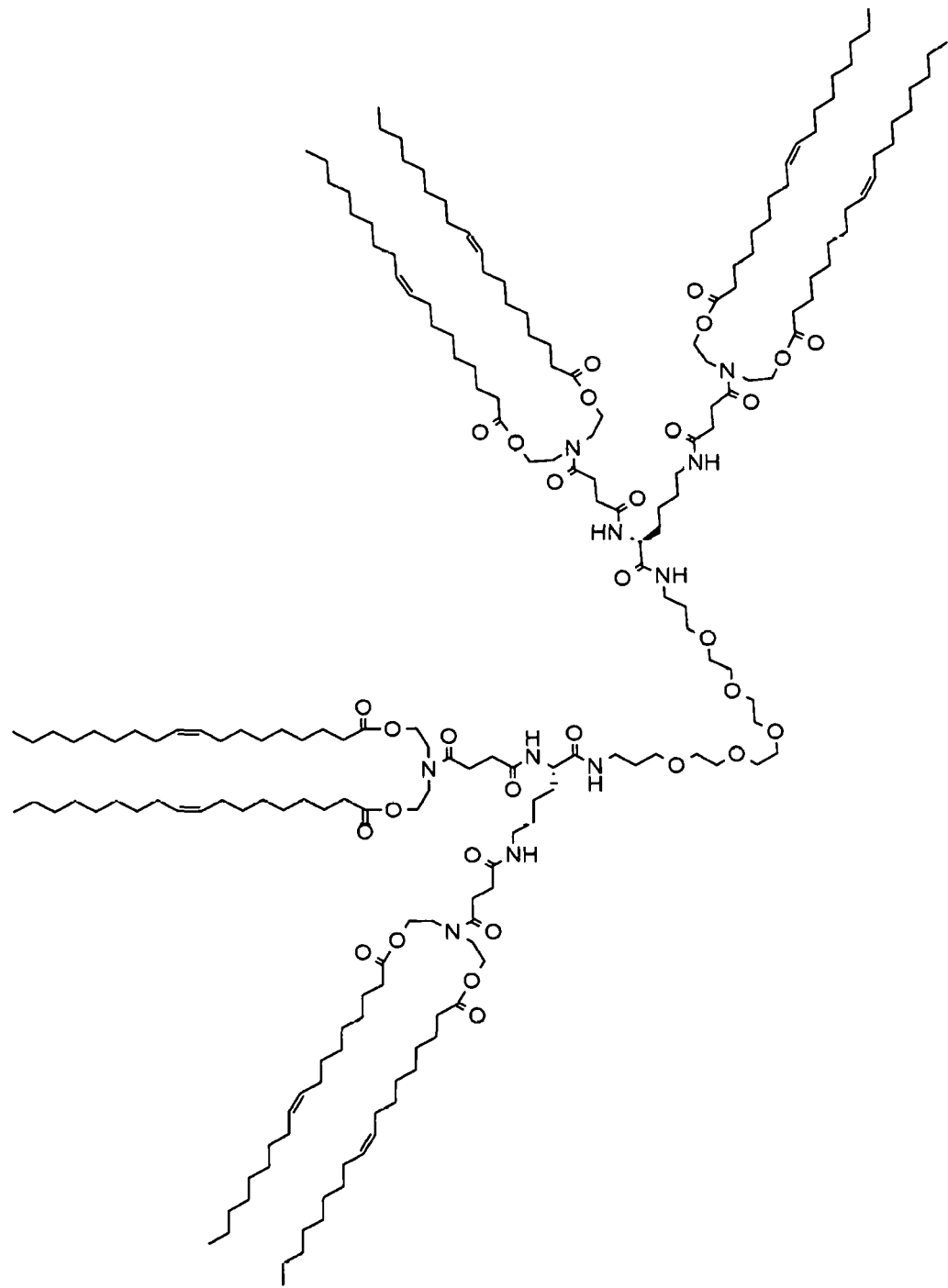
FIG. 13B shows the structure of Compound S7.
Figure 14A:
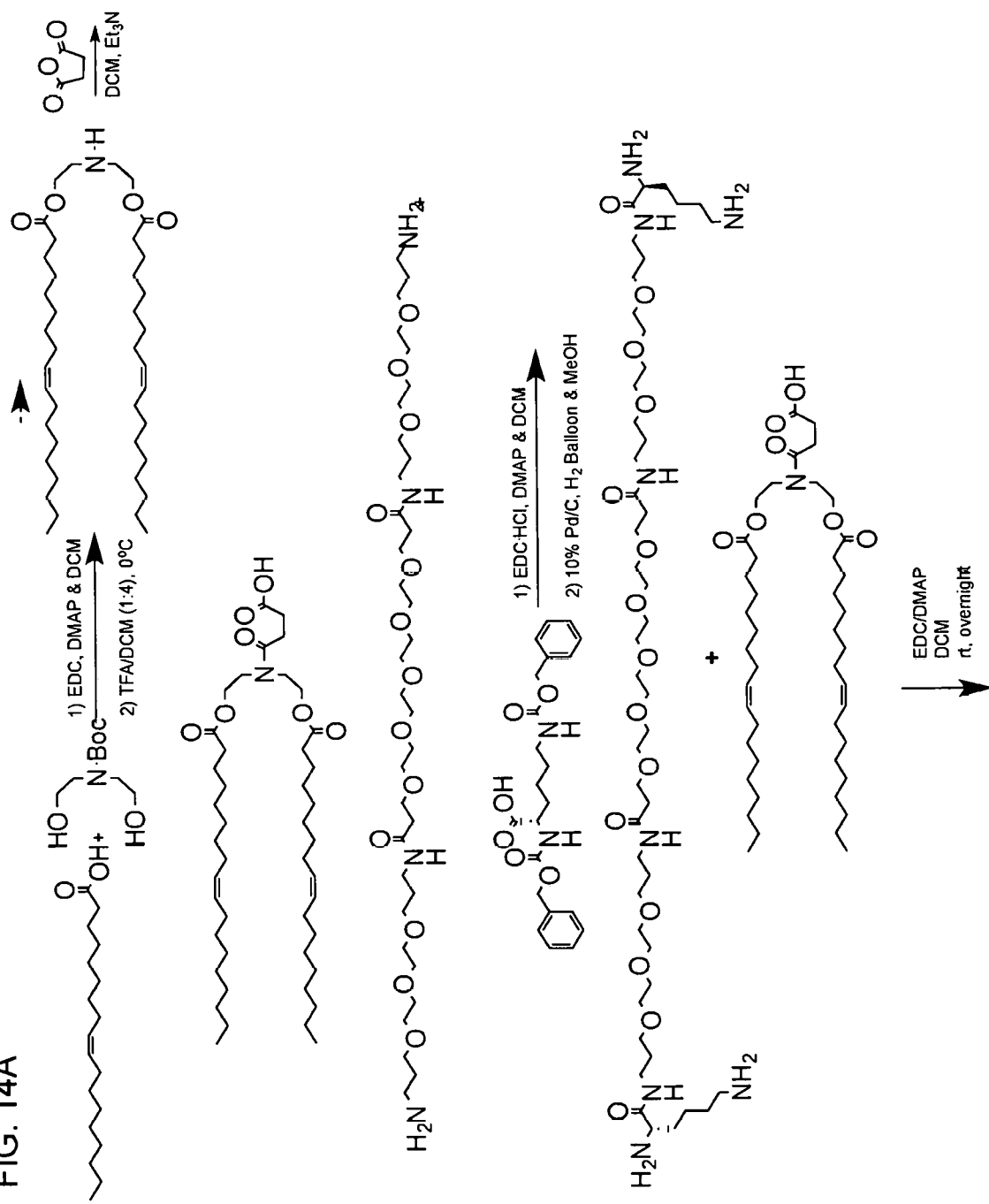
FIG. 14A shows a scheme for the preparation of Compound S8.
Figure 14B:
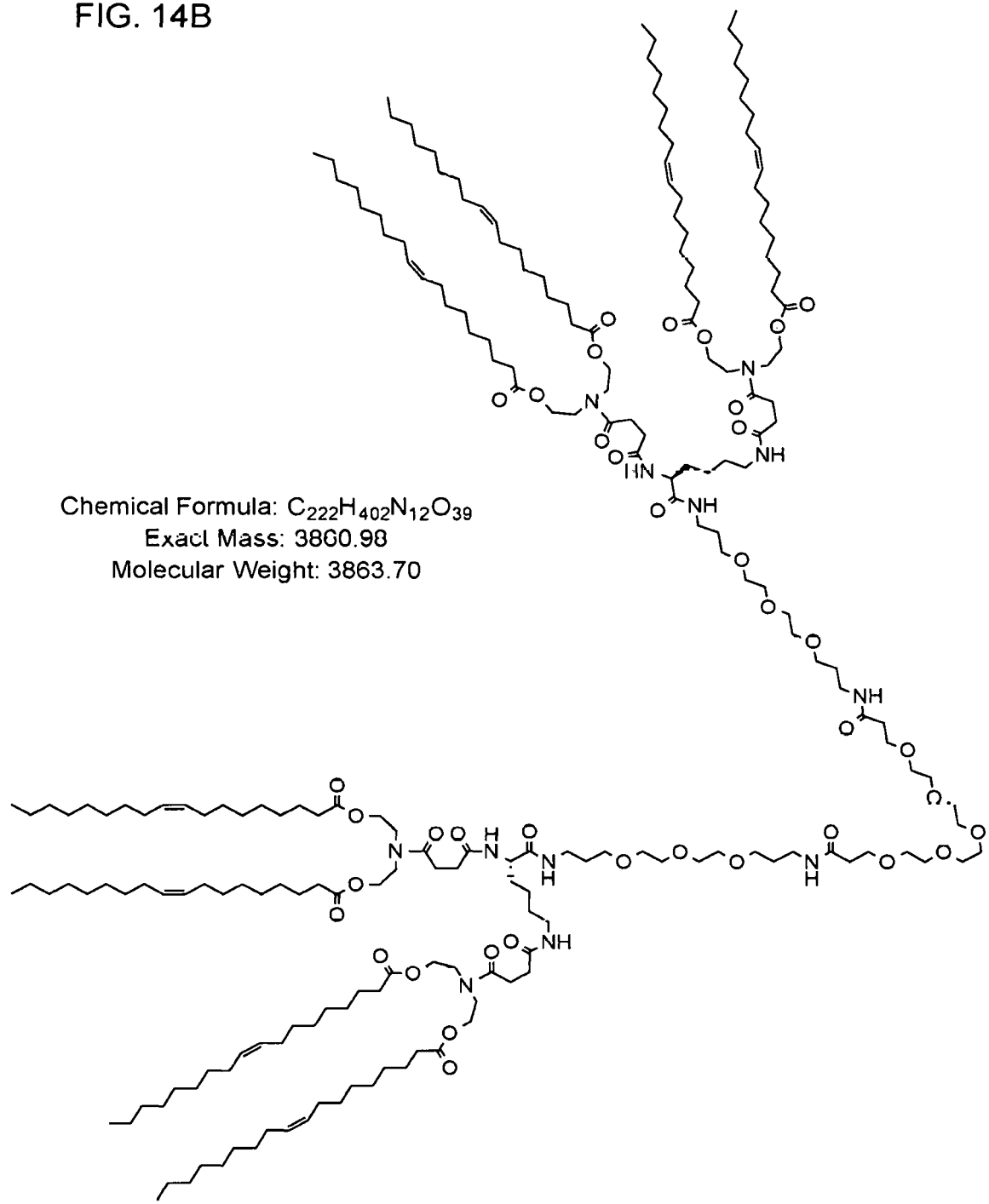
FIG. 14B shows the structure of Compound S8.
Figure 15A:
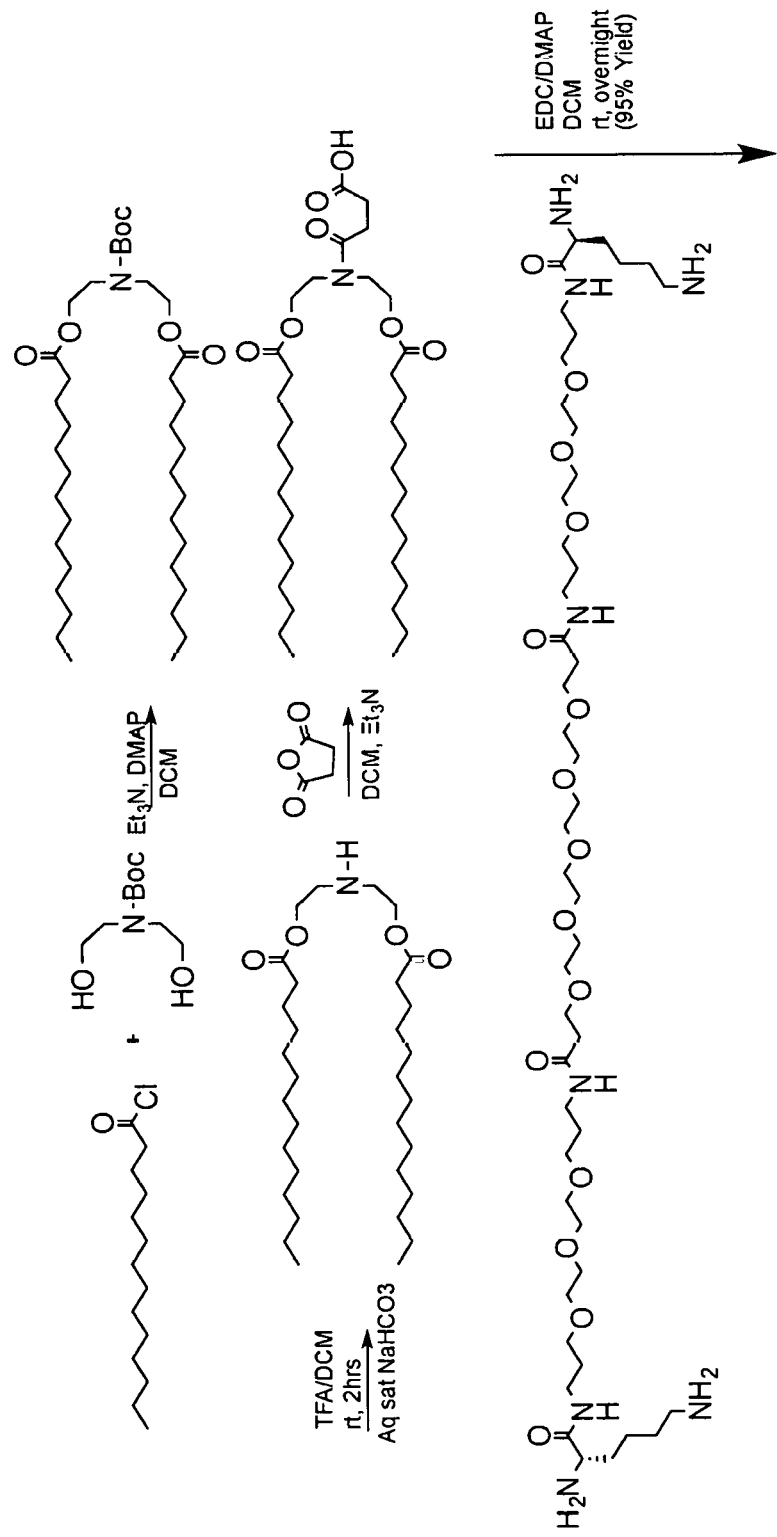
FIG. 15A shows a scheme for the preparation of Compound T1.
Figure 15B:
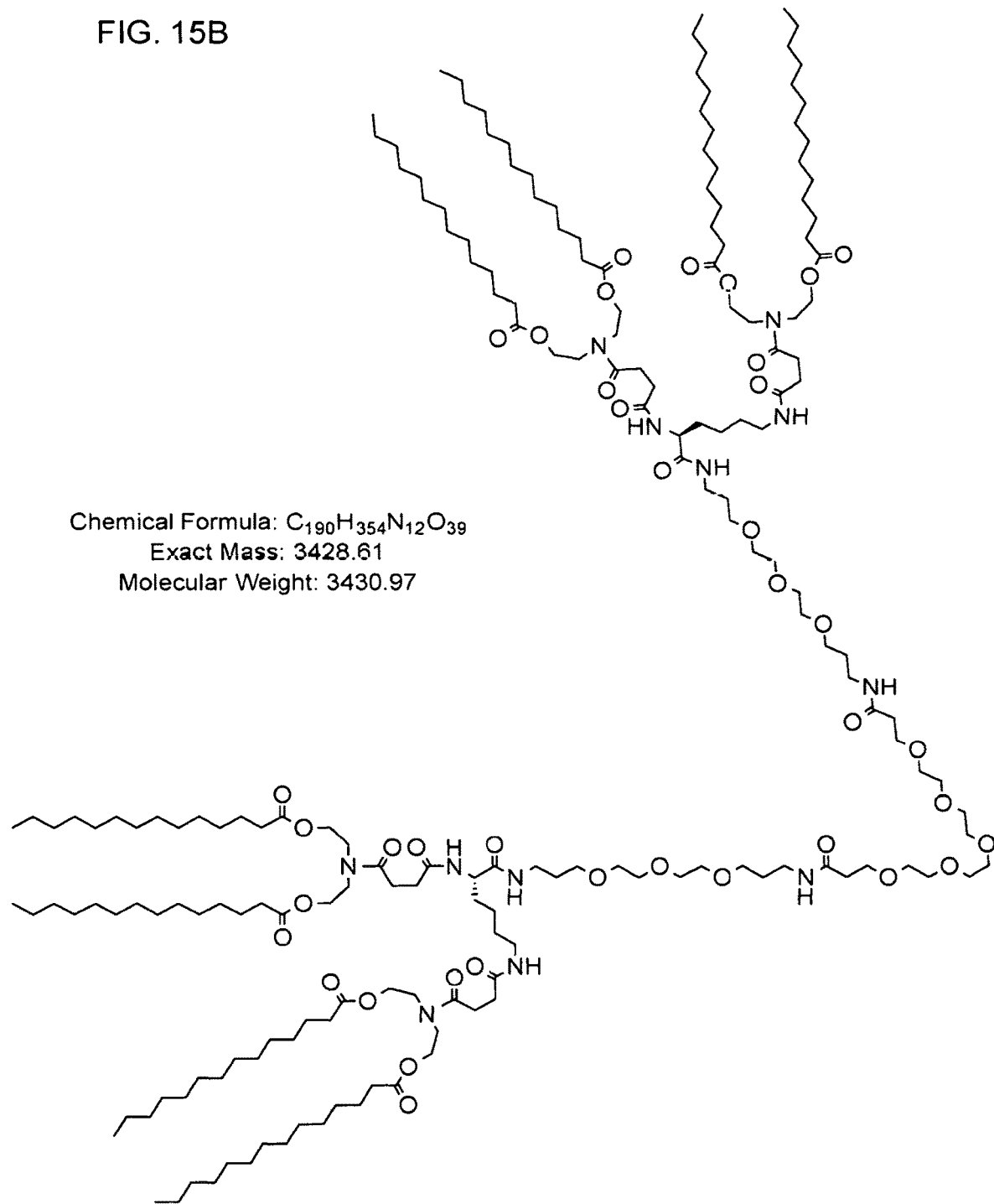
FIG. 15B shows the structure of Compound T1.
Figure 16A:
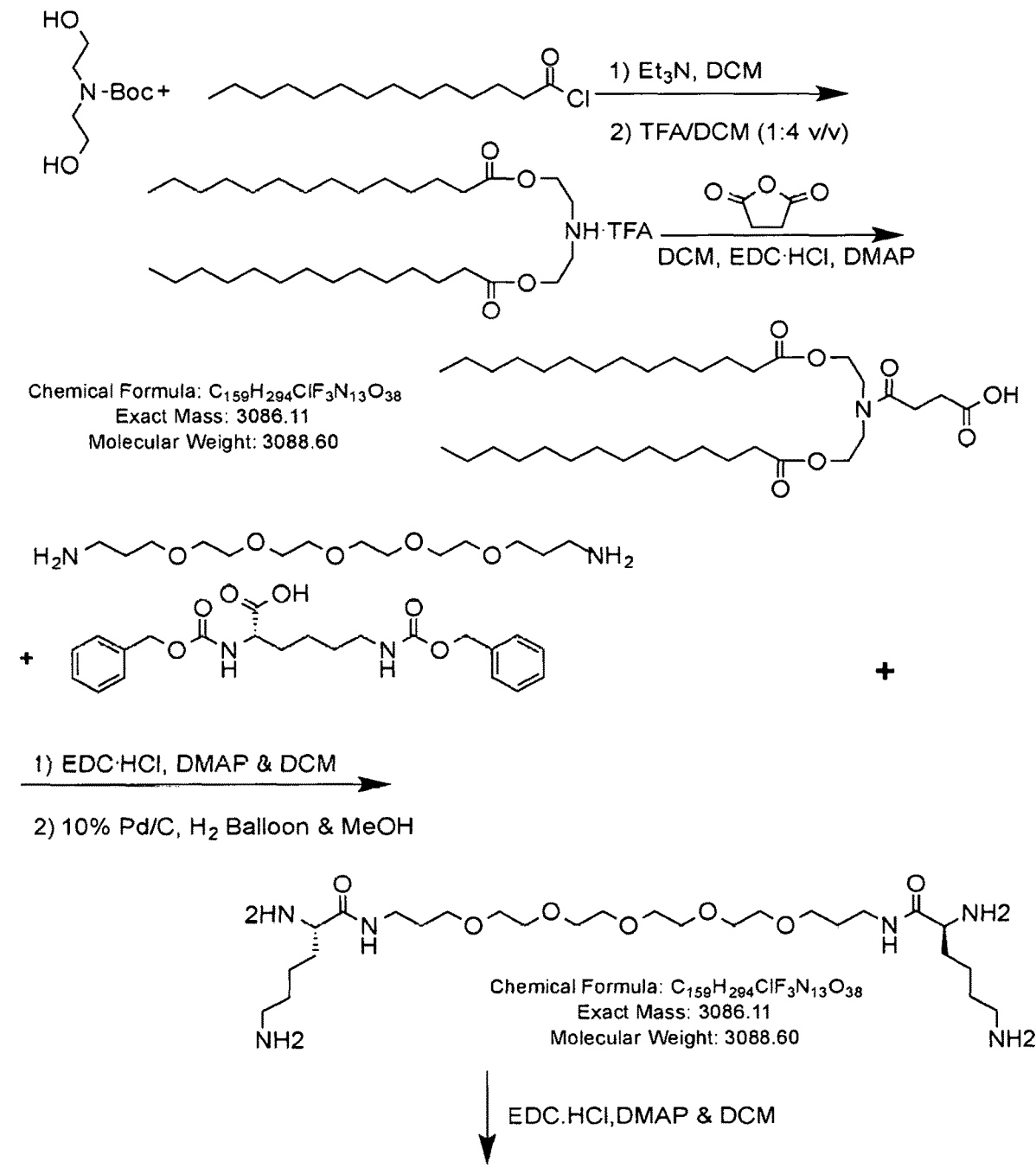
FIG. 16A shows a scheme for the preparation of Compound T2.
Figure 16B:
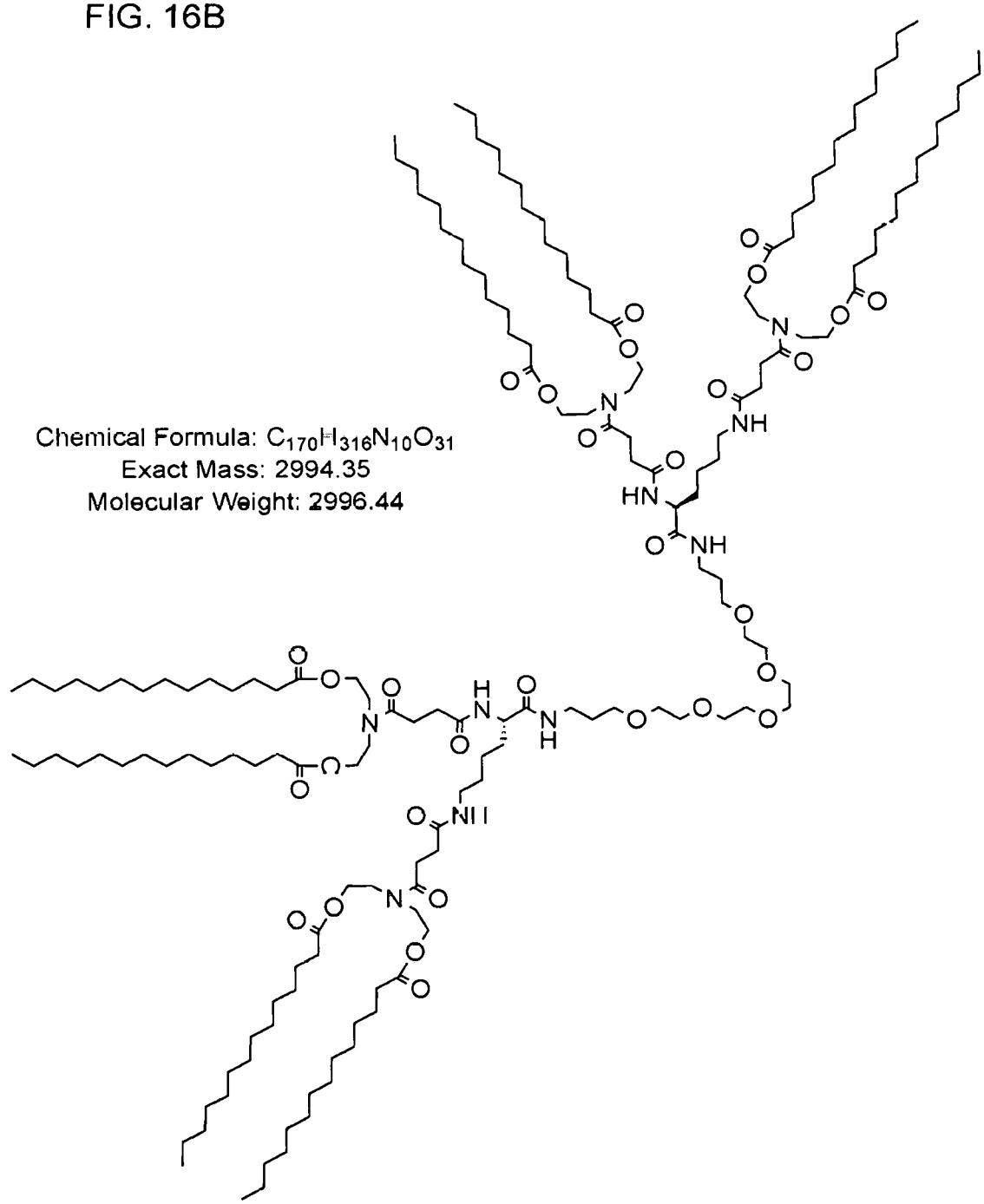
FIG. 16B shows the structure of Compound T2.
Figure 17A:
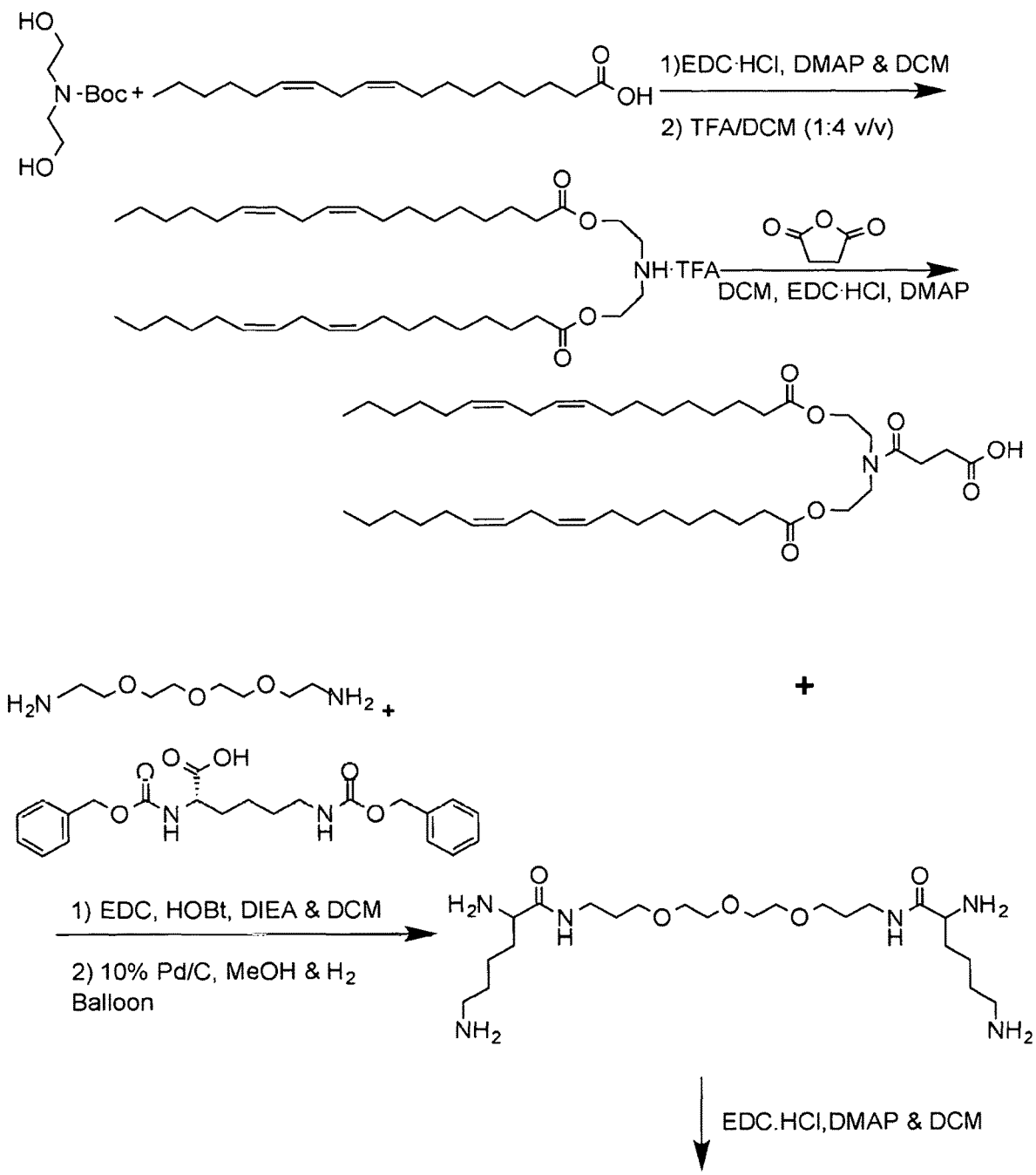
FIG. 17A shows a scheme for the preparation of Compound T4.
Figure 17B:
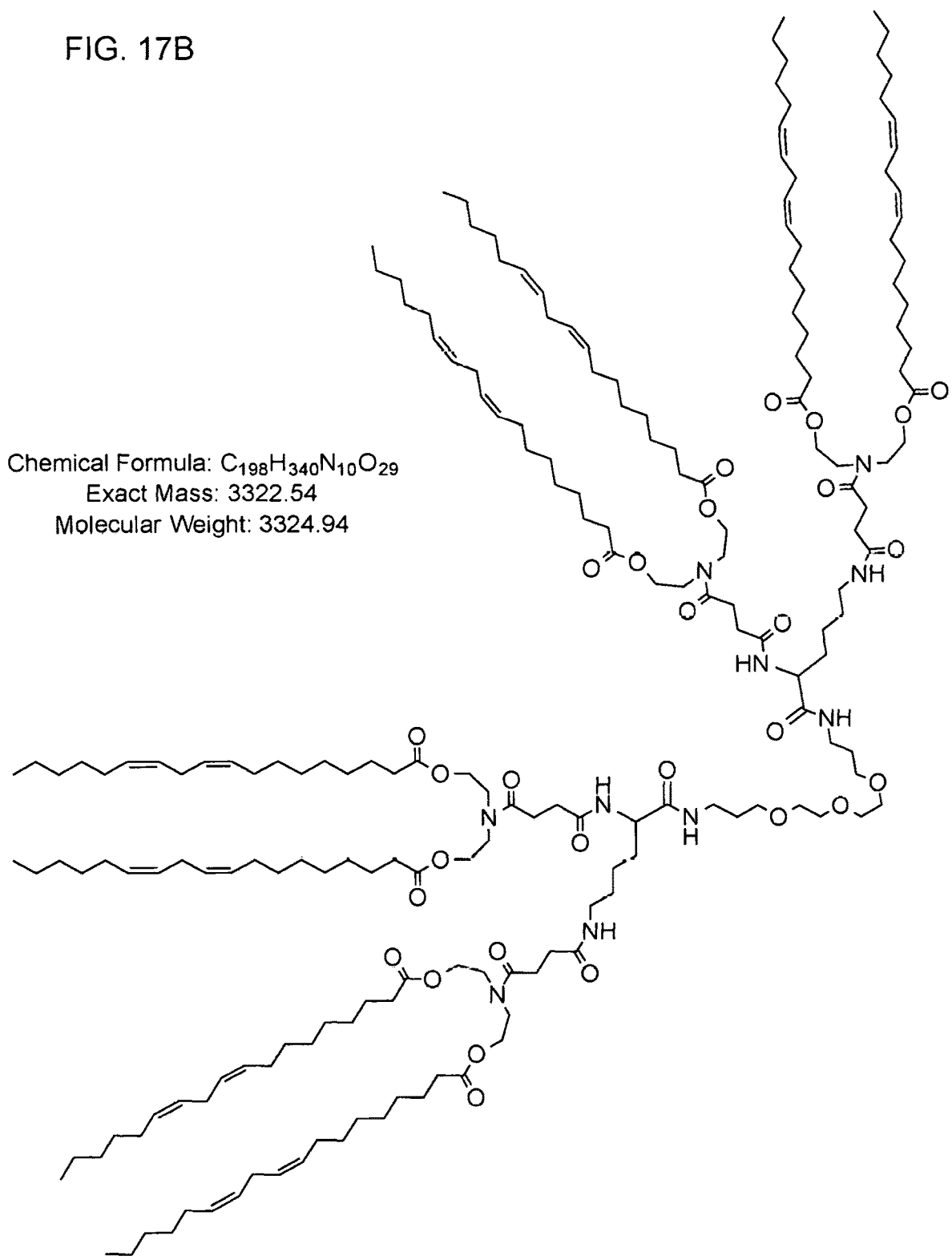
FIG. 17B shows the structure of Compound T4.
Figure 18A:
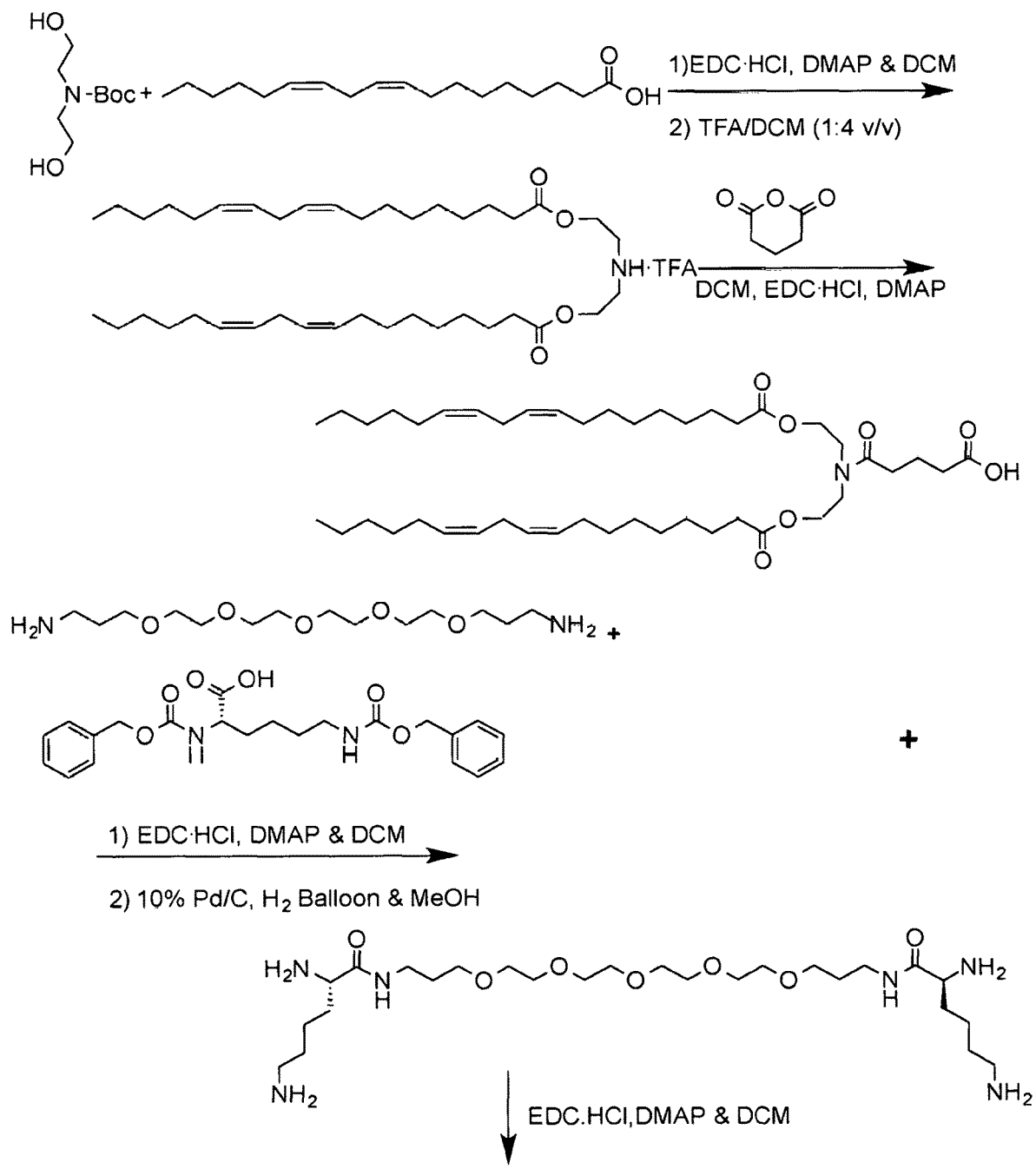
FIG. 18A shows a scheme for the preparation of Compound T5.
Figure 18B:
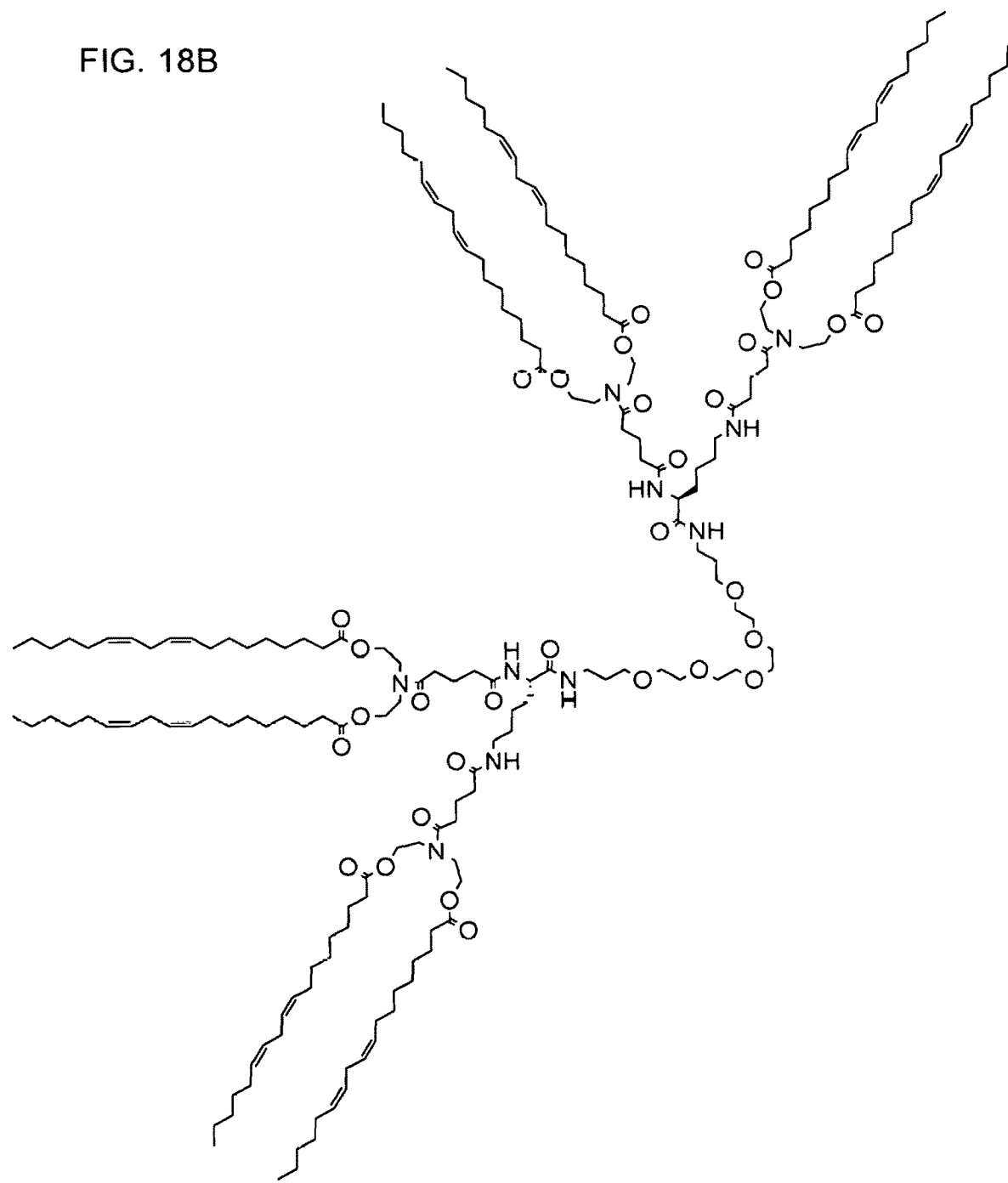
FIG. 18B shows the structure of Compound T5.
Figure 19A:
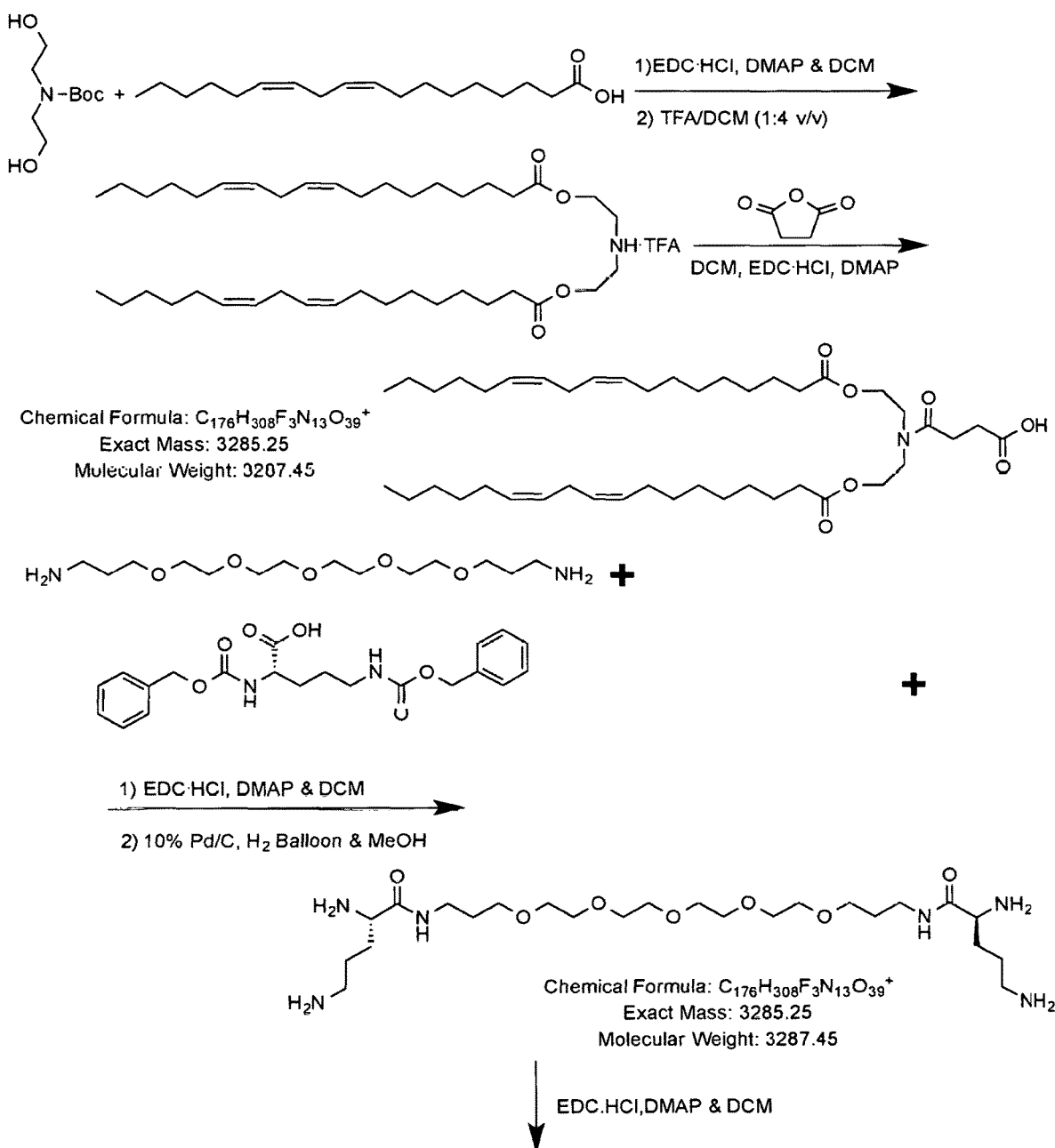
FIG. 19A shows a scheme for the preparation of Compound T6.
Figure 19B:
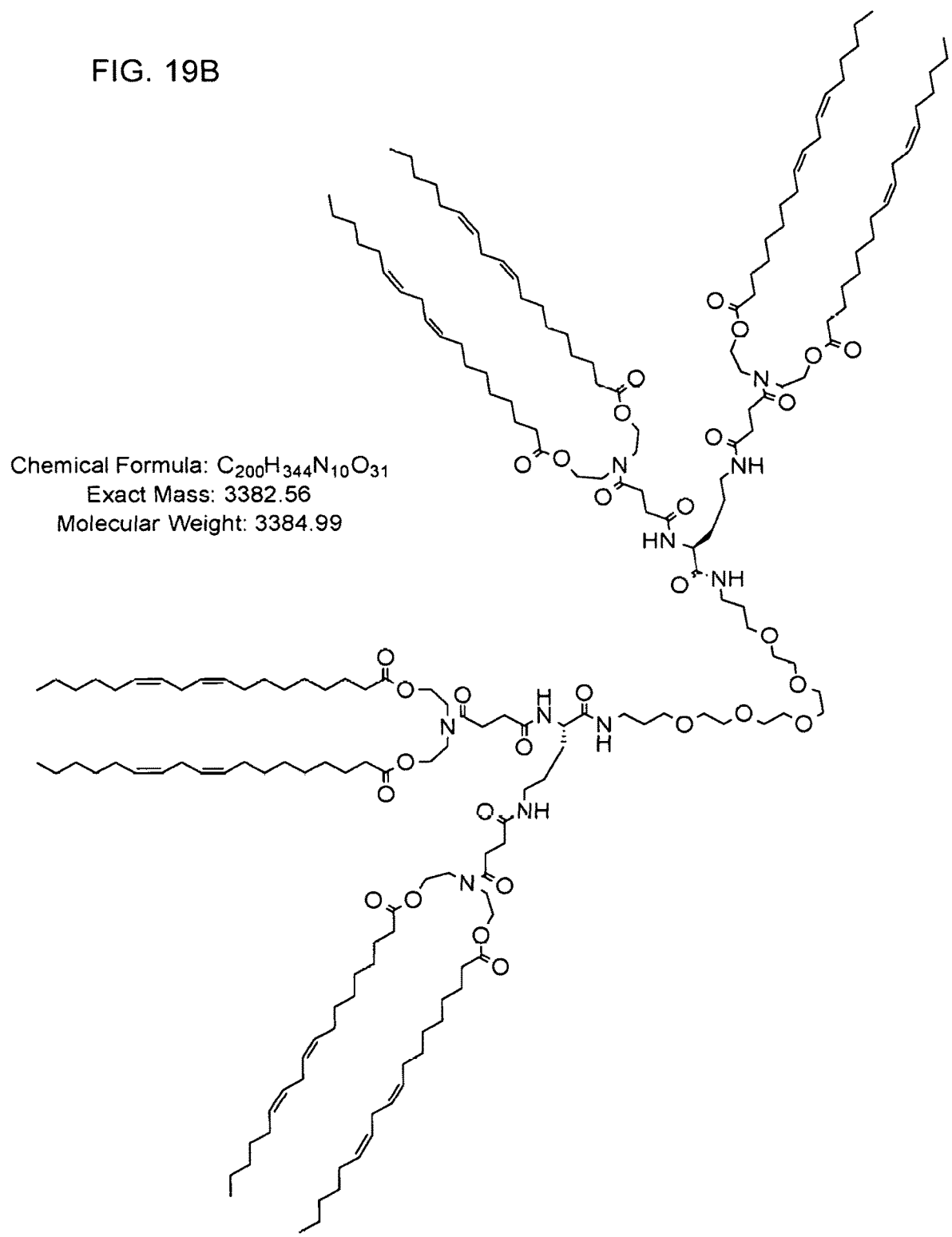
FIG. 19B shows the structure of Compound T6.
Figure 20A:
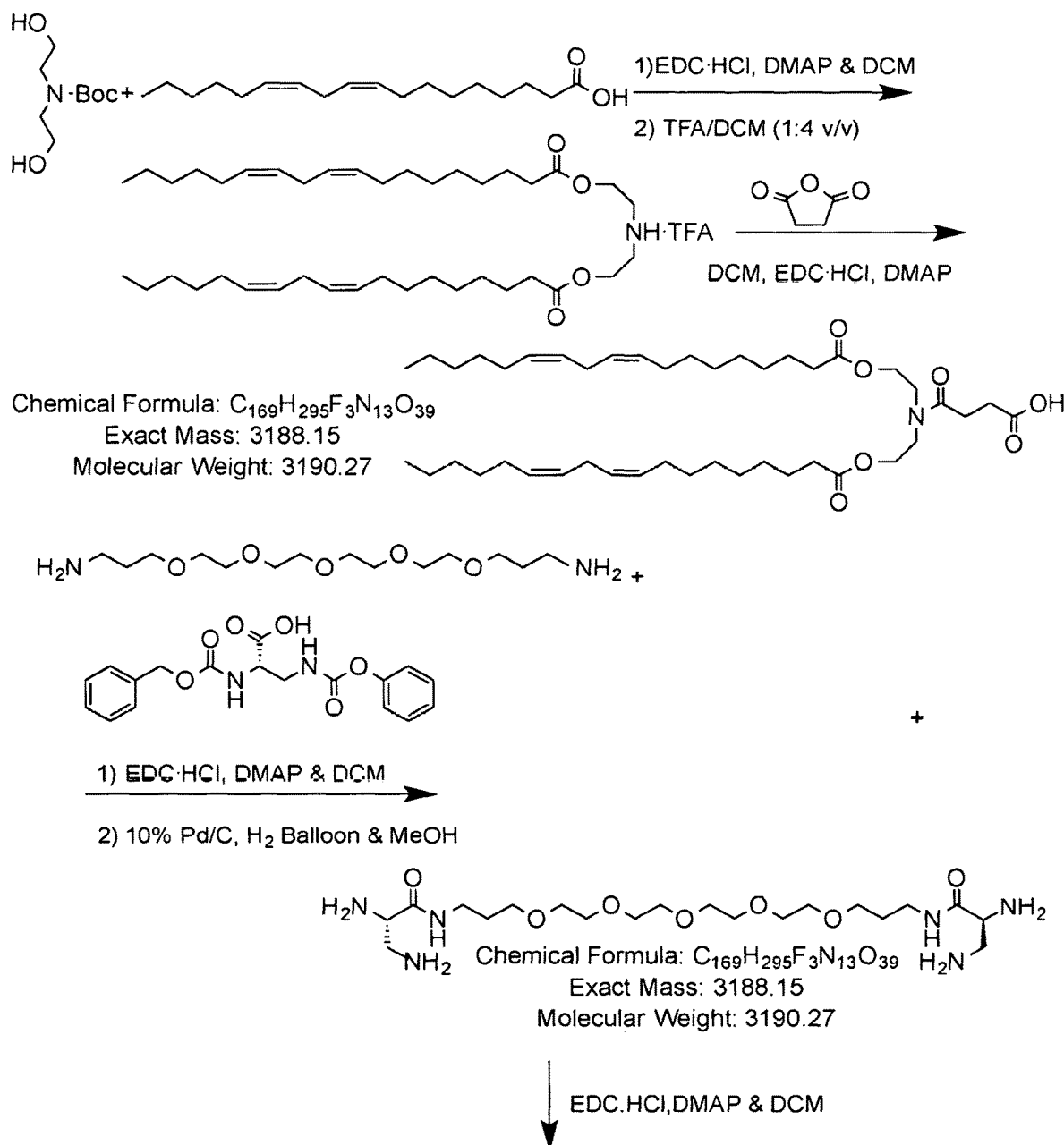
FIG. 20A shows a scheme for the preparation of Compound T7.
Figure 20B:
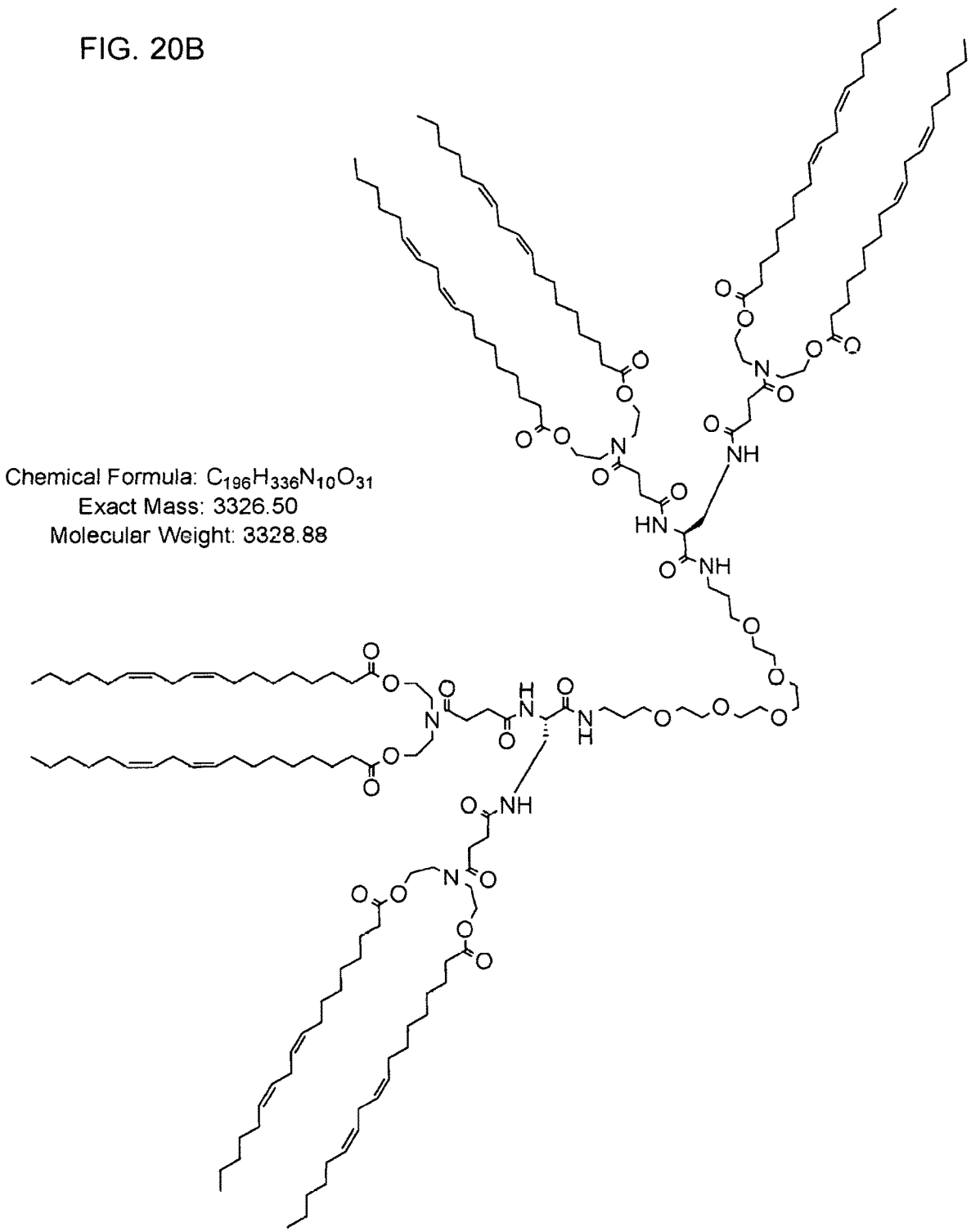
FIG. 20B shows the structure of Compound T7.
Figure 21A:
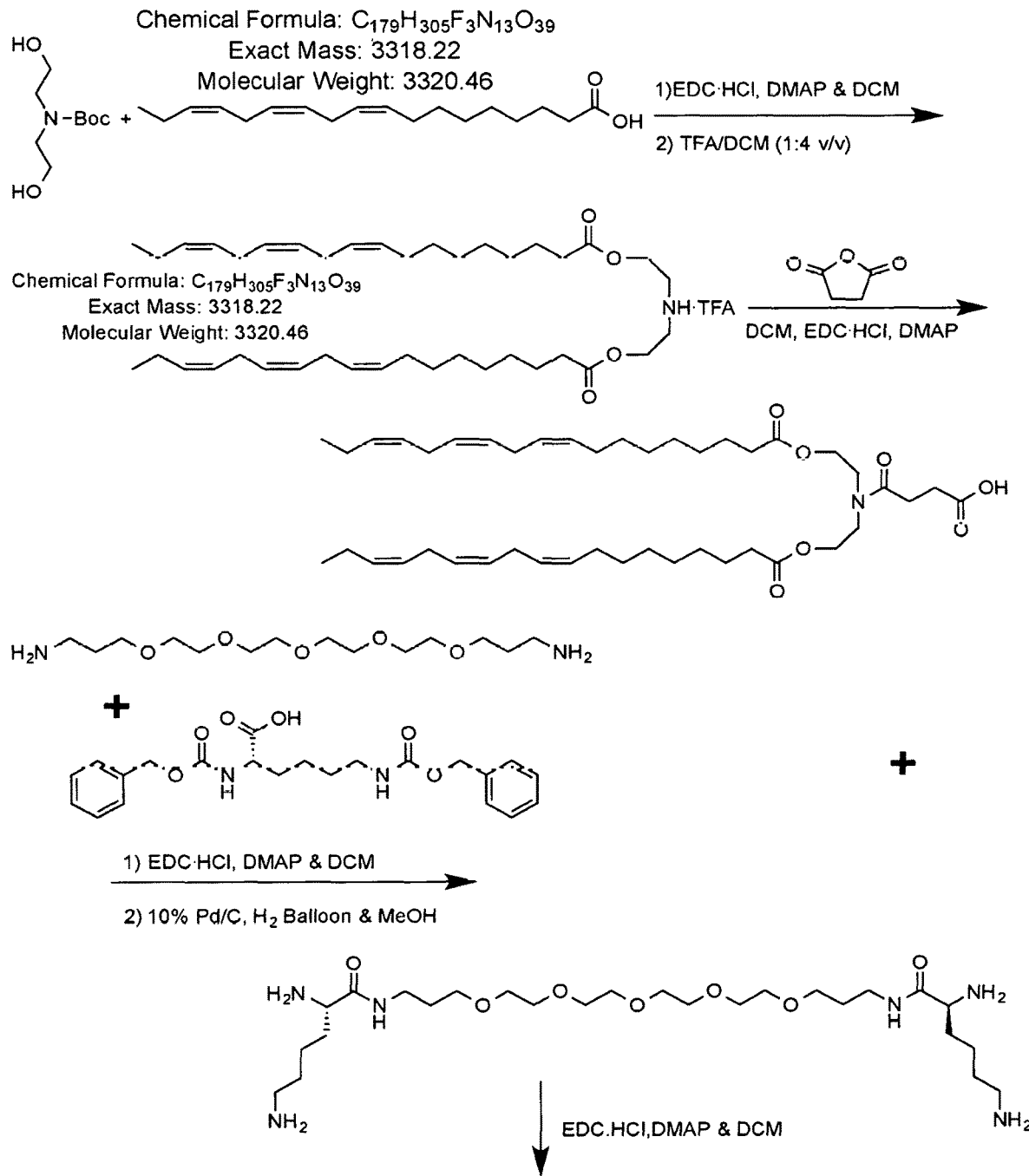
FIG. 21A shows a scheme for the preparation of Compound T8.
Figure 21B:
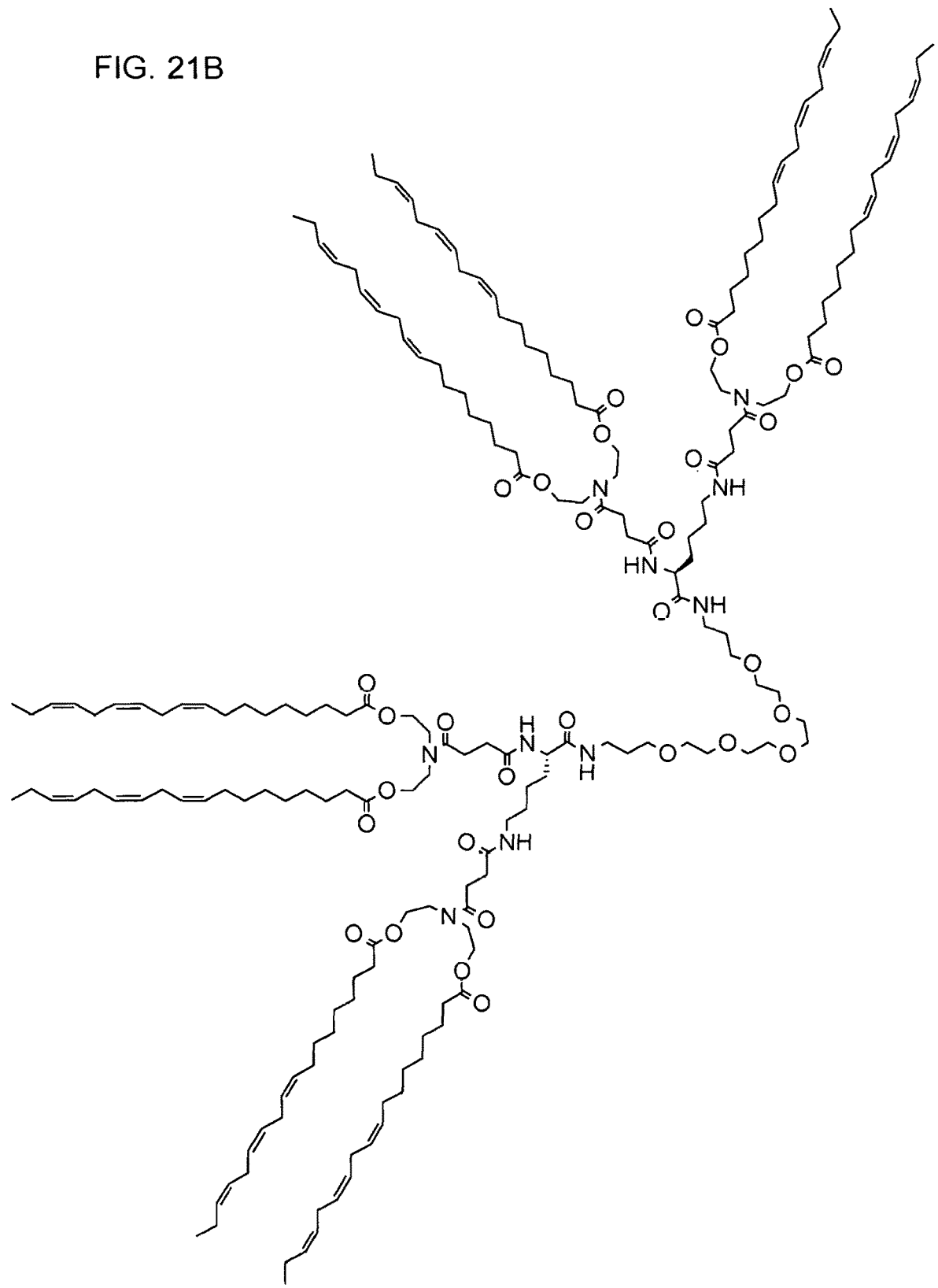
FIG. 21B shows the structure of Compound T8.
Figure 22A:
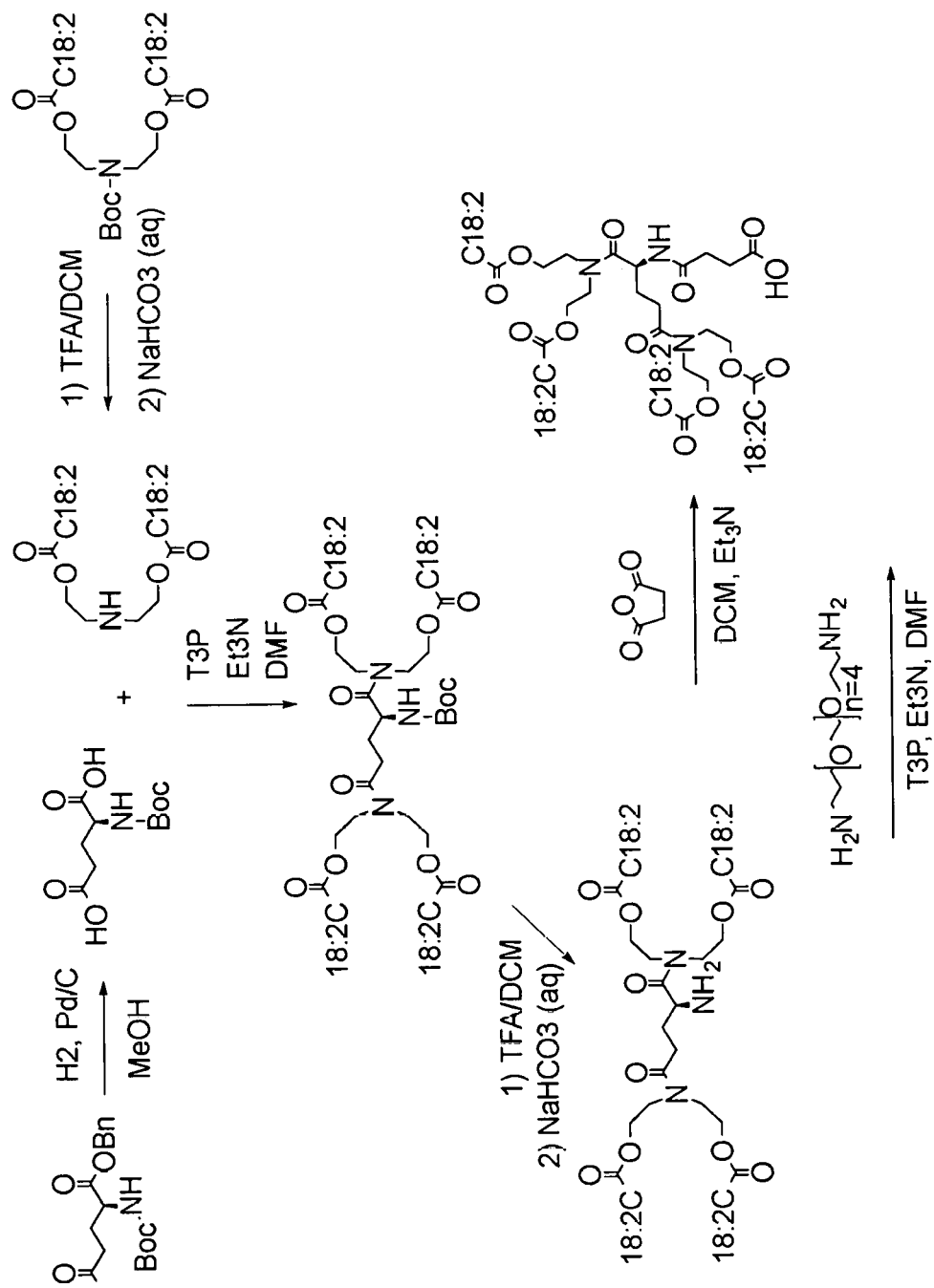
FIG. 22A shows a scheme for the preparation of Compound T9.
Figure 22B:
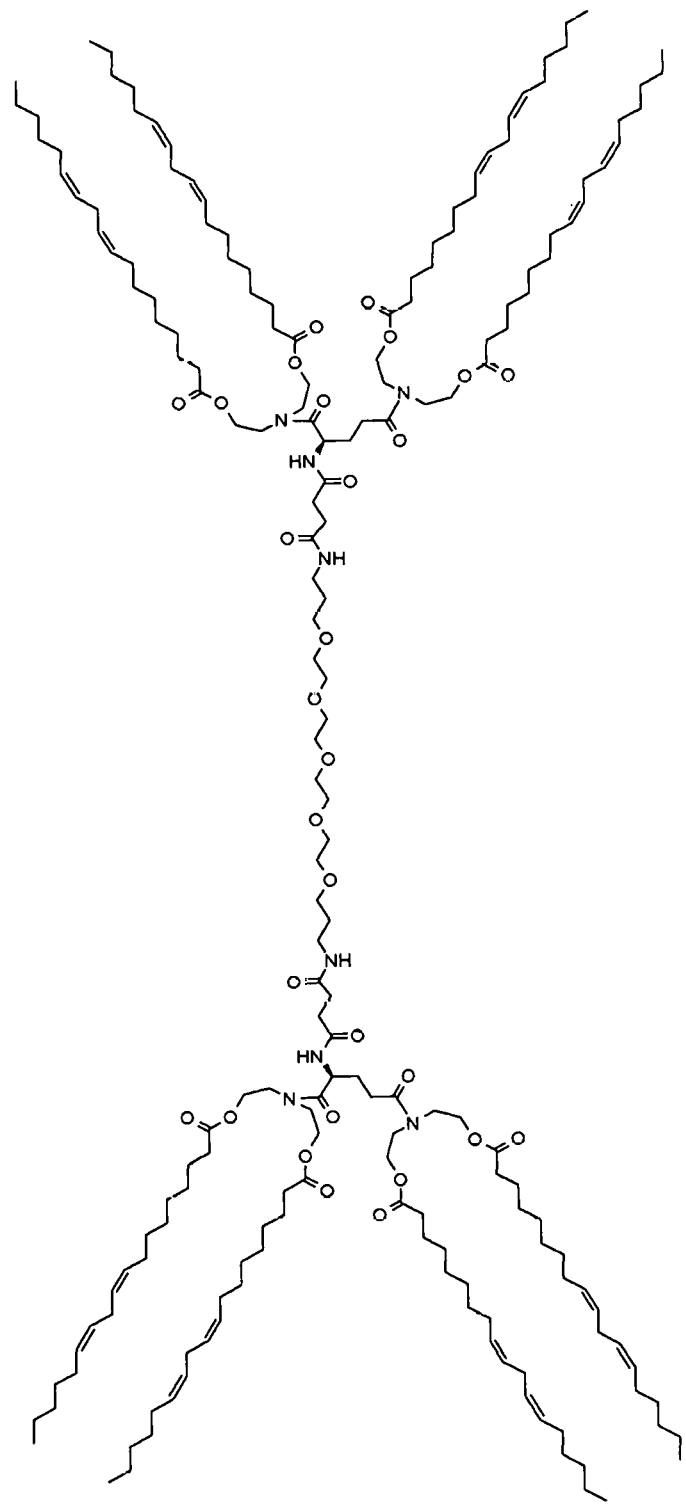
FIG. 22B shows the structure of Compound T9.
Figure 23A:
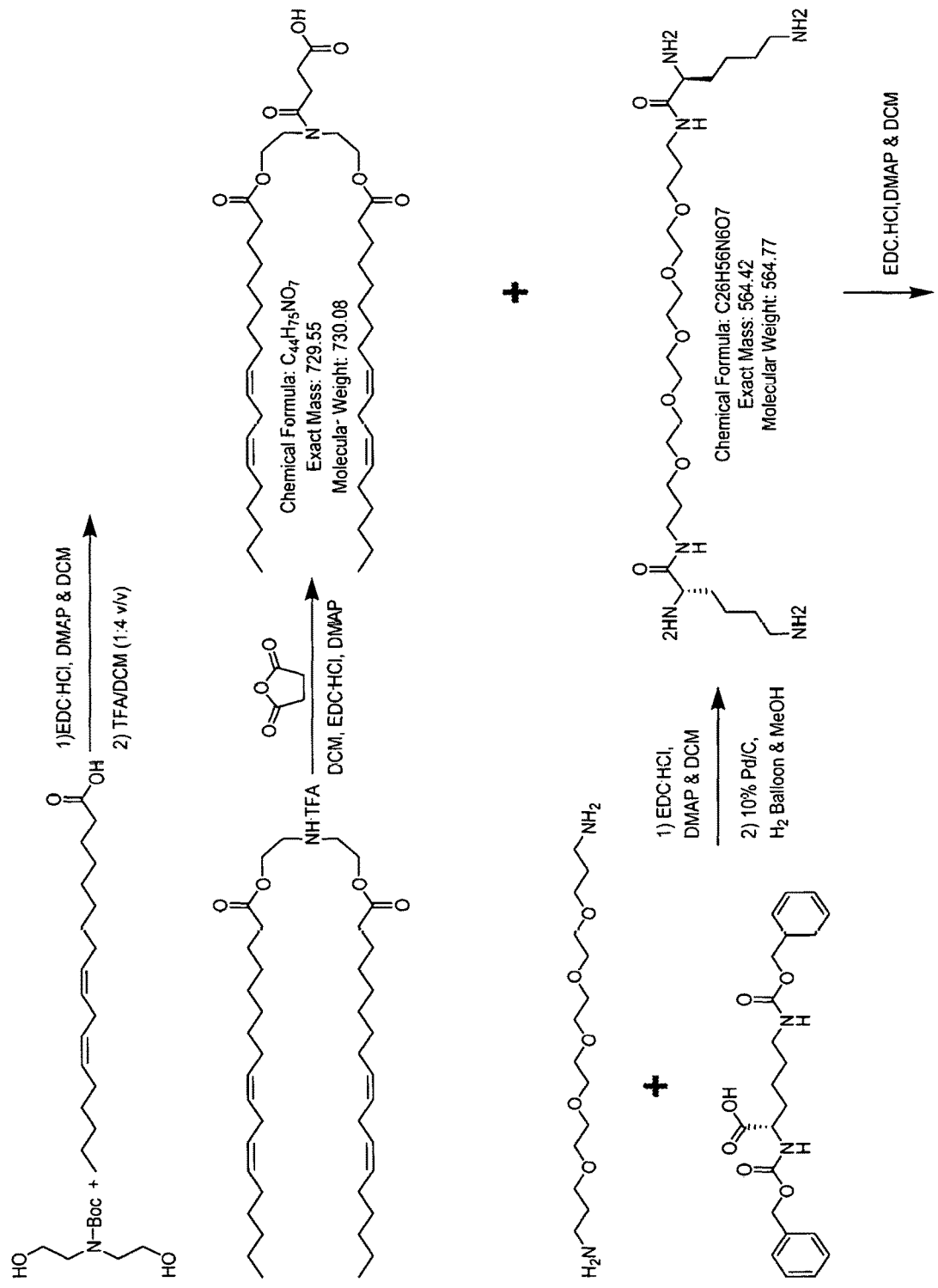
FIG. 23A shows a scheme for the preparation of Compound T3.
Figure 23B:
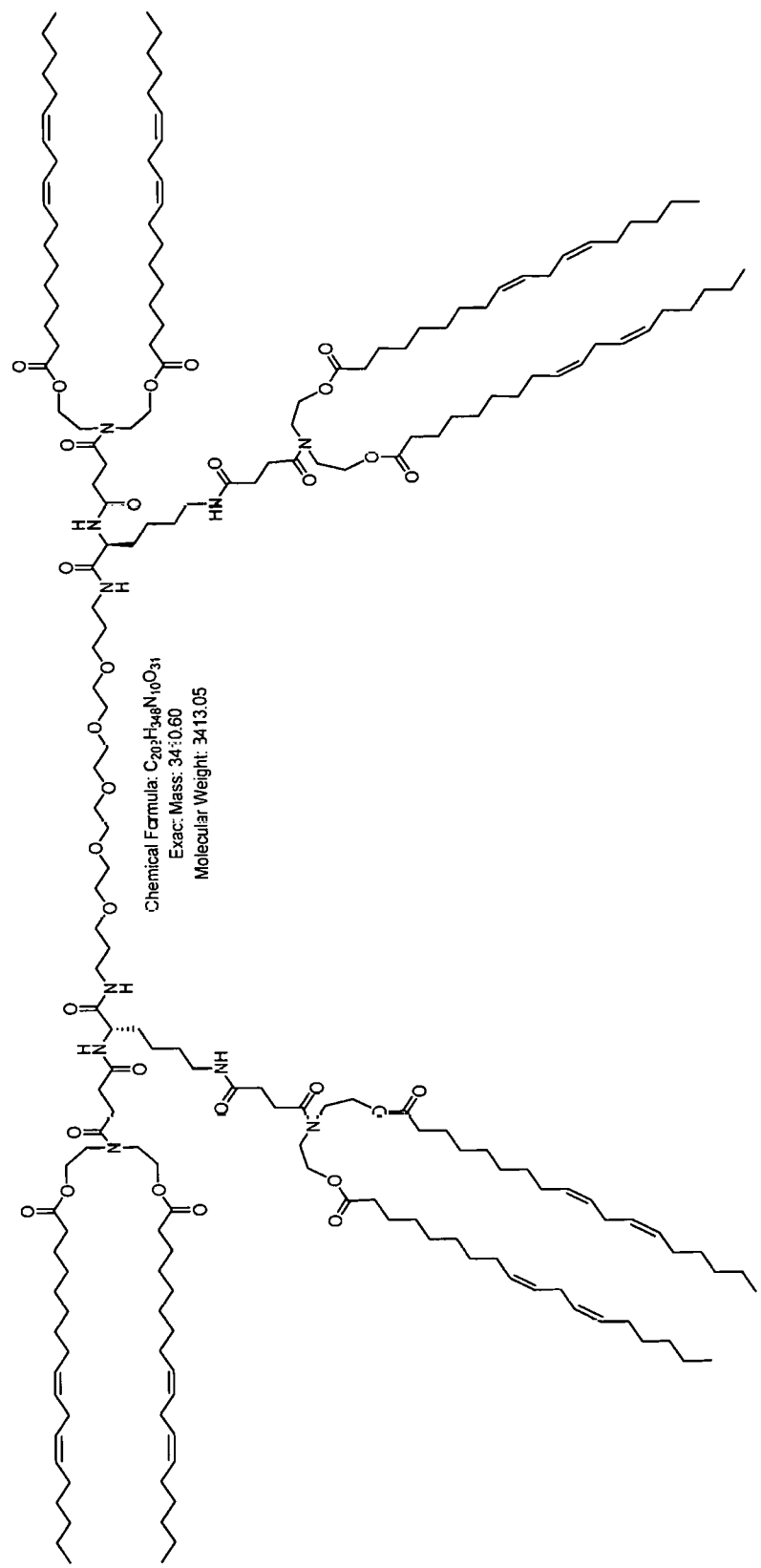
FIG. 23B shows the structure of Compound T3.
Figure 27:
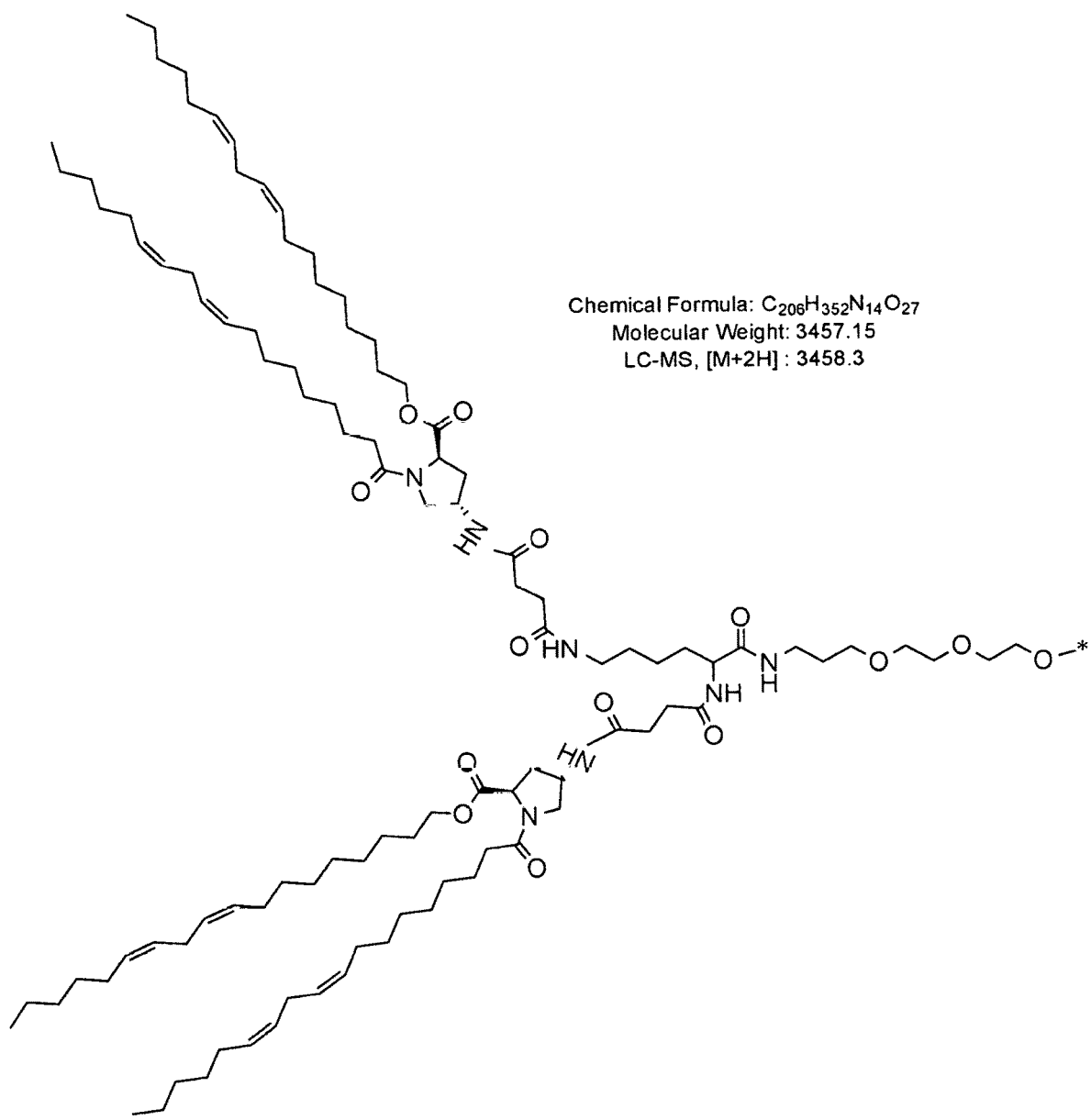
FIG. 27 shows the left half of the structure of Compound T10.
Figure 28:
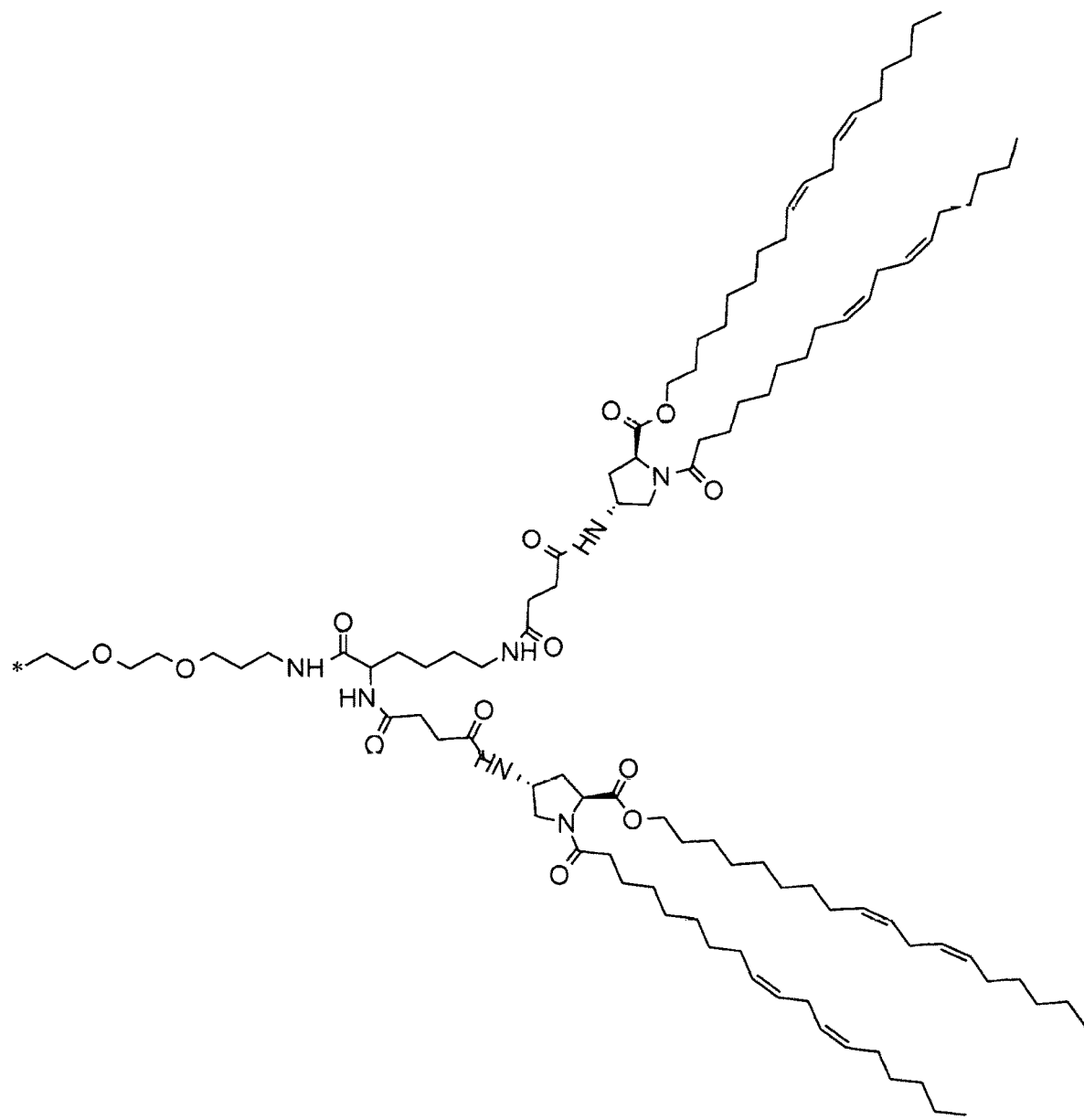
FIG. 28 shows the right half of the structure of Compound T10.
Figure 29:
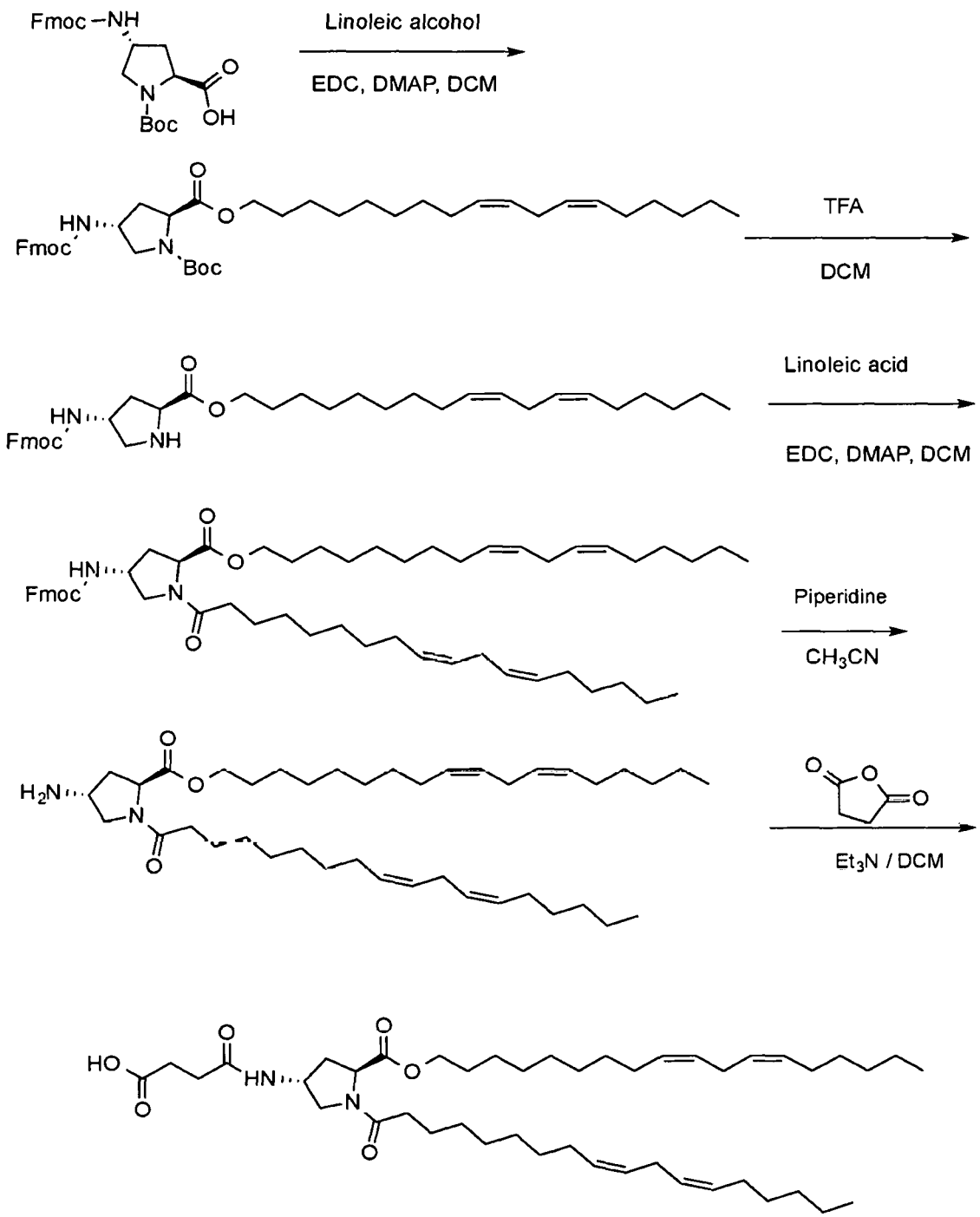
FIG. 29 shows a scheme for the preparation of Compound T10.
Figure 30:
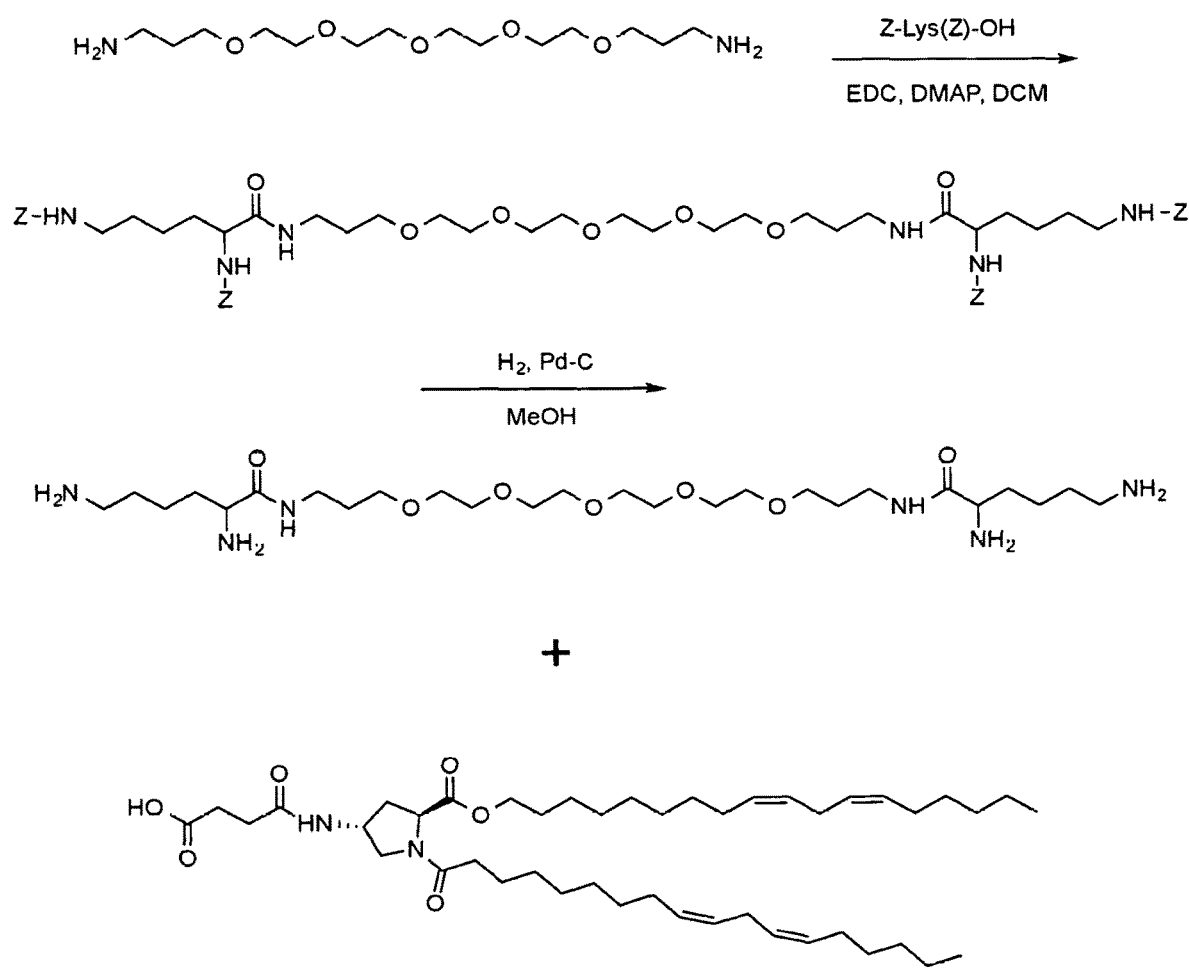
FIG. 30 shows a scheme for the preparation of Compound T10.
Figure 31:
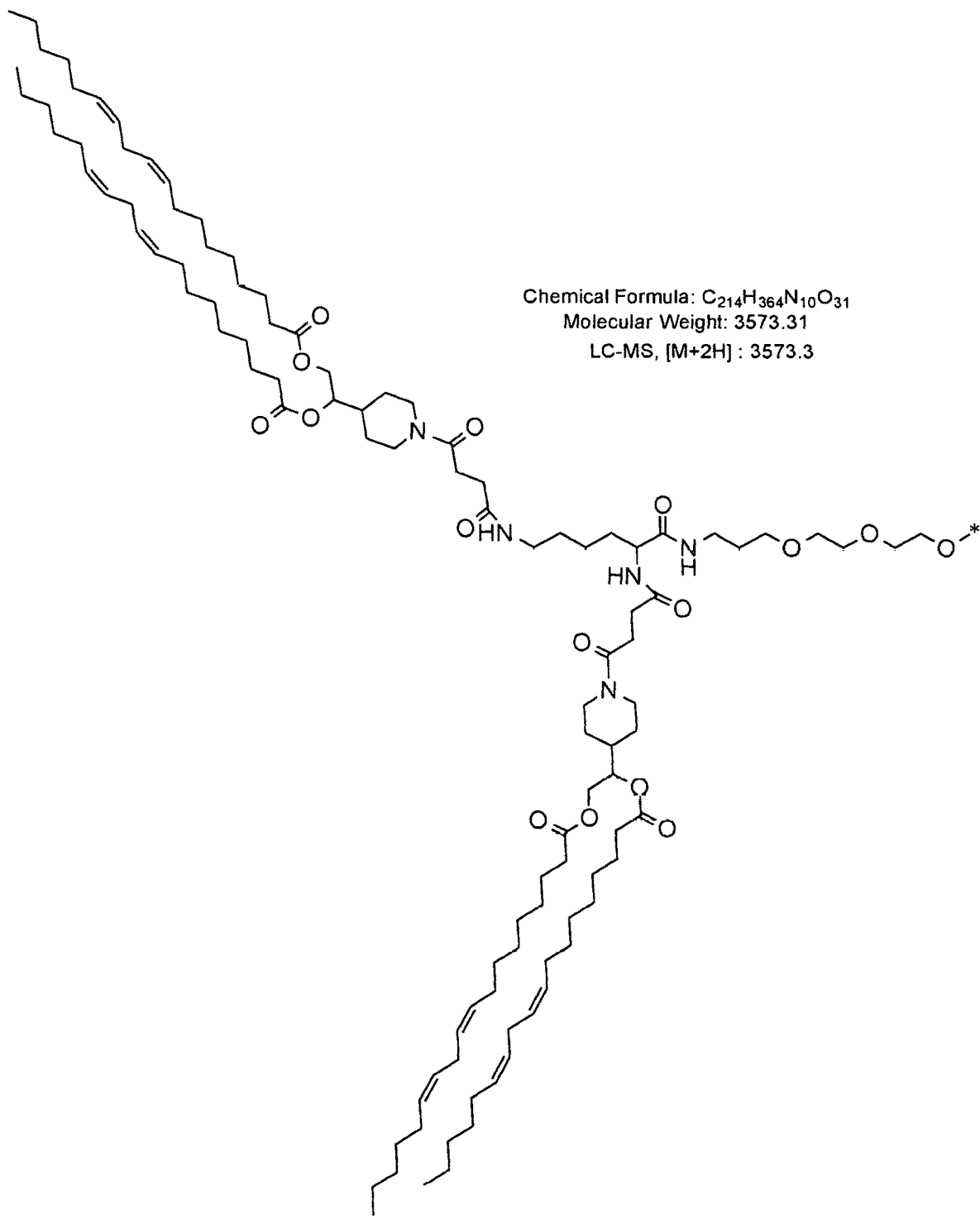
FIG. 31 shows the left half of the structure of Compound T11.
Figure 32:
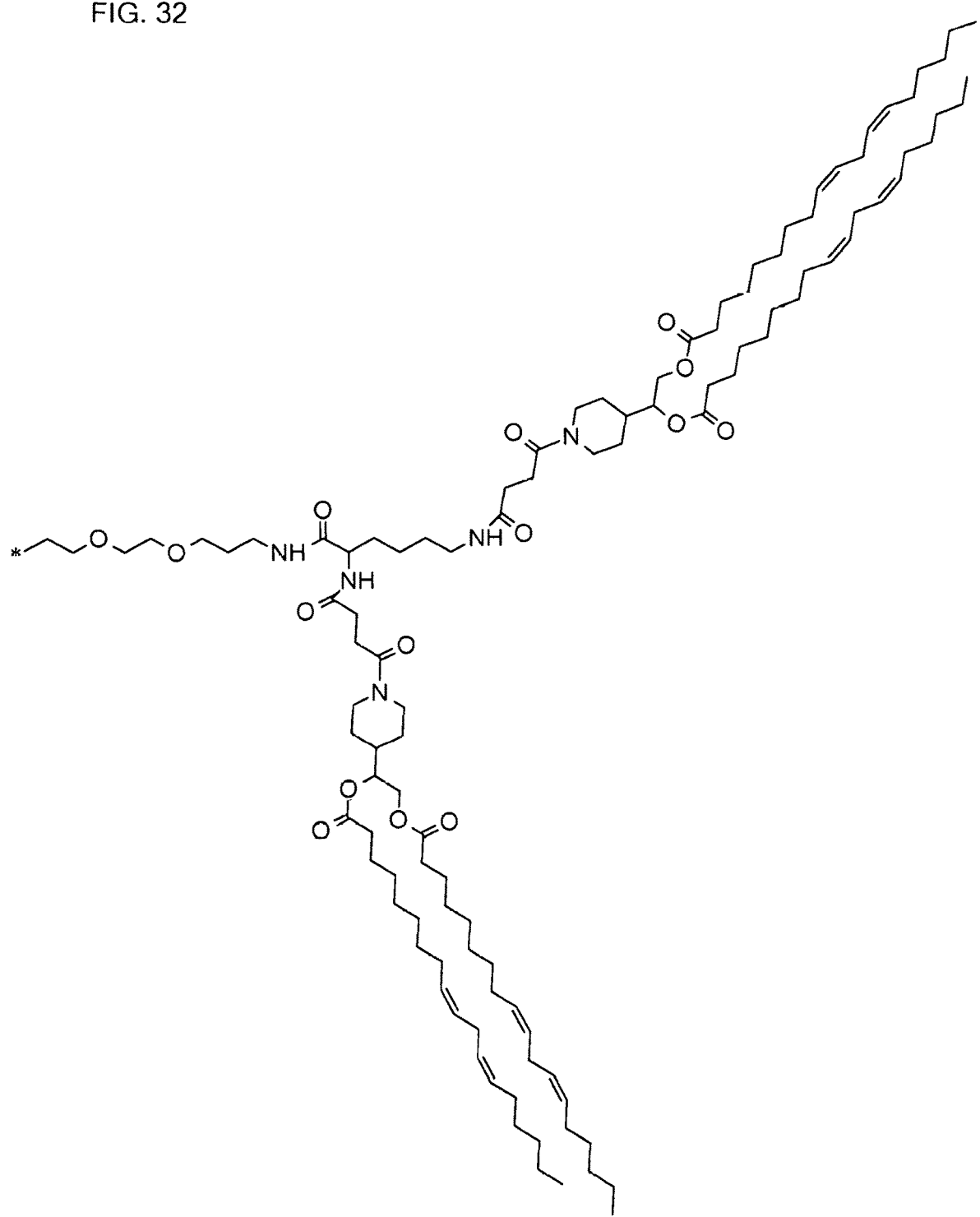
FIG. 32 shows the right half of the structure of Compound T11.
Figure 33:
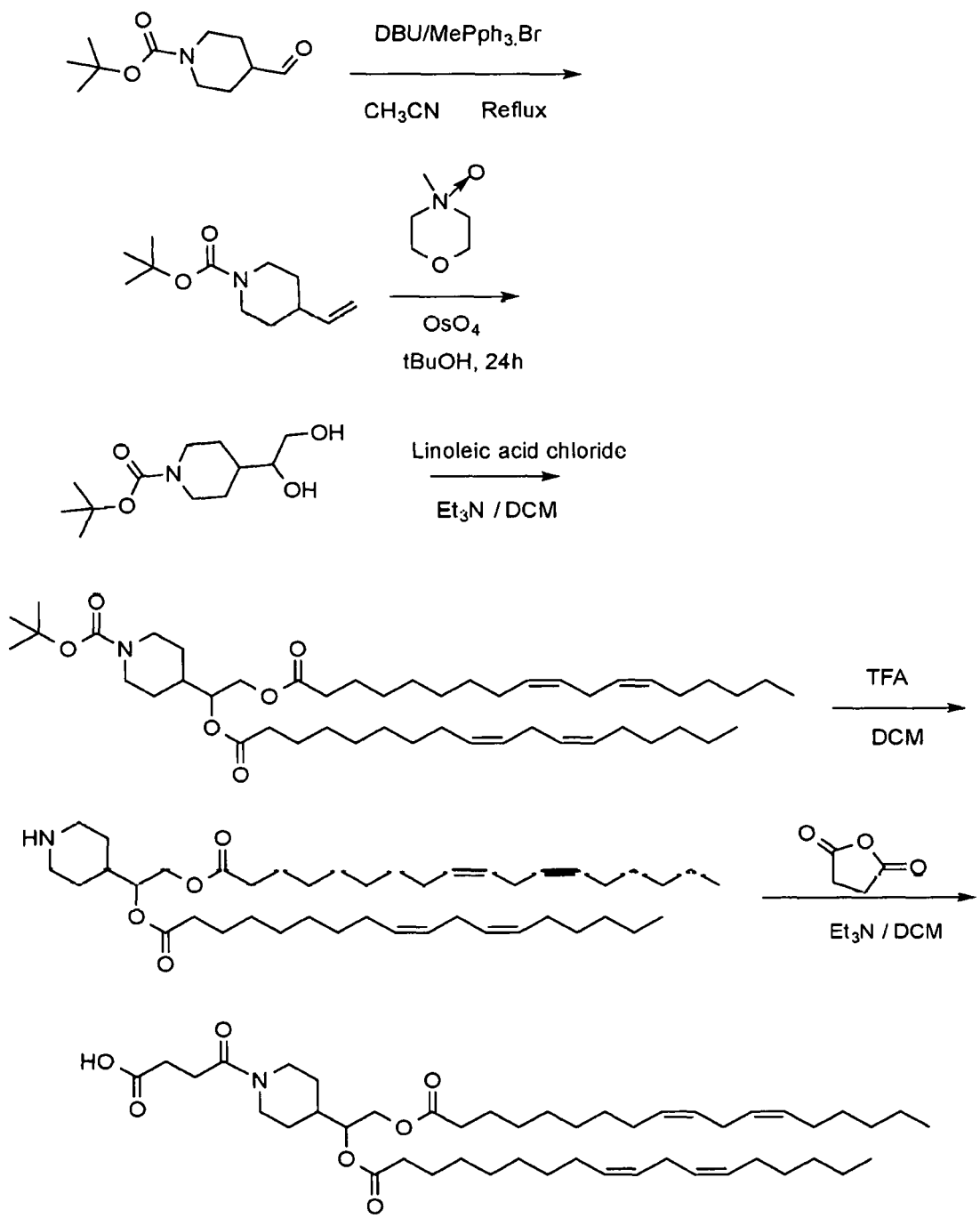
FIG. 33 shows a scheme for the preparation of Compound T11.
Figure 34:
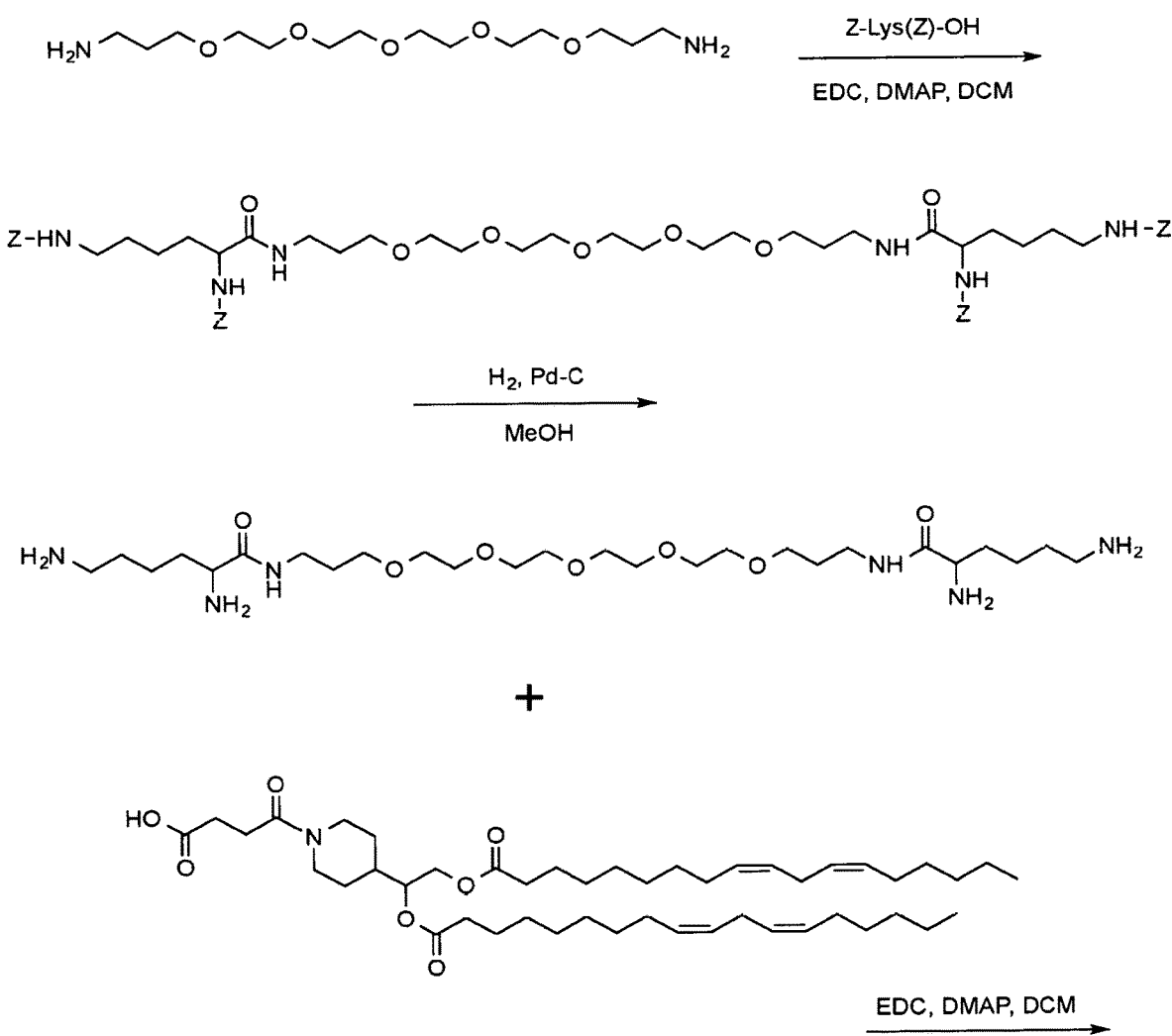
FIG. 34 shows a scheme for the preparation of Compound T11.
Figure 35:
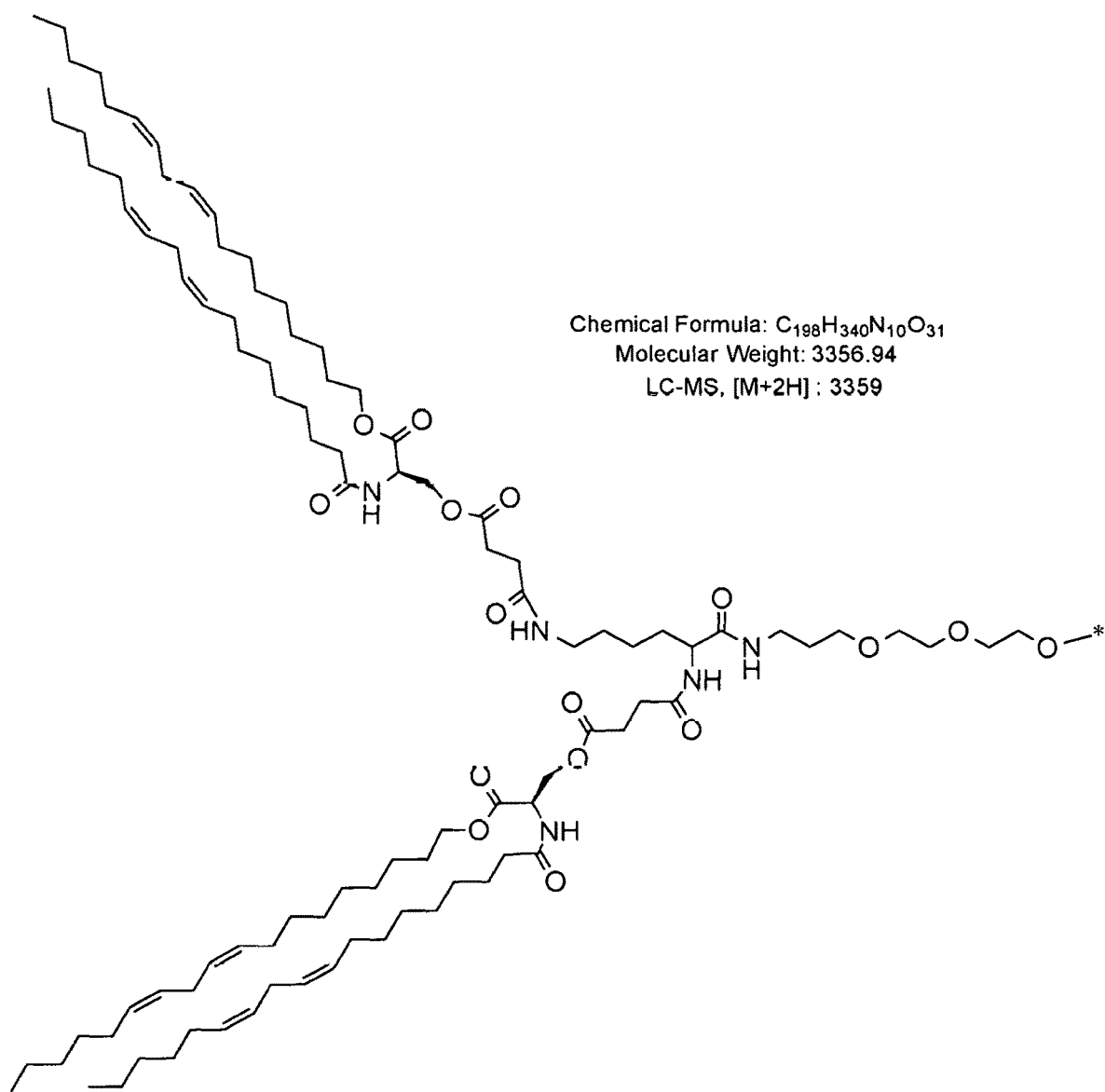
FIG. 35 shows the left half of the structure of Compound T12.
Figure 36:
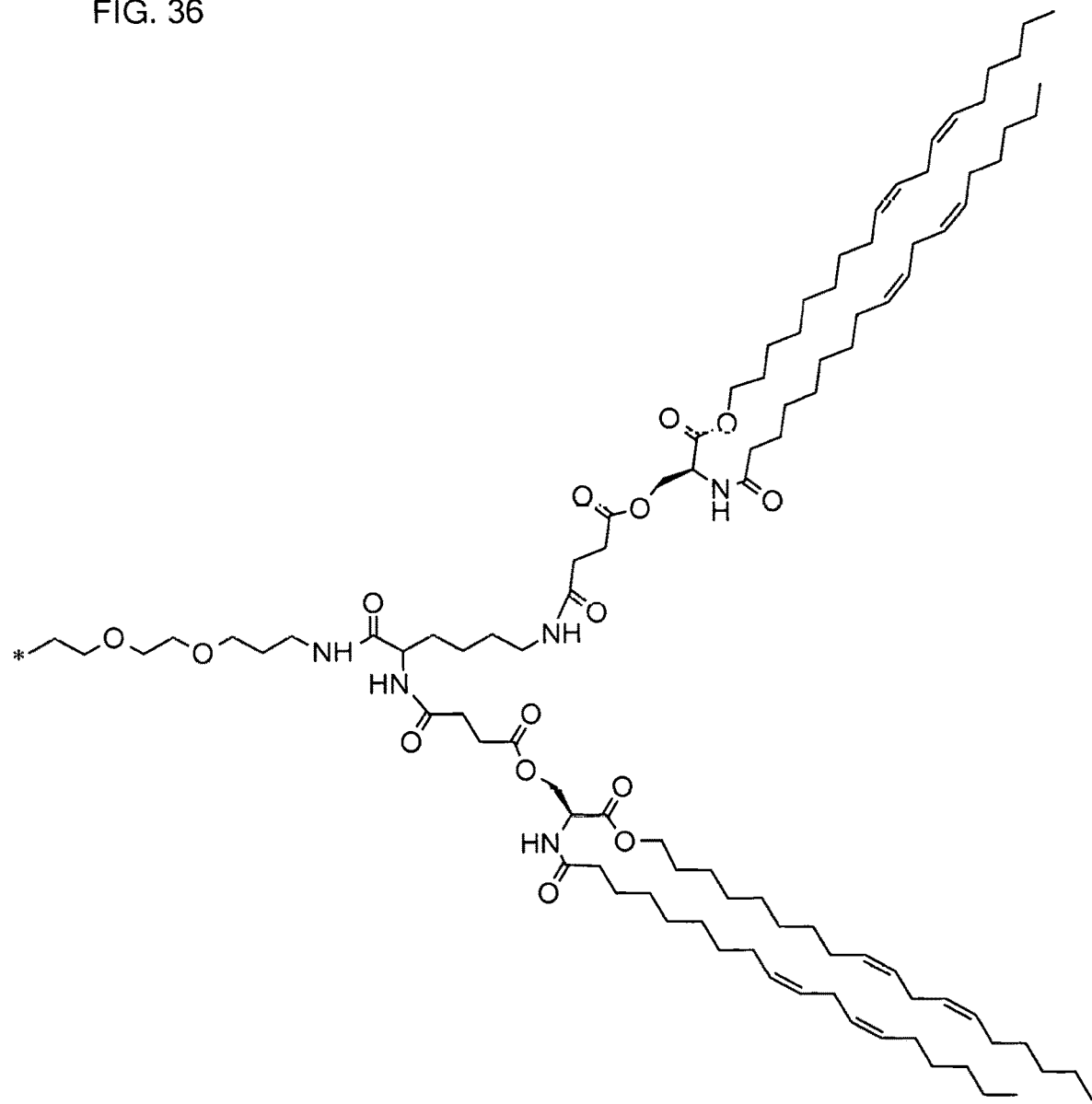
FIG. 36 shows the right half of the structure of Compound T12.
Figure 37:
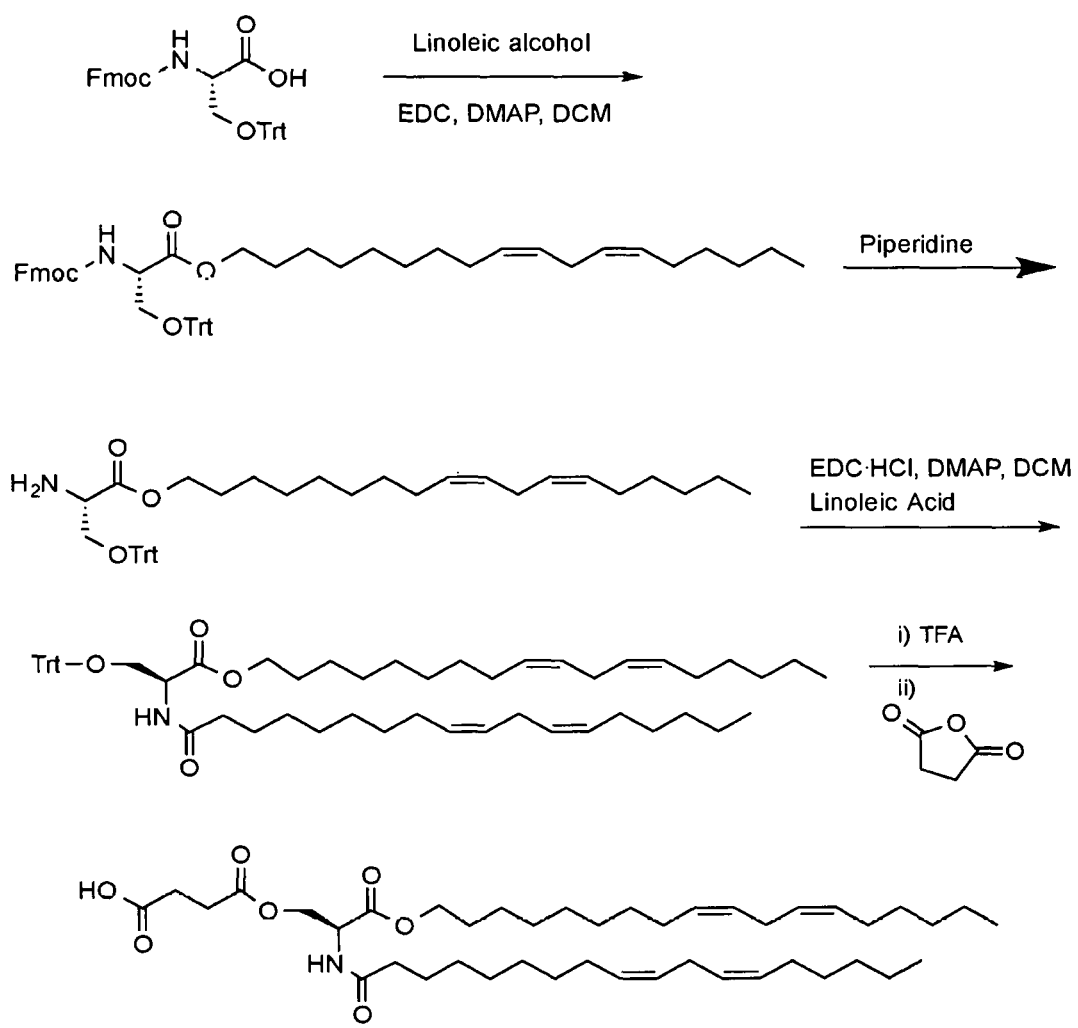
FIG. 37 shows a scheme for the preparation of Compound T12.
Figure 38:
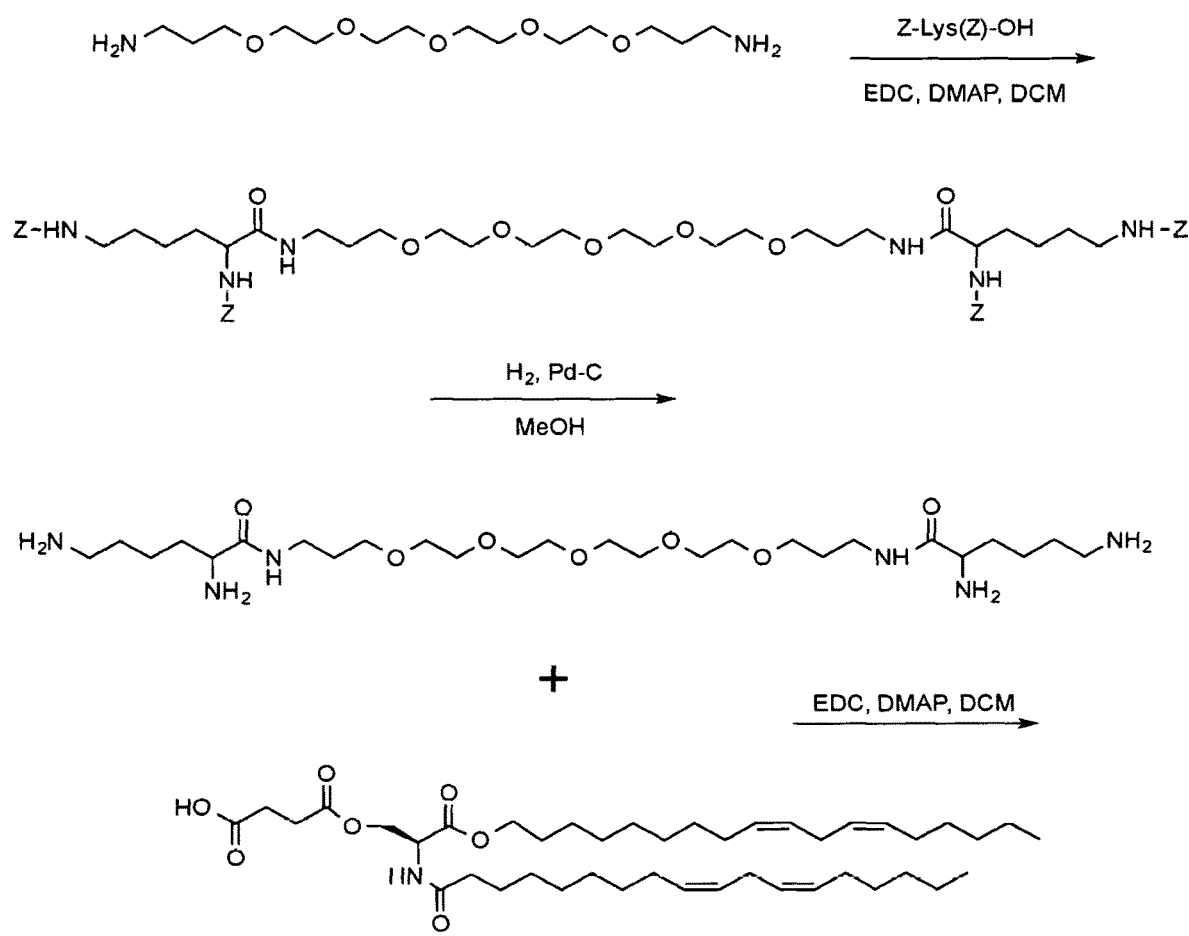
FIG. 38 shows a scheme for the preparation of Compound T12.
Figure 39:
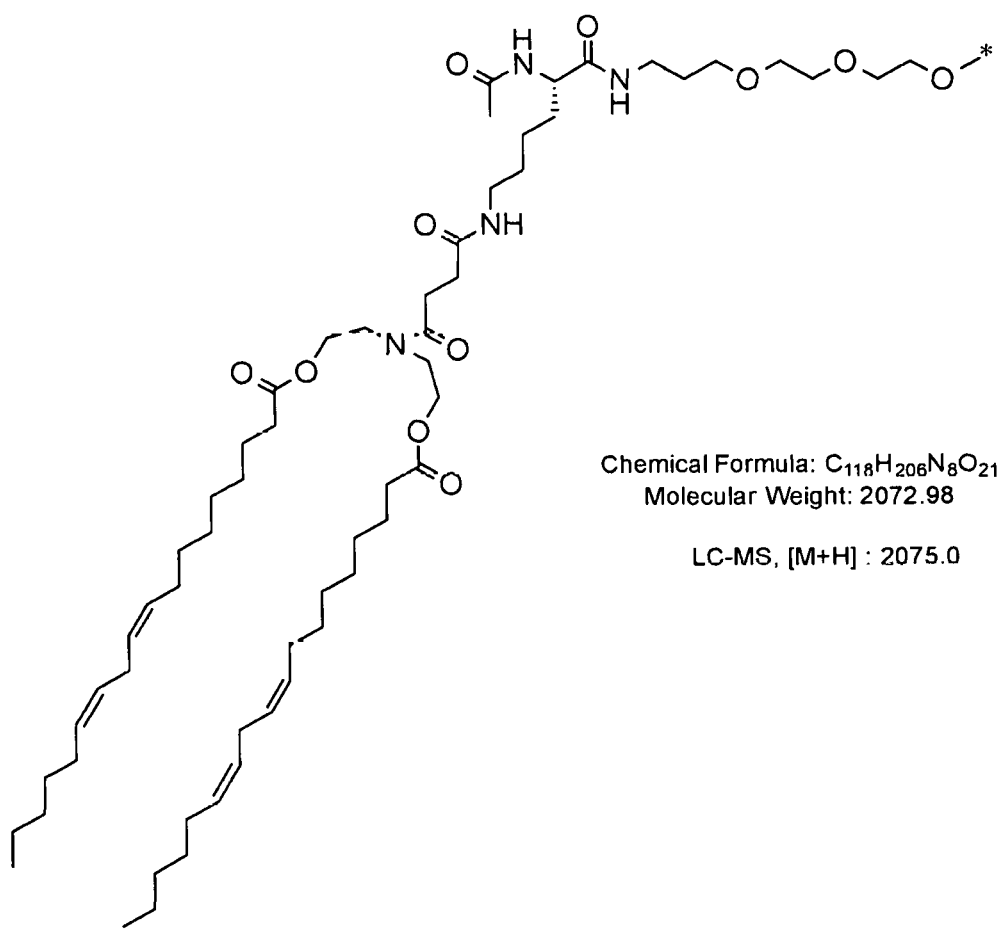
FIG. 39 shows the left half of the structure of Compound T13.
Figure 40:
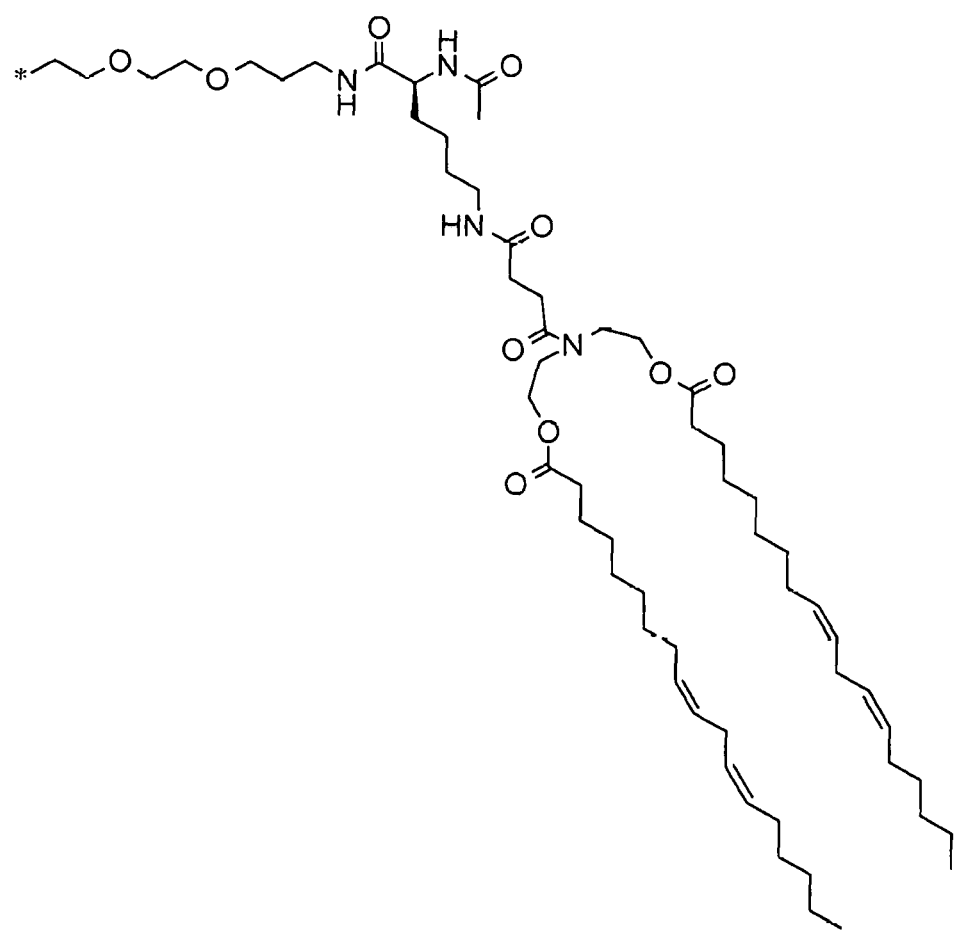
FIG. 40 shows the right half of the structure of Compound T13.
Figure 41:
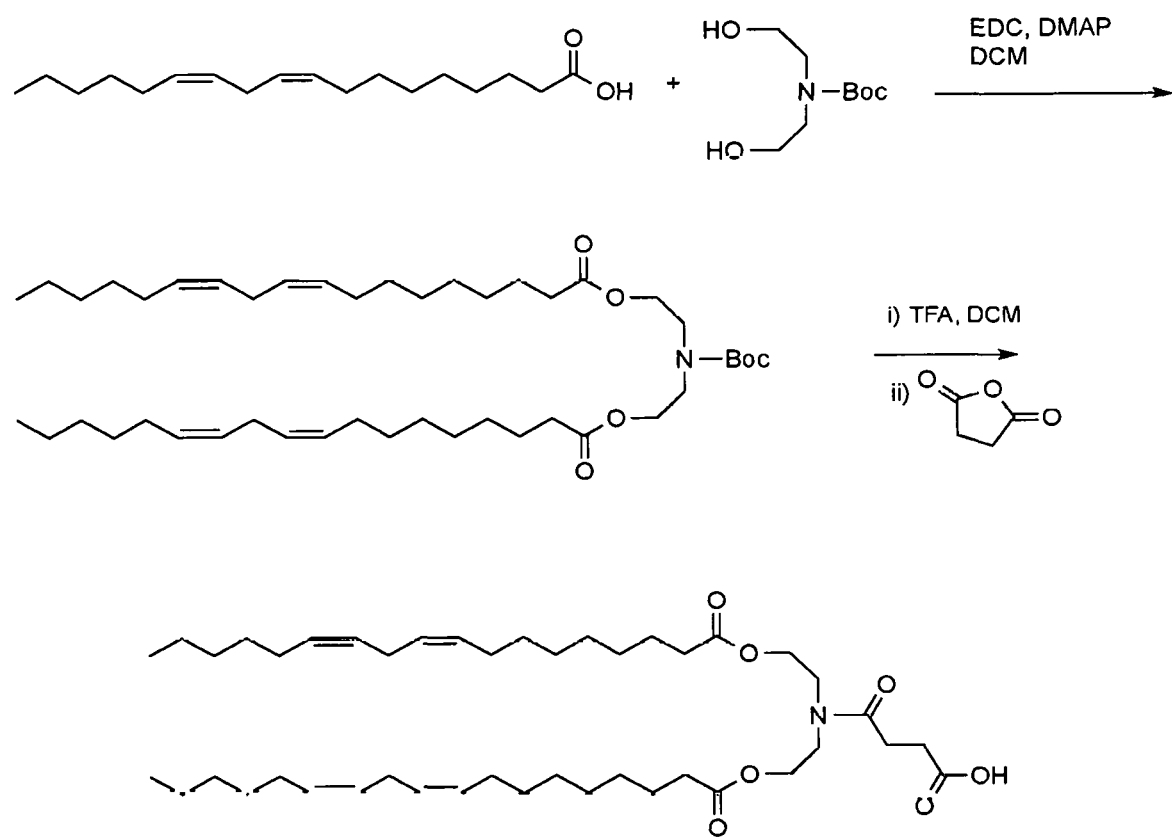
FIG. 41 shows a scheme for the preparation of Compound T13.
Figure 42:
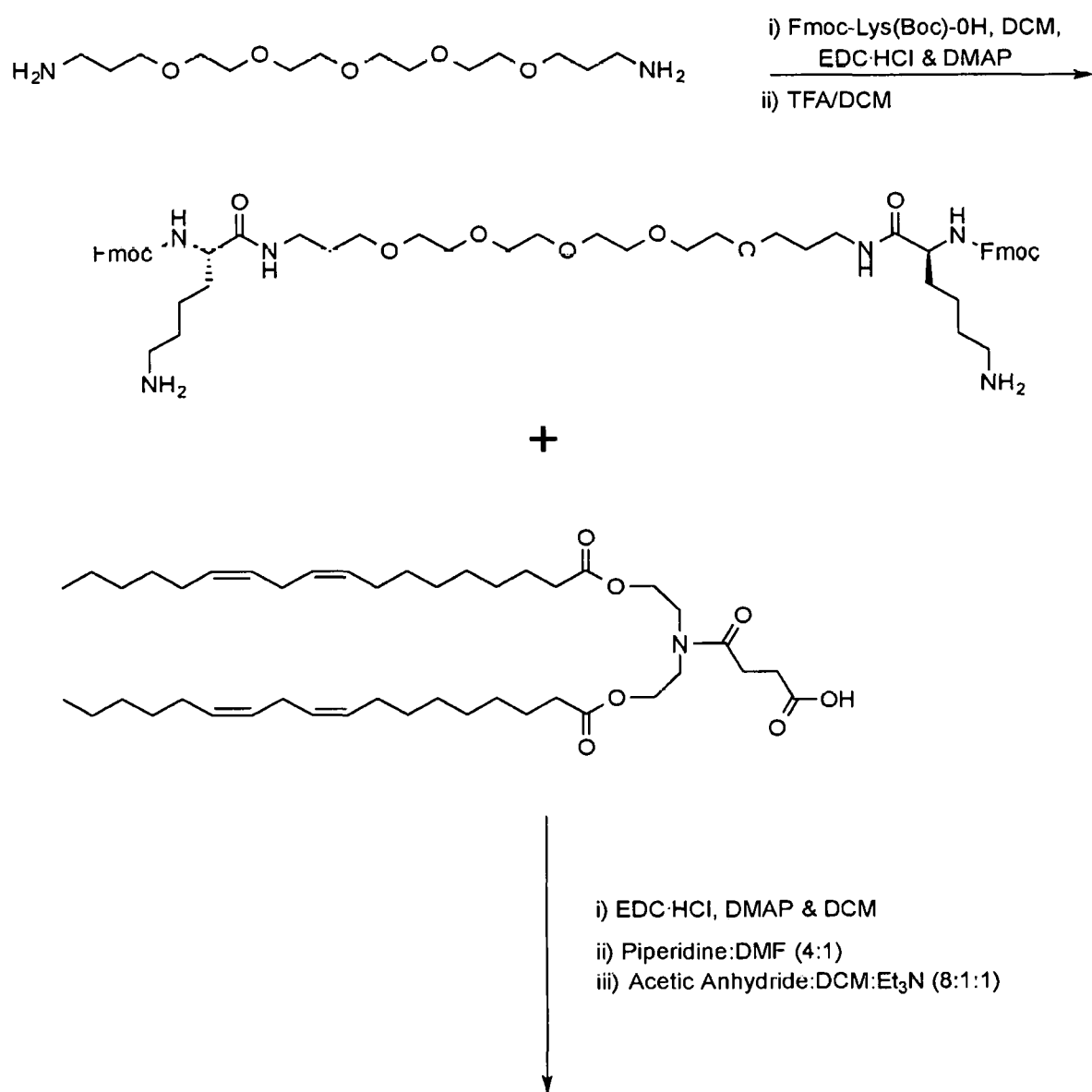
FIG. 42 shows a scheme for the preparation of Compound T13.
Figure 43:
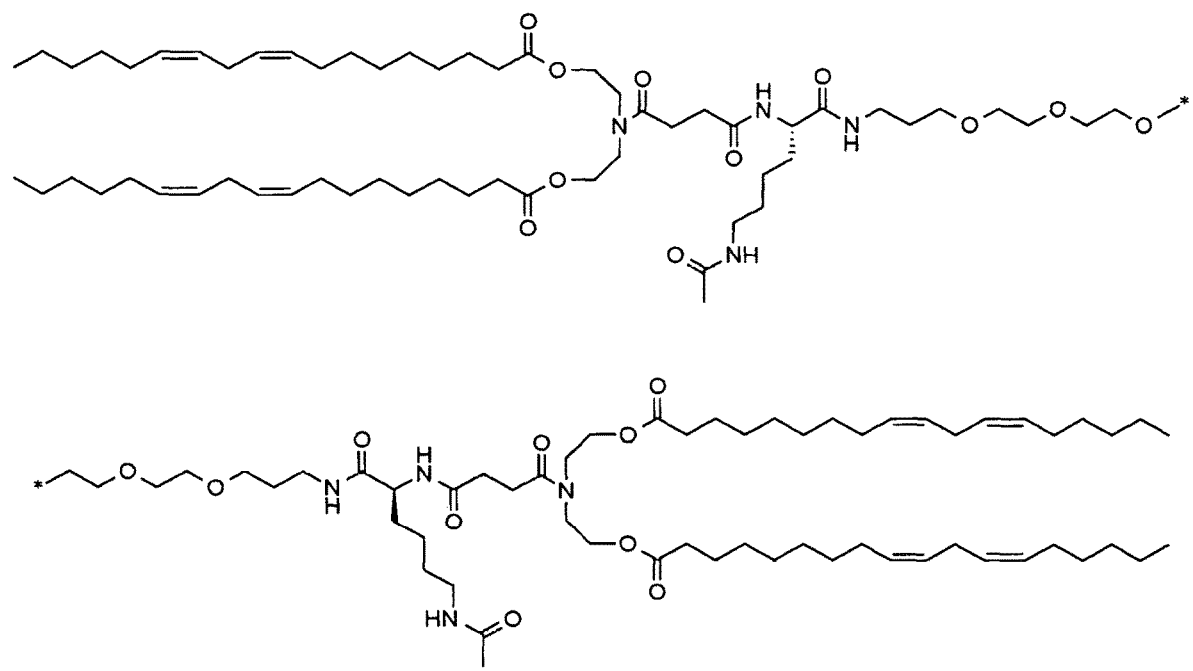
FIG. 43 shows the right and left halves of the structure of Compound T14.
Figure 44:
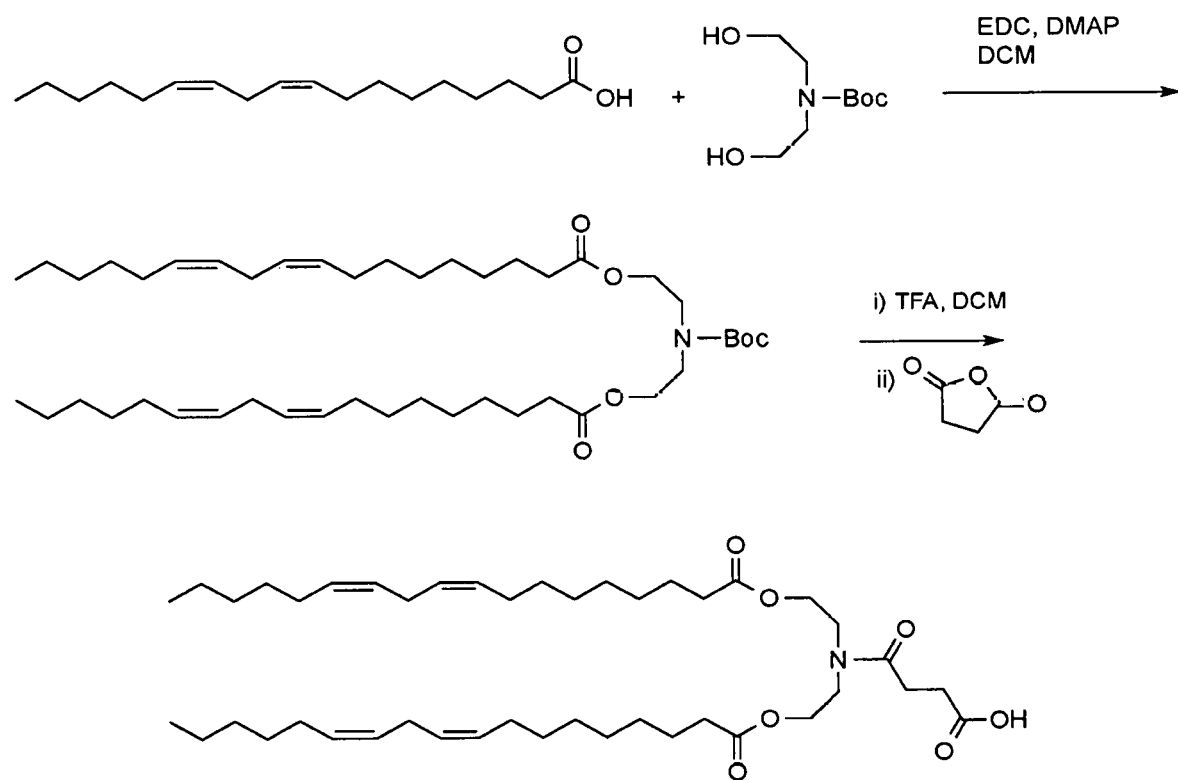
FIG. 44 shows a scheme for the preparation of Compound T14.
Figure 45:
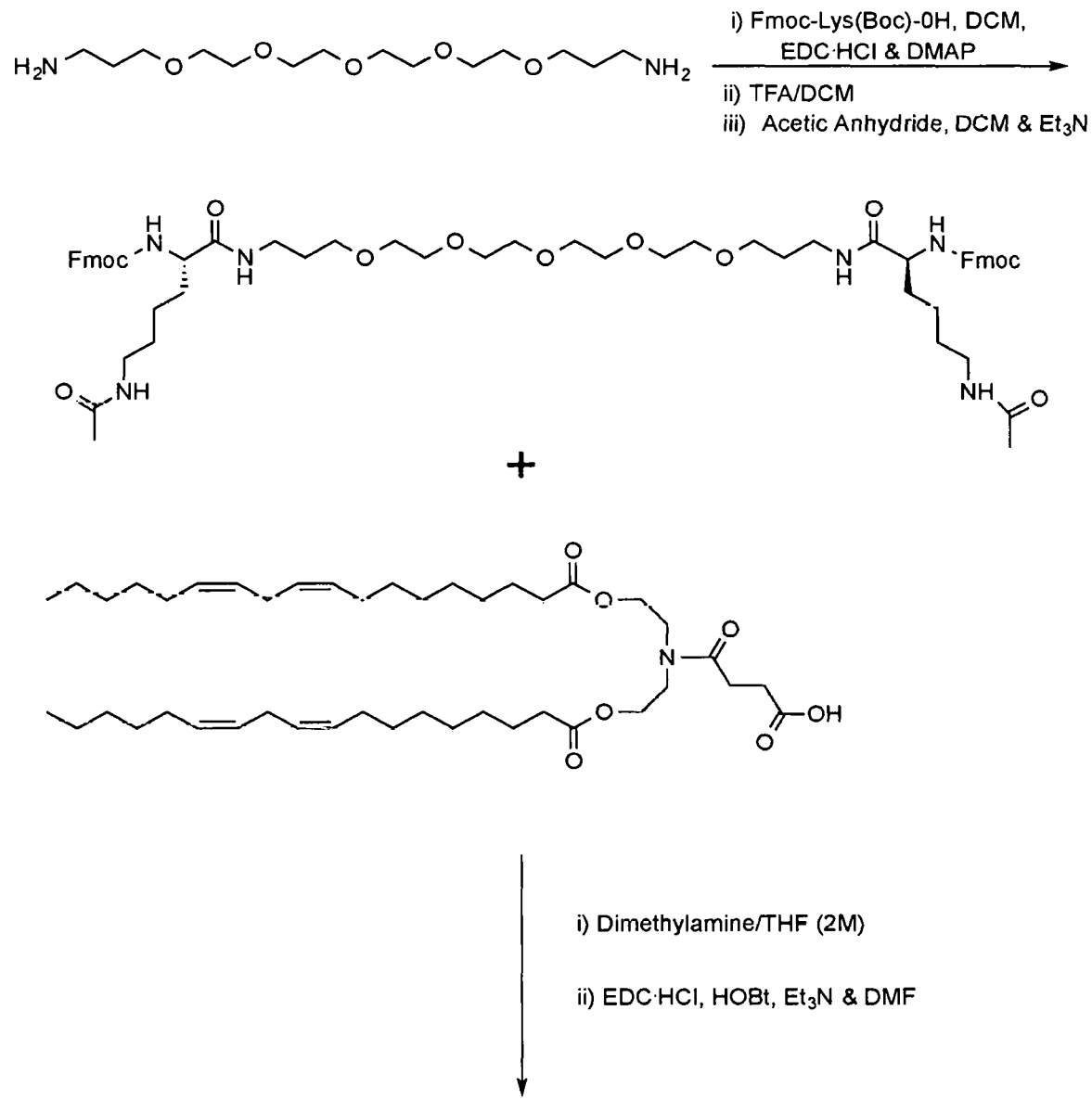
FIG. 45 shows a scheme for the preparation of Compound T14.

Examples of a fusogenic compound of this invention include, but are not limited to, a compound R4 shown in FIG. 4B; a compound S6 shown in FIG. 12B; a compound S7 shown in FIG. 13B; a compound S8 shown in FIG. 14B; a compound T1 shown in FIG. 15B; a compound T2 shown in FIG. 16B; a compound T4 shown in FIG. 17B; a compound T5 shown in FIG. 18B; a compound T6 shown in FIG. 19B; a compound T7 shown in FIG. 20B; a compound T8 shown in FIG. 21B; a compound T9 shown in FIG. 22B; a compound T3 shown in FIG. 23B; a compound T10 shown in FIGS. 27 and 28; a compound T11 shown in FIGS. 31 and 32; a compound T12 shown in FIGS. 35 and 36; a compound T13 shown in FIGS. 39 and 40; a compound T14 shown in FIG. 43.

Compounds shown in FIGS. 1, 2, 3A, 3B, and 6-11 are shown for purposes of illustrating methods of synthesis of compounds.

In some aspects, this invention provides a range fusogenic molecules, which can be used in formulations for forming and utilizing lipid nanoparticles for delivering active agents to cells and subjects.

A fusogenic compound of this invention can have one or two amphiphiles attached to an amino acid group, which amino acid group is attached by a linker to a separate amino acid group carrying one or two additional amphiphiles.

The lipophilic chains of an amphiphile can each independently contain 8 to 22 carbon atoms.

An amphiphile group can be a lipid-like group, having one or two lipophilic chains attached to an organic chemical group. The organic chemical group may have up to 400 atoms, or 20-400 atoms, or 10-400 atoms, or 4-400 atoms, or 3-400 atoms, or 2-400 atoms, or 1-400 atoms selected from carbon, oxygen, nitrogen, sulfur, fluorine, and hydrogen, and may have any structure suitable for attaching the one or two lipophilic chains, and attaching to the amino acid group. The organic chemical group may be neutral, or zwitterionic, or can provide a hydrophilic nature. In certain embodiments, the organic chemical group may be ionizable. Examples of an organic chemical group include, alkyl, alkenyl, alkynyl, and acetyl, as well as protective groups such as Boc, Fmoc, TFA, and CBZ (benzyloxycarbonyl).

Without wishing to be bound by any particular theory, an amphiphile may have a lipid-like structure so that the amphiphile may enter a lipid bilayer in an orientation similar to lipid molecules of the bilayer, while remaining attached to the larger fusogenic compound. A fusogenic compound of this invention may disrupt the dynamical structure of the bilayer to enhance fusogenicity to cells.

An amino acid group of a fusogenic compound (designated AA or AA$^a$) may be modified with substituents. An amino acid group of a fusogenic compound may be any D or L amino acid group having the formula —NR$^N$—CR$^1$R$^2$—(C=O)—, where R$^1$ is a substituted or unsubstituted side chain of certain natural amino acids. R$^2$ and R$^N$ may be each independently hydrogen, or an organic group consisting of carbon, oxygen, nitrogen, sulfur, and hydrogen atoms, and having from 1 to 20 carbon atoms, or can be C(1-6)alkyl, cycloalkyl, cycloalkylalkyl, C(2-6)alkenyl, C(2-6)alkynyl, C(1-6)alkanoyl, C(1-6)alkanoyloxy, C(1-6)alkoxy, C(1-6)alkoxy-C(1-6)alkyl, C(1-6)alkoxy-C(1-6)alkoxy.

As used herein, the term "which is attached to AA" is used to designate the point of attachment of a group to AA. For example, the term "-alkyl-(C=O)—, which is attached to AA" refers to attachment to AA through the (C=O)— group, so that -alkyl-(C=O)-AA is formed. Unless otherwise stated, it is intended that the last group which appears next to the phrase "which is attached to AA" is the group attached to AA.

This invention can provide compositions for use in distributing an active agent in cells, tissues or organs, organisms, and subjects, where the composition includes one or more of the fusogenic molecules of this invention.

The fusogenic compounds of this invention can provide compositions and formulations for use in delivering therapeutic agents to cells, tissues and subjects advantageously without significant aggregation of the components of the composition.

A fusogenic compound of this invention can provide a liposomal formulation for use in delivering therapeutic agents to cells, tissues and subjects advantageously without significant aggregation of the liposomes of the composition.

Compositions of this invention may include one or more of the fusogenic molecules, along with a structural lipid, and one or more lipids for reducing immunogenicity of the composition.

In some aspects, this invention provides novel fusogenic lipids that facilitate the delivery of biologically active molecules into cells. The fusogenic lipids can be incorporated into formulations, such as nanoparticles or liposomes, to deliver therapeutic molecules including nucleic acids or oligonucleotides to cells, including tumors. In certain embodiments, nanoparticles or liposomes containing fusogenic lipids may fuse with a plasma membrane of a cell, or intracellular membrane of a cell, and facilitate the release of therapeutic molecules, as well as increase transfection efficacy.

In further embodiments, a range of novel fusogenic lipids can be synthesized and incorporated into nanoparticles or liposomes. The nanoparticles or liposomes may incorporate, or encapsulate therapeutic molecules, including nucleic acid based molecules such as siRNA, miRNA or mRNA, as well as small molecule drugs and any active therapeutic agent that can be delivered with the nanoparticles or liposomes.

The particle size of nanoparticles or liposomes may be in the range of 50-200 nm, with a polydispersity less than 0.2. The transfection efficacy of the nanoparticles or liposomes in various cell lines can be enhanced relative to nanoparticles or liposomes lacking one or more of the novel fusogenic lipids.

In additional embodiments, cellular uptake of nanoparticles or liposomes of this invention by an endocytotic pathway or micropinocytosis mechanism, among others, can be enhanced.

Nanoparticles or liposomes of this invention may also reduce lysosomal degradation of therapeutic molecules in delivery.

In some embodiments, this invention includes compositions containing one or more of the fusogenic molecules, along with other lipid molecules for forming nanoparticles. In certain embodiments, the fusogenic molecules may comprise 0.1 to 40 mol % of the lipids of the composition. In further embodiments, the fusogenic compound may comprise 1 to 20 mol % of the lipids of the composition. In additional embodiments, the fusogenic compound may comprise 1 to 10 mol %, or 2 to 10 mol % of the lipids of the composition. In further embodiments, the fusogenic molecules may comprise 2 mol % of the lipids of the composition.

In some embodiments, a fusogenic compound may comprise a fourth or fifth component of the lipids of the composition, or the fusogenic molecules may replace one of the components of the lipids of the composition.

The fusogenic molecules of this invention can be composed of a platform structure, and having attached to the platform structure from one to four amphiphile groups with suitable chemical linkages.

A composition of this invention can include a fusogenic molecule of this disclosure. The fusogenic molecule may be 1-10 mol % of the composition, or more. The composition may form a nanoparticle or liposome.

In some embodiments, a composition of this invention may include a cationic lipid, an ionizable lipid, and a fusogenic lipid molecule, which can combine to form a lipid nanoparticle. In certain embodiments, a lipid nanoparticle may have a bilayer of lipid molecules.

In certain embodiments, one or two amphiphiles may be absent, and when absent may be replaced by a protective group $R^P$.

In additional embodiments, one or two amphiphiles may be absent, and when absent may be replaced by an alkyl, alkenyl, or alkynyl group, or an organic chemical group having up to 400 atoms, or 20-400 atoms, or 10-400 atoms, or 4-400 atoms, or 3-400 atoms, or 2-400 atoms, or 1-400 atoms selected from carbon, oxygen, nitrogen, sulfur, fluorine, and hydrogen.

Methods to prepare various organic groups and protective groups are known in the art and their use and modification is generally within the ability of one of skill in the art. See, e.g., Stanley R. Sandler and Wolf Karo, Organic Functional Group Preparations (1989); Greg T. Hermanson, Bioconjugate Techniques (1996); Leroy G. Wade, Compendium Of Organic Synthetic Methods (1980); some examples of protective groups are found in T. W. Greene and P. G. M. Wuts, Protective Groups In Organic Synthesis (3rd ed. 1991). See, e.g., Helmut Vorbrüggen, Handbook of Nucleoside Synthesis (2001).

Examples of a protective group $R^P$ include Fmoc (fluorenylmethyloxycarbonyl).

Examples of a protective group $R^P$ include Boc (tert-butyloxycarbonyl).

Examples of a protective group $R^P$ include OTrt (O triphenylmethyl).

Examples of an amino protective group $R^P$ include Ac (acetamide (C=O)CH$_3$).

Examples of amino protecting group include Fmoc, Boc, Trt, Dde and Alloc.

Examples of protective alkoxy groups include OTrt, OClt, OMmt, OMtt, ODpm and OtBu.

Examples of a protective group include t-butylether.

Examples of a carboxylic acid protecting group include benzyl ester.

Cationic Lipids and Ionizable Lipids

Examples of the cationic lipids and the ionizable lipids of this disclosure are given in US20130022665A and US20130330401A.

The structure of HEDC is shown in US2013/0022665A at [0146].

The structure of 5104 is shown in US 2013/0115274A1 at [0046].

Compositions with Three or More Components

As used herein, a component of a formulation, such as a "lipid," can be a single compound, or can be a combination of one or more suitable lipid compounds. For example, "a stabilizer lipid" can refer to a single stabilizer lipid, or to a combination of one or more suitable stabilizer lipids. One skilled in the art can readily appreciate that certain combinations of the compounds described herein can be used without undue experimentation, and that various combinations of compounds are encompassed by the description of a component of a formulation.

The ionizable compounds of a composition of this invention can be from 20 mol % to 80 mol % of the lipid components of the composition. In certain embodiments, the ionizable molecules of a composition can be from 55 mol % to 65 mol % of the lipid components of the composition. In further embodiments, the ionizable molecules of a composition can be about 60 mol % of the lipid components of the composition.

The structural lipid of a composition of this invention can be from 20 mol % to 50 mol % of the lipid components of the composition. In certain embodiments, the structural lipid of a composition can be from 35 mol % to 45 mol % of the lipid components of the composition.

The one or more lipids for reducing immunogenicity of the composition can be from a total of 1 mol % to 8 mol % of the lipid components of the composition. In certain embodiments, the one or more lipids for reducing immunogenicity of the composition can be from a total of 1 mol % to 5 mol % of the lipid components of the composition.

In additional aspects, a composition of this invention can further include a cationic lipid, which can be from 5 mol % to 25 mol % of the lipid components of the composition. In certain embodiments, a composition of this invention can further include a cationic lipid, which can be from 5 mol % to 15 mol % of the lipid components of the composition. In these aspects, the molar ratio of the concentrations of the cationic lipid to the ionizable molecules of a composition of this invention can be from 5:80 to 25:50.

In compositions of this invention, the entirety of the lipid components may include one or more of the ionizable compound molecular components, a structural lipid, and one or more lipids for reducing immunogenicity of the composition.

In addition to the components above, a composition of this invention can further include a fusogenic molecule of this disclosure. The fusogenic molecule may be 1-10 mol % of the composition.

Compositions with Four or More Components

The ionizable molecules of a composition of this invention can be from 15 mol % to 40 mol % of the lipid components of the composition. In certain embodiments, the ionizable molecules of a composition can be from 20 mol % to 35 mol % of the lipid components of the composition. In further embodiments, the ionizable molecules of a composition can be from 25 mol % to 30 mol % of the lipid components of the composition.

The structural lipid of a composition of this invention can be from 25 mol % to 40 mol % of the lipid components of the composition. In certain embodiments, the structural lipid of a composition can be from 30 mol % to 35 mol % of the lipid components of the composition.

The sum of the stabilizer lipids of a composition of this invention can be from 25 mol % to 40% mol % of the lipid components of the composition. In certain embodiments, the sum of the stabilizer lipids of a composition can be from 30 mol % to 40 mol % of the lipid components of the composition.

In some embodiments, a composition of this invention can include two or more stabilizer lipids, where each of the stabilizer lipids individually can be from 5 mol % to 35 mol % of the lipid components of the composition. In certain embodiments, a composition of this invention can include two or more stabilizer lipids, where each of the stabilizer lipids individually can be from 10 mol % to 30 mol % of the lipid components of the composition.

In certain embodiments, the sum of the one or more stabilizer lipids can be from 25 mol % to 40 mol % of the lipids of the composition, wherein each of the stabilizer lipids individually can be from 5 mol % to 35% mol %.

In certain embodiments, the sum of the one or more stabilizer lipids can be from 30 mol % to 40 mol % of the lipids of the composition, wherein each of the stabilizer lipids individually can be from 10 mol % to 30% mol %.

The one or more lipids for reducing immunogenicity of the composition can be from a total of 1 mol % to 8 mol % of the lipid components of the composition. In certain embodiments, the one or more lipids for reducing immunogenicity of the composition can be from a total of 1 mol % to 5 mol % of the lipid components of the composition.

In additional aspects, a composition of this invention can further include a cationic lipid, which can be from 5 mol % to 25 mol % of the lipid components of the composition. In certain embodiments, a composition of this invention can further include a cationic lipid, which can be from 5 mol % to 15 mol % of the lipid components of the composition. In these aspects, the molar ratio of the concentrations of the cationic lipid to the ionizable molecules of a composition of this invention can be from 5:35 to 25:15.

In certain embodiments, the entirety of the lipid components of a composition may include one or more of the ionizable compound molecular components, a structural lipid, one or more lipids for reducing immunogenicity of the composition, and one or more stabilizer lipids.

In addition to the components above, a composition of this invention can further include a fusogenic molecule of this disclosure. The fusogenic molecule may be 1-10 mol % of the composition.

Examples of Lipid Compositions

In some embodiments, a composition may contain one or more ionizable molecules, a structural lipid, one or more lipids for reducing immunogenicity of the composition, and a fusogenic molecule of this invention, which would represent 100% of the lipid components of the composition. In certain embodiments, a cationic lipid can be included.

Examples of compositions of this invention are shown in Table 1.

TABLE 1

Compositions of lipid components (each in mol % of total)

| Ionizable | Cationic | Structural | Reduce immun. | Fusogenic |
|---|---|---|---|---|
| 60 | 0 | 30 | 8 | 2 |
| 60 | 0 | 33 | 5 | 2 |
| 55 | 0 | 42 | 1 | 2 |
| 65 | 0 | 31 | 3 | 1 |
| 60 | 0 | 33 | 4 | 3 |
| 65 | 0 | 28 | 3 | 4 |
| 70 | 0 | 20 | 5 | 5 |
| 66 | 0 | 20 | 6 | 8 |
| 73 | 0 | 15 | 2 | 10 |
| 50 | 10 | 33 | 5 | 2 |
| 55 | 15 | 23 | 5 | 2 |
| 55 | 19 | 19 | 5 | 2 |

Examples of compositions of this invention are shown in Table 2.

TABLE 2

Compositions of lipid components (each in mol % of total)

| Ionizable | Cationic | Structural | Stabilizer | Reduce immun. | Fusogenic |
|---|---|---|---|---|---|
| 17 | 0 | 35 | 38 | 8 | 2 |
| 20 | 0 | 32 | 40 | 5 | 3 |
| 25 | 0 | 35 | 37 | 1 | 2 |
| 25 | 0 | 34 | 34 | 5 | 2 |
| 25 | 0 | 28 | 38 | 5 | 4 |
| 25 | 0 | 40 | 27 | 5 | 3 |
| 30 | 0 | 25 | 38 | 5 | 2 |
| 35 | 0 | 24 | 34 | 5 | 2 |
| 40 | 0 | 29 | 24 | 5 | 2 |
| 25 | 5 | 30 | 32 | 5 | 3 |
| 25 | 10 | 28 | 28 | 5 | 4 |
| 25 | 15 | 25 | 30 | 3 | 2 |

Structural Lipids

Examples of structural lipids include cholesterols, sterols, and steroids.

Examples of structural lipids include cholanes, cholestanes, ergostanes, campestanes, poriferastanes, stigmastanes, gorgostanes, lanostanes, gonanes, estranes, androstanes, pregnanes, and cycloartanes.

Examples of structural lipids include sterols and zoosterols such as cholesterol, lanosterol, zymosterol, zymostenol, desmosterol, stigmastanol, dihydrolanosterol, and 7-dehydrocholesterol.

Examples of structural lipids include pegylated cholesterols, and cholestane 3-oxo-(C1-22)acyl compounds, for example, cholesteryl acetate, cholesteryl arachidonate, cholesteryl butyrate, cholesteryl hexanoate, cholesteryl myristate, cholesteryl palmitate, cholesteryl behenate, cholesteryl stearate, cholesteryl caprylate, cholesteryl n-decanoate, cholesteryl dodecanoate, cholesteryl nervonate, cholesteryl pelargonate, cholesteryl n-valerate, cholesteryl oleate, cholesteryl elaidate, cholesteryl erucate, cholesteryl heptanoate, cholesteryl linolelaidate, and cholesteryl linoleate.

Examples of structural lipids include sterols such as phytosterols, beta-sitosterol, campesterol, ergosterol, brassicasterol, delta-7-stigmasterol, and delta-7-avenasterol.

Stabilizer Lipids

Examples of stabilizer lipids include zwitterionic lipids.

Examples of stabilizer lipids include compounds such as phospholipids.

Examples of phospholipids include phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine and ordilinoleoylphosphatidylcholine.

Examples of stabilizer lipids include phosphatidyl ethanolamine compounds and phosphatidyl choline compounds.

Examples of stabilizer lipids include 1,2-dioleoyl-sn-Glycero-3-Phosphocholine (DOPC).

Examples of stabilizer lipids include diphytanoyl phosphatidyl ethanolamine (DPhPE) and 1,2-Diphytanoyl-sn-Glycero-3-Phosphocholine (DPhPC).

Examples of stabilizer lipids include 1,2-distearoyl-sn-glycero-3-phosphocholine (DSPC), 1,2-dipalmitoyl-sn-glycero-3-phosphocholine (DPPC), 1,2-dipalmitoyl-sn-glycero-3-phosphoethanolamine (DPPE), and 1,2-dioleoyl-sn-glycero-3-phosphoethanolamine (DOPE).

Examples of stabilizer lipids include 1,2-dilauroyl-sn-glycerol (DLG); 1,2-dimyristoyl-sn-glycerol (DMG); 1,2-dipalmitoyl-sn-glycerol (DPG); 1,2-distearoyl-sn-glycerol (DSG); 1,2-diarachidoyl-sn-glycero-3-phosphocholine (DAPC); 1,2-dilauroyl-sn-glycero-3-phosphocholine (DLPC); 1,2-dimyristoyl-sn-glycero-3-phosphocholine (DMPC); 1,2-dipalmitoyl-sn-glycero-O-ethyl-3-phosphocholine (DPePC); 1,2-dilauroyl-sn-glycero-3-phosphoethanolamine (DLPE); 1,2-dimyristoyl-sn-glycero-3-phosphoethanolamine (DMPE); 1,2-distearoyl-sn-glycero-3-phosphoethanolamine (DSPE); 1-palmitoyl-2-linoleoyl-sn-glycero-3-phosphocholine; 1-palmitoyl-2-oleoyl-sn-glycero-3-phosphocholine (POPC); 1-palmitoyl-2-lyso-sn-glycero-3-phosphocholine (P-Lyso-PC); and 1-Stearoyl-2-lyso-sn-glycero-3-phosphocholine (S-Lyso-PC).

Lipids for Reducing Immunogenicity

Examples of lipids for reducing immunogenicity include polymeric compounds and polymer-lipid conjugates.

Examples of lipids for reducing immunogenicity include pegylated lipids having polyethyleneglycol (PEG) regions. The PEG regions can be of any molecular mass. In some embodiments, a PEG region can have a molecular mass of 200, 300, 350, 400, 500, 550, 750, 1000, 1500, 2000, 3000, 3500, 4000 or 5000 Da.

Examples of lipids for reducing immunogenicity include compounds having a methoxypolyethyleneglycol region.

Examples of lipids for reducing immunogenicity include compounds having a carbonyl-methoxypolyethyleneglycol region.

Examples of lipids for reducing immunogenicity include compounds having a multi-branched PEG region.

Examples of lipids for reducing immunogenicity include compounds having a polyglycerine region.

Examples of lipids for reducing immunogenicity include polymeric lipids such as DSPE-mPEG, DMPE-mPEG, DPPE-mPEG, and DOPE-mPEG.

Examples of lipids for reducing immunogenicity include PEG-phospholipids and PEG-ceramides.

Cationic Lipids

Examples of cationic lipids include cationic HEDC (2-(bis(2-(tetradecanoyloxy)ethyl)amino)-N-(2-hydroxyethyl)-N,N-dimethyl-2-oxoethan-aminium bromide) compounds as described in US 2013/0330401 A1. Some examples of cationic lipids are given in US 2013/0115274 A1.

Lipid Compositions

In some embodiments, a composition can contain a fusogenic molecule, an ionizable compound, cholesterol, lipids DOPC and DOPE, and DPPE-mPEG. In certain embodiments, the fusogenic molecule can be 1-20 mol % of the composition, the ionizable molecule can be 15 to 25 mol % of the composition; the cholesterol, DOPC, and DOPE combined can be 75 to 85 mol % of the composition; and DPPE-mPEG can be 2-5 mol % of the composition.

In one embodiment, the fusogenic molecule can be 2 mol % of the composition, the ionizable molecule can be 24 mol % of the composition; cholesterol can be 29 mol % of the composition, DOPC can be 20 mol % of the composition, DOPE can be 20 mol % of the composition; and DPPE-mPEG(2000) can be 5 mol % of the composition.

Nanoparticles

Embodiments of this invention can provide liposome nanoparticle compositions. The fusogenic molecules of this invention can be used to form liposome compositions, which can have one or more bilayer structures of lipid-like molecules.

A nanoparticle composition can have one or more of the fusogenic molecules of this invention in a liposomal structure, a bilayer structure, a micelle, a lamellar structure, or a mixture thereof.

In some embodiments, a composition can include one or more liquid vehicle components. A liquid vehicle suitable for delivery of active agents of this invention can be a pharmaceutically acceptable liquid vehicle. A liquid vehicle can include an organic solvent, or a combination of water and an organic solvent.

Embodiments of this invention can provide lipid nanoparticles having a size of from 10 to 1000 nm. In some embodiments, the liposome nanoparticles can have a size of from 10 to 150 nm.

Pharmaceutical Compositions

This invention further contemplates methods for distributing an active agent to an organ of a subject for treating fibrosis by administering to the subject a composition of this invention. Organs that can be treated include lung, liver, pancreas, kidney, colon, heart, bone marrow, skin, intestine, brain and eye.

In some embodiments, this invention provides methods for treating a lung fibrosis disease by administering to the subject a composition of this invention.

Examples of fibrosis disease include idiopathic lung fibrosis and liver cirrhosis.

In further aspects, this invention provides a range of pharmaceutical formulations.

A pharmaceutical formulation herein can include an active agent, as well as a drug carrier, or a lipid of this invention, along with a pharmaceutically acceptable carrier or diluent.

In general, active agents of this description include siRNAs, active agents for fibrosis, as well as any small molecule drug. An active agent can be a nucleic acid, a siRNA, a mRNA or a microRNA.

A pharmaceutical formulation of this invention may contain one or more of each of the following: a surface active agent, a diluent, an excipient, a preservative, a stabilizer, a dye, and a suspension agent.

Some pharmaceutical carriers, diluents and components for a pharmaceutical formulation, as well as methods for formulating and administering the compounds and compositions of this invention are described in Remington's Pharmaceutical Sciences, 18th Ed., Mack Publishing Co., Easton, Pa. (1990).

Examples of preservatives include sodium benzoate, ascorbic acid, and esters of p-hydroxybenzoic acid.

Examples of surface active agents include alcohols, esters, sulfated aliphatic alcohols.

Examples of excipients include sucrose, glucose, lactose, starch, crystallized cellulose, mannitol, light anhydrous silicate, magnesium aluminate, magnesium metasilicate aluminate, synthetic aluminum silicate, calcium carbonate, sodium acid carbonate, calcium hydrogen phosphate, and calcium carboxymethyl cellulose.

Examples of suspension agents include coconut oil, olive oil, sesame oil, peanut oil, soya, cellulose acetate phthalate, methylacetate-methacrylate copolymer, and ester phthalates.

Structures of Molecular Tails

A compound of this invention may have one or more lipophilic tails that contain one or more alkyl or alkenyl groups. Examples of lipophilic tails having alkenyl groups include C(14:1(5))alkenyl, C(14:1(9))alkenyl, C(16:1(7)) alkenyl, C(16:1(9))alkenyl, C(18:1(3))alkenyl, C(18:1(5)) alkenyl, C(18:1(7))alkenyl, C(18:1(9))alkenyl, C(18:1(11)) alkenyl, C(18:1(12))alkenyl, C(18:2(9,12))alkenyl, C(18:2 (9,11))alkenyl, C(18:3(9,12,15))alkenyl, C(18:3(6,9,12)) alkenyl, C(18:3(9,11,13))alkenyl, C(18:4(6,9,12,15)) alkenyl, C(18:4(9,11,13,15))alkenyl, C(20:1(9))alkenyl, C(20:1(11))alkenyl, C(20:2(8,11))alkenyl, C(20:2(5,8))alkenyl, C(20:2(11,14))alkenyl, C(20:3(5,8,11))alkenyl, C(20: 4(5,8,11,14))alkenyl, C(20:4(7,10,13,16))alkenyl, C(20:5(5, 8,11,14,17))alkenyl, C(20:6(4,7,10,13,16,19))alkenyl, C(22: 1(9))alkenyl, C(22:1(13))alkenyl, and C(24:1(9))alkenyl. Some examples of tail structures are found at Donald Voet and Judith Voet, *Biochemistry*, 3rd Edition (2005), p. 383.

Some examples of lipophilic tails include the following structures:

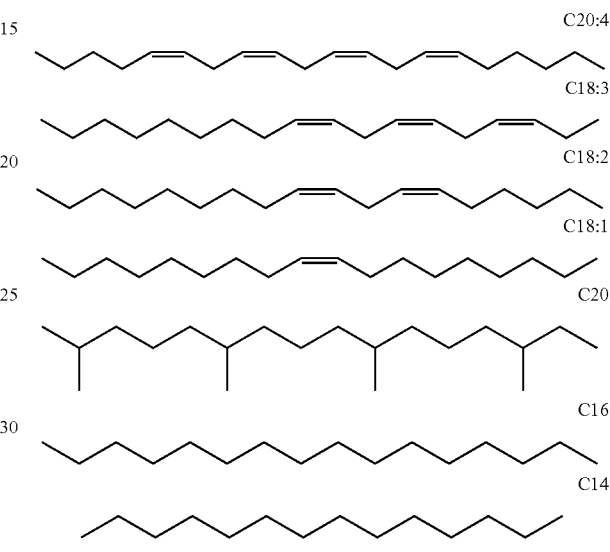

Any of these example structures of lipophilic tails may have one or more additional chemical branches.

Additional Embodiments

Embodiments of this invention further include:

A compound of formula (A)

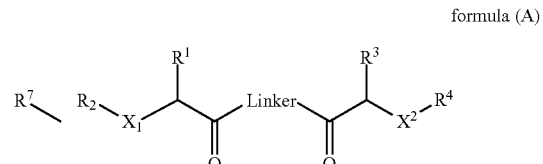

formula (A)

wherein linker is a divalent group comprising PEG portion,
$X_1$ and $X_2$ are independently C1-C5 alkanediyl group,
$R_1$, $R_2$, $R_3$ and $R_4$ are independently

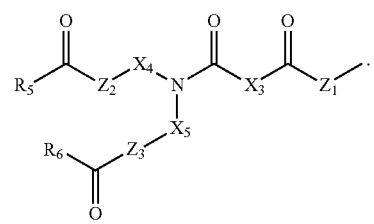

$X_3$ is single bond, C1-C5 alkanediyl group or C2-C5 alkenediyl group,
$X_4$ and $X_5$ are independently C2-5 alkanediyl group,
$Z_1$, $Z_2$ and $Z_3$ are independently —O—, —S— or —NH—, and
$R_5$ and $R_6$ are independently C11-23 alkyl or C11-23 alkenyl group.

A compound of formula (B)

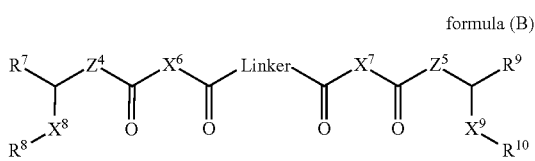

formula (B)

wherein linker is a divalent group comprising PEG portion,
$X_6$ and $X_7$ are independently C1-C5 alkanediyl group,
$X_8$ and $X_9$ are independently C1-C5 alkanediyl group,
$Z_4$ and $Z_5$ are independently —O—, —S— or —NH—,
$R_7$, $R_8$, $R_9$ and $R_{10}$ are independently

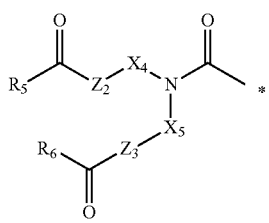

$X_4$ and $X_5$ are independently C2-5 alkanediyl group,
$Z_2$ and $Z_3$ are independently —O—, —S— or —NH—, and
$R_5$ and $R_6$ are independently C11-23 alkyl or C11-23 alkenyl group.

The compound above, wherein the linker is

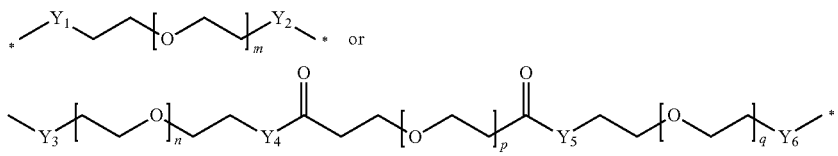

wherein m is an integer of 1-12,
$Y_1$ is —O—, —NH— or —NHCH$_2$—,
$Y_2$ is —O—, —NH— or —CH$_2$NH—,
n and q are independently an integer of 1-5,
p is integer of 0-5,
$Y_3$ and $Y_5$ are independently —O—, —NH— or —NHCH$_2$—, and
$Y_4$ and $Y_6$ are independently —O—, —NH— or —CH$_2$NH—.

The compound above, wherein $X_1$ and $X_2$ are independently C1-C5 straight alkanediyl group, preferably C2-C4 straight alkanediyl group, more preferably C4 straight alkanediyl group.

The compound above, wherein $R_1$, $R_2$, $R_3$ and $R_4$ are same group.

The compound above, wherein $X_3$ is single bond or C1-05 straight alkanediyl group, $X_3$ is preferably C2-C4 straight alkanediyl group, more preferably ethylene, i.e. ethanediyl group.

The compound above, wherein $X_4$ and $X_5$ are independently C2-5 straight alkanediyl group, $X_4$ and $X_5$ are preferably C2-4 straight alkanediyl group, more preferably ethylene, i.e. ethanediyl group.

The compound above, wherein $Z_1$ is —NH—.
The compound above, wherein $Z_2$ and $Z_3$ are —O—.
The compound above, wherein $R_5$ and $R_6$ are independently C11-23 straight alkenyl group.
The compound above, wherein $R_5$ and $R_6$ are independently C11-23 straight alkenyl group with 1-6 double-bond(s), wherein the number of double bonds is preferably 1-3, more preferably 2-3, further more preferably 2.
The compound above, wherein $R_5$ and $R_6$ are independently C11-23 straight alkenyl group with 2 double-bonds.
The compound above, wherein $R_5$ and $R_6$ are independently C13-17 straight alkenyl group, $R_5$ and $R_6$ are preferably C15-17 straight alkenyl group, more preferably C17 straight alkenyl group.
The compound above, wherein $R_5$ and $R_6$ are independently C17 straight alkenyl group.
The compound above, wherein $R_5$ and $R_6$ is heptadeca-8,11-dienyl group.

A composition which comprises a cationic lipid, an ionizable lipid and a lipid of the compound above in a lipid nanoparticle comprising a bilayer of lipid molecules.
The composition above, which further comprises a nucleic acid.
The composition above, wherein the nucleic acid is siRNA, mRNA or microRNA.
The composition above, wherein the composition is a pharmaceutical composition.

Chemical Definitions

The term "alkyl" as used herein refers to a hydrocarbyl radical of a saturated aliphatic group, which can be of any length unless otherwise specified. An alkyl group can be a branched or unbranched, substituted or unsubstituted aliphatic group containing from 1 to 22 carbon atoms. This definition also applies to the alkyl portion of other groups such as, for example, cycloalkyl, alkoxy, alkanoyl, and aralkyl, for example.

As used herein, for example, a term such as "C(1-5)alkyl" includes C(1)alkyl, C(2)alkyl, C(3)alkyl, C(4)alkyl, and C(5)alkyl. Likewise, for example, the term "C(3-22)alkyl" includes C(1)alkyl, C(2)alkyl, C(3)alkyl, C(4)alkyl, C(5)alkyl, C(6)alkyl, C(7)alkyl, C(8)alkyl, C(9)alkyl, C(10)alkyl, C(11)alkyl, C(12)alkyl, C(13)alkyl, C(14)alkyl, C(15)alkyl, C(16)alkyl, C(17)alkyl, C(18)alkyl, C(19)alkyl, C(20)alkyl, C(21)alkyl, and C(22)alkyl.

As used herein, an alkyl group may be designated by a term such as Me (methyl, —CH$_3$), Et (ethyl, —CH$_2$CH$_3$), Pr (any propyl group), $^n$Pr (n-Pr, n-propyl), $^i$Pr (i-Pr, isopropyl), Bu (any butyl group), $^n$Bu (n-Bu, n-butyl), $^i$Bu (i-Bu, isobutyl), $^s$Bu (s-Bu, sec-butyl), and $^t$Bu (t-Bu, tert-butyl).

The term "alkenyl" as used herein refers to hydrocarbyl radical having at least one carbon-carbon double bond. An alkenyl group can be branched or unbranched or unsubstituted hydrocarbyl radical having 2 to 22 carbon atoms and at least one carbon-carbon double bond. An "alkenyl" group has one or more carbon-carbon double bonds.

The term "substituted" as used herein refers to an atom having one or more substitutions or substituents which can be the same or different and may include a hydrogen substituent. Thus, the terms alkyl, cycloalkyl, alkenyl, alkoxy, alkanoyl, and aryl, for example, refer to groups which can include substituted variations. Substituted variations include linear, branched, and cyclic variations, and groups having a substituent or substituents replacing one or more hydrogens attached to any carbon atom of the group.

In general, a compound may contain one or more chiral centers. Compounds containing one or more chiral centers may include those described as an "isomer," a "stereoisomer," a "diastereomer," an "enantiomer," an "optical isomer," or as a "racemic mixture." Conventions for stereochemical nomenclature, for example the stereoisomer naming rules of Cahn, Ingold and Prelog, as well as methods for the determination of stereochemistry and the separation of stereoisomers are known in the art. See, for example, Michael B. Smith and Jerry March, March's Advanced Organic Chemistry, 5th edition, 2001. The compounds and structures of this disclosure, including chemical drawings, are meant to encompass all possible isomers, chemically reasonable positional isomers, stereoisomers, diastereomers, enantiomers, and/or optical isomers that would be understood to exist for the specified compound or structure, including any mixture, racemic or otherwise, thereof.

This invention encompasses any and all tautomeric, solvated or unsolvated, hydrated or unhydrated forms, as well as any atom isotope forms of the compounds and compositions disclosed herein.

This invention encompasses any and all crystalline polymorphs or different crystalline forms of the compounds and compositions disclosed herein.

Abbreviations used:
DMAP—4-N,N-Dimethylaminopyridine
DCM—Dichloromethane
TEA—Triethylamine
EDC—1-(3-Dimethylaminopropyl)-3-ethylcarbodimimde hydrochloride
$Na_2SO_4$—Sodium sulphate
EtOAc—Ethyl acetate
DMF—N,N-Dimethylformide
ELSD—Evaporating Light Scattering Detector
NaCl—Sodium chloride
$K_2CO_3$—Potassium carbonate
MeOH—Methanol
TFA—Trifluoroacetic acid
DIEA—N,N-Diisopropylethylamine
PEG—polyethylene glycol, a.k.a. polyethylene oxide
$MgSO_4$—Magnesium sulphate
LCMS—Liquid chromatography-mass spectrometry
$NaHCO_3$—Sodium bicarbonate
$H_2O$—Water
HCl—Hydrochloride
KI—Potassium idoide
DMSO—Dimethyl sulfoxide
TBAF—tetra-N-Butylammonium fluoride
$NaBH_4$—Sodium borohydride
THF—Tetrahydrofuran
TBDMS—tert-Butyldimethylsilyl
LiOH—Lithium hydroxide
MeI—Methyl iodide
BOC—tert-Butyloxycarbonyl
Fmoc—Fluorenylmethyloxycarbonyl

EXAMPLES

Example 1: Fusogenic molecules of this invention were useful for delivering one or more biologically active agents in cells. In this example, fusogenic molecules of this invention were shown to provide surprisingly active delivery of an example siRNA targeted to HSP47 for gene expression knockdown. The example siRNA was delivered in a liposomal formulation containing the fusogenic molecules. The presence of the fusogenic molecules of this invention in the delivery formulation surprisingly provided high activity of the formulation for gene expression knockdown by the example siRNA.

The in vitro activity for gene expression knockdown using an siRNA was measured using rat stellate cells in DMEM medium according to the following protocol: One day before the transfection, plate the cells in a 96-well plate at $3\times10^3$ cells per well for Stellate cells with 100 µl of medium containing 10% FBS and culture in a 37° C. incubator containing a humidified atmosphere of 5% $CO_2$ in air. Before transfection, change medium to 90 µl of medium without antibiotics. Prepare the appropriate dilutions of the solution collected from the tubing in PBS buffer so that the addition of 10 µl into each well is sufficient to reach the desired concentration. 48 hours after transfection, wash the cells once with ice-cold PBS. Lyse the cells with 50 µl of Cell-to-Ct Lysis Buffer for 5-30 minutes at ambient temperature. Add 5 µl of Stop Solution and incubate for 2 minutes at ambient temperature. Measure mRNA level by qPCR with TAQMAN immediately. Alternatively, the samples can be frozen at −80° C. and assayed at later times. For qRT-PCR assay: Thaw all reagents on ice. Mix the pooled reagents in 0.2 ml PCR tubes. Dispense the set-up mixture into 384 well plate, 10 µl/well×3. Seal the plate with film, spin down mixture into the bottom of wells. Perform qRT-PCR assay.

In this example, an HSP47 siRNA was used to knockdown HSP47 gene. For TaqMan gene expression assays, HSP47 gene specific TaqMan probe was used.

Experimental results for the in vitro gene silencing activity in rat stellate cells is shown in Tables 3 and 4.

TABLE 3

| | In vitro activity in rat stellate cells | | | | |
|---|---|---|---|---|---|
| | % of Expression at Dose (nM) | | % of Expression at Dose (nM) | | |
| Sample | 50 nM | 200 nM | 18 nM | 75 nM | 300 nM |
| Control (PBS) | 110 | 92 | 80 | 80 | 36 |
| Compound R4 | 44 | 15 | 16 | 10 | 6 |
| Compound S6 | | | 97 | 80 | 33 |
| Compound S7 | | | 57 | 48 | 27 |
| Compound S8 | | | 74 | 64 | 42 |
| Compound T1 | | | 76 | 68 | 44 |
| Compound T2 | | | 82 | 70 | 44 |
| Compound T3 | | | 10 | 8 | 5 |
| Compound T4 | | | 82 | 70 | 44 |

TABLE 4

In vitro activity in rat stellate cells

| Sample | % of Expression at Dose (nM) | | |
|---|---|---|---|
| | 18 nM | 75 nM | 300 nM |
| Control (PBS) | 88 | 88 | 88 |
| Compound T3 | 36 | 15 | 3 |
| Compound T4 | 27 | 10 | 8 |
| Compound T5 | 29 | 13 | 11 |
| Compound T6 | 30 | 12 | 5 |
| Compound T7 | 51 | 20 | 8 |
| Compound T8 | 29 | 9 | 8 |
| Compound T9 | 100 | 65 | 36 |

These data show that a siRNA formulation containing a fusogenic molecule of this invention was surprisingly effective for delivering an active siRNA agent in cells. Fusogenic molecules of this invention were shown to provide surprisingly active delivery for gene expression knockdown of an example siRNA targeted to HSP47.

Example 2: A broad range of fusogenic molecules of this invention were shown to be useful for delivering an active agent in cells. In this example, a range of fusogenic molecules of this invention were shown to provide surprisingly active delivery of an example siRNA targeted to HSP47 for gene expression knockdown. The example siRNA was delivered in a liposomal formulation containing the fusogenic molecules.

The in vitro activity for gene expression knockdown measured in stellate cells using an example siRNA in a liposomal formulation containing various fusogenic molecules of this invention is shown in Table 5.

TABLE 5

% of HSP47 expression in Stellate Cell

| Sample | Conc siRNA | | |
|---|---|---|---|
| | 18 nM | 75 nM | 300 nM |
| Cell Only | 108 | 108 | 108 |
| Cell + PBS | 100 | 100 | 100 |
| Compound T10 | 11.1 | 4.2 | 1.9 |
| Compound T11 | 11.1 | 4.5 | 1.8 |
| Compound T12 | 40.2 | 8.4 | 2.7 |
| Compound T13 | 21.8 | 6.4 | 3.1 |
| Compound T14 | 103.3 | 59.1 | 5.2 |
| Compound T3 | 13.2 | 4.5 | 2.3 |

As shown in Table 5, the presence of the fusogenic molecules of this invention in the liposomal delivery formulation surprisingly provided high activity of the formulation for gene expression knockdown by the example siRNA.

Example 3: Fusogenic molecules of this invention were surprisingly active for increasing the delivery activity of an active agent in cells. The activity of an agent delivered in a liposomal formulation containing a fusogenic molecule of this invention was greatly increased as compared to activity of a liposomal formulation which did not contain a fusogenic molecule of this invention.

In this example, the activity for gene expression knockdown of an example siRNA targeted to HSP47 was surprisingly increased using a liposomal delivery formulation which included the presence of compound R4 of this invention.

The liposomal delivery formulation was prepared according to the following protocol: HEDC (2-(bis(2-(tetradecanoyloxy)ethyl)amino)-N-(2-hydroxyethyl)-N,N-dimethyl-2-oxoethan-aminium bromide) and S104 (((2,4(2-(dimethylamino)ethyl)thio)acetyl)azanediyl)bis(ethane-2,1-diyl)ditetradecanoate) were solubilized in absolute EtOH (200 proof) at a molar ratio of 1:1. The HSP47 siRNA was solubilized in 50 mM citrate buffer and the temperature was adjusted to 35-40° C. The ethanol/lipid mixture was then added to the siRNA-containing buffer while stirring to spontaneously form siRNA loaded liposomes. Lipids were combined with siRNA to reach a final total lipid to siRNA ratio of 5:1 to 15:1 (wt:wt). The siRNA loaded liposomes were diafiltered against 10× volumes of PBS (pH 7.2) to remove ethanol and exchange the buffer. Final product was filtered through 0.22 sterilizing grade, PES filter for bioburden reduction.

Figure 46:
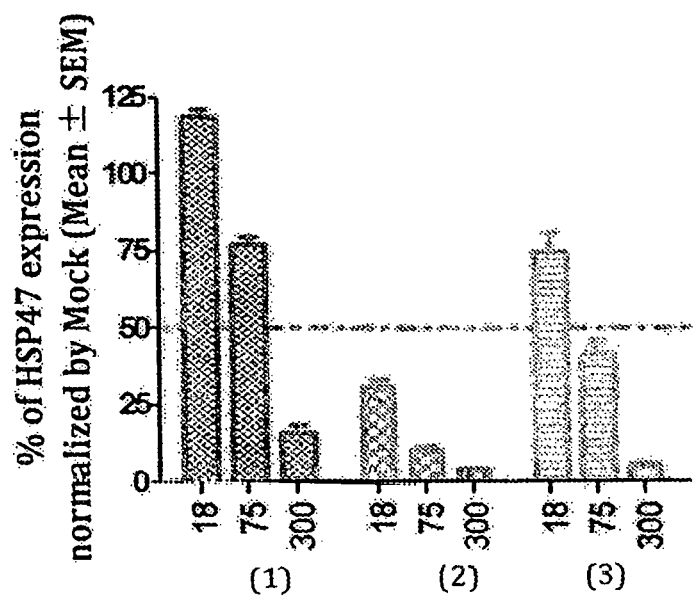
FIG. 46 shows in vitro activity for gene expression knockdown using an example siRNA in rat stellate cells for liposomal formulations containing a fusogenic compound of this invention. (1) Results for a liposomal formulation comprised of lipids HEDC and S104, which did not contain a fusogenic compound of this invention. (2) Results for a liposomal formulation similar to (1), except which contained 2% (of total lipids) of the fusogenic compound R4. (3) Results for a liposomal formulation similar to (1), except which contained 10% (of total lipids) of the fusogenic compound R4. The presence of fusogenic compound R4 in the formulation greatly increased the delivered activity of the example siRNA, and the increased activity was directly attributable to the presence of fusogenic compound R4.

In this example, the in vitro activity for gene expression knockdown using an example siRNA in rat stellate cells was conducted in the same manner as Example 1. The results are shown in FIG. 46. The liposomal formulation comprised lipids HEDC and S104, as well as the fusogenic compound.

In FIG. 46, the results for a liposomal formulation comprised of lipids HEDC and S104, which did not contain fusogenic compound is designated (1). The HSP47 gene expression knockdown for this control formulation was substantial only at the highest concentration of 300 nm.

In FIG. 46, the results for a liposomal formulation comprised of lipids HEDC and S104, which contained the fusogenic compound R4 is designated (2). The amount of fusogenic compound R4 in this formulation was 2% of the total lipids. The HSP47 gene expression knockdown for this formulation was greatly and surprisingly increased at all concentrations of siRNA, as compared to the control formulation which did not contain the fusogenic compound R4. Thus, the presence of fusogenic compound R4 in the formulation greatly increased the delivered activity of the example siRNA, and the increased activity was directly attributable to the presence of fusogenic compound R4.

In FIG. 46, the results for a liposomal formulation comprised of lipids HEDC and S104, which contained the fusogenic compound R4 is designated (3). The amount of fusogenic compound R4 in this formulation was 10% of the total lipids. The HSP47 gene expression knockdown for this formulation was greatly and surprisingly increased at all concentrations of siRNA, as compared to the control formulation which did not contain the fusogenic compound R4. Thus, the presence of fusogenic compound R4 in the formulation greatly increased the delivered activity of the example siRNA, and the increased activity was directly attributable to the presence of fusogenic compound R4.

As shown in FIG. 46, for liposomal delivery formulations comprising lipids HEDC and S104 the activity for gene expression knockdown in stellate cells of an example siRNA targeted to HSP47 was surprisingly increased in formulations containing from 2-10% (of total lipids) of fusogenic compound R4.

Example 4: Fusogenic molecules of this invention provided surprisingly increased activity of an active nucleic acid agent in cells. The activity of a nucleic acid agent delivered in a liposomal formulation containing a fusogenic molecule of this invention was greatly increased as compared to activity of a liposomal formulation which did not contain a fusogenic molecule of this invention.

Figure 47:
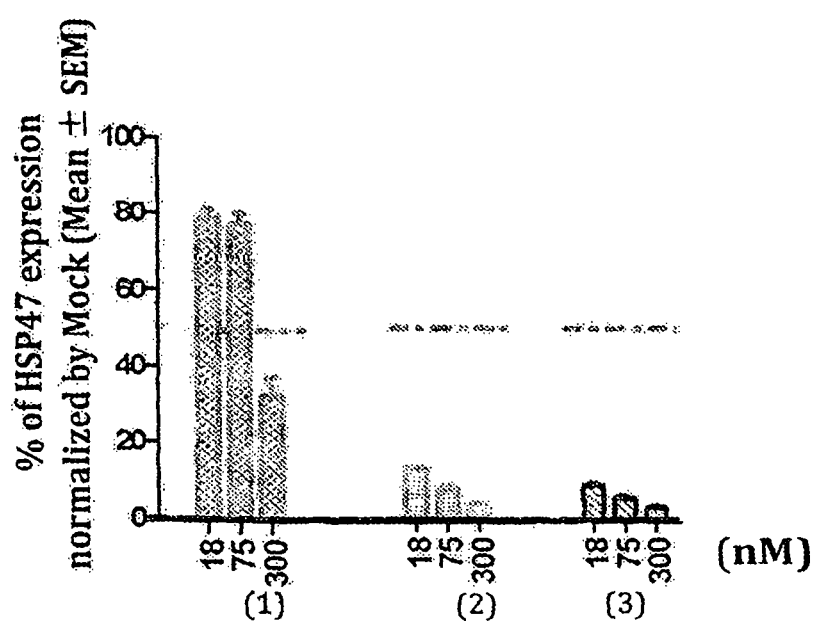
FIG. 47 shows in vitro activity for gene expression knockdown using an example siRNA in rat stellate cells using a liposomal formulation containing a fusogenic compound of this invention. (1) Results for a liposomal formulation comprised of lipids HEDC and S104, which did not contain a fusogenic compound of this invention. (2) Results for a liposomal formulation similar to (1), except which contained 2% (of total lipids) of the fusogenic compound R4. (3) Results for a liposomal formulation similar to (1), except which contained 2% (of total lipids) of the fusogenic compound T3. The presence of fusogenic compounds R4 and T3, respectively, in the formulations greatly increased the delivered activity of the example siRNA, and the increased activity was directly attributable to the presence of fusogenic compounds R4 and T3.

In this example, the in vitro activity for gene expression knockdown using an example siRNA in rat stellate cells was conducted in a similar manner as Example 1. The results are shown in FIG. 47. The liposomal formulation comprised lipids HEDC and S104, as well as the fusogenic compound.

In FIG. 47, the results for a liposomal formulation comprised of lipids HEDC and S104, which did not contain any fusogenic compound of this invention is designated (1). The HSP47 gene expression knockdown for this control formulation was substantial only at the highest concentration of 300 nm siRNA.

In FIG. 47, the results for a liposomal formulation comprised of lipids HEDC and S104, which contained the fusogenic compound R4 is designated (2). The amount of fusogenic compound R4 in this formulation was 2% of the total lipids. The HSP47 gene expression knockdown for this formulation was greatly and surprisingly increased at all concentrations of siRNA, as compared to the control formulation which did not contain the fusogenic compound R4. Thus, the presence of fusogenic compound R4 in the formulation greatly increased the delivered activity of the example siRNA, and the increased activity was directly attributable to the presence of fusogenic compound R4.

In FIG. 47, the results for a liposomal formulation comprised of lipids HEDC and S104, which contained the fusogenic compound T3 is designated (3). The amount of fusogenic compound T3 in this formulation was 2% of the total lipids. The HSP47 gene expression knockdown for this formulation was greatly and surprisingly increased at all concentrations of siRNA, as compared to the control formulation which did not contain the fusogenic compound T3. Thus, the presence of fusogenic compound T3 in the formulation greatly increased the delivered activity of the example siRNA, and the increased activity was directly attributable to the presence of fusogenic compound T3.

Example 5: Fusogenic molecules of this invention were active for delivering one or more biologically active molecules in vitro. For example, the activity for gene expression knockdown using an siRNA (HSP47 siRNA, see Example 1) was surprisingly increased due to the presence of a fusogenic compound of this invention in a liposomal delivery formulation.

In this Example, liposomal delivery formulations were prepared for comparative compounds, as well as fusogenic compound R4. The liposomal delivery formulations were prepared in the same manner as that of Example 1, with the compositions shown in Table 6 (CH refers to cholesterol).

TABLE 6

| No. | Formulation | Descr. | Kind | Final siRNA conc. (nM) |
|---|---|---|---|---|
| 1 | HEDC:S104:DOPE:CH:DMPE-PEG | bulk | Control | 2000 |
| 2 | HEDC:S104:DOPE:CH:DMPE-PEG:R1 | bulk | experimental | 2000 |
| 3 | HEDC:S104:DOPE:CH:DMPE-PEG:R2 | bulk | experimental | 2000 |
| 4 | HEDC:S104:DOPE:CH:DMPE-PEG:R3 | bulk | experimental | 2000 |
| 5 | HEDC:S104:DOPE:CH:DMPE-PEG:R4 | bulk | experimental | 2000 |
| 6 | HEDC:S104:DOPE:CH:DMPE-PEG:R5 | bulk | experimental | 2000 |
| 7 | HEDC:S104:DOPE:CH:DMPE-PEG:S1 | bulk | experimental | 2000 |
| 8 | HEDC:S104:DOPE:CH:DMPE-PEG:S2 | bulk | experimental | 2000 |
| 9 | HEDC:S104:DOPE:CH:DMPE-PEG:S3 | bulk | experimental | 2000 |
| 10 | HEDC:S104:DOPE:CH:DMPE-PEG:S4 | bulk | experimental | 2000 |

Figure 24:
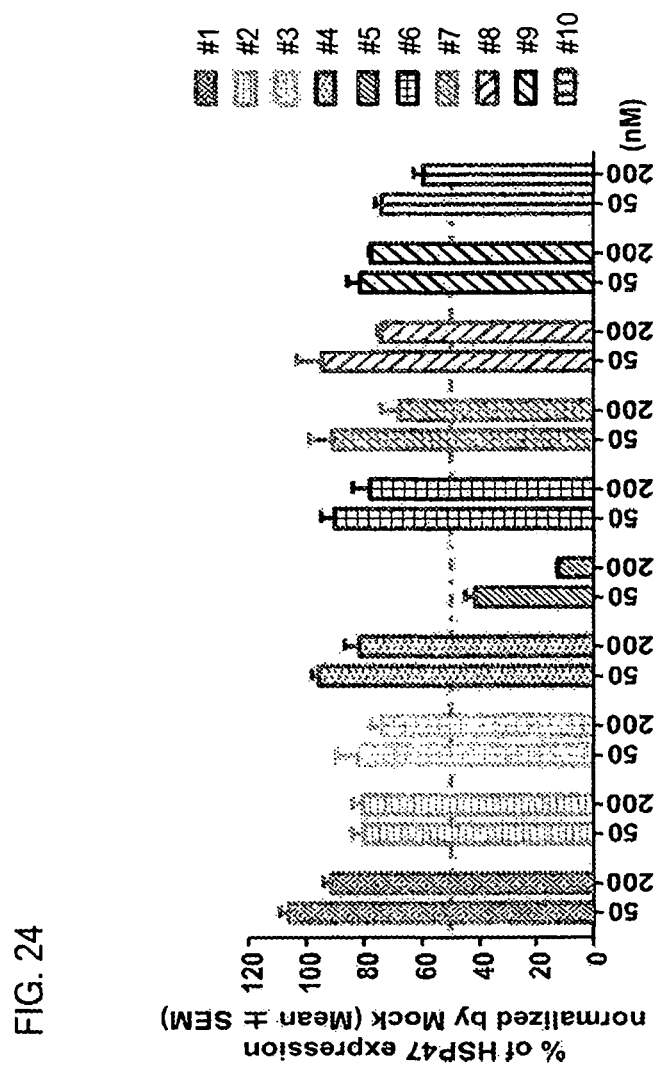
FIG. 24 shows results for delivery of biologically active molecules in vitro using fusogenic molecules of this invention.

As shown in FIG. 24, for the liposomal delivery formulations of Table 6, the activity for gene expression knockdown in stellate cells of an example siRNA targeted to HSP47 was surprisingly increased in formulations containing 2% (of total lipids) of a fusogenic compound R4 of this invention, as compared to the control formulation which did not contain a fusogenic compound of this invention. The structure of fusogenic compound R4 of this invention provided surprising delivery activity for gene expression knockdown in stellate cells of an example siRNA.

Example 6: Fusogenic lipid molecules of this invention were active for delivering one or more biologically active molecules in cells. In this example, liposomal delivery formulations containing an example siRNA (HSP47 siRNA, see Example 1), as well as a fusogenic compound of this invention provided activity for gene expression knockdown. In this Example, as shown in Table 7, liposomal delivery formulations of the siRNA were prepared containing various compounds T3 to T9 (No. 1 to No. 7), each containing 2% (of total lipids) of a fusogenic compound of this invention. The liposomal delivery formulations were prepared in the same manner as that of Example 1.

TABLE 7

Fusogenic liposomal formulations

| No. | Formulation |
|---|---|
| 1 | HEDC:S104:DOPE:CH:DMPE-PEG:T4 |
| 2 | HEDC:S104:DOPE:CH:DMPE-PEG:T5 |
| 3 | HEDC:S104:DOPE:CH:DMPE-PEG:T6 |
| 4 | HEDC:S104:DOPE:CH:DMPE-PEG:T7 |
| 5 | HEDC:S104:DOPE:CH:DMPE-PEG:T8 |
| 6 | HEDC:S104:DOPE:CH:DMPE-PEG:T9 |
| 7 | HEDC:S104:DOPE:CH:DMPE-PEG:T3 |

Figure 25:
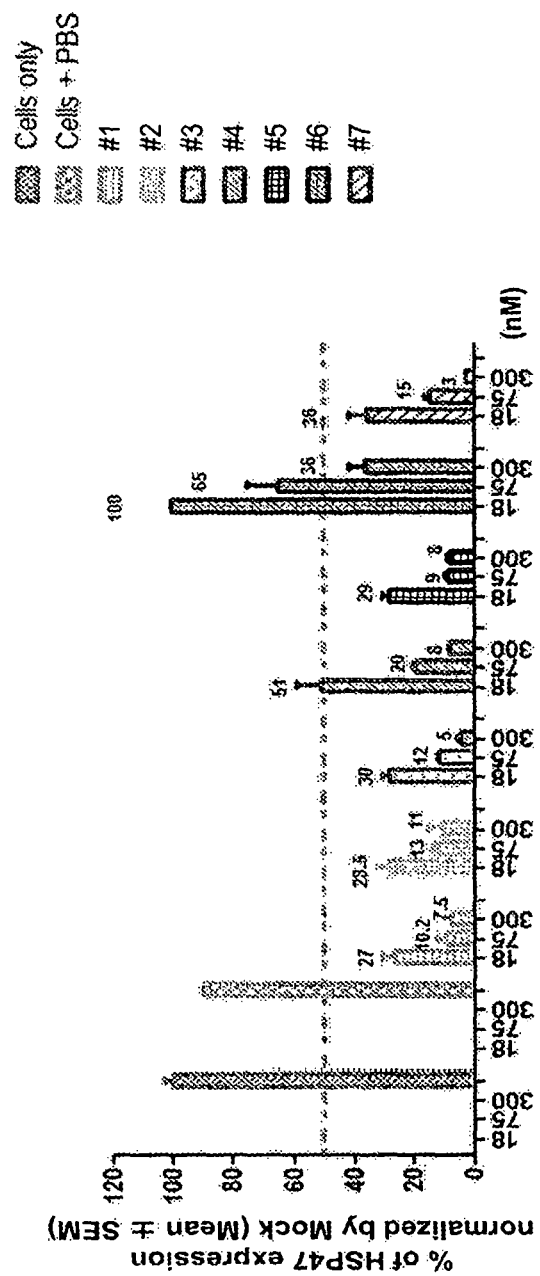
FIG. 25 shows results for delivery of biologically active molecules in vitro using fusogenic molecules of this invention. The activity for HSP47 gene expression knockdown of several siRNA liposomal delivery formulations was measured. The formulations provided high activity for gene expression knockdown in stellate cells. The formulations contained 2% (of total lipids) of a fusogenic compound of this invention, and provided high activity of the siRNA targeted to HSP47.

As shown in FIG. 25, in this measurement of the activity of siRNA liposomal delivery formulations of Table 7, the formulations provided high activity for gene expression knockdown in stellate cells. Thus, formulations containing 2% (of total lipids) of a fusogenic compound of this invention provided high activity of the siRNA targeted to HSP47.

Example 7: In vivo activity for fusogenic formulations. Fusogenic molecules of this invention were useful for delivering an active agent in vivo. For example, liposomal delivery formulations for gene expression knockdown using an example siRNA targeted to HSP47 were active due to the presence of a fusogenic compound of this invention.

Figure 26:
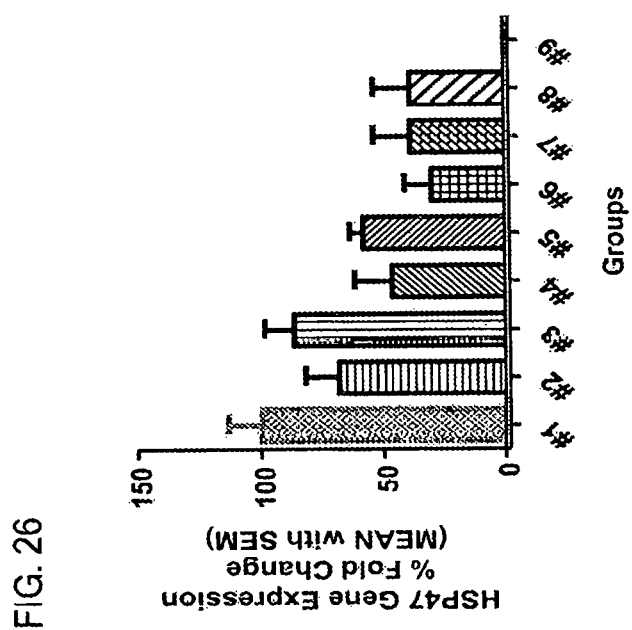
FIG. 26 shows results for delivery of biologically active molecules in vivo using fusogenic molecules of this invention. Liposomal delivery formulations showed activity for gene expression knockdown in vivo (mice), using an siRNA targeted to HSP47. The active formulations #2-#8 contained 2% (of total lipids) of a designated fusogenic compound of this invention.

As shown in FIG. 26, liposomal delivery formulations showed activity for gene expression knockdown in vivo (mice), using an siRNA targeted to HSP47. The formulations contained 2% (of total lipids) of the designated fusogenic compound of this invention. The formulations were delivered by infusion bolus. The parameters for the delivery are shown in Table 8.

TABLE 8

Fusogenic liposomal formulations in vivo

| Group No. | Formulation | Dose | Conc. (mg/ml) |
|---|---|---|---|
| #1 | Vehicle Saline 10 mpk@day 0-2 | | |
| #2 | HEDC:S104:DOPE:CH:DMPE-PEG:T4 | 0.5 mg/kg | 0.17 |
| #3 | HEDC:S104:DOPE:CH:DMPE-PEG:T5 | 0.5 mg/kg | 0.17 |
| #4 | HEDC:S104:DOPE:CH:DMPE-PEG:T6 | 0.5 mg/kg | 0.17 |
| #5 | HEDC:S104:DOPE:CH:DMPE-PEG:T7 | 0.5 mg/kg | 0.17 |
| #6 | HEDC:S104:DOPE:CH:DMPE-PEG:T8 | 0.5 mg/kg | 0.17 |
| #7 | HEDC:S104:DOPE:CH:DMPE-PEG:T9 | 0.5 mg/kg | 0.17 |
| #8 | HEDC:S104:DOPE:CH:DMPE-PEG:T3 | 0.5 mg/kg | 0.17 |
| #9 | Sham saline | | |

An example of a protocol for these results is as follows.

1.1. Animals

Eighty male Sprague-Dawley rats at ~49 days of age were purchased from Charles River Laboratories and delivered to the test facility. The average weight of the animals upon receipt was about 200-210 grams. The animals were housed in standard caging systems with 2 animals per cage under an alternating 12-hour light/dark cycle. The room temperature was maintained at 64-79° F. (18-26° C.) and humidity at 30-70%, with at least 10 air changes per hour using 100% fresh air with no re-circulation. Animals were provided with an irradiated certified standard fresh rodent chow and tap water ad-libitum.

Seventy-two animals were subjected to DMN treatment from Days 0-5 and then randomly divided into 9 groups, 8 rats per group, based on their body weight so that there was no significant difference in the body weight among the groups prior to siRNA treatment. This was confirmed using a one-way ANOVA analysis. As expected, these DMN-treated animals showed a significantly lower body weight than the naïve animals 1.2. DMN Treatment DMN was obtained from Wako (lot number DSP2369) and formulated for intraperitoneal (IP) injection in phosphate buffered saline (PBS) by dissolving the compound at 5 mg/mL. Seventy-two of the rats were dosed daily with DMN at 10 mg/kg in a dose volume of 2 mL/kg from Day 0 through Day 2 and then 5 mg/kg in a dose volume of 1 mL/kg from Day 3 through Day 5; eight animals, being not treated with DMN, were used as shams for this procedure. Animals were weighed daily and the DMN dose was adjusted accordingly.

1.3. siRNA Treatment

On experimental Day 5, the animals were assigned to different treatment groups and dosed with an appropriate dosing regimen. Test articles were used for treatment Groups 2 to 8 (#1 to #8), respectively; whereas animals in Group 1 (#1) received only vehicle (saline) at 3 mL/kg by single intravenous injection into the lateral tail vein. Animals in Group 9 (Naïve group, #9) got no treatment.

1.4. Euthanasia and Necropsy

On experimental Day 6, 24 hours post-treatment, the animals were euthanized via overdose inhalation of carbon dioxide. The liver was immediately flushed with PBS, pH 7.4 (40 mL at a rate of 20 mL/min) through the hepatic portal vein to remove residual blood and blood-associated formulation. One 2-mm thick transverse liver section was collected from the left lateral lobe and immediately submerged in 2 mL RNAlater in a microcentrifuge tube. Samples were stored at 4° C. until further processing for RNA isolation.

1.6. RNA Analysis

HSP47 mRNA abundance in the liver samples was evaluated. Total RNA was extracted using RNeasy columns (Qiagen) according to the manufacturer's instructions. The RNA concentration for each sample was quantified using a Nanodrop spectrophotometer and then diluted to 10 ng/μl using nuclease-free water. For each PCR reaction, 20 ng of total RNA was used. In brief, total RNA from a section of left lobe of liver tissue will be extracted using RNeasy columns (Qiagen) according to the manufacturer's instructions. A Nanodrop spectrophotometer was used for RNA quantification. RNA was adjusted to 10 ng/μL with nuclease free water. Real-time PCR was performed on the ViiA7 system in a 96-well format. Each sample was measured in triplicate using the TaqMan Gene Expression Master Mix. The cycling program was set as 48° C. for 15 min, 95° C. for 10 min followed by 40 cycles at 95° C. for 15 sec and 60° C. for 1 min. The average cycle threshold value for housekeeping gene MRP119 was used to normalize the raw cycle threshold data and ΔCt calculation. The ΔΔCt for each Gene of Interest (GOI) was calculated by deducting the average ΔCt of GOI in the control sample from the ΔCt of each GOI in the target samples. Data for each animal was expressed both as percent of the mean vehicle treated group and as fold change from the naive group. Differences between siRNA treatment groups and vehicle-treated group were analyzed using one-way ANOVA followed by Dunnett's multiple comparisons post hoc test. For all analyses, a p-value less than 0.05 was considered significant.

Example 8: Preparation of mRNA nanoparticle. Cationic lipids such as HEDC or HE2DC (2-(bis(2-(palmitoyloxy)ethyl)amino)-N,N-bis(2-hydroxyethyl)-N-methyl-2-oxo-ethan-1-aminium bromide), ionizable lipids such as S104, or TU104 Dlin ((9Z,9'Z,12Z,12'Z)-((2-((2-(dimethylamino)ethyl)thio)acetyl)azanediyl)bis(ethane-2,1-diyl)bis(octa-deca-9,12-dienoate)), and helper lipids cholesterol, DOPE were dissolved in ethanol. mRNA was dissolved in 50 mM Citrate buffer (pH 3.5). Lipid nanoparticles (LNPs) were prepared by injecting an appropriate amount of an ethanolic solution of the lipids into Citrate buffer containing the mRNA, with the flow rate of 25 mL/min at 37° C. The molar percentage ratio for the LNP composition was 20% HEDC, 20% S104, 30% DOPE (1,2-dioleoyl-sn-glycero-3-phosphoethanolamine) (Avanti Polar Lipid), 25% Cholesterol (Puriss grade) (Wilshire Technologies), 5% DMPE-Peg (1,2-dimyristoyl-sn-glycero-3-phosphoethanolamine-N-[methoxy(polyethylene glycol)-2000] (ammonium salt), and 2% of the fusogenic molecule of this invention, for example Compound T3.

High speed injection yielded high encapsulation of mRNA, as well as controlled particle size distribution. The mixed LNPs solution was then diluted with 20 mM HEPES Buffer in 9% sucrose (w/v) in 1:1 ratio, which reduced the ethanol content in the LNP solution from 35% to 17.5%. The diluted LNP solution was transferred over to the tangential flow filtration (TFF) process for ultrafiltration and diafiltration with 20 mM HEPES Buffer in 9% sucrose (w/v). To remove ethanol from the LNPs solution, a total of 10 diafiltration volumes of HEPES Buffer in 9% sucrose was used. The concentrated LNP solution from the TFF was aliquoted into centrifugal filter vials (EMD Millipore) for further concentration, however, this step was required only for a small scale batch. After final concentration, LNPs were filtered through 0.2 μm filters. Encapsulation efficiency and mRNA yield was calculated by using the RiboGreen method.

Example 9: Transfection delivery of mRNA to cells in vitro. Transfection of cells in vitro with mRNA was performed in three different cell lines: Hek-293, A549, and Lung fibroblast. JET MESSENGER (Polyplus Transfection Company) was used as a positive transfection control. GFP mRNA (TriLink) that was encapsulated in the LNP nanoparticles of this invention, or mixed with JET MESSENGER Control, was used to transfect the cells at different concentrations. After 24, 48 and 72 hours of transfection, cells were viewed under a confocal microscope and the fluorescence generated from expressed GFP in cells was then detected and captured. GFP mRNA was well transfected into all three lines of cells with the LNP nanoparticles of this invention, and the mRNA was translated.

Example 10: Transfection delivery of mRNA to cells in vivo. mRNA was transfected into tissues and cells in vivo with the LNP nanoparticles of this invention. Two different mRNA having different sizes, GFP mRNA and luciferase mRNA (TriLink), were delivered and transfected into Balb/c mice. In some luciferase mRNA delivery studies, the mRNA was also delivered using a Viromer in vivo mRNA transfection reagent as positive control. The animals were intravenously given a single injection with the mRNA encapsulated in the LNP nanoparticles of this invention, or in the positive control particles at a dose of 1.0, 2.0 or 4.0 mg/kg. Mice were anesthetized 6-8 hours after mRNA injection, and whole body fluorescence for luciferase mRNA delivery studies was detected and analyzed with an IVIS system. Animals xwere then sacrificed immediately, and different organs were harvested and saved under −80° C. until further analysis. Delivery of the mRNA to various tissues and cells was determined with a MAXDISCOVER GFP ELISA kit to analyze GFP protein level in the tissues from the GFP mRNA delivery studies. For luciferase mRNA delivery studies, tissues were homogenized in CCLR lysis buffer and centrifuged. The resultant supernatants were used for luciferase activity assay using Promega E4510 assay reagents. Surprisingly, both GFP mRNA and luciferase mRNA were predominantly transfected and/or translated in lung and spleen with much lower transfection and/or translation in other tissues.

Example 11: Transfection delivery of mRNA to cells in vitro.

Figure 48:
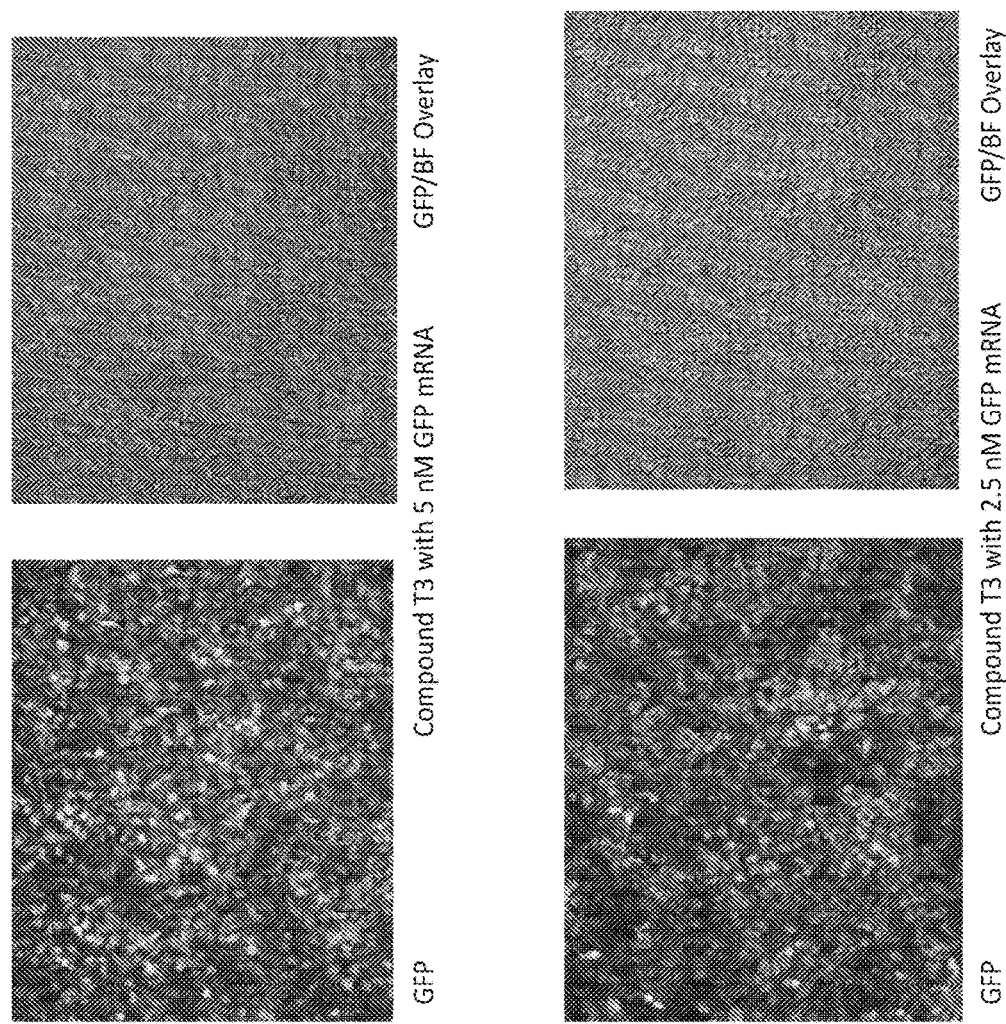
FIG. 48 shows results for delivery and transfection of GFP mRNA at 5 nM (Top) and 2 nM (bottom) into A549 cells in vitro with LNP nanoparticles of this invention having the composition HEDC:S104:CH:DOPE:DMPE-PEG2000:Compound T3. Fluorescence images (left) of GFP expression were acquired 48 hrs. after transfection with a fluorescence microscope. Overlay image (right) of fluorescence and bright field (BF) images demonstrate that close to 100% of the cells were transfected and are expressing GFP.

According to a method described in Examples 9 and 10 above, GFP mRNA (CleanCap EGFP mRNA, 5 moU) was transfected into A549 cells in vitro with the LNP nanoparticles of this invention having the composition HEDC:S104:CH:DOPE:DMPE-PEG2000:Compound T3. Results after 48 hrs of transfection are shown in FIG. 48. Cells were viewed under a confocal microscope and the fluorescence generated from expressed GFP in cells was detected. The results showed that GFP mRNA was transfected and translated in A549 cells.

Example 12: Transfection delivery of mRNA to cells in vivo. According to a method described in Examples 9 and 10 above, GFP mRNA (CleanCap EGFP mRNA, 5 moU) was transfected into Balb/c mice with the LNP nanoparticles of this invention having the composition HEDC:S104:CH:DOPE:DMPE-PEG2000:Compound T3, as shown in Table 9:

TABLE 9

In vivo transfection in Balb/c mice

| Group | Animal Number | Treatment | Dosage | Endpoint |
|---|---|---|---|---|
| 1 | 4 | iv, QD | 1 mpk | 8 hour after treatment, IVIS imaging, Tissues (Muscle, Liver, Heart, Lung and kidney) collection, measure GFP protein by ELISA |
| 2 | 4 | iv, QD | 4 mpk | |
| 3 | 3 | N/A | N/A | |

Figure 49:
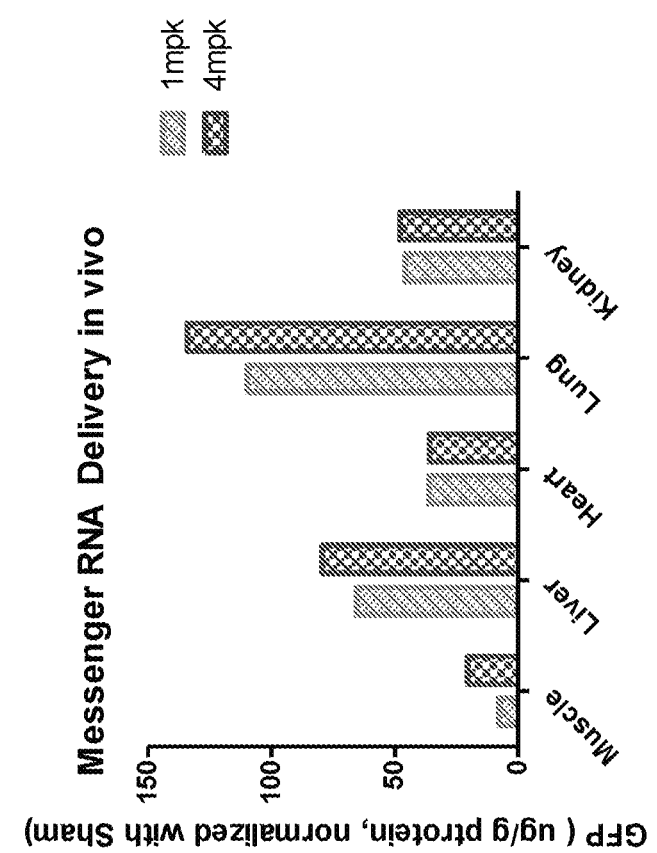
FIG. 49 shows results for delivery of GFP mRNA in vivo using fusogenic lipid-like molecules of this invention. GFP mRNA was transfected into Balb/c mice with the LNP nanoparticles of this invention having the composition HEDC:S104:CH:DOPE:DMPE-PEG2000:Compound T3.
Figure 49:
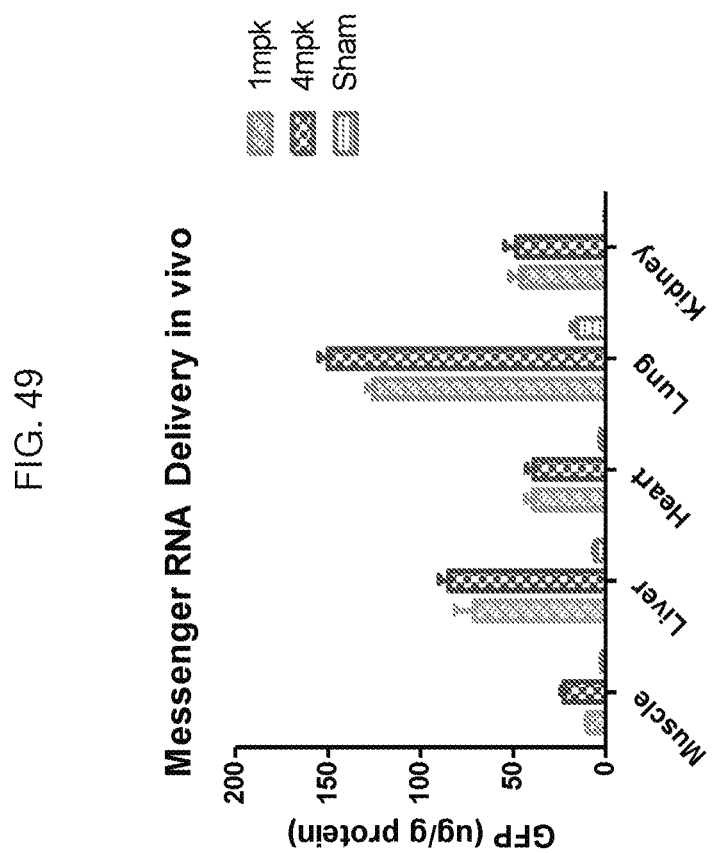

As shown in FIG. 49, delivery of the mRNA to various tissues and cells was determined with a MAXDISCOVER GFP ELISA. Surprisingly, GFP mRNA was selectively transfected and/or translated in lung, with lower transfection and/or translation in muscle, liver, heart, and kidney.

Example 13: Transfection delivery of mRNA to cells in vivo. According to a method described in Examples 9 and 10 above, Luciferase mRNA (Fluc mRNA (5meC)) was transfected into Balb/c mice with the LNP nanoparticles of this invention having the composition HEDC:S104:CH:DOPE:DMPE-PEG2000:Compound T3, as shown in Table 10:

TABLE 10

In vivo transfection in Balb/c mice

| Group | Animal Number | Dosage | endpoint |
|---|---|---|---|
| 1 | 3 | | IVIS imaging |
| 2 | 3 | 1 mpk (20 ug/each) | Tissue luciferase analysis |
| 3 | 3 | 2 mpk (40 ug/each) | |
| 4 | 1 | 10 ug | |
| 5 | 1 | 30 ug | |
| 6 | 3 | 40 ug | |

Figure 50:
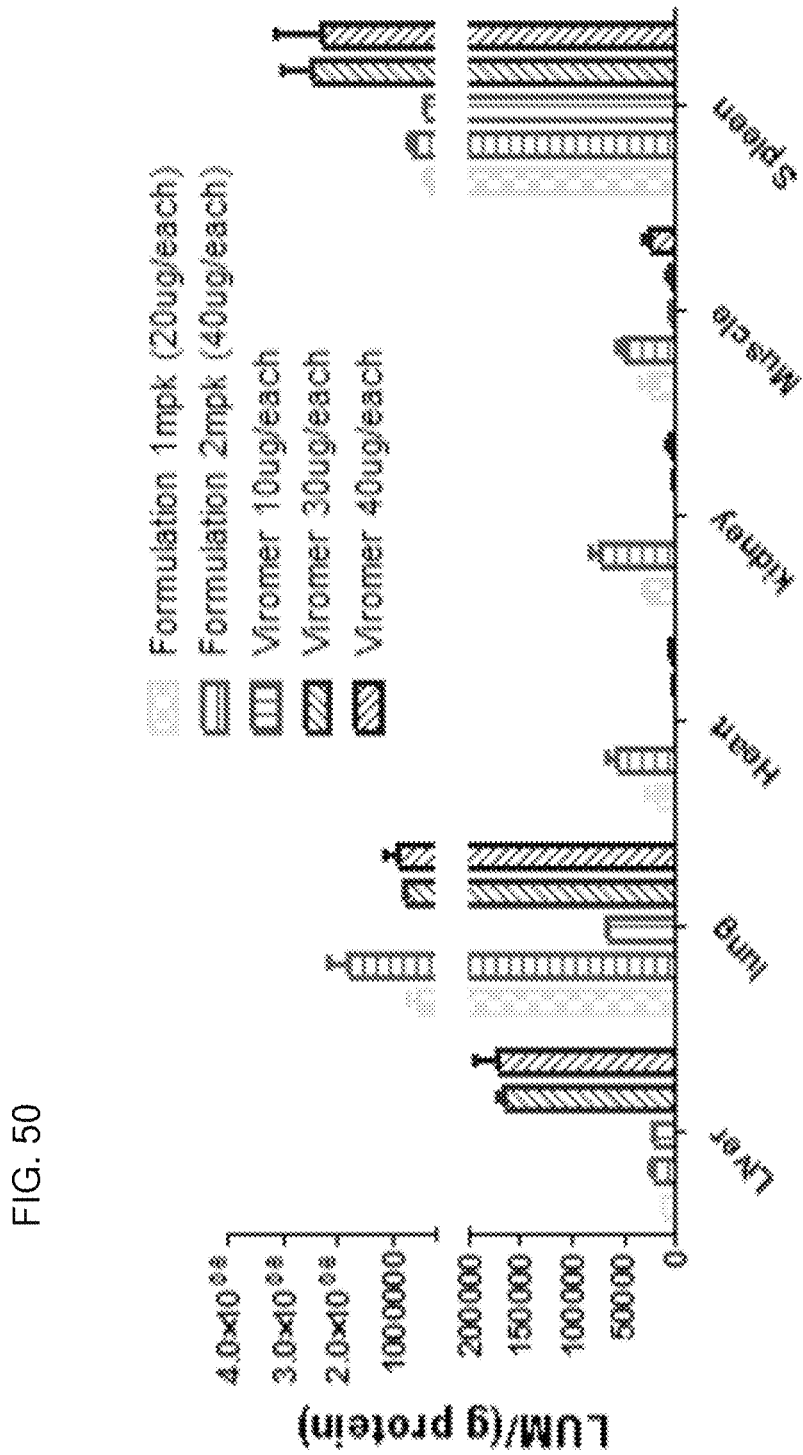
FIG. 50 shows results for delivery of Luciferase mRNA in vivo using fusogenic lipid-like molecules of this invention. Luciferase mRNA was transfected into Balb/c mice with the LNP nanoparticles of this invention having the composition HEDC:S104:CH:DOPE:DMPE-PEG2000: Compound T3.

As shown in FIG. 50, the relative delivery, transfection, and/or translation of the mRNA in various tissues and cells was determined with a Promega E4510 assay kit. Surprisingly, Fluc mRNA was selectively delivered, transfected, and/or translated in lung and spleen, with lower delivery, transfection, and/or translation in liver, heart, kidney, and muscle.

Example 14: Transfection delivery of mRNA to cells in vivo. According to a method described in Examples 9 and 10 above, Luciferase mRNA (Fluc mRNA (5meC)) was transfected into Balb/c mice with the LNP nanoparticles of this invention having the composition:
(−01)   HE2DC:S104:CH:DOPE:DMPE-PEG2000:Compound T3, or
(−02)   HEDC:S104:CH:DOPE:DMPE-PEG2000:Compound T3, injected at 2 mpk, with luminescence imaging 7 hours after injection.

Figure 51:
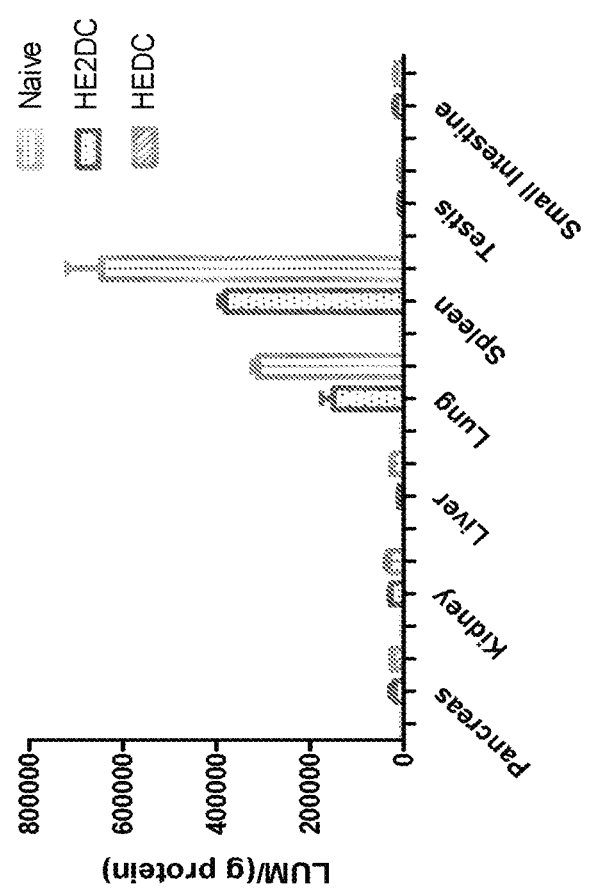
FIG. 51 shows results for delivery of Luciferase mRNA in vivo using fusogenic lipid-like molecules of this invention. Luciferase mRNA was transfected into Balb/c mice with the LNP nanoparticles of this invention having the composition: (−01) HE2DC:S104:CH:DOPE:DMPE-PEG2000:Compound T3, or (−02) HEDC:S104:CH:DOPE: DMPE-PEG2000:Compound T3, injected at 2 mpk.

As shown in FIG. 51, the relative delivery, transfection, and/or translation of the mRNA in various tissues and cells was determined with a Promega E4510 assay. Surprisingly, Fluc mRNA was selectively delivered, transfected, and/or translated in lung and spleen, with lower delivery, transfection, and/or translation in pancreas, kidney, liver, testis, and small intestine.

Figure 52:
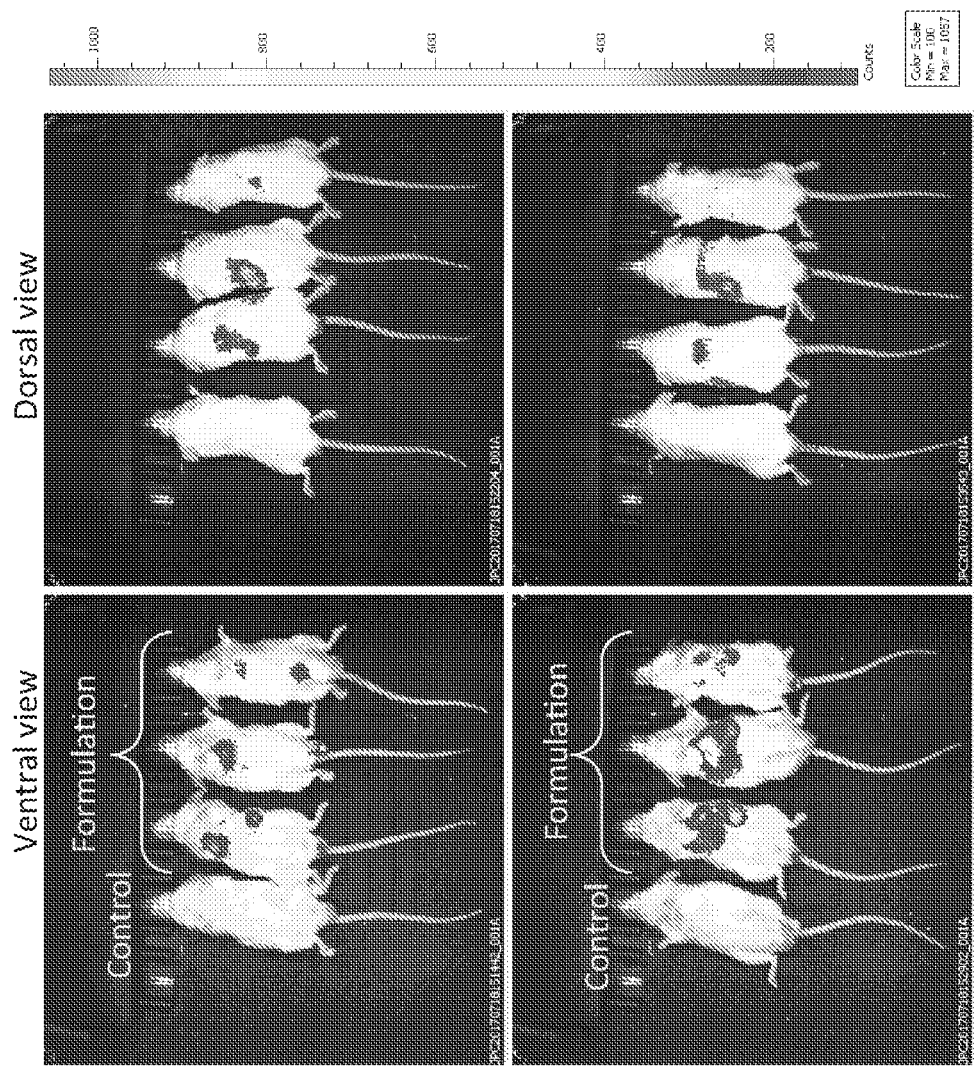
FIG. 52 shows bioluminescence results for delivery of Luciferase mRNA in vivo mouse using fusogenic lipid-like molecules of this invention.

As shown in FIG. 52, the relative delivery, transfection, and/or translation of the mRNA in various tissues was determined with luminescence imaging 7 hours after injection. In FIG. 52, a set of photographs in upper row indicates Balb/c mice transfected with the LNP nanoparticles of the (-01). A set of photographs in lower row indicates Balb/c mice transfected with the LNP nanoparticles of the (-02).

Example 15: Delivery of mRNA to cells in vivo with fusogenic compounds. The fusogenic compounds of this invention greatly enhance delivery of active agents to cells, organs and tissues in vivo.

In this example, formulations for delivery of an mRNA in vivo were prepared with a fusogenic compound T3 and compared to the same formulation without the fusogenic compound, as shown in Table 11.

TABLE 11

In vivo mouse delivery formulations

| mRNA | Formulation | PS nm | PDI | EE % |
|---|---|---|---|---|
| 2035-03-03 | HEDC:S104:DOPE:CH:DMPE-PEG2K:Compound T3 (20:20:30:25:5:5) | 81 | 0.10 | 93 |
| 2035-13-01 | HEDC:S104:DOPE:CH:DMPE-PEG2K (20:20:30:25:5) | 83 | 0.148 | 78 |

Figure 53:
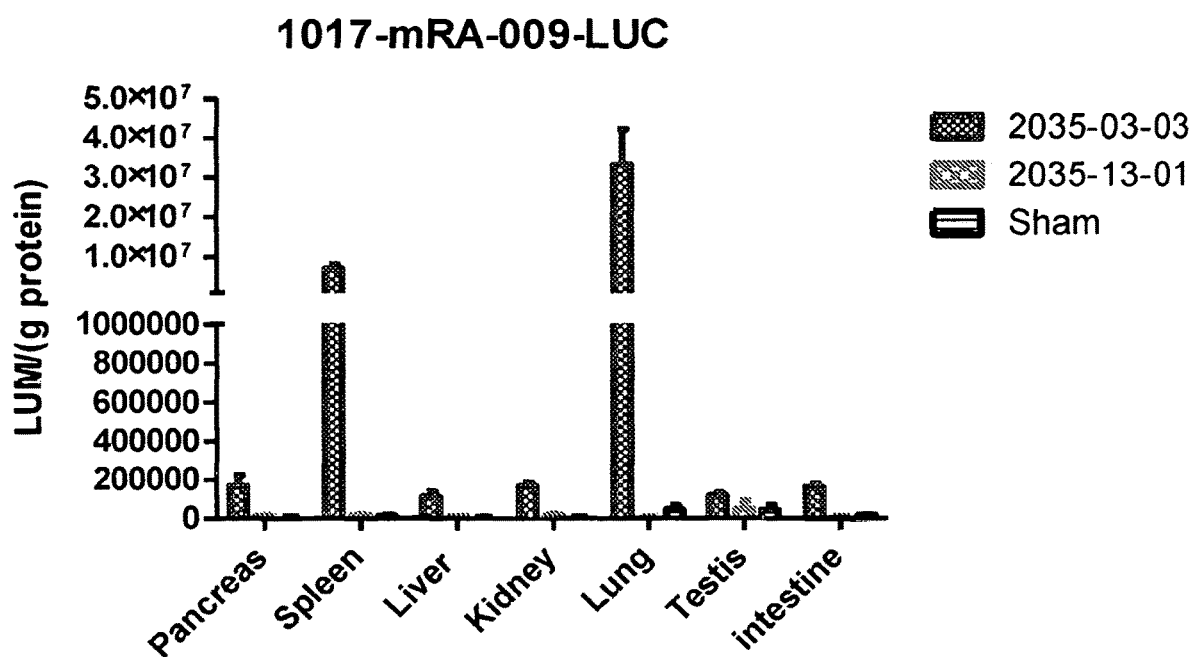
FIG. 53 shows results for delivery of Luciferase mRNA in vivo mouse using fusogenic lipid-like molecules of this invention.

FIG. 53 shows results for delivery of Luciferase mRNA in vivo mouse using fusogenic lipid-like molecules of this invention. As shown in FIG. 53, the relative delivery of mRNA was far greater in formulations containing the fusogenic molecule of this invention (2035-03-03) than for the same formulation without the fusogenic molecule (2035-13-01). In all organs observed, including pancreas, spleen, liver, kidney, lung, testis, and intestine, the delivery was advantageously and surprisingly higher for the formulation containing fusogenic compound T3.

The embodiments described herein are not limiting and one skilled in the art can readily appreciate that specific combinations of the modifications described herein can be tested without undue experimentation toward identifying nucleic acid molecules with improved RNAi activity.

All publications, patents and literature specifically mentioned herein are incorporated by reference in their entirety for all purposes.

It is understood that this invention is not limited to the particular methodology, protocols, materials, and reagents described, as these may vary. It is also to be understood that the terminology used herein is for the purpose of describing particular embodiments only, and is not intended to limit the scope of the present invention. It will be readily apparent to one skilled in the art that varying substitutions and modifications can be made to the description disclosed herein without departing from the scope and spirit of the description, and that those embodiments are within the scope of this description and the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprises," "comprising", "containing," "including", and "having" can be used interchangeably, and shall be read expansively and without limitation.

Recitation of ranges of values herein are merely intended to serve as a shorthand method of referring individually to each separate value falling within the range, unless otherwise indicated herein, and each separate value is incorporated into the specification as if it were individually recited herein. For Markush groups, those skilled in the art will recognize that this description includes the individual members, as well as subgroups of the members of the Markush group.

A compound, molecule or composition of this invention may have an ionic form for which the corresponding counterion or counterions are not shown. A person of skill in the art will immediately understand that the counterion or counterions will exist as necessary. Examples of counterions include alkali metal ions, Cl⁻, and pharmaceutically acceptable counterions.

For example, when a list of examples or components is given, such as a list of compounds, molecules or compositions suitable for this invention, it will be apparent to those skilled in the art that mixtures of the listed compounds, molecules or compositions may also be suitable.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever.

All of the features disclosed in this specification may be combined in any combination. Each feature disclosed in this specification may be replaced by an alternative feature serving the same, equivalent, or similar purpose.

Drawings in the appended claims are adjusted to fit on the page, and the appearance of molecules in drawings does not necessarily reflect any significant shape or properties of the compound depicted.

What is claimed is:

1. A fusogenic compound having Formula I

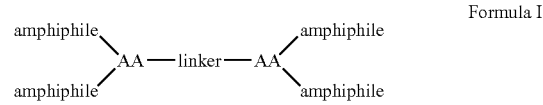

wherein each AA is independently an amino acid selected from the following structures, and any stereoisomer thereof:

111
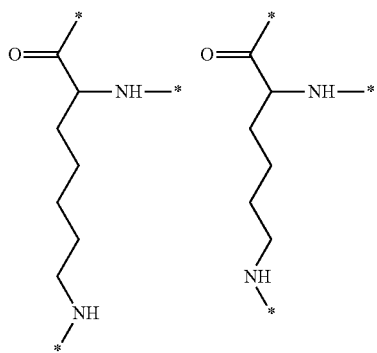
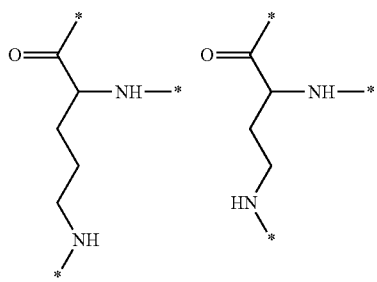
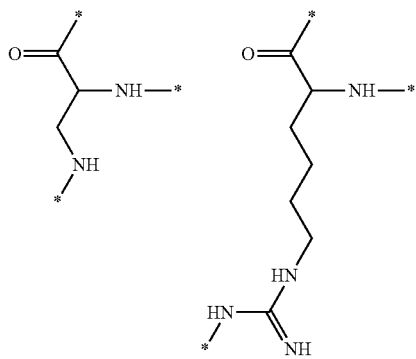
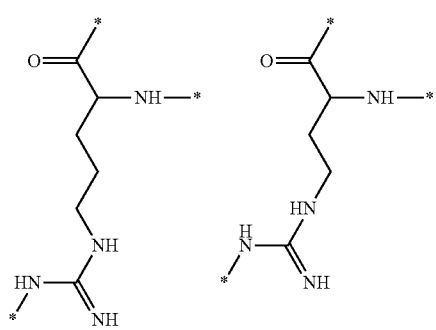
112
-continued
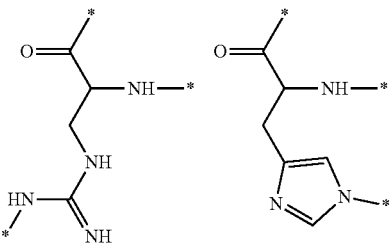
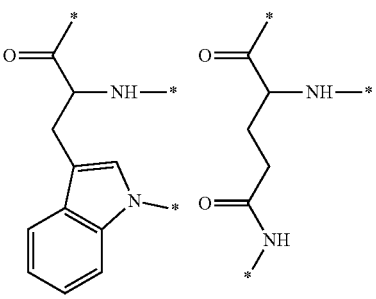
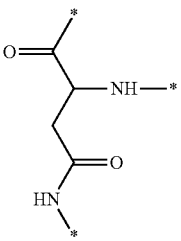
wherein the amino acid is attached to an amphiphile at each of its amino groups and is attached to the linker at its C terminus;
wherein linker has the structure
—NH(CH$_2$)$_n$(OCH$_2$CH$_2$)$_m$(CH$_2$)$_p$NH—
or
Q$^2$—(CH$_2$)$_q$X(C=O)CH$_2$CH$_2$(OCH$_2$CH$_2$)$_{\overline{m}}$(C=O)X(CH$_2$)$_t$—Q$^3$ wherein Q² is

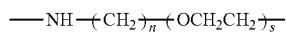

wherein Q³ is

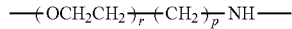

wherein X is —O—, —S—, or —NH—;
wherein n, p, q and t are independently for each occurrence 1 to 3;
wherein m is independently 1 to 10;
wherein r and s are independently for each occurrence 1 to 5; and
wherein each amphiphile is independently selected from Formula (II), Formula (IV), Formula (V), and Formula (VI), as follows:

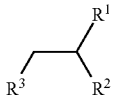

Formula (II)

wherein R¹ in Formula (II) is $CH_2(CH_2)_nO(C=O)R^4$, $CH_2(CH_2)_nNH(C=O)R^4$, $CH_2(CH_2)_n(C=O)OR^4$, or $CH_2(CH_2)_n(C=O)NHR^4$;
wherein R² in Formula (II) is $CH_2(CH_2)_mO(C=O)R^5$, $CH_2(CH_2)_mNH(C=O)R^5$, $CH_2(CH_2)_m(C=O)OR^5$, or $CH_2(CH_2)_m(C=O)NHR^5$;
wherein n and m in Formula (II) are each independently from 1 to 2; and R⁴ and R⁵ are independently for each occurrence a C(12-20) alkyl group, or a C(12-20) alkenyl group; and
wherein R³ in Formula (II) is branched or unbranched C(1-8) alkandiyl;

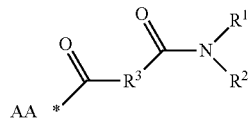

Formula (IV)

wherein R¹ in Formula (IV) is (C=O)R⁴;
wherein R² in Formula (IV) is (C=O)OR⁵;
wherein R⁴ and R⁵ in Formula (IV) are independently for each occurrence a C(12-20) alkyl group, or a C(12-20) alkenyl group;
wherein Z in Formula (IV) is NH;
wherein p in Formula (IV) is 1 to 4;
wherein R³ in Formula (IV) is
—C(1-12) alkyl group that is substituted with a —(C=O)— which is attached to AA;

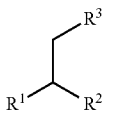

Formula (V)

wherein R¹ in Formula (V) is (C=O)OR⁴;
wherein R² in Formula (V) is NH(C=O)R⁵;
wherein R⁴ and R⁵ in Formula (V) are independently for each occurrence a C(12-20) alkyl group, or a C(12-20) alkenyl group;
wherein R³ in Formula (V) is branched or unbranched —O(C=O)—C(1-8)alkandiyl-(C=O)— which is attached to AA;

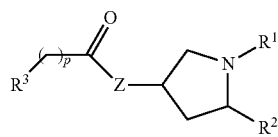

Formula (VI)

wherein R¹ in Formula (VI) is O(C=O)R⁴;
wherein R² in Formula (VI) is O(C=O)R⁵;
wherein R⁴ and R⁵ in Formula (VI) are independently for each occurrence a C(12-20) alkyl group, or a C(12-20) alkenyl group;
wherein R³ in formula (VI) is

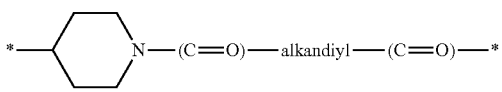

which is attached to AA
wherein one or two of the amphiphiles may optionally be absent and replaced by a pharmaceutically acceptable organic chemical group selected from an alkyl group, alkenyl, alkynyl, acetyl, Boc, Fmoc, TFA, and CBZ, having 1-400 atoms selected from carbon, oxygen, nitrogen, sulfur, fluorine, and hydrogen.

2. The fusogenic compound of claim 1, wherein one or two of the amphiphiles are absent and replaced by the pharmaceutically acceptable organic chemical group.

3. The fusogenic compound of claim 2, wherein the pharmaceutically acceptable organic chemical group is alkyl, alkenyl, alkynyl, acetyl, Boc, Fmoc, TFA, or CBZ.

4. The fusogenic compound of claim 2, wherein the compound is selected from the following:
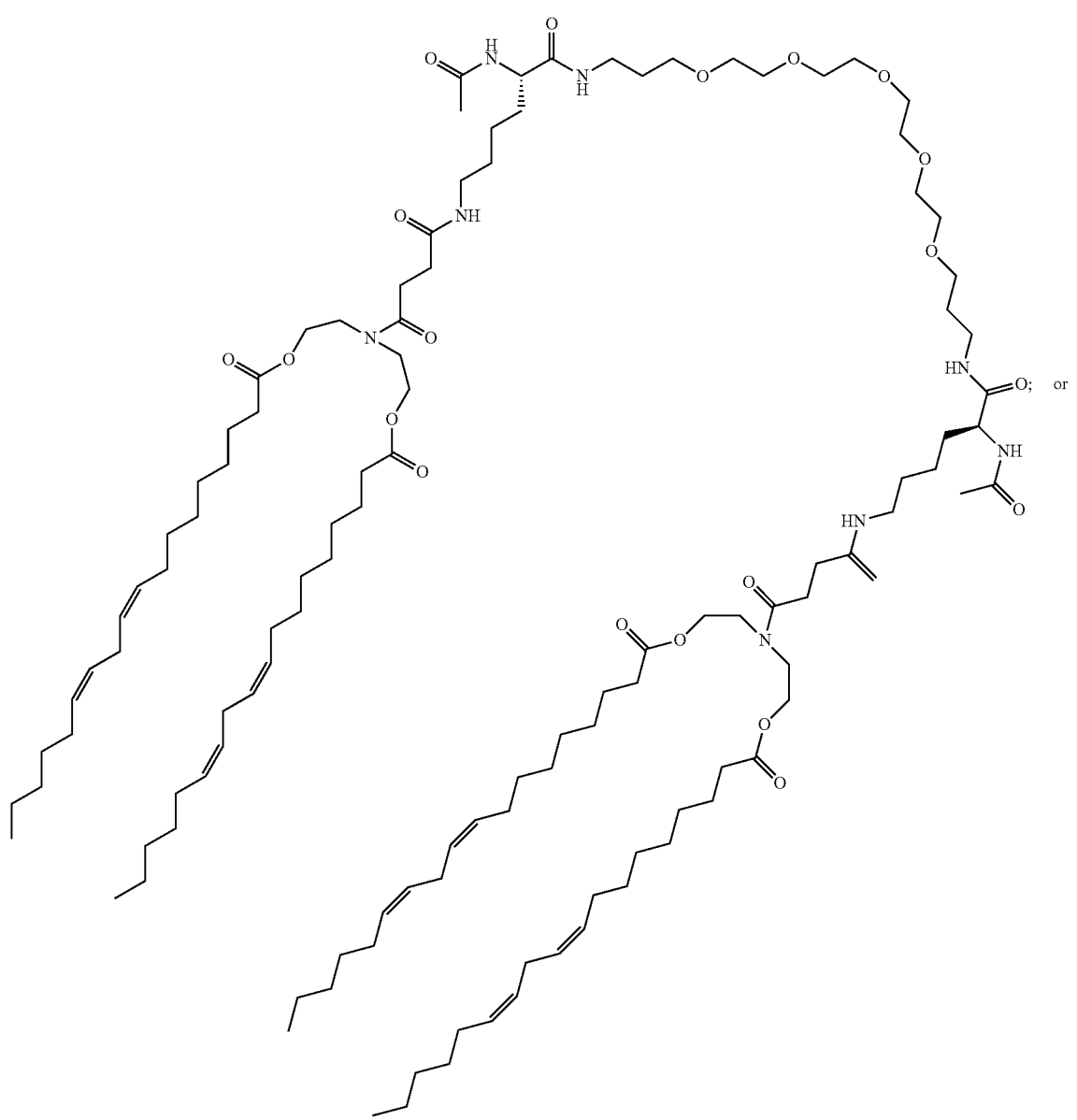
Compound T13

-continued
Compound T14
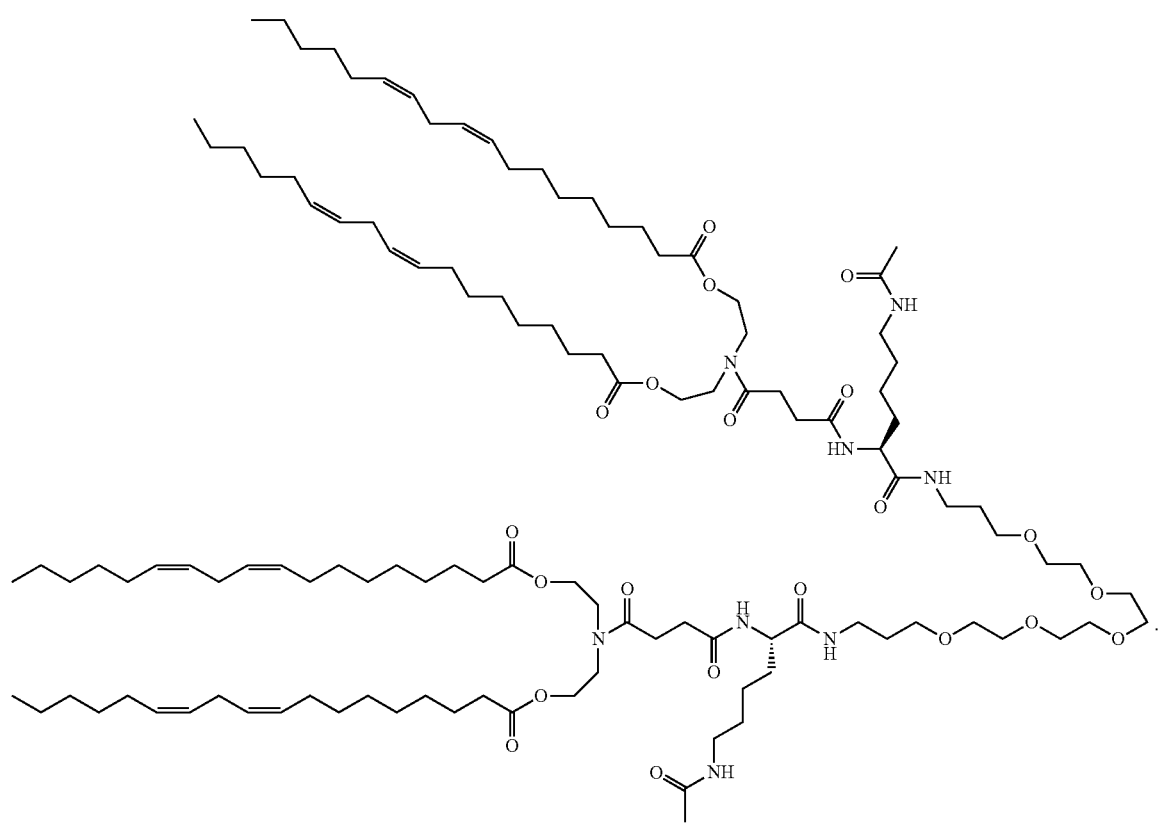
5. The fusogenic compound of claim 1, wherein $R^3$ in Formula (II) is branched or unbranched C(2-8)alkandiyl.
6. The fusogenic compound of claim 1, wherein the compound is selected from the following:

Compound R4
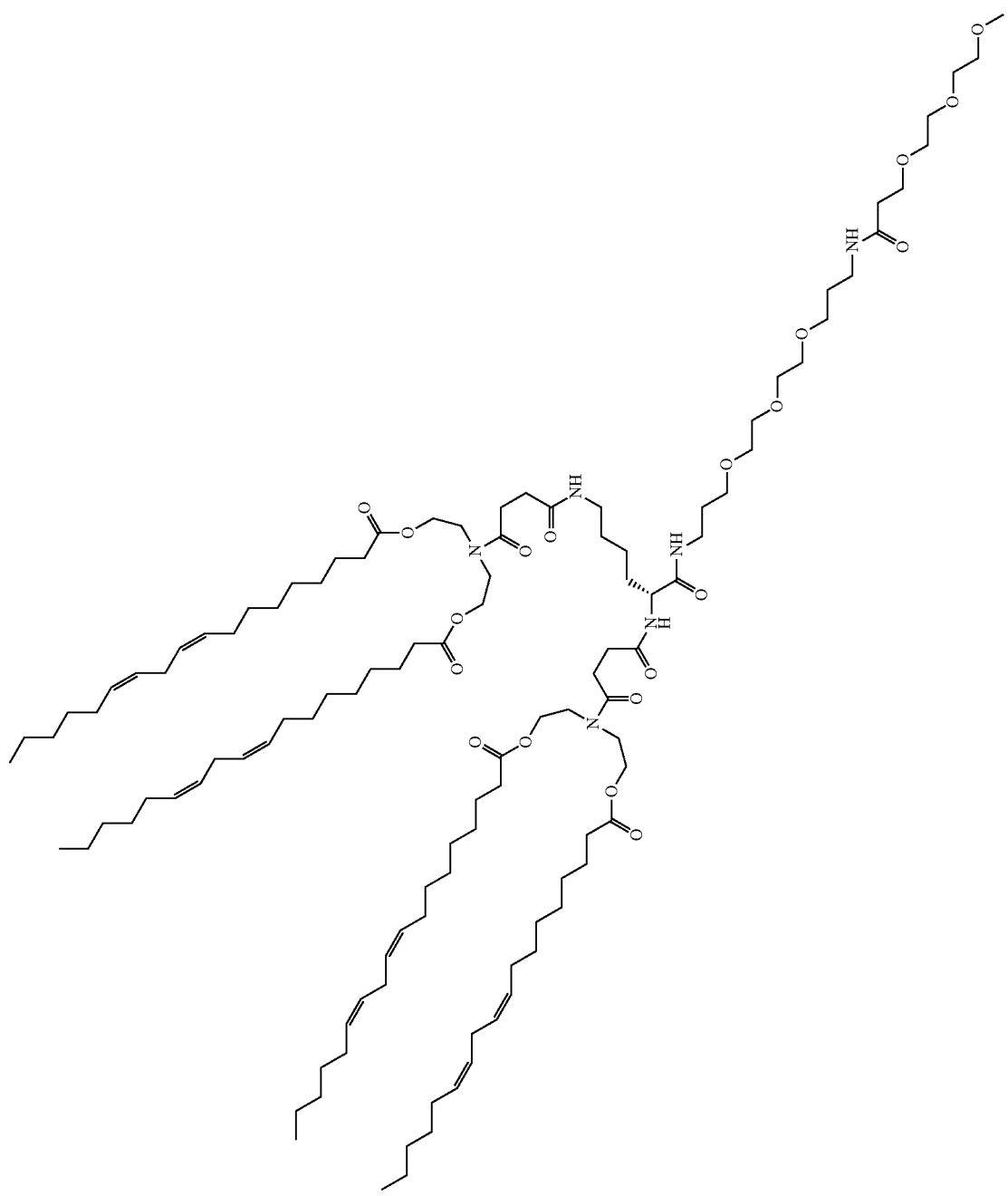

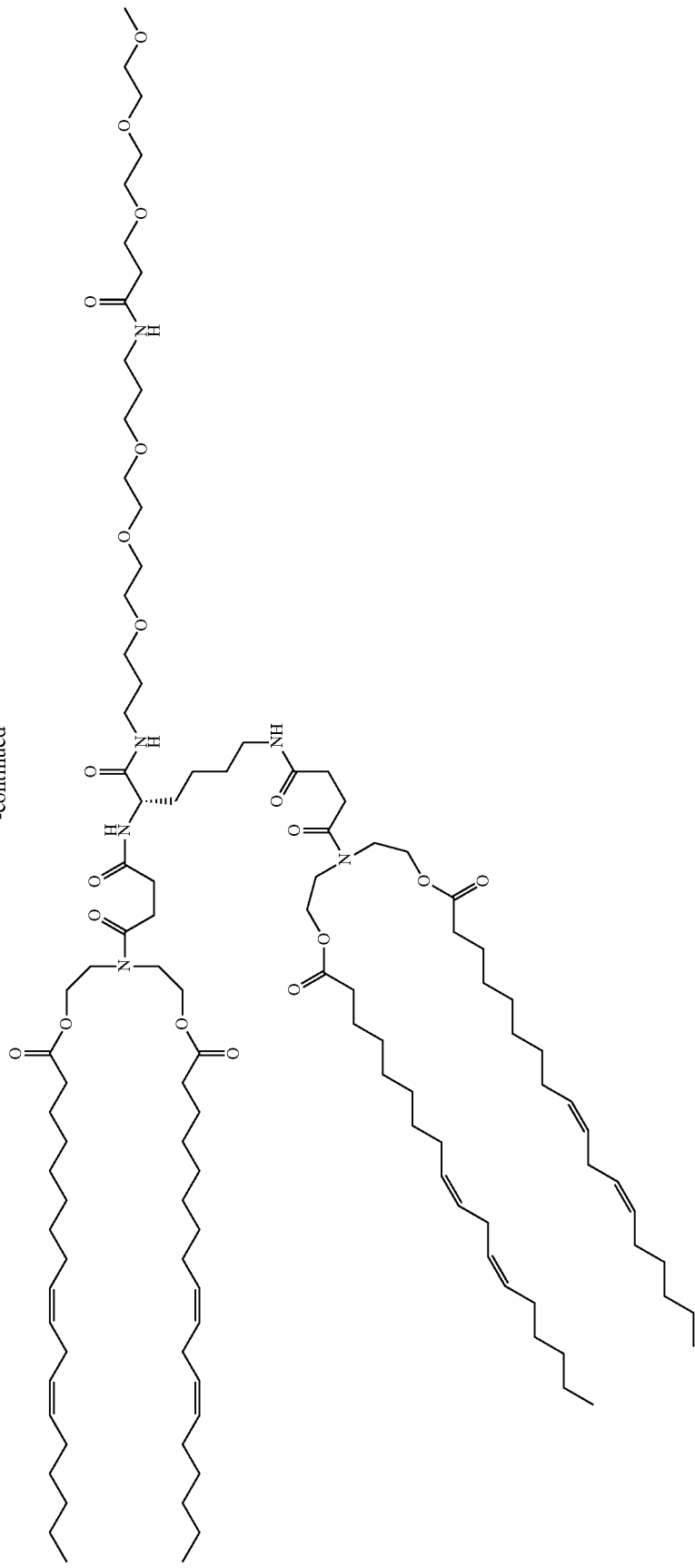

Compound S6
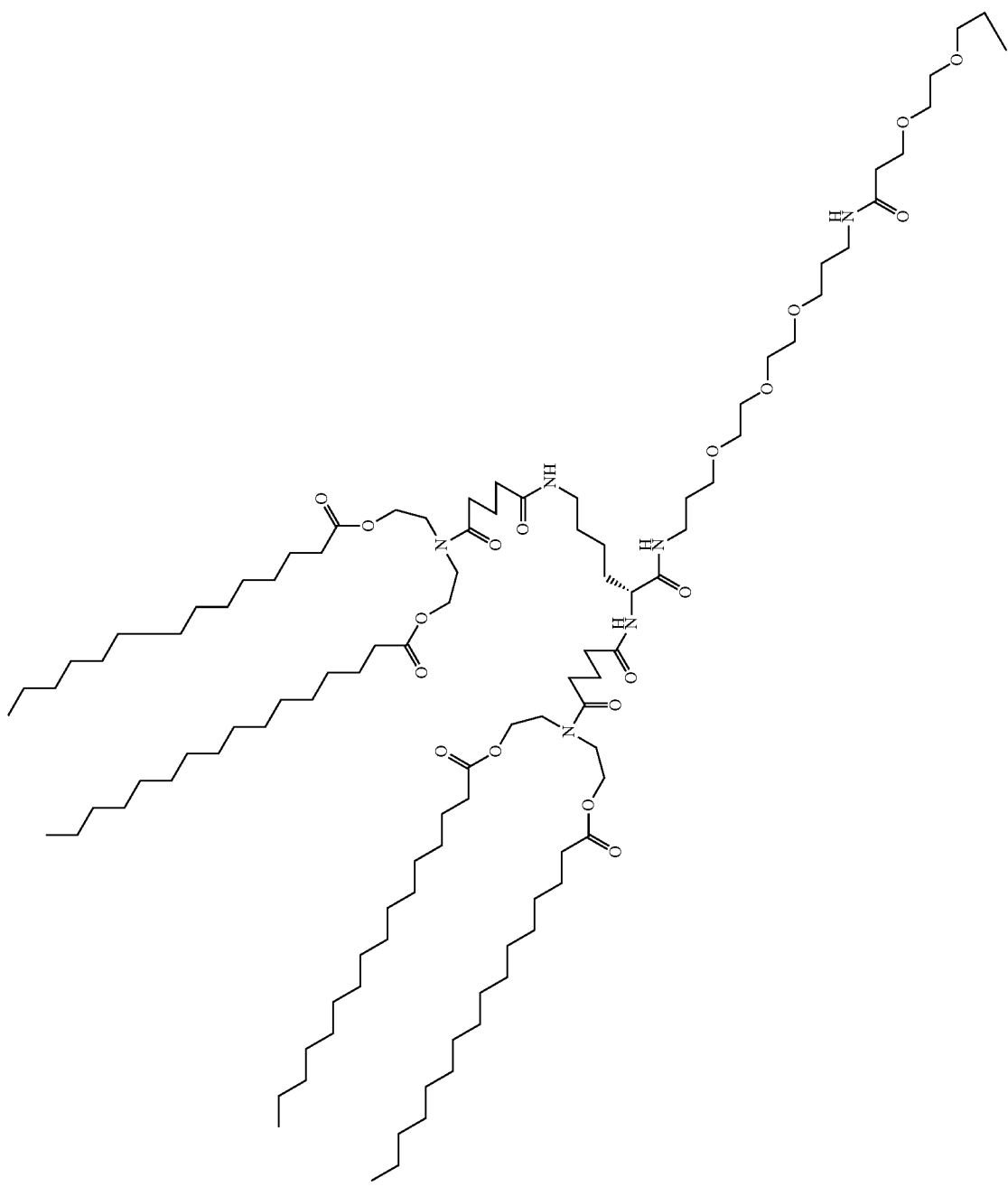

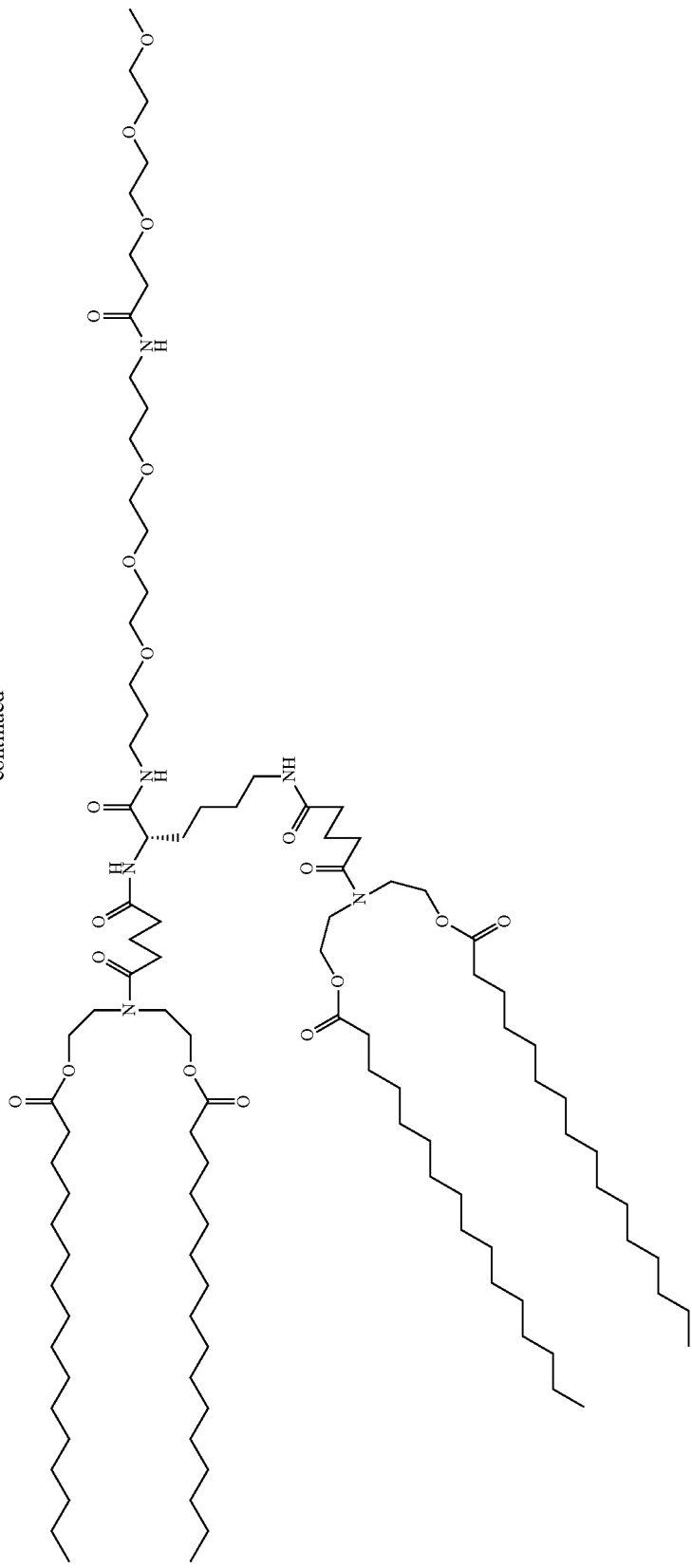

-continued
Compound S7
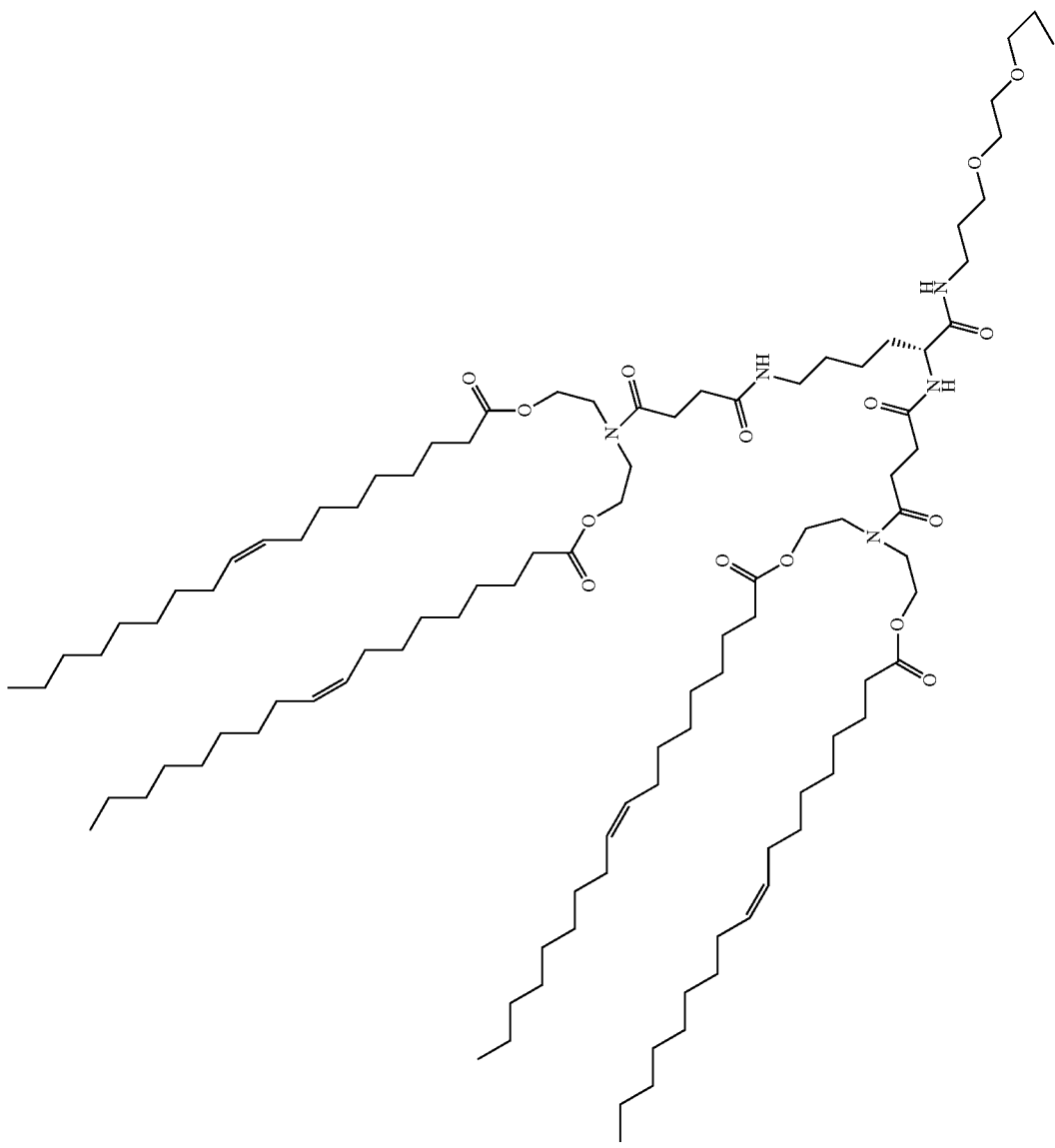

-continued
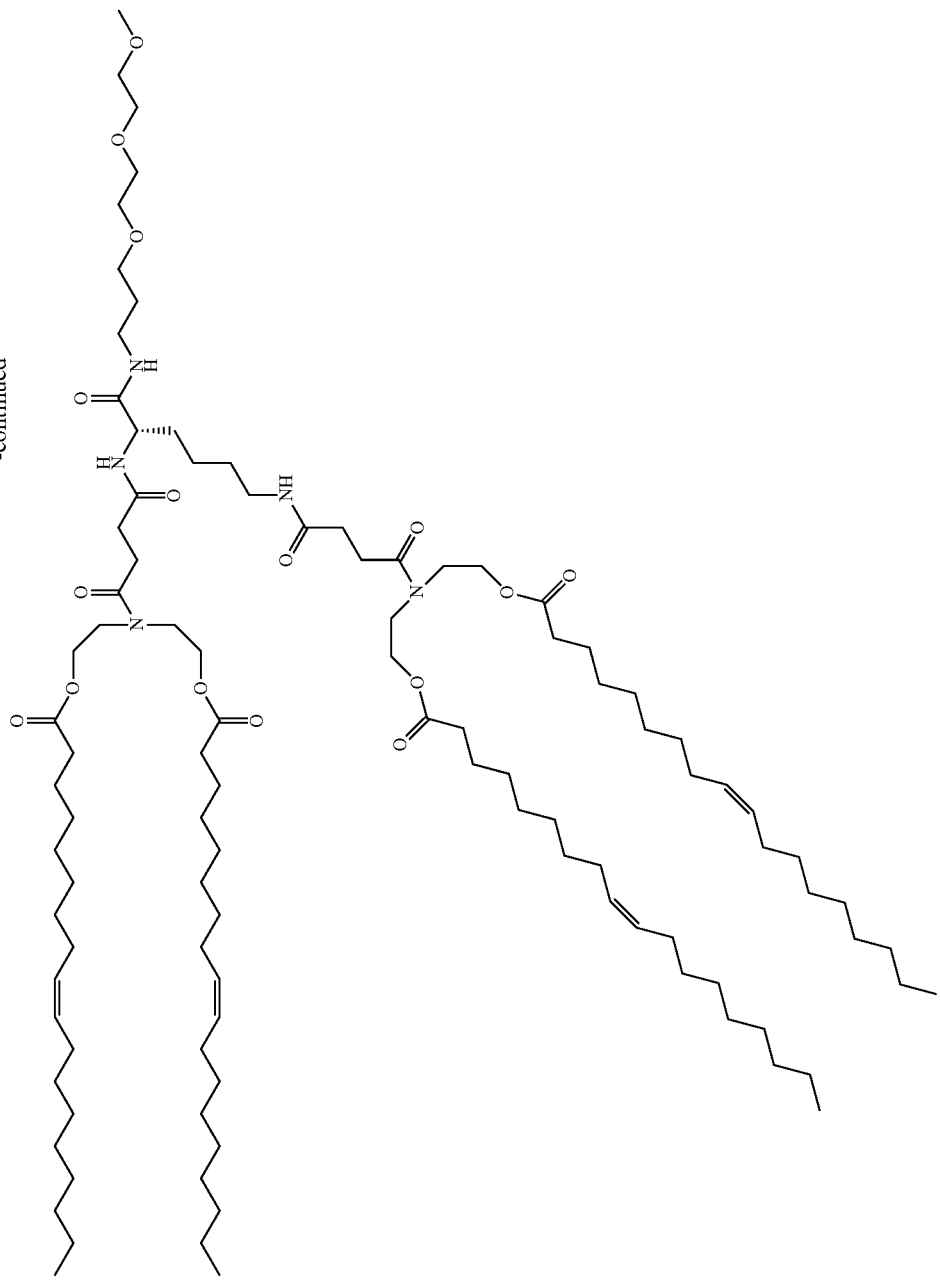

Compound T1
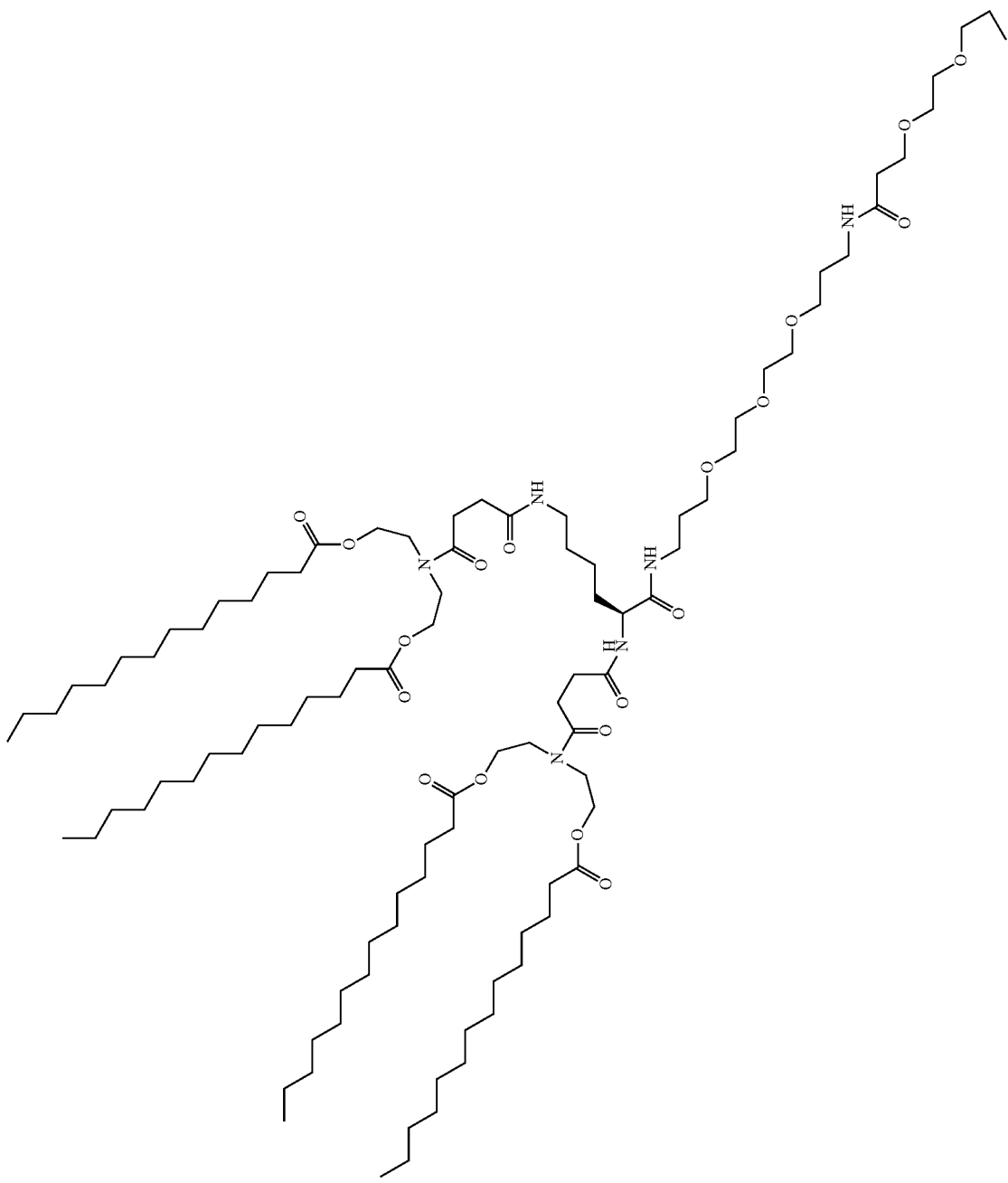

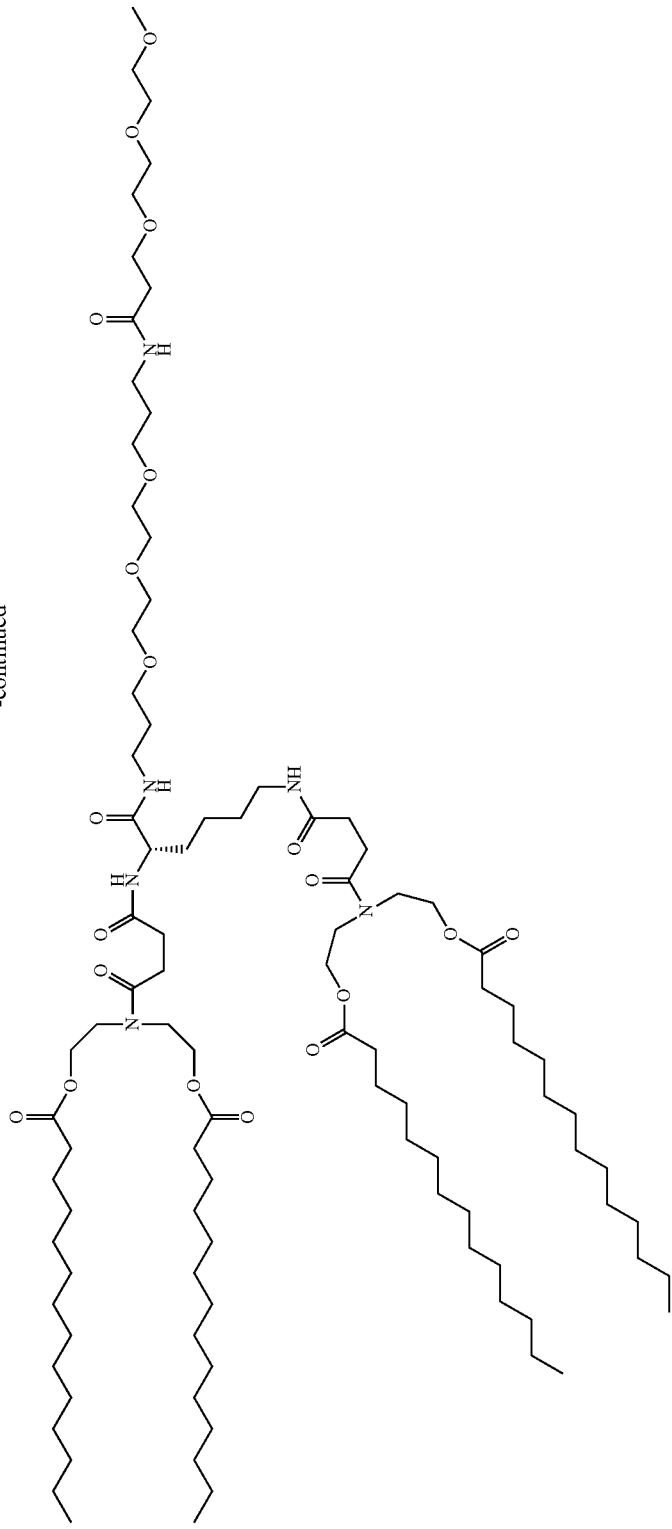

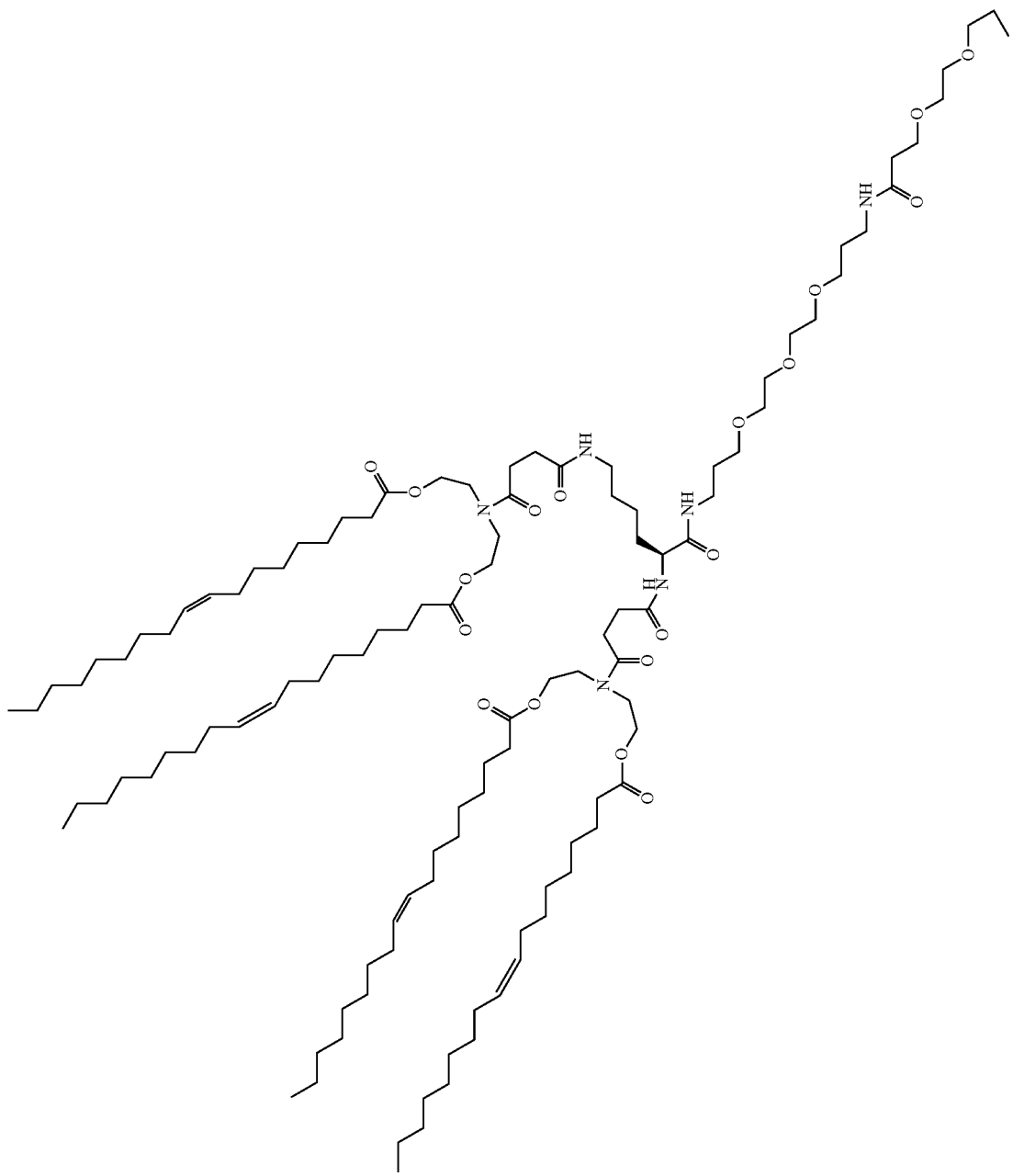
Compound S8

-continued
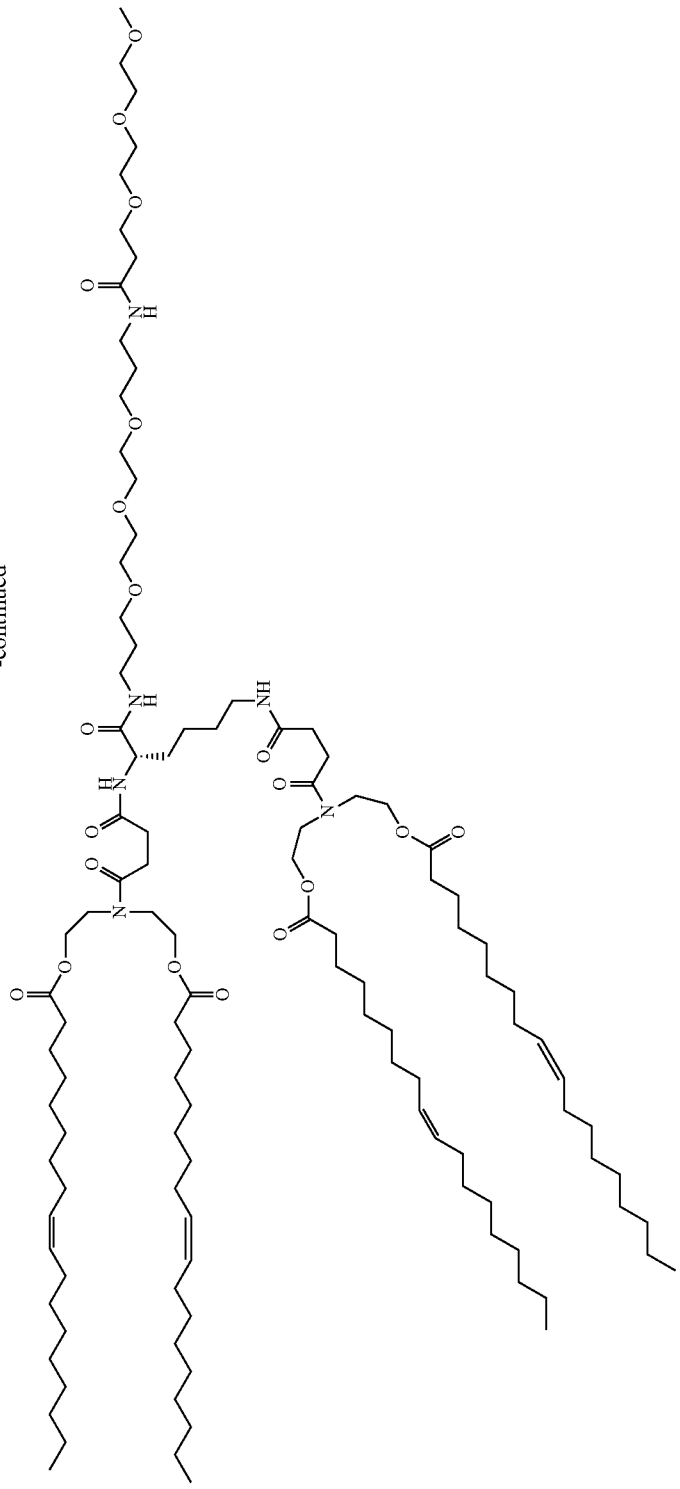

-continued
Compound T2
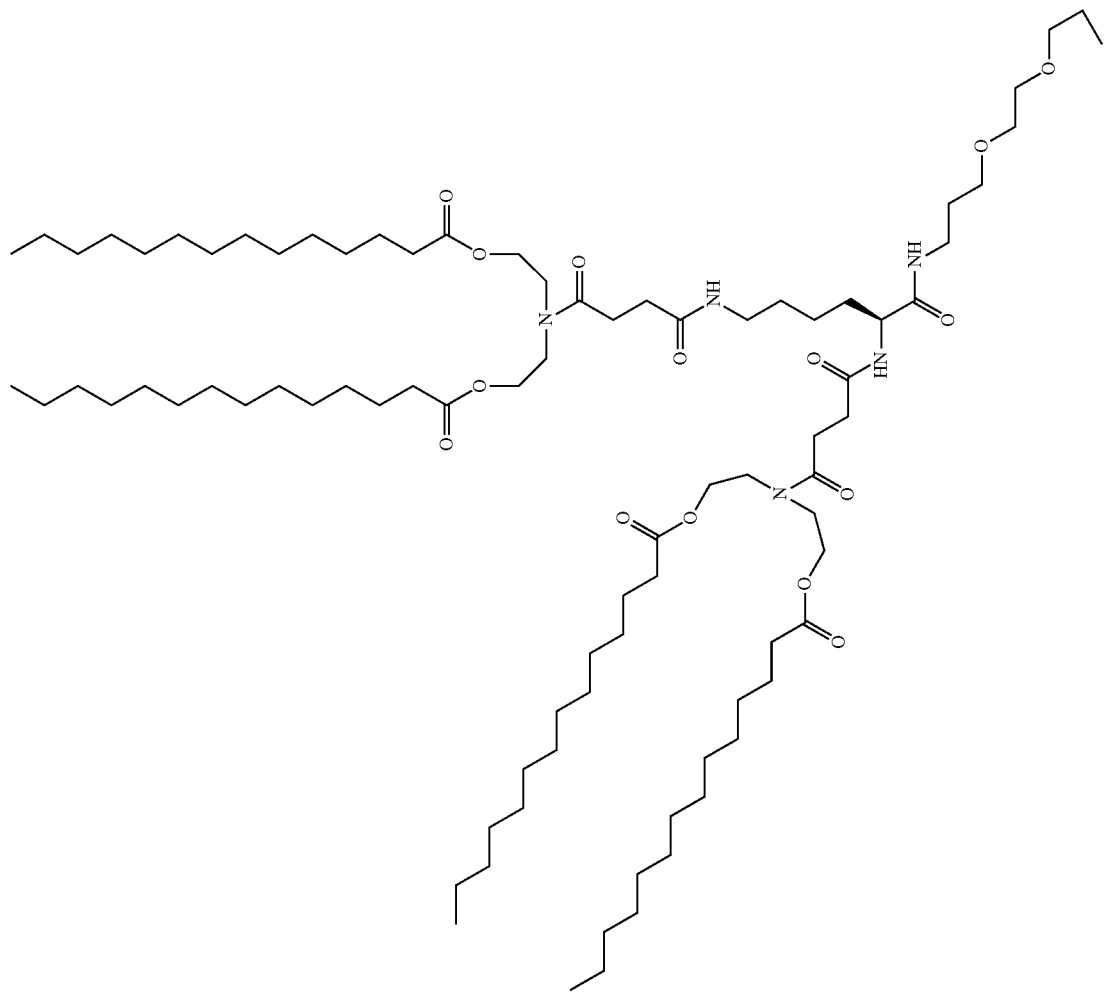

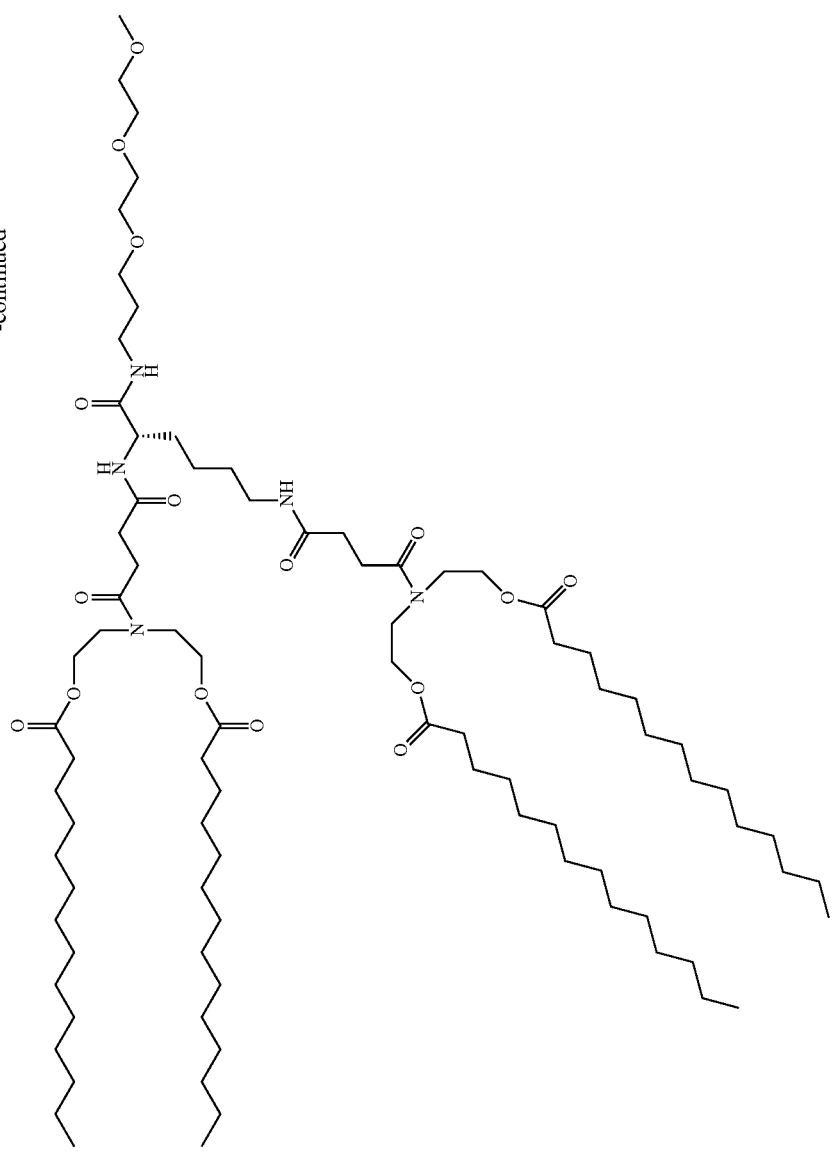

-continued
Compound T4
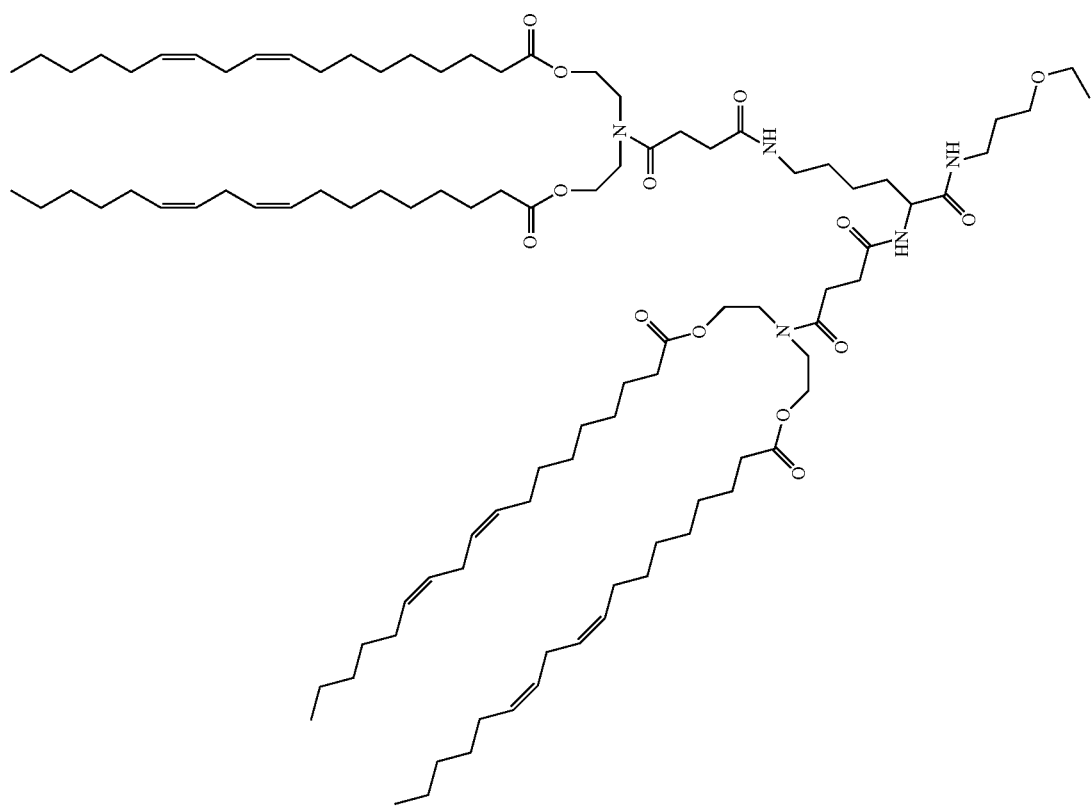

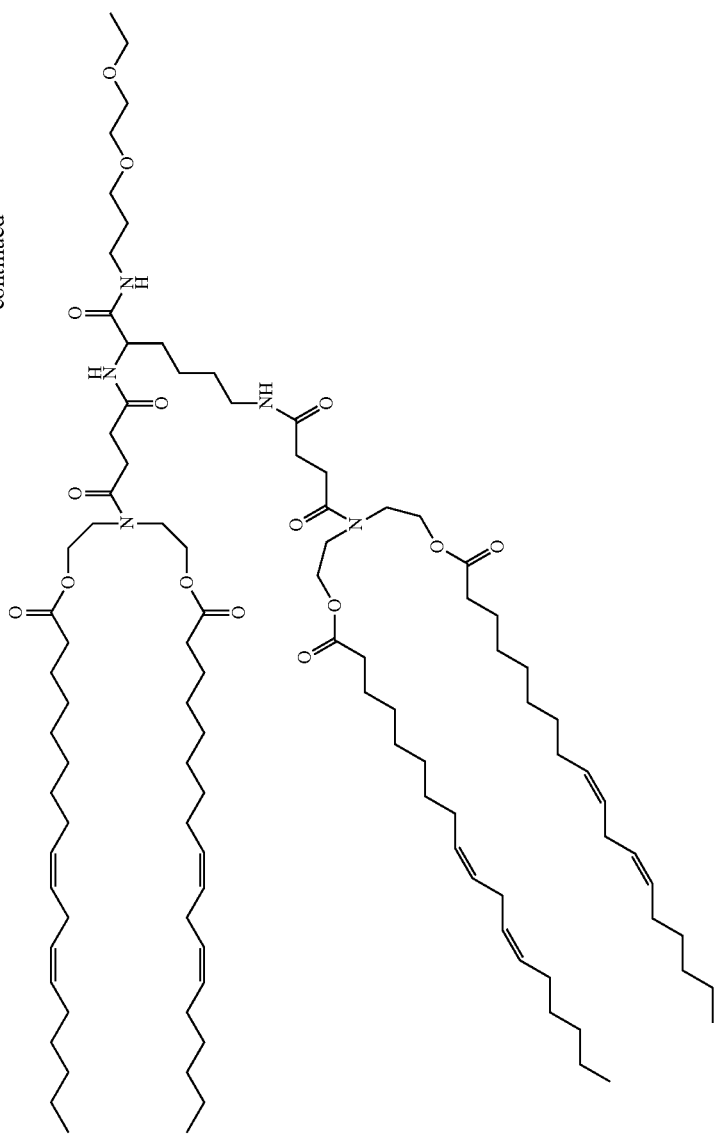

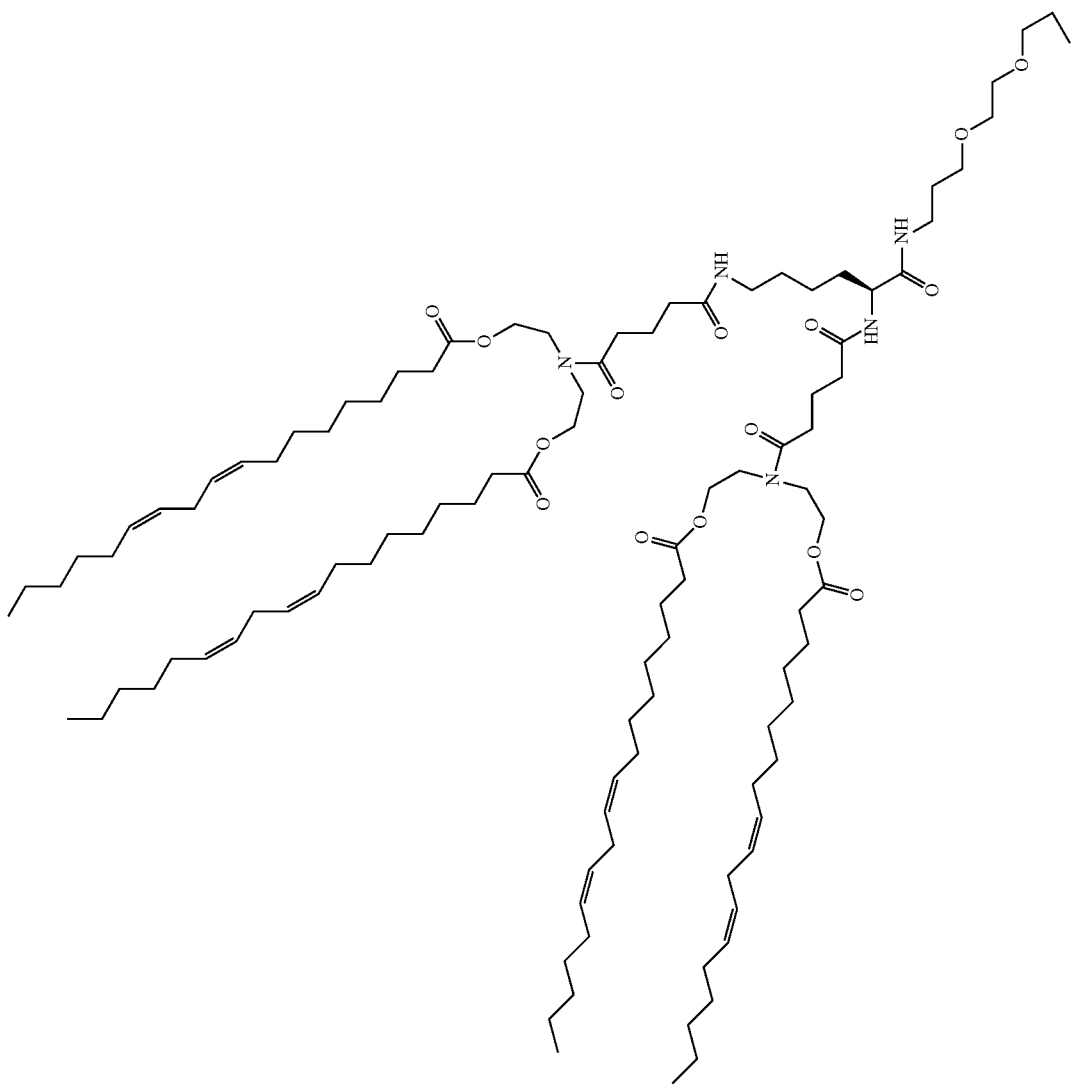
Compound T5

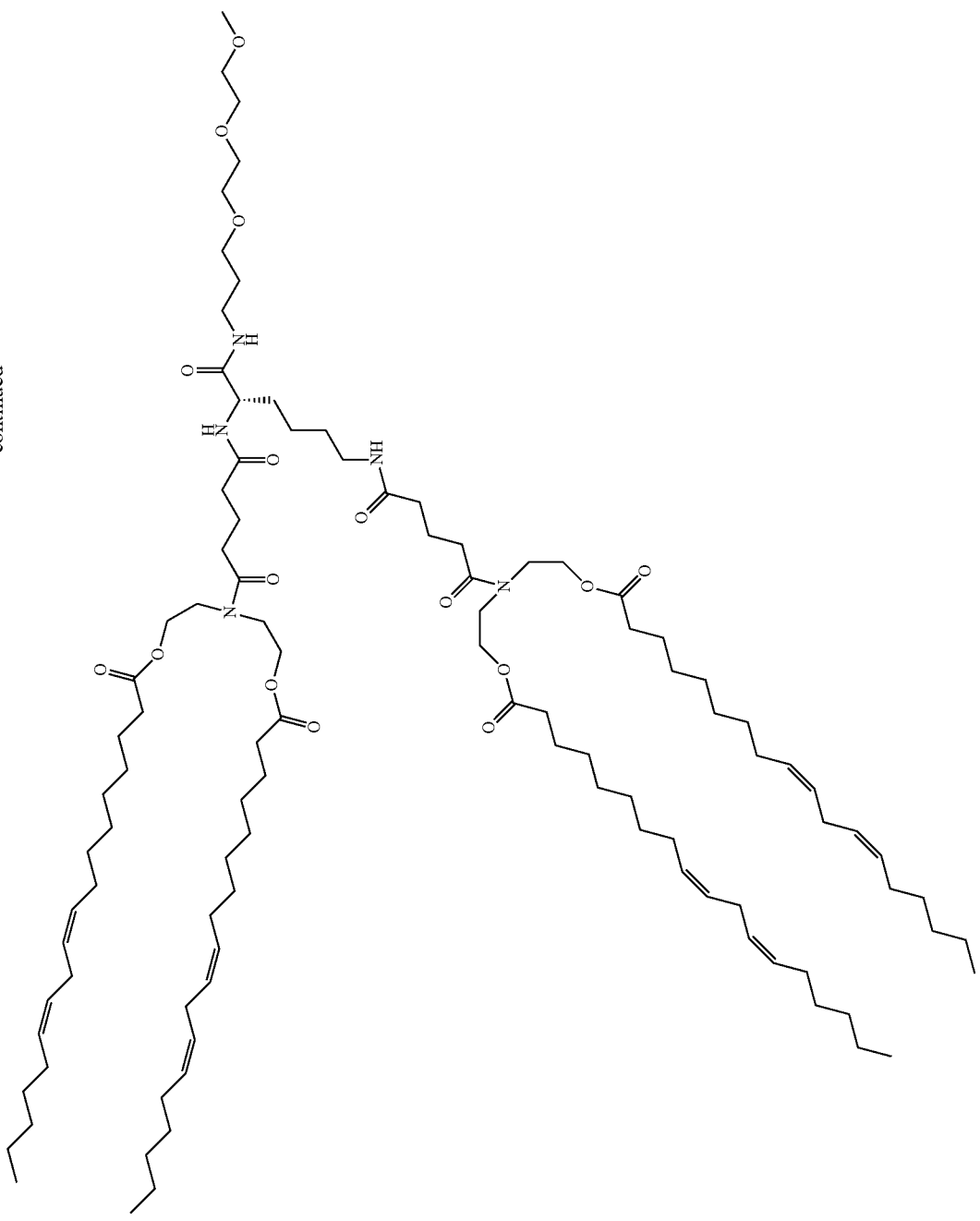

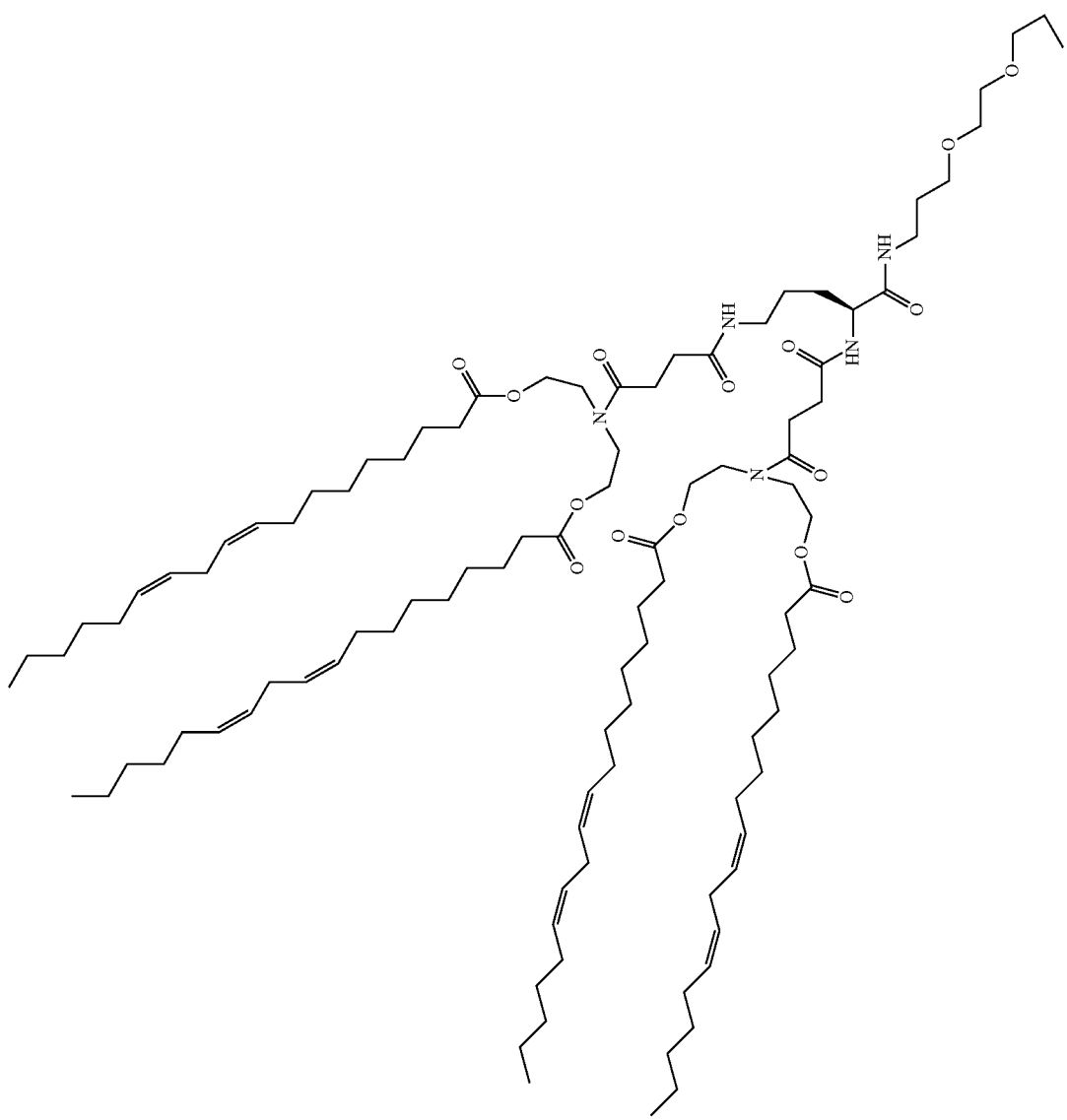
Compound T6

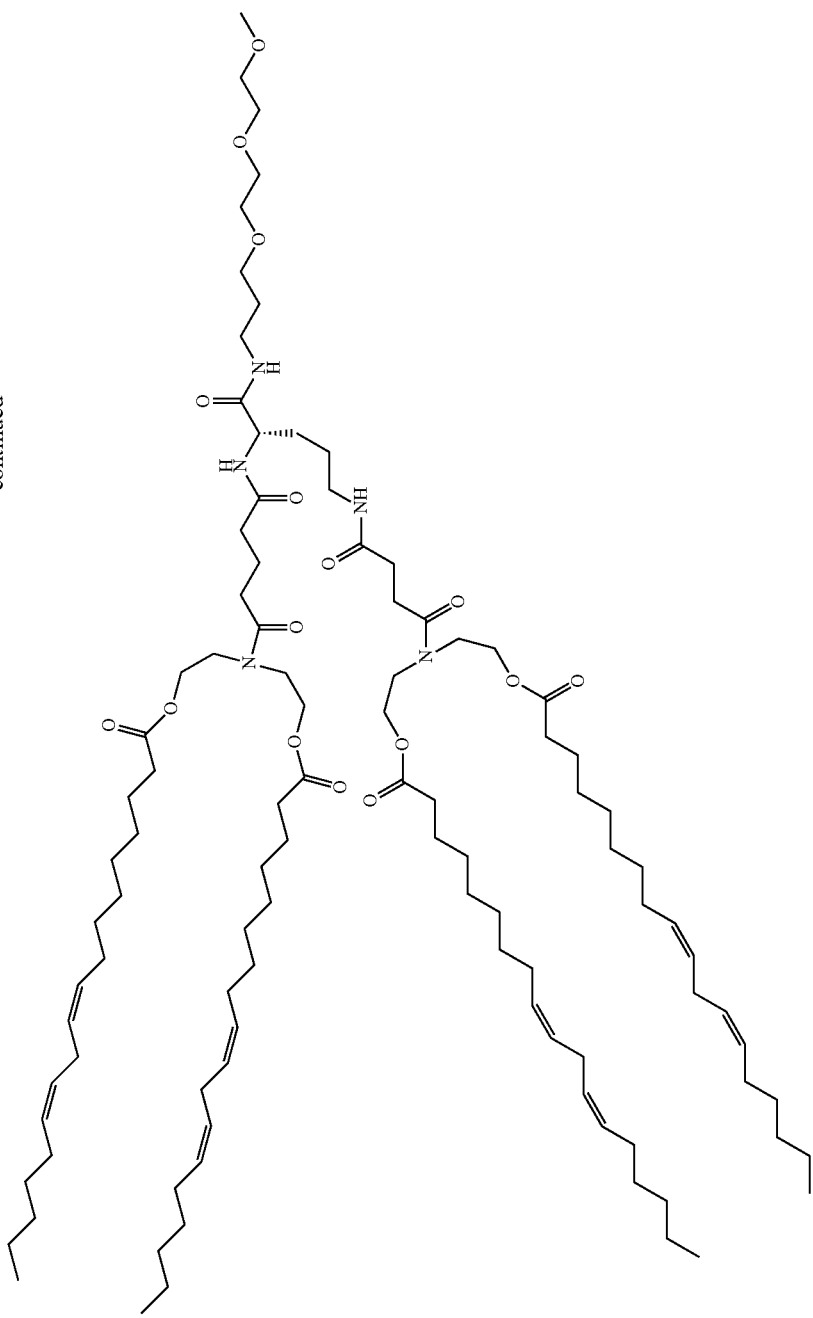

-continued
Compound T7
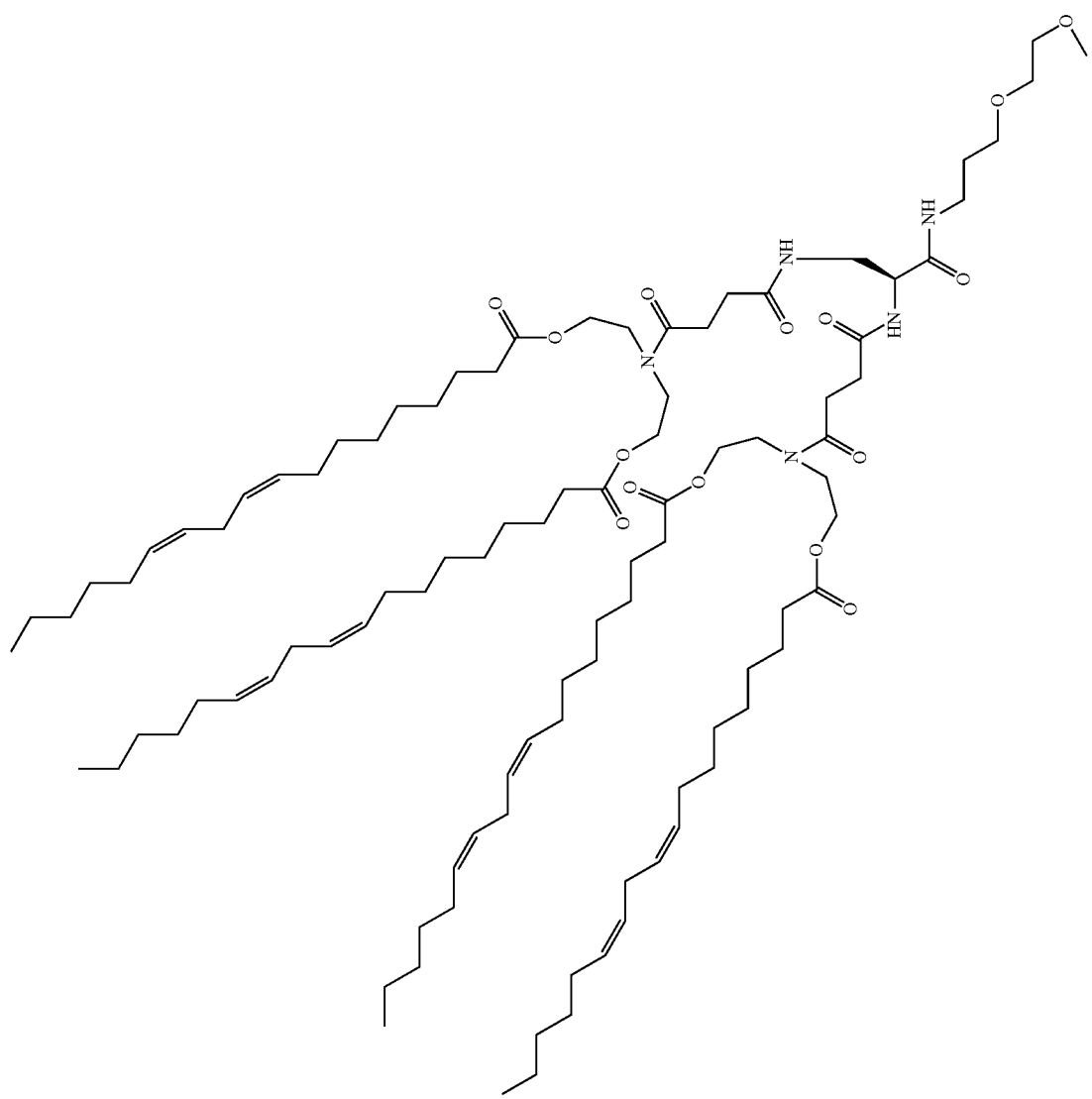

-continued
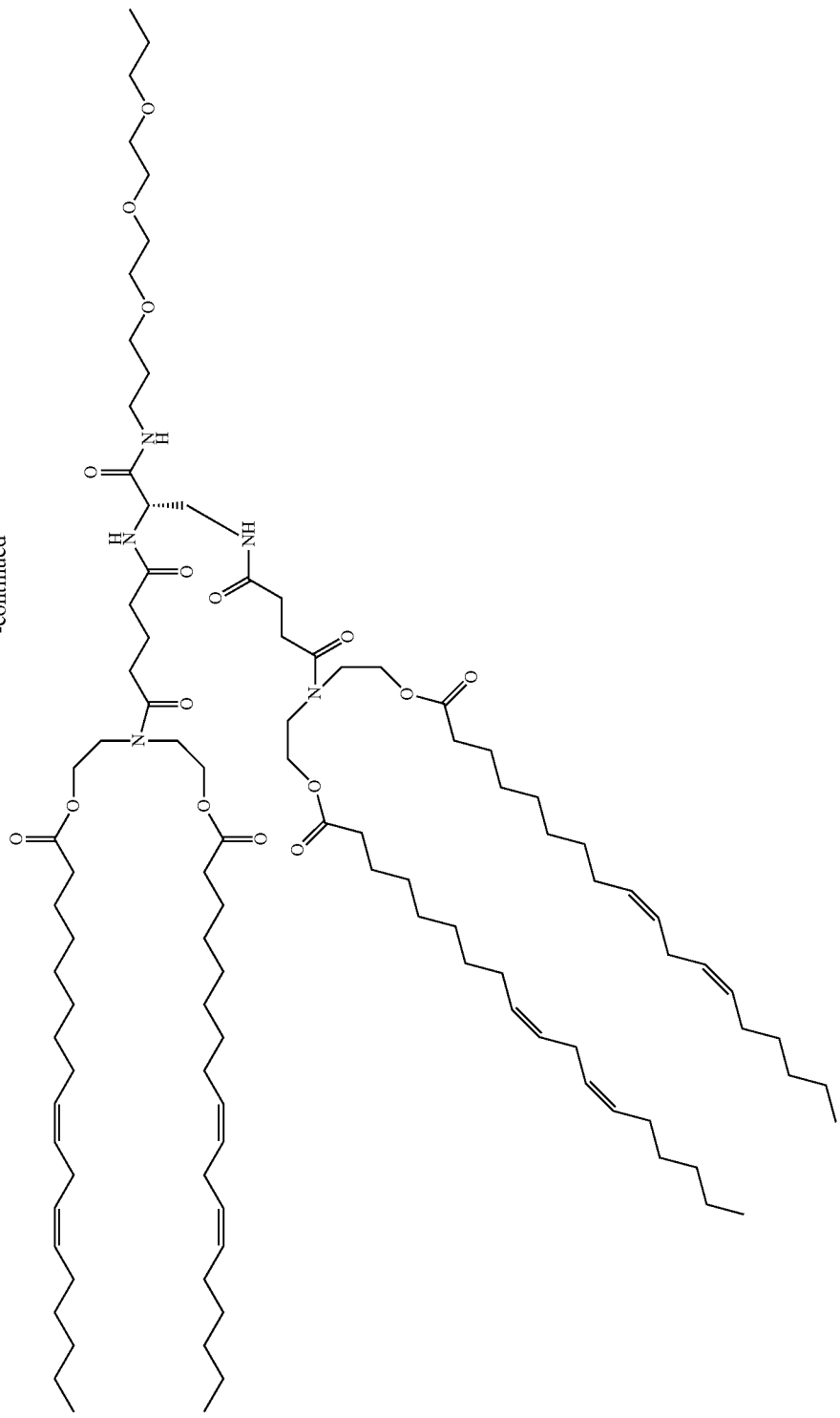

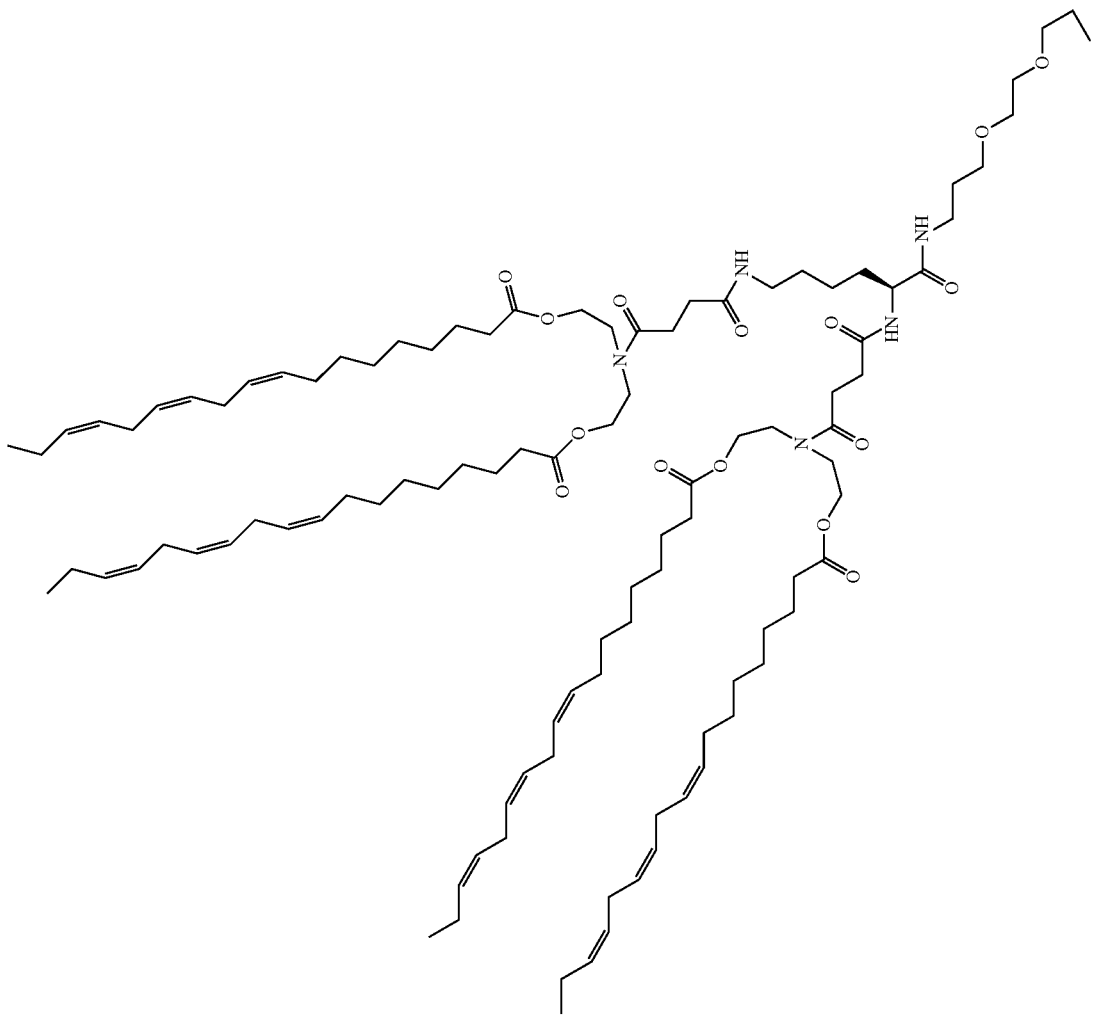
Compound T8

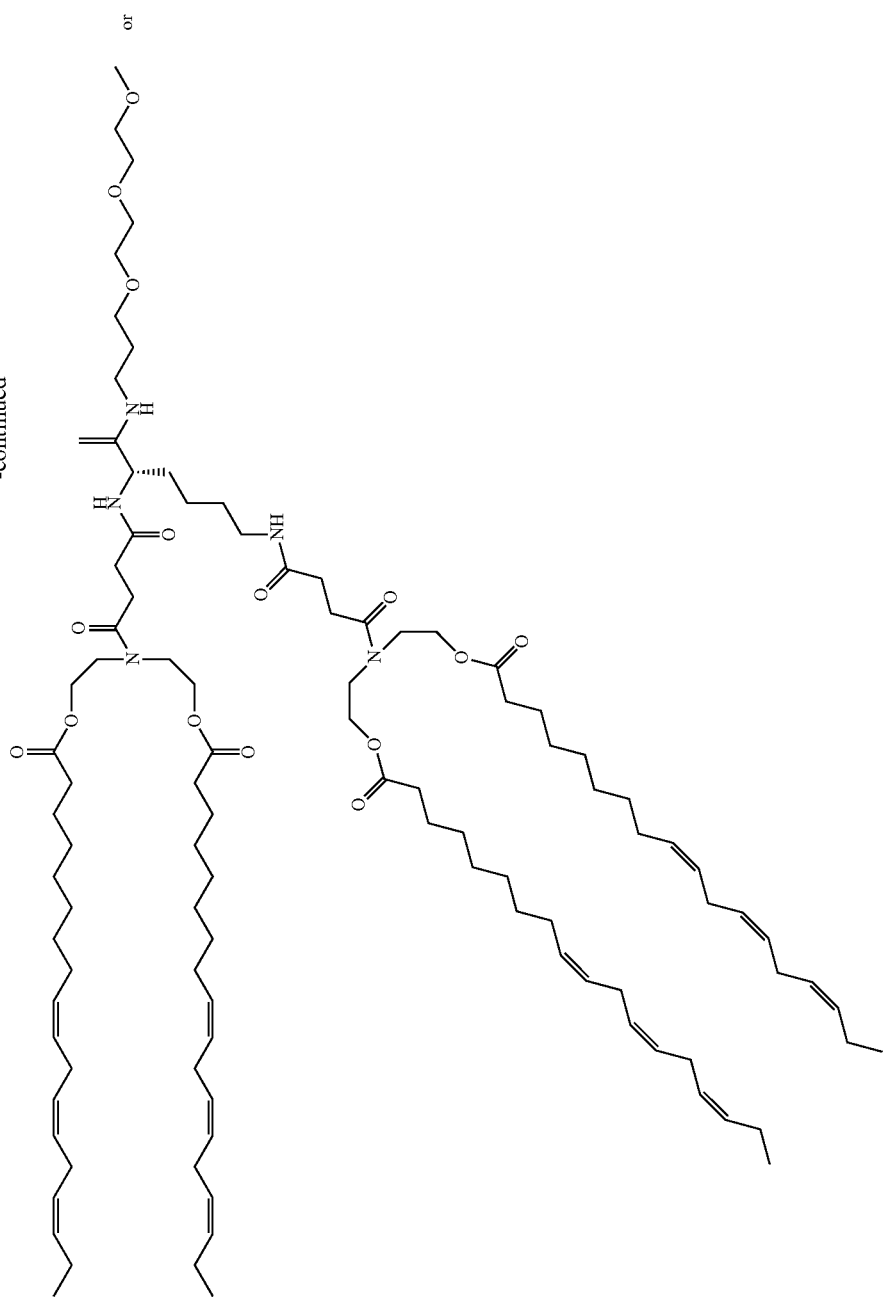

-continued
Compound T3
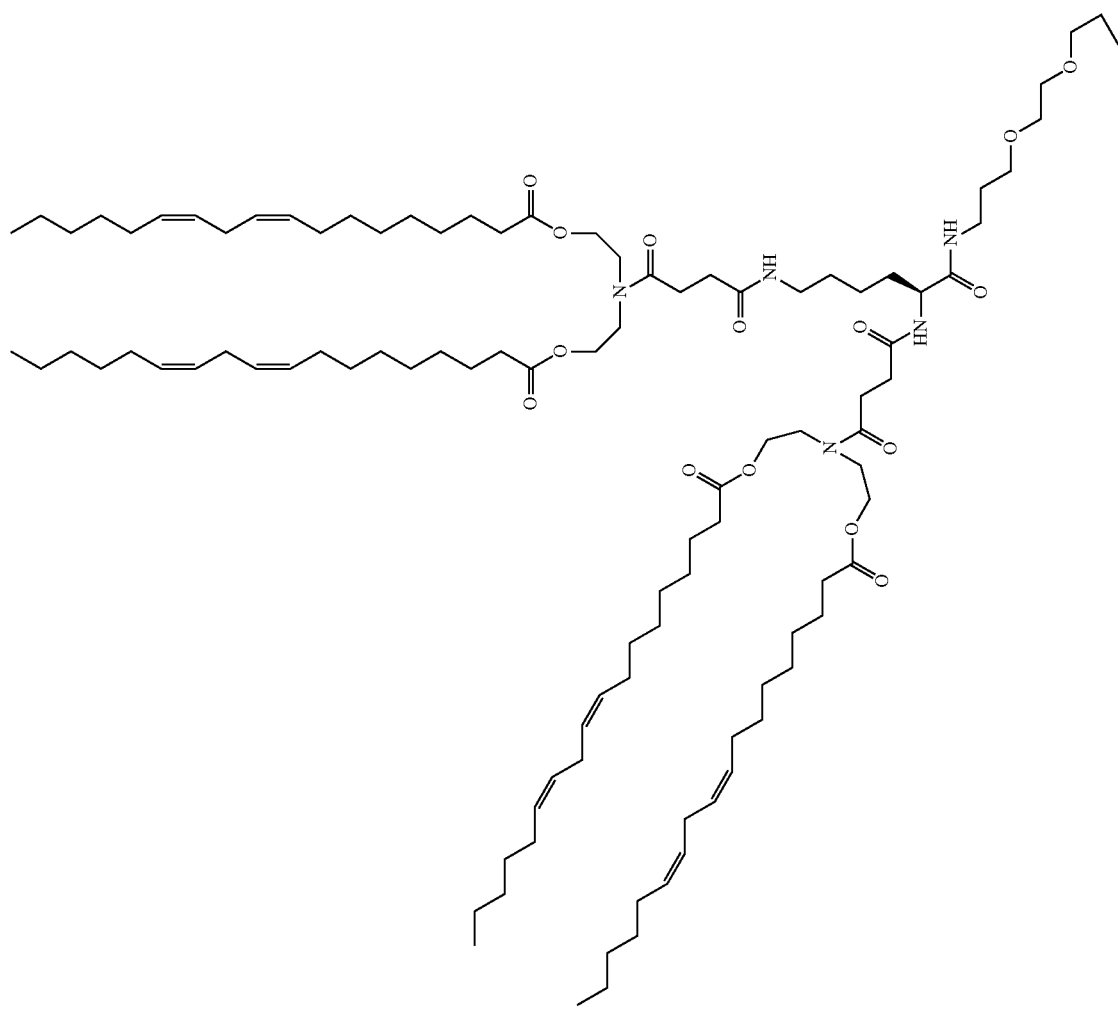

-continued
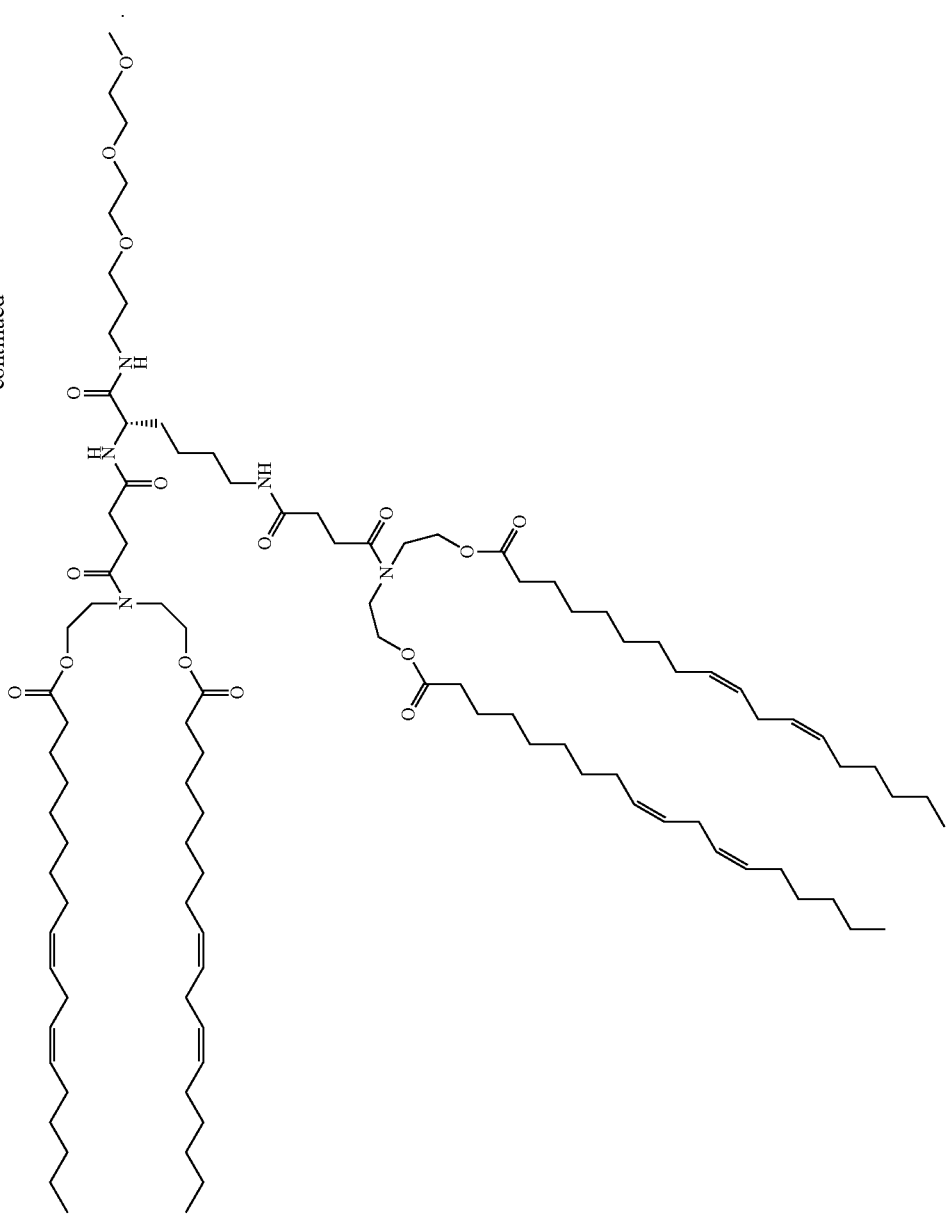

7. The fusogenic compound of claim 1, wherein $R^4$ and $R^5$ in Formula (IV) are independently for each occurrence a C(14-18) alkyl group, or a C(14-18) alkenyl group.
8. The fusogenic compound of claim 1, wherein the compound is compound T10:
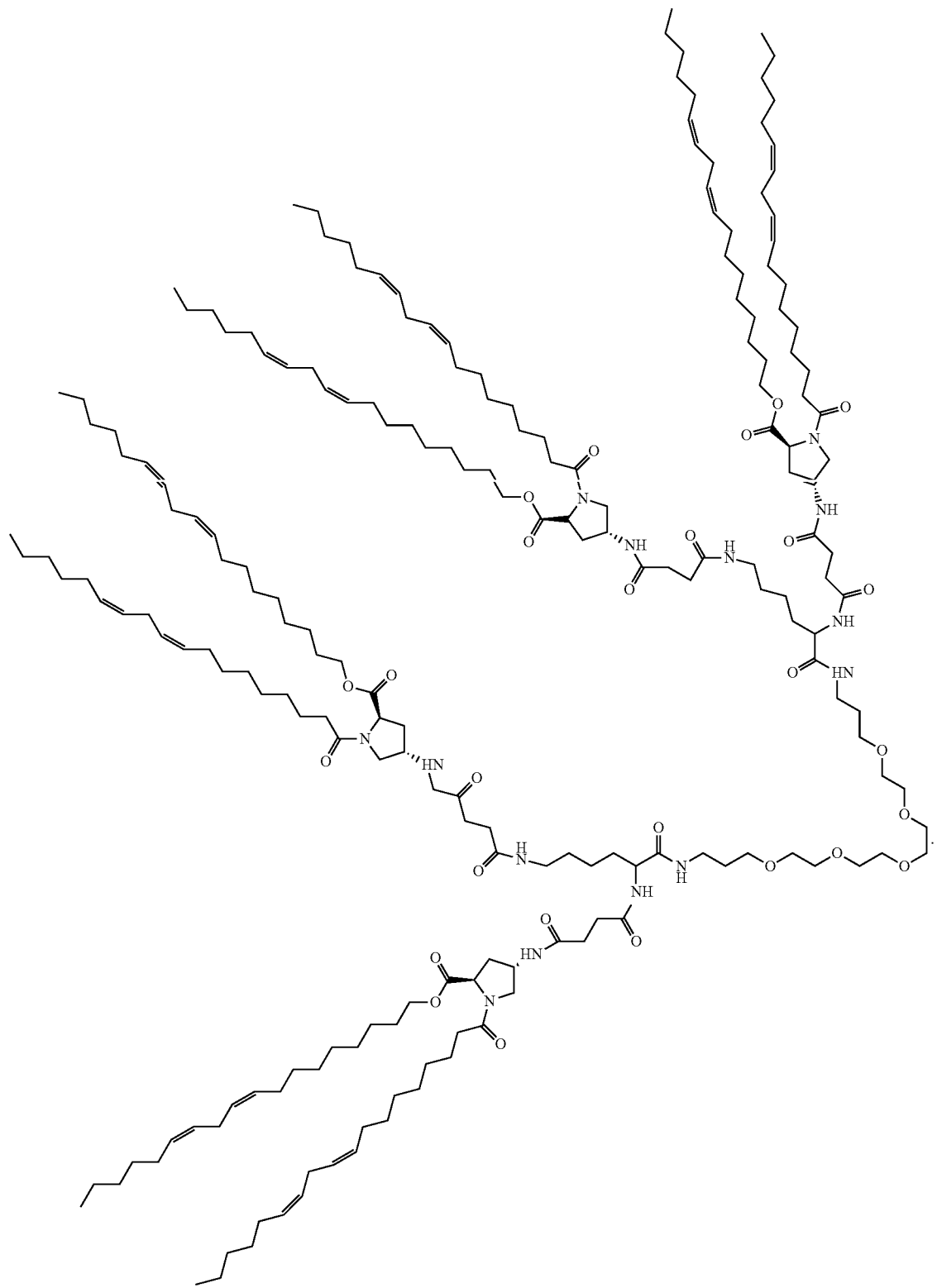
Compound T10

9. The fusogenic compound of claim 1, wherein $R^4$ and $R^5$ in Formula (V) are independently for each occurrence a C(14-18) alkyl group, or a C(14-18) alkenyl group.
10. The fusogenic compound of claim 1, wherein the compound is compound T12:
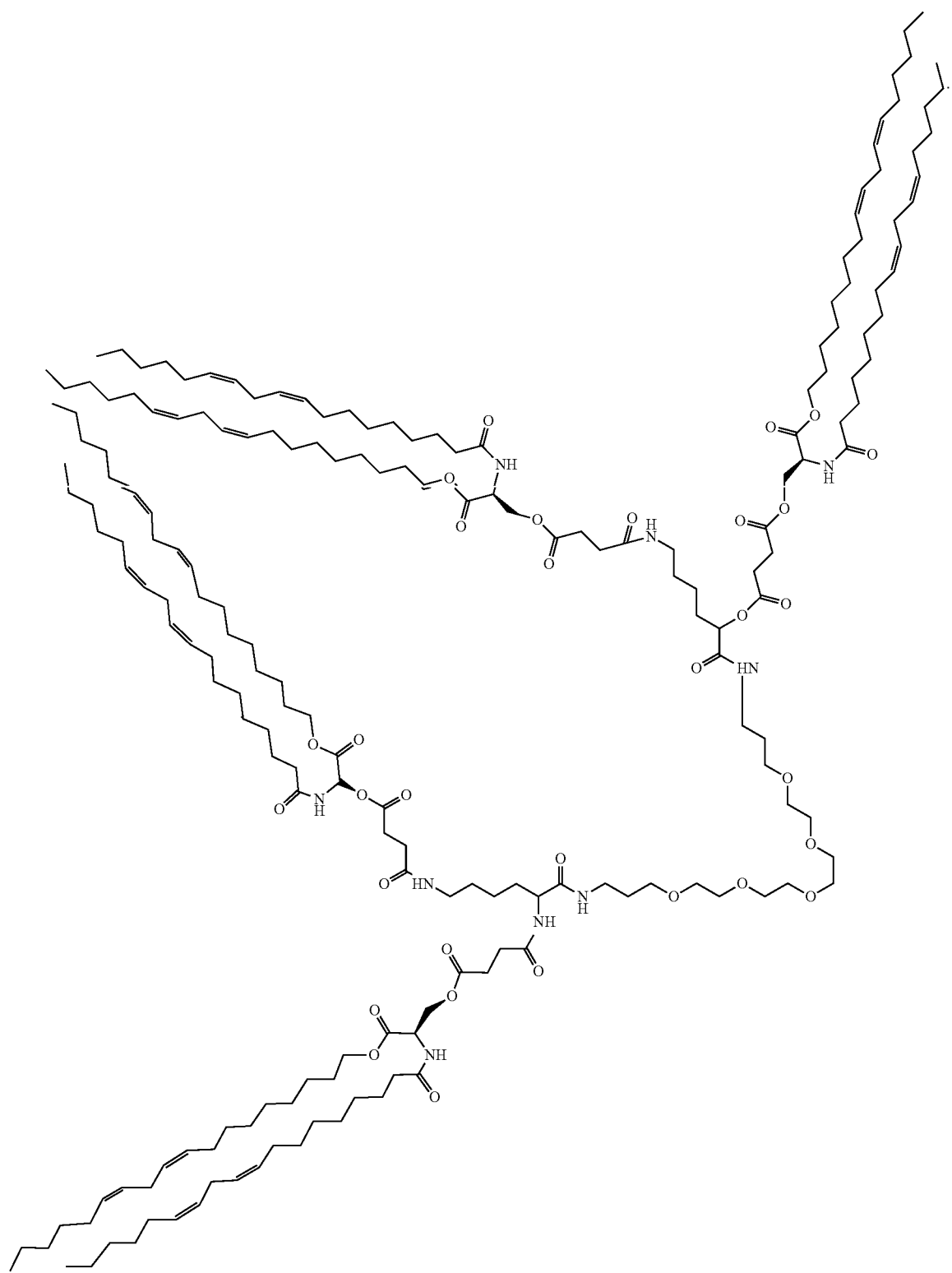
Compound T12

11. The fusogenic compound of claim 1, wherein $R^4$ and $R^5$ in Formula (VI) are independently for each occurrence a C(14-18) alkyl group, or a C(14-18) alkenyl group.
12. The fusogenic compound of claim 1, wherein the compound is compound T11
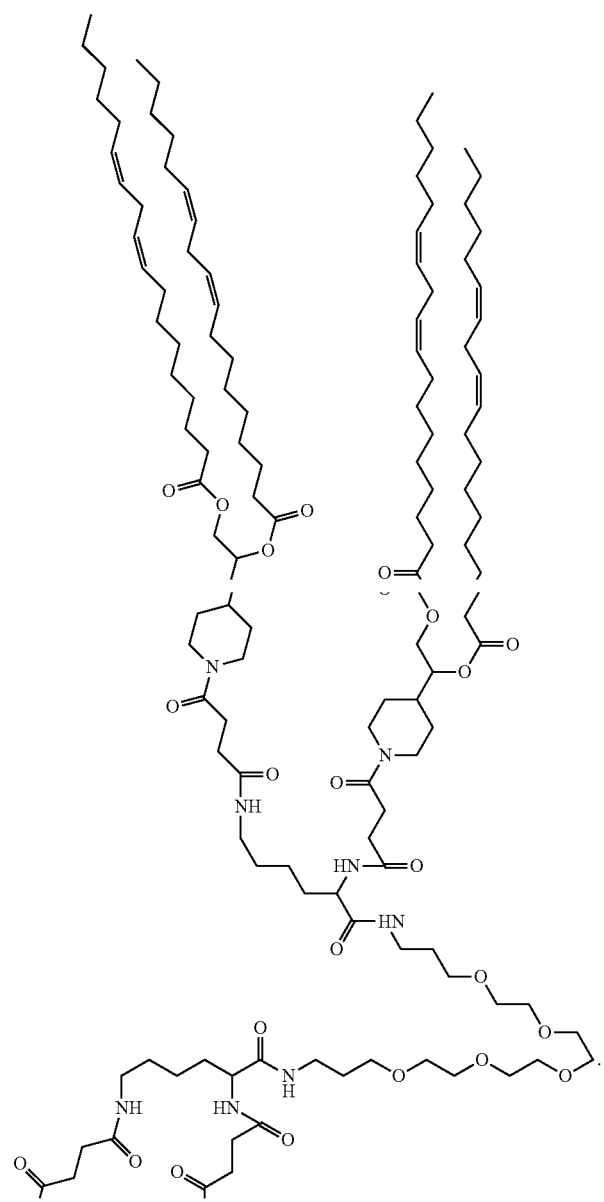
Compound T11

-continued

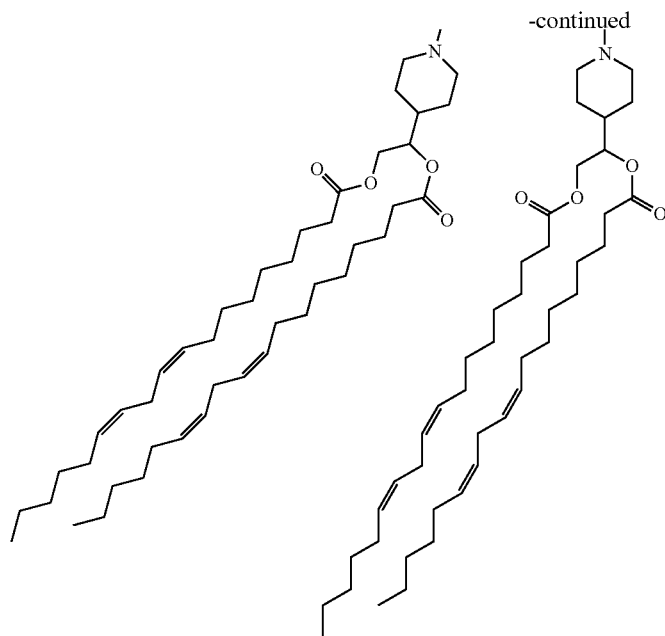

13. A composition comprising a fusogenic compound of claim 1 and a pharmaceutically acceptable carrier.

14. The composition of claim 13, wherein the composition comprises nanoparticles or liposomes.

15. A pharmaceutical composition comprising a fusogenic compound of claim 1, an active agent, and a pharmaceutically acceptable carrier.

16. The composition of claim 15, wherein the fusogenic compound is from 0.01 mol % to 20 mol % of the lipids of the composition.

17. The composition of claim 15, wherein the composition comprises nanoparticles or liposomes.

18. The composition of claim 15, wherein the active agent is one or more nucleic acids.

19. The composition of claim 15, wherein the active agent is one or more DNAs, RNAs, mRNAs, siRNAs, or microRNAs.

20. The composition of claim 15, wherein the active agent is one or more RNA molecules.

21. The composition of claim 15, wherein the active agent is selected from one or more RNAi molecules, one or more mRNA molecules, and modified forms thereof.

22. A composition comprising an active agent, a fusogenic compound of claim 1, an ionizable lipid, a structural lipid, a stabilizer lipid, and a lipid for reducing immunogenicity of the composition.

23. The composition of claim 22, wherein the active agent is one or more nucleic acids.

* * * * *